United States Patent
Siegel et al.

(10) Patent No.: US 10,487,318 B1
(45) Date of Patent: *Nov. 26, 2019

(54) COMPOSITIONS AND METHODS FOR TREATING CELIAC SPRUE DISEASE

(71) Applicant: UNIVERSITY OF WASHINGTON THROUGH ITS CENTER FOR COMMERCIALIZATION, Seattle, WA (US)

(72) Inventors: Justin Bloomfield Siegel, Seattle, WA (US); David Baker, Seattle, WA (US); Ingrid Swanson Pultz, Seattle, WA (US)

(73) Assignee: University of Washington Through its Center for Commercialization, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/360,190

(22) Filed: Mar. 21, 2019

Related U.S. Application Data

(63) Continuation of application No. 14/911,630, filed as application No. PCT/US2014/050835 on Aug. 13, 2014, now Pat. No. 10,266,815.

(60) Provisional application No. 61/865,787, filed on Aug. 14, 2013.

(51) Int. Cl.
*C12N 9/52* (2006.01)
*C12N 9/64* (2006.01)
*A61K 38/00* (2006.01)

(52) U.S. Cl.
CPC ............... *C12N 9/52* (2013.01); *C12N 9/64* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 7,202,216 B2 | 4/2007 | Sollid et al. |
| 7,265,093 B2 | 9/2007 | Khosla et al. |
| 7,303,871 B2 | 12/2007 | Hausch et al. |
| 7,320,788 B2 | 1/2008 | Shan et al. |
| 7,462,688 B2 | 12/2008 | Khosla et al. |
| 7,534,426 B2 | 5/2009 | Piper et al. |
| 7,563,864 B2 | 7/2009 | Marti et al. |
| 7,579,313 B2 | 8/2009 | Khosla et al. |
| 7,605,150 B2 | 10/2009 | Khosla et al. |
| 7,628,985 B2 | 12/2009 | Shan et al. |
| 7,776,545 B2 | 8/2010 | Khosla et al. |
| 7,910,541 B2 | 3/2011 | Hausch et al. |
| 7,923,532 B2 | 4/2011 | Hausch et al. |
| 7,928,056 B2 | 4/2011 | Hausch et al. |
| 7,943,312 B2 | 5/2011 | Hausch et al. |
| 8,071,316 B2 | 12/2011 | Khosla et al. |
| 8,143,210 B2 | 3/2012 | Shan et al. |
| 8,153,593 B2 | 4/2012 | Khosla et al. |
| 8,426,145 B2 | 4/2013 | Khosla et al. |
| 8,470,782 B2 | 6/2013 | Khosla et al. |
| 8,796,201 B2 | 8/2014 | Shan et al. |
| 8,871,718 B2 | 10/2014 | Khosla et al. |
| 8,962,545 B2 | 2/2015 | Hausch et al. |
| 2006/0269538 A1 | 11/2006 | Kolterman et al. |
| 2009/0117092 A1 | 5/2009 | Kappler et al. |
| 2009/0280555 A1 | 11/2009 | Hausch et al. |
| 2011/0171201 A1 | 7/2011 | Siegel et al. |
| 2011/0293724 A1 | 12/2011 | Hausch et al. |

FOREIGN PATENT DOCUMENTS

| | | |
|---|---|---|
| JP | 2002078489 | 3/2002 |
| WO | 2013/023151 A2 | 2/2013 |
| WO | 2013/083338 A1 | 6/2013 |
| WO | 2015/023728 | 2/2015 |

OTHER PUBLICATIONS

Akobeng, et al., "Systematic review: tolerable amount of gluten for people with coeliac disease," Alimentary Pharmacology & Therapeutics, 27: 1044-1052 (2008).
Arentz-Hansen, et al., "The Intestinal T Cell Response to a-Gliadin in Adult Celiac Disease Is Focused on a Single Deamidated Glutamine Targeted by Tissue Transglutaminase," J. Exp. Med., 191(4): 603-612, 2000.
Armstrong, et al., "Advances in coeliac disease," Curr Opin Gastroenterol 2012, 28:104-112.
Arnold, "Combinatorial and computational challenges for biocatalyst design," Nature, 409: 253-257, Jan. 2001.
Bershtein, et al., "Advances in laboratory evolution of enzymes," Current Opinion in Chemical Biology 2008, 12:151-158.
Bethune, et al., "Heterologous Expression, Purification, Refolding, and Structural-Functional Characterization of EP-B2, a Self-Activating Barley Cysteine Endoprotease," Chemistry & Biology 13, 637-647, Jun. 2006.
Bethune, et al., "Oral Enzyme Therapy for Celiac Sprue," Methods in Enzymology, 502: 241-270, 2012.
Camacrca, et al., "Intestinal T Cell Responses to Gluten Peptides Are Largely Heterogeneous: Implications for a Peptide-Based Therapy in Celiac Disease," The Journal of Immunology, 2009, 4158-4166.
Castillo, et al., "The present and the future in the diagnosis and management of celiac disease," Gastroenterology Report, 3(1), 2015, 3-11.
Catassi, et al., "World Perspective and Celiac Disease Epidemiology," Dig Dis 2015;33:141-146.
Catassi, et al., "A prospective, double-blind, placebo-controlled trial to establish a safe gluten threshold for patients with celiac disease," Am J Clin Nutr 2007;85:160-6.
Chand, et al., "Celiac Disease Current Concepts in Diagnosis and Treatment," J Clin Gastroenterol 2006;40:3-14.
Chang, et al., "A Novel Placement Method of the Bravo Wireless pH Monitoring Capsule for Measuring Intragastric pH," Dig Dis Sci (2009) 54:578-585.

(Continued)

*Primary Examiner* — Manjunath N Rao
*Assistant Examiner* — Jae W Lee
(74) *Attorney, Agent, or Firm* — McDonnell Boehnen Hulbert & Berghoff LLP

(57) ABSTRACT

The invention provides compositions and methods for treating celiac sprue.

29 Claims, 4 Drawing Sheets

Specification includes a Sequence Listing.

(56) References Cited

OTHER PUBLICATIONS

Ehern, et al., "A Food-Grade Enzyme Preparation with Modest Gluten Detoxification Properties," PLoS ONE 4(7): e6313. doi:10.1371/journal.pone.0006313, Jul. 2009.
Ehern, et al., "Protein engineering of improved prolyl endopeptidases for celiac sprue therapy," Protein Engineering, Design & Selection vol. 21 No. 12 pp. 699-707, 2008.
Eiben, et al., "Increased Diels-Alderase activity through backbone remodeling guided by Foldit players," Nature Biotechnology, 30(2): 190-194, 2012.
Fleishman, et al., "Computational Design of Proteins Targeting the Conserved Stem Region of Influenza Hemagglutinin," Science, 332:816-821, May 2011.
Gardner, et al., Measurement of meal-stimulated gastric acid secretion by in vivo gastric autotitration, J Appl Physiol 92: 427-434, 2002.
Gass, et al., "Combination Enzyme Therapy for Gastric Digestion of Dietary Gluten in Patients With Celiac Sprue," Gastroenterology 2007;133:472-480.
Gass, et al., "Effect of Barley Endoprotease EP-B2 on Gluten Digestion in the Intact Rat," The Journal of Pharmacology and Experimental Therapeutics vol. 318, No. 3, pp. 1178-1186, 2006.
Gordon, et al., "Computational Design of an α-Gliadin Peptidase," J. Am. Chem. Soc. 2012, 134, 20513-20520.
Hausch, et al., "Intestinal digestive resistance of immunodominant gliadin peptides," Am J Physiol Gastrointest Liver Physiol 283: G996-G1003, 2002.
Houghton, et al., "Relationship of the Motor Activity of the Antrum, Pylorus, and Duodenum to Gastric Emptying of a Solid Liquid Mixed Meal," Gatroenterology, 1988; 94:1285-91.
International Search Report PCT/US2012/050364, dated Apr. 18, 2013.
International Search Report PCT/US2014/050835, dated Dec. 2, 2014.
Kuhlman, et al., "Design of a Novel Globular Protein Fold with Atomic-Level Accuracy," Science, 302: 1364-1368, Nov. 2003.
Kunkel, "Rapid and efficient site-specific mutagenesis without phenotypic selection," Proc. Natl. Acad. Sci. USA vol. 82, pp. 488-492, Jan. 1985.
Lahdeaho, et al., "Glutenase ALV003 Attenuates Gluten-Induced Mucosal Injury in Patients With Celiac Disease," Gastroenterology 2014;146:1649-1658.
Leaver-Fay, et al., "ROSETTA3: An Object-Oriented Software Suite for the Simulation and Design of Macromolecules," Methods in Enzymology, vol. 487:545-574, 2011.
Lupo, et al., "Validation Study of the Veratox R5 Rapid ELISA for Detection of Gliadin," Journal of AOA C International vol. 96, No. 1, 2013.
Moron, et al., "Sensitive detection of cereal fractions that are toxic to celiac disease patients by using monoclonal antibodies to a main immunogenic wheat peptide," Am J Clin Nutr 2008;87:405-14.
Mustalahti, et al., "The prevalence of celiac disease in Europe: Results of a centralized, international mass screening project," Annals of Medicine, 42:8, 587-595, Nov. 2010.
Oda, et al., "Subsite Preferences of Pepstatin-Insensitive Carboxyl Proteinases from Prokaryotes: Kumamolysin, a Thermostable Pepstatin-Insensitive Carboxyl Proteinase," J. Biochem. 128,499-607 (2000).
Okubo, et al., "Processing, catalytic activity and crystal structures of kumamolisin-As with an engineered active site," FEBS Journal 273 (2006) 2563-2576.
Oyama, et al., "A CLN2-Related and Thermostable Serine-Carboxyl Proteinase, Kumamolysin: Cloning, Expression, and Identification of Catalytic Serine Residue," J. Biochem. 131, 757-766 (2002).
Pera, et al., "Influence of Mastication on Gastric Emptying," J Dent Res 81(3):179-181, 2002.
Petersen, et al., "T-cell receptor recognition of HLA-DQ2-gliadin complexes associated with celiac disease," Nature Structural & Molecular Biology, 21(5): 480-490, May 2014.

Picariello, et al., "Proteomics, Peptidomics, and Immunogenic Potential of Wheat Beer (Weissbier)," J. Agric. Food Chem. 2015, 63, 3579-3586.
Richter, et al., "De Novo Enzyme Design Using Rosetta3," PLoS ONE 6(5): e19230. doi:10.1371/journal.pone.0019230, May 2011.
Romero, et al., "Exploring protein fitness landscapes by directed evolution," Nature Reviews: Molecular cell Biology, 10: 866-876, Dec. 2009.
Rubio-Tapia, et al., "The Prevalence of Celiac Disease in the United States," Am J Gastroenterol 2012; 107:1538-1544; doi: 10.1038/ajg.2012.219; published online Jul. 31, 2012.
Shan, et al., "Comparative biochemical analysis of three bacterial prolyl endopeptidases: implications for coeliac sprue," Biochem. J. (2004) 383, 311-318.
Shan, et al., "Identification and Analysis of Multivalent Proteolytically Resistant Peptides from Gluten: Implications for Celiac Sprue," Journal of Proteome Research 2005, 4, 1732-1741.
Shan, et al., "Structural Basis for Gluten Intolerance in Celiac Sprue," Science, 297:2275-2279, Sep. 2002.
Siegel, et al., "Rational Design of Combination Enzyme Therapy for Celiac Sprue," Chemistry & Biology 13, 649-658, Jun. 2006.
Siegel, et al., "Safety, Tolerability, and Activity of ALV003: Results from Two Phase 1 Single, Escalating-Dose Clinical Trials," Dig Dis Sci (2012) 57:440-450.
Sollid, et al., "Nomenclature and listing of celiac disease relevant gluten T-cell epitopes restricted by HLA-DQ molecules," Immunogenetics (2012) 64:455-460.
Sollid, et al., "Coeliac Disease: Dissecting a Complex Inflammatory Disorder," Nature Reviews: Immunology, 2:847-855, Sep. 2002.
Stepniak, et al., "Highly efficient gluten degradation with a newly identified prolyl endoprotease: implications for celiac disease," Am J Physiol Gastrointest Liver Physiol 291: G621-G629, May 2006.
Tye-Din, et al., "Comprehensive, Quantitative Mapping of T Cell Epitopes in Gluten in Celiac Disease," Sci Transl Med 2, 41ra51 (2010).
Office Action dated Dec. 23, 2015 in EP 12748354.3.
International Search Report and Written Opinion for PCT/US2016/036356, dated Aug. 10, 2016.
Database Uniparc, XP002760283, Jan. 15, 2010.
Wolf, et al., "Engineering of Kuma 030: A Gliadin peptidase that rapidly degrades immunogenic gliadin peptides in gastric conditions," Journal of the American Chemical Society, 137(40): 13106-13113, Oct. 2015.
Kumar, et al., (2013) Uniprot database accession No. K8RMLO_9BURK.
Ehren, Jennifer, Sridhar Govindarajan, Belâen Morâon, Jeremy Minshull, and Chaitan Khosla. 2008. "Protein engineering of improved prolyl endopeptidases for celiac sprue therapy". Protein Engineering, Design & Selection. 21 (12): 699-707.
Mustalahti K, C Catassi, A Reunanen, E Fabiani, M Heier, S McMillan, L Murray, et al. 2010. "The prevalence of celiac disease in Europe: results of a centralized, international mass screening project". Annals of Medicine. 42 (8): 587-95.
Shan L, Ø Molberg, I Parrot, F Hausch, F Filiz, GM Gray, LM Sollid, and C Khosla. 2002. "Structural basis for gluten intolerance in celiac sprue". Science (New York, N.Y.). 297 (5590): 2275-9.
Wlodawer A, M Li, A Gustchina, N Tsuruoka, M Ashida, H Minakata, H Oyama, K Oda, T Nishino, and T Nakayama. 2004. "Crystallographic and biochemical investigations of kumamolisin-As, a serine-carboxyl peptidase with collagenase activity". The Journal of Biological Chemistry. 279 (20): 21500-10.
Vora Harmit, et al., (2007) "A scaleable manufacturing process for pro-EP-B2, a cysteine protease from barley indicated for celiac psrue," Biotechnology and Bioengineering, 98(1): 177-185.
Oyama Hiroshi, et al., (2002) "A CLN2-related and thermostable serine-carboxyl proteinase, kumamolysin: cloning, expression, and identification of catalytic serine residue," Biochemistry, 131(5):757-765.
International Search Report for PCT/US12/50364, dated Apr. 18, 2013.
Dunn, et al., "Engineered Enzyme," Encyclopedia of Life Sciences, 2005, p. 1-8.

(56) References Cited

OTHER PUBLICATIONS

Wieser, "Chemistry of gluten proteins," Food Microbiology 24 (2007) 115-119.
GenBank: BAC41257.1, kumamolisin-As precursor, Jun. 2003.
Arentz-Hansen et al. (Sep. 2002) "Celiac lesion T cells recognize epitopes that cluster in regions of gliadins rich in proline residues," Gastroenterology, 123(3):803-809.
Siegel et al. (Jul. 2010) "Computational Design of an Enzyme Catalyst for a Stereoselective Bimolecular Diels-Alder Reaction," Science, 329(5989):309-313.
Uniprot C8WU40—Retrieved from ,http://www.uniprot.org/uniprot/C8WU40> on Jan. 29, 2015.
Cornellas-Bigler, et al., "1.2 A crystal structure of the serine carboxyl porteinase pro-kumamolisin: structure of an intact pro-subtilase," Structure, 12: 1313-1323, Jul. 2004.
GenBank: 1SIO_A, Chain A, Structure of Kumamolisin-As Complex, Sep. 2008.
Genbank: ACV57803.1, Peptidase S53 propeptide, Sep. 2009.
Peptidase S53 propeptide [Acidimicrobium ferrooxidans DSM 10331] (Genbank accession No. ACU54006.1, publically available since Aug. 18, 2009, retrieved from the internet: <https://www.ncbi.nlm.nih.gov/protein/ACU54006?report=genbank&log$=protalign&blast_rank=1&RID=E6Z6PR8P015, retrieved on Apr. 27, 2018).

SEQUENCE LISTING

<160> NUMBER OF SEQ ID NOS: 112

<210> SEQ ID NO 1
<211> LENGTH: 573
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (119)..(119)
<223> OTHER INFORMATION: X can be V or D
<220> FEATURE:
<221> NAME/KEY: MISC_FEATURE
<222> LOCATION: (262)..(262)
<223> OTHER INFORMATION: X can be S, K or G
<220> FEATURE:
<221> NAME/KEY: MISC_FEATURE
<222> LOCATION: (291)..(291)
<223> OTHER INFORMATION: X can be N or D
<220> FEATURE:
<221> NAME/KEY: MISC_FEATURE
<222> LOCATION: (292)..(292)
<223> OTHER INFORMATION: X can be T or S
<220> FEATURE:
<221> NAME/KEY: MISC_FEATURE
<222> LOCATION: (293)..(293)
<223> OTHER INFORMATION: X can be D, A, T, or N
<220> FEATURE:
<221> NAME/KEY: MISC_FEATURE
<222> LOCATION: (319)..(319)
<223> OTHER INFORMATION: X can be G or S
<220> FEATURE:
<221> NAME/KEY: MISC_FEATURE
<222> LOCATION: (354)..(354)
<223> OTHER INFORMATION: X can be S or N
<220> FEATURE:
<221> NAME/KEY: MISC_FEATURE
<222> LOCATION: (357)..(357)
<223> OTHER INFORMATION: X can be T or A
<220> FEATURE:
<221> NAME/KEY: MISC_FEATURE
<222> LOCATION: (358)..(358)
<223> OTHER INFORMATION: X can be D, N or G
<220> FEATURE:
<221> NAME/KEY: MISC_FEATURE
<222> LOCATION: (361)..(361)
<223> OTHER INFORMATION: X can be Q or D
<220> FEATURE:
<221> NAME/KEY: MISC_FEATURE
<222> LOCATION: (368)..(368)
<223> OTHER INFORMATION: X can be D, S, or H

<400> SEQUENCE: 1

```
Met Ser Asp Met Glu Lys Pro Trp Lys Glu Gly Glu Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Leu Arg
        35                  40                  45

Arg Gln Arg Ala Gly Glu Leu Ala Ala His Val Glu Arg Gln Ala Ala
    50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Xaa Asp Ala Ile Asn Arg Ala Phe Gly Val
        115                 120                 125
```

```
Glu Leu Arg His Phe Asp His Pro Asp Gly Ser Tyr Arg Ser Tyr Leu
    130                 135                 140
Gly Glu Val Thr Val Pro Ala Ser Ile Ala Pro Met Ile Glu Ala Val
145                 150                 155                 160
Leu Gly Leu Asp Thr Arg Pro Val Ala Arg Pro His Phe Arg Met Gln
                165                 170                 175
Arg Arg Ala Glu Gly Phe Glu Ala Arg Ser Gln Ala Ala Ala Pro
            180                 185                 190
Thr Ala Tyr Thr Pro Leu Asp Val Ala Gln Ala Tyr Gln Phe Pro Glu
        195                 200                 205
Gly Leu Asp Gly Gln Gly Gln Cys Ile Ala Ile Ile Glu Leu Gly Gly
    210                 215                 220
Gly Tyr Asp Glu Ala Ser Leu Ala Gln Tyr Phe Ala Ser Leu Gly Val
225                 230                 235                 240
Pro Ala Pro Gln Val Val Ser Val Ser Val Asp Gly Ala Ser Asn Gln
                245                 250                 255
Pro Thr Gly Asp Pro Xaa Gly Pro Asp Gly Glu Val Glu Leu Asp Ile
            260                 265                 270
Glu Val Ala Gly Ala Leu Ala Pro Gly Ala Lys Phe Ala Val Tyr Phe
        275                 280                 285
Ala Pro Xaa Xaa Xaa Ala Gly Phe Leu Asp Ala Ile Thr Thr Ala Ile
    290                 295                 300
His Asp Pro Thr Leu Lys Pro Ser Val Val Ser Ile Ser Trp Xaa Gly
305                 310                 315                 320
Pro Glu Asp Ser Trp Thr Ser Ala Ala Ile Ala Ala Met Asn Arg Ala
                325                 330                 335
Phe Leu Asp Ala Ala Leu Gly Val Thr Val Leu Ala Ala Ala Gly
            340                 345                 350
Asp Xaa Gly Ser Xaa Xaa Gly Glu Xaa Asp Gly Leu Tyr His Val Xaa
        355                 360                 365
Phe Pro Ala Ala Ser Pro Tyr Val Leu Ala Cys Gly Gly Thr Arg Leu
    370                 375                 380
Val Ala Ser Gly Gly Arg Ile Ala Gln Glu Thr Val Trp Asn Asp Gly
385                 390                 395                 400
Pro Asp Gly Gly Ala Thr Gly Gly Val Ser Arg Ile Phe Pro Leu
                405                 410                 415
Pro Ala Trp Gln Glu His Ala Asn Val Pro Pro Ser Ala Asn Pro Gly
            420                 425                 430
Ala Ser Ser Gly Arg Gly Val Pro Asp Leu Ala Gly Asn Ala Asp Pro
        435                 440                 445
Ala Thr Gly Tyr Glu Val Val Ile Asp Gly Ala Thr Val Ile Gly
    450                 455                 460
Gly Thr Ser Ala Val Ala Pro Leu Phe Ala Ala Leu Val Ala Arg Ile
465                 470                 475                 480
Asn Gln Lys Leu Gly Lys Ala Val Gly Tyr Leu Asn Pro Thr Leu Tyr
                485                 490                 495
Gln Leu Pro Ala Asp Val Phe His Asp Ile Thr Glu Gly Asn Asn Asp
            500                 505                 510
Ile Ala Asn Arg Ala Gln Ile Tyr Gln Ala Gly Pro Gly Trp Asp Pro
        515                 520                 525
Cys Thr Gly Leu Gly Ser Pro Ile Gly Val Arg Leu Leu Gln Ala Leu
    530                 535                 540
```

-continued

```
Leu Pro Ser Ala Ser Gln Pro Gln Pro Gly Ser Thr Glu Asn Leu Tyr
545                 550                 555                 560

Phe Gln Ser Gly Ala Leu Glu His His His His His His
                565                 570

<210> SEQ ID NO 2
<211> LENGTH: 573
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (119)..(119)
<223> OTHER INFORMATION: X can be V or D
<220> FEATURE:
<221> NAME/KEY: MISC_FEATURE
<222> LOCATION: (262)..(262)
<223> OTHER INFORMATION: X can be S, K or G
<220> FEATURE:
<221> NAME/KEY: MISC_FEATURE
<222> LOCATION: (291)..(291)
<223> OTHER INFORMATION: All mutants with more than 10-fold activity
      have this substitution
<220> FEATURE:
<221> NAME/KEY: MISC_FEATURE
<222> LOCATION: (292)..(292)
<223> OTHER INFORMATION: X can be T or S
<220> FEATURE:
<221> NAME/KEY: MISC_FEATURE
<222> LOCATION: (293)..(293)
<223> OTHER INFORMATION: X can be D, A, T or N
<220> FEATURE:
<221> NAME/KEY: MISC_FEATURE
<222> LOCATION: (319)..(319)
<223> OTHER INFORMATION: X can be G or S
<220> FEATURE:
<221> NAME/KEY: MISC_FEATURE
<222> LOCATION: (354)..(354)
<223> OTHER INFORMATION: X can be S or N
<220> FEATURE:
<221> NAME/KEY: MISC_FEATURE
<222> LOCATION: (357)..(357)
<223> OTHER INFORMATION: X can be T or A
<220> FEATURE:
<221> NAME/KEY: MISC_FEATURE
<222> LOCATION: (358)..(358)
<223> OTHER INFORMATION: X can be D, N or G
<220> FEATURE:
<221> NAME/KEY: MISC_FEATURE
<222> LOCATION: (361)..(361)
<223> OTHER INFORMATION: X can be Q or D
<220> FEATURE:
<221> NAME/KEY: MISC_FEATURE
<222> LOCATION: (368)..(368)
<223> OTHER INFORMATION: X can be D, S or H

<400> SEQUENCE: 2

Met Ser Asp Met Glu Lys Pro Trp Lys Glu Gly Glu Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Leu Arg
        35                  40                  45

Arg Gln Arg Ala Gly Glu Leu Ala Ala His Val Glu Arg Gln Ala Ala
    50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95
```

```
Asp Ala His Gly Leu Ala Leu Asp Arg Ala Asn Val Ala Ala Gly Thr
            100                 105                 110
Ala Val Leu Ser Gly Pro Xaa Asp Ala Ile Asn Arg Ala Phe Gly Val
        115                 120                 125
Glu Leu Arg His Phe Asp His Pro Asp Gly Ser Tyr Arg Ser Tyr Leu
    130                 135                 140
Gly Glu Val Thr Val Pro Ala Ser Ile Ala Pro Met Ile Glu Ala Val
145                 150                 155                 160
Leu Gly Leu Asp Thr Arg Pro Val Ala Arg Pro His Phe Arg Met Gln
                165                 170                 175
Arg Arg Ala Glu Gly Gly Phe Glu Ala Arg Ser Gln Ala Ala Ala Pro
            180                 185                 190
Thr Ala Tyr Thr Pro Leu Asp Val Ala Gln Ala Tyr Gln Phe Pro Glu
        195                 200                 205
Gly Leu Asp Gly Gln Gly Gln Cys Ile Ala Ile Ile Glu Leu Gly Gly
    210                 215                 220
Gly Tyr Asp Glu Ala Ser Leu Ala Gln Tyr Phe Ala Ser Leu Gly Val
225                 230                 235                 240
Pro Ala Pro Gln Val Val Ser Val Ser Val Asp Gly Ala Ser Asn Gln
                245                 250                 255
Pro Thr Gly Asp Pro Xaa Gly Pro Asp Gly Glu Val Glu Leu Asp Ile
            260                 265                 270
Glu Val Ala Gly Ala Leu Ala Pro Gly Ala Lys Phe Ala Val Tyr Phe
        275                 280                 285
Ala Pro Asp Xaa Xaa Ala Gly Phe Leu Asp Ala Ile Thr Thr Ala Ile
    290                 295                 300
His Asp Pro Thr Leu Lys Pro Ser Val Val Ser Ile Ser Trp Xaa Gly
305                 310                 315                 320
Pro Glu Asp Ser Trp Thr Ser Ala Ala Ile Ala Ala Met Asn Arg Ala
                325                 330                 335
Phe Leu Asp Ala Ala Ala Leu Gly Val Thr Val Leu Ala Ala Ala Gly
            340                 345                 350
Asp Xaa Gly Ser Xaa Xaa Gly Glu Xaa Asp Gly Leu Tyr His Val Xaa
        355                 360                 365
Phe Pro Ala Ala Ser Pro Tyr Val Leu Ala Cys Gly Gly Thr Arg Leu
    370                 375                 380
Val Ala Ser Gly Gly Arg Ile Ala Gln Glu Thr Val Trp Asn Asp Gly
385                 390                 395                 400
Pro Asp Gly Gly Ala Thr Gly Gly Val Ser Arg Ile Phe Pro Leu
                405                 410                 415
Pro Ala Trp Gln Glu His Ala Asn Val Pro Pro Ser Ala Asn Pro Gly
            420                 425                 430
Ala Ser Ser Gly Arg Gly Val Pro Asp Leu Ala Gly Asn Ala Asp Pro
        435                 440                 445
Ala Thr Gly Tyr Glu Val Val Ile Asp Gly Glu Ala Thr Val Ile Gly
    450                 455                 460
Gly Thr Ser Ala Val Ala Pro Leu Phe Ala Ala Leu Val Ala Arg Ile
465                 470                 475                 480
Asn Gln Lys Leu Gly Lys Ala Val Gly Tyr Leu Asn Pro Thr Leu Tyr
                485                 490                 495
Gln Leu Pro Ala Asp Val Phe His Asp Ile Thr Glu Gly Asn Asn Asp
            500                 505                 510
Ile Ala Asn Arg Ala Gln Ile Tyr Gln Ala Gly Pro Gly Trp Asp Pro
```

```
                515                 520                 525
Cys Thr Gly Leu Gly Ser Pro Ile Gly Val Arg Leu Leu Gln Ala Leu
        530                 535                 540

Leu Pro Ser Ala Ser Gln Pro Gln Pro Gly Ser Thr Glu Asn Leu Tyr
545                 550                 555                 560

Phe Gln Ser Gly Ala Leu Glu His His His His His His
                565                 570

<210> SEQ ID NO 3
<211> LENGTH: 573
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (119)..(119)
<223> OTHER INFORMATION: X can be V or D
<220> FEATURE:
<221> NAME/KEY: MISC_FEATURE
<222> LOCATION: (262)..(262)
<223> OTHER INFORMATION: X can be S, K, or G
<220> FEATURE:
<221> NAME/KEY: MISC_FEATURE
<222> LOCATION: (291)..(291)
<223> OTHER INFORMATION: All mutants with more than 20-fold activity
     increase have this substitution together with 358 substitution
<220> FEATURE:
<221> NAME/KEY: MISC_FEATURE
<222> LOCATION: (292)..(292)
<223> OTHER INFORMATION: X is T or S
<220> FEATURE:
<221> NAME/KEY: MISC_FEATURE
<222> LOCATION: (293)..(293)
<223> OTHER INFORMATION: X is D, A, T or N
<220> FEATURE:
<221> NAME/KEY: MISC_FEATURE
<222> LOCATION: (319)..(319)
<223> OTHER INFORMATION: X is G or S
<220> FEATURE:
<221> NAME/KEY: MISC_FEATURE
<222> LOCATION: (354)..(354)
<223> OTHER INFORMATION: X is S or N
<220> FEATURE:
<221> NAME/KEY: MISC_FEATURE
<222> LOCATION: (357)..(357)
<223> OTHER INFORMATION: X is T or A
<220> FEATURE:
<221> NAME/KEY: MISC_FEATURE
<222> LOCATION: (358)..(358)
<223> OTHER INFORMATION: X is N or G (most have G at this position)
<220> FEATURE:
<221> NAME/KEY: MISC_FEATURE
<222> LOCATION: (361)..(361)
<223> OTHER INFORMATION: X is Q or D
<220> FEATURE:
<221> NAME/KEY: MISC_FEATURE
<222> LOCATION: (368)..(368)
<223> OTHER INFORMATION: X is D, S, or H

<400> SEQUENCE: 3

Met Ser Asp Met Glu Lys Pro Trp Lys Glu Gly Glu Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Leu Arg
        35                  40                  45

Arg Gln Arg Ala Gly Glu Leu Ala Ala His Val Glu Arg Gln Ala Ala
    50                  55                  60

Ile Ala Pro His Ala Arg Glu His Leu Lys Arg Glu Ala Phe Ala Ala
```

```
                65                  70                  75                  80
        Ser His Gly Ala Ser Leu Asp Asp Phe Ala Glu Leu Arg Arg Phe Ala
                            85                  90                  95

Asp Ala His Gly Leu Ala Leu Asp Arg Ala Asn Val Ala Ala Gly Thr
                    100                 105                 110

Ala Val Leu Ser Gly Pro Xaa Asp Ala Ile Asn Arg Ala Phe Gly Val
                    115                 120                 125

Glu Leu Arg His Phe Asp His Pro Asp Gly Ser Tyr Arg Ser Tyr Leu
                130                 135                 140

Gly Glu Val Thr Val Pro Ala Ser Ile Ala Pro Met Ile Glu Ala Val
        145                 150                 155                 160

Leu Gly Leu Asp Thr Arg Pro Val Ala Arg Pro His Phe Arg Met Gln
                        165                 170                 175

Arg Arg Ala Glu Gly Gly Phe Glu Ala Arg Ser Gln Ala Ala Ala Pro
                    180                 185                 190

Thr Ala Tyr Thr Pro Leu Asp Val Ala Gln Ala Tyr Gln Phe Pro Glu
                    195                 200                 205

Gly Leu Asp Gly Gln Gly Gln Cys Ile Ala Ile Ile Glu Leu Gly Gly
                    210                 215                 220

Gly Tyr Asp Glu Ala Ser Leu Ala Gln Tyr Phe Ala Ser Leu Gly Val
        225                 230                 235                 240

Pro Ala Pro Gln Val Val Ser Val Ser Val Asp Gly Ala Ser Asn Gln
                        245                 250                 255

Pro Thr Gly Asp Pro Xaa Gly Pro Asp Gly Glu Val Glu Leu Asp Ile
                    260                 265                 270

Glu Val Ala Gly Ala Leu Ala Pro Gly Ala Lys Phe Ala Val Tyr Phe
                    275                 280                 285

Ala Pro Asp Xaa Xaa Ala Gly Phe Leu Asp Ala Ile Thr Thr Ala Ile
                    290                 295                 300

His Asp Pro Thr Leu Lys Pro Ser Val Val Ser Ile Ser Trp Xaa Gly
        305                 310                 315                 320

Pro Glu Asp Ser Trp Thr Ser Ala Ala Ile Ala Ala Met Asn Arg Ala
                        325                 330                 335

Phe Leu Asp Ala Ala Ala Leu Gly Val Thr Val Leu Ala Ala Ala Gly
                    340                 345                 350

Asp Xaa Gly Ser Xaa Xaa Gly Glu Xaa Asp Gly Leu Tyr His Val Xaa
                    355                 360                 365

Phe Pro Ala Ala Ser Pro Tyr Val Leu Ala Cys Gly Gly Thr Arg Leu
                370                 375                 380

Val Ala Ser Gly Gly Arg Ile Ala Gln Glu Thr Val Trp Asn Asp Gly
        385                 390                 395                 400

Pro Asp Gly Gly Ala Thr Gly Gly Val Ser Arg Ile Phe Pro Leu
                    405                 410                 415

Pro Ala Trp Gln Glu His Ala Asn Val Pro Ser Ala Asn Pro Gly
                    420                 425                 430

Ala Ser Ser Gly Arg Gly Val Pro Asp Leu Ala Gly Asn Ala Asp Pro
                    435                 440                 445

Ala Thr Gly Tyr Glu Val Val Ile Asp Gly Glu Ala Thr Val Ile Gly
                    450                 455                 460

Gly Thr Ser Ala Val Ala Pro Leu Phe Ala Ala Leu Val Ala Arg Ile
        465                 470                 475                 480

Asn Gln Lys Leu Gly Lys Ala Val Gly Tyr Leu Asn Pro Thr Leu Tyr
                        485                 490                 495
```

```
Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
        515                 520                 525

Cys Thr Gly Leu Gly Ser Pro Ile Gly Val Arg Leu Leu Gln Ala Leu
    530                 535                 540

Leu Pro Ser Ala Ser Gln Pro Gln Pro Gly Ser Thr Glu Asn Leu Tyr
545                 550                 555                 560

Phe Gln Ser Gly Ala Leu Glu His His His His His His
                565                 570

<210> SEQ ID NO 4
<211> LENGTH: 573
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (119)..(119)
<223> OTHER INFORMATION: X is V or D
<220> FEATURE:
<221> NAME/KEY: MISC_FEATURE
<222> LOCATION: (262)..(262)
<223> OTHER INFORMATION: X is S, K or G
<220> FEATURE:
<221> NAME/KEY: MISC_FEATURE
<222> LOCATION: (291)..(291)
<223> OTHER INFORMATION: All mutants with more than 50-fold activity
      increase have this substitution together with 319, 358, and 368
      substitutions
<220> FEATURE:
<221> NAME/KEY: MISC_FEATURE
<222> LOCATION: (292)..(292)
<223> OTHER INFORMATION: X is T or S
<220> FEATURE:
<221> NAME/KEY: MISC_FEATURE
<222> LOCATION: (293)..(293)
<223> OTHER INFORMATION: X is D, A, T, or N
<220> FEATURE:
<221> NAME/KEY: MISC_FEATURE
<222> LOCATION: (354)..(354)
<223> OTHER INFORMATION: X is S or N
<220> FEATURE:
<221> NAME/KEY: MISC_FEATURE
<222> LOCATION: (357)..(357)
<223> OTHER INFORMATION: X is T or A
<220> FEATURE:
<221> NAME/KEY: MISC_FEATURE
<222> LOCATION: (361)..(361)
<223> OTHER INFORMATION: X is Q or D

<400> SEQUENCE: 4

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Leu Arg
        35                  40                  45

Arg Gln Arg Ala Gly Glu Leu Ala Ala His Val Glu Arg Gln Ala Ala
    50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
```

```
                100             105                 110
Ala Val Leu Ser Gly Pro Xaa Asp Ala Ile Asn Arg Ala Phe Gly Val
            115                 120             125
Glu Leu Arg His Phe Asp His Pro Asp Gly Ser Tyr Arg Ser Tyr Leu
        130                 135             140
Gly Glu Val Thr Val Pro Ala Ser Ile Ala Pro Met Ile Glu Ala Val
145                 150                 155                 160
Leu Gly Leu Asp Thr Arg Pro Val Ala Arg Pro His Phe Arg Met Gln
                165                 170             175
Arg Arg Ala Glu Gly Phe Glu Ala Arg Ser Gln Ala Ala Ala Pro
            180                 185             190
Thr Ala Tyr Thr Pro Leu Asp Val Ala Gln Ala Tyr Gln Phe Pro Glu
        195                 200             205
Gly Leu Asp Gly Gln Gly Gln Cys Ile Ala Ile Ile Glu Leu Gly Gly
    210                 215                 220
Gly Tyr Asp Glu Ala Ser Leu Ala Gln Tyr Phe Ala Ser Leu Gly Val
225                 230                 235                 240
Pro Ala Pro Gln Val Val Ser Val Ser Val Asp Gly Ala Ser Asn Gln
                245                 250             255
Pro Thr Gly Asp Pro Xaa Gly Pro Asp Gly Glu Val Glu Leu Asp Ile
            260                 265             270
Glu Val Ala Gly Ala Leu Ala Pro Gly Ala Lys Phe Ala Val Tyr Phe
        275                 280             285
Ala Pro Asp Xaa Xaa Ala Gly Phe Leu Asp Ala Ile Thr Thr Ala Ile
    290                 295                 300
His Asp Pro Thr Leu Lys Pro Ser Val Val Ser Ile Ser Trp Ser Gly
305                 310                 315                 320
Pro Glu Asp Ser Trp Thr Ser Ala Ala Ile Ala Ala Met Asn Arg Ala
                325                 330             335
Phe Leu Asp Ala Ala Leu Gly Val Thr Val Leu Ala Ala Ala Gly
            340                 345             350
Asp Xaa Gly Ser Xaa Gly Gly Glu Xaa Asp Gly Leu Tyr His Val His
        355                 360             365
Phe Pro Ala Ala Ser Pro Tyr Val Leu Ala Cys Gly Gly Thr Arg Leu
    370                 375                 380
Val Ala Ser Gly Gly Arg Ile Ala Gln Glu Thr Val Trp Asn Asp Gly
385                 390                 395                 400
Pro Asp Gly Gly Ala Thr Gly Gly Val Ser Arg Ile Phe Pro Leu
                405                 410             415
Pro Ala Trp Gln Glu His Ala Asn Val Pro Pro Ser Ala Asn Pro Gly
            420                 425             430
Ala Ser Ser Gly Arg Gly Val Pro Asp Leu Ala Gly Asn Ala Asp Pro
        435                 440             445
Ala Thr Gly Tyr Glu Val Val Ile Asp Gly Glu Ala Thr Val Ile Gly
    450                 455                 460
Gly Thr Ser Ala Val Ala Pro Leu Phe Ala Ala Leu Val Ala Arg Ile
465                 470                 475                 480
Asn Gln Lys Leu Gly Lys Ala Val Gly Tyr Leu Asn Pro Thr Leu Tyr
                485                 490             495
Gln Leu Pro Ala Asp Val Phe His Asp Ile Thr Glu Gly Asn Asn Asp
            500                 505             510
Ile Ala Asn Arg Ala Gln Ile Tyr Gln Ala Gly Pro Gly Trp Asp Pro
        515                 520             525
```

```
Cys Thr Gly Leu Gly Ser Pro Ile Gly Val Arg Leu Leu Gln Ala Leu
            530                 535                 540

Leu Pro Ser Ala Ser Gln Pro Gln Pro Gly Ser Thr Glu Asn Leu Tyr
545                 550                 555                 560

Phe Gln Ser Gly Ala Leu Glu His His His His His His
                565                 570

<210> SEQ ID NO 5
<211> LENGTH: 573
<212> TYPE: PRT
<213> ORGANISM: Artificial Sequence
<220> FEATURE:
<223> OTHER INFORMATION: Synthetic

<400> SEQUENCE: 5

Met Ser Asp Met Glu Lys Pro Trp Lys Glu Gly Glu Glu Ala Arg Ala
1               5                   10                  15

Val Leu Gln Gly His Ala Arg Ala Gln Ala Pro Gln Ala Val Asp Lys
                20                  25                  30

Gly Pro Val Ala Gly Asp Glu Arg Met Ala Val Thr Val Leu Arg
            35                  40                  45

Arg Gln Arg Ala Gly Glu Leu Ala Ala His Val Glu Arg Gln Ala Ala
        50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Val Asp Ala Ile Asn Arg Ala Phe Gly Val
        115                 120                 125

Glu Leu Arg His Phe Asp His Pro Asp Gly Ser Tyr Arg Ser Tyr Leu
130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
        195                 200                 205

Gly Leu Asp Gly Gln Gly Gln Cys Ile Ala Ile Ile Glu Leu Gly Gly
210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Ser Gly Pro Asp Gly Glu Val Glu Leu Asp Ile
            260                 265                 270

Glu Val Ala Gly Ala Leu Ala Pro Gly Ala Lys Phe Ala Val Tyr Phe
        275                 280                 285

Ala Pro Asn Thr Asp Ala Gly Phe Leu Asp Ala Ile Thr Thr Ala Ile
290                 295                 300

His Asp Pro Thr Leu Lys Pro Ser Val Val Ser Ile Ser Trp Gly Gly
305                 310                 315                 320
```

Pro Glu Asp Ser Trp Thr Ser Ala Ala Ile Ala Ala Met Asn Arg Ala
            325                 330                 335

Phe Leu Asp Ala Ala Ala Leu Gly Val Thr Val Leu Ala Ala Ala Gly
        340                 345                 350

Asp Ser Gly Ser Thr Asn Gly Glu Gln Asp Gly Leu Tyr His Val Asp
    355                 360                 365

Phe Pro Ala Ala Ser Pro Tyr Val Leu Ala Cys Gly Gly Thr Arg Leu
370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
                405                 410                 415

Pro Ala Trp Gln Glu His Ala Asn Val Pro Ser Ala Asn Pro Gly
            420                 425                 430

Ala Ser Ser Gly Arg Gly Val Pro Asp Leu Ala Gly Asn Ala Asp Pro
        435                 440                 445

Ala Thr Gly Tyr Glu Val Val Ile Asp Gly Glu Ala Thr Val Ile Gly
    450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
        515                 520                 525

Cys Thr Gly Leu Gly Ser Pro Ile Gly Val Arg Leu Leu Gln Ala Leu
530                 535                 540

Leu Pro Ser Ala Ser Gln Pro Gln Pro Gly Ser Thr Glu Asn Leu Tyr
545                 550                 555                 560

Phe Gln Ser Gly Ala Leu Glu His His His His His
                565                 570

<210> SEQ ID NO 6
<211> LENGTH: 573
<212> TYPE: PRT
<213> ORGANISM: Artificial Sequence
<220> FEATURE:
<223> OTHER INFORMATION: Synthetic

<400> SEQUENCE: 6

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
                20                  25                  30

Gly Pro Val Ala Gly Asp Glu Arg Met Ala Val Thr Val Val Leu Arg
            35                  40                  45

Arg Gln Arg Ala Gly Glu Leu Ala Ala His Val Glu Arg Gln Ala Ala
        50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

```
Ala Val Leu Ser Gly Pro Val Asp Ala Ile Asn Arg Ala Phe Gly Val
            115                 120                 125

Glu Leu Arg His Phe Asp His Pro Asp Gly Ser Tyr Arg Ser Tyr Leu
            130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
                180                 185                 190

Thr Ala Tyr Thr Pro Leu Asp Val Ala Gln Ala Tyr Gln Phe Pro Glu
                195                 200                 205

Gly Leu Asp Gly Gln Gly Gln Cys Ile Ala Ile Ile Glu Leu Gly Gly
            210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Ser Gly Pro Asp Gly Glu Val Gly Leu Asp Ile
                260                 265                 270

Glu Val Ala Gly Ala Leu Ala Pro Gly Ala Lys Phe Ala Val Tyr Phe
            275                 280                 285

Ala Pro Asp Thr Asp Ala Gly Phe Leu Asp Ala Ile Thr Thr Ala Ile
290                 295                 300

His Asp Pro Thr Leu Lys Pro Ser Val Val Ser Ile Ser Trp Gly Gly
305                 310                 315                 320

Pro Glu Asp Ser Trp Thr Ser Ala Ala Ile Ala Ala Met Asn Arg Ala
                325                 330                 335

Phe Leu Asp Ala Ala Ala Leu Gly Val Thr Val Leu Ala Ala Ala Gly
                340                 345                 350

Asp Ser Gly Ser Thr Asp Gly Glu Gln Asp Gly Leu Tyr His Val Asp
            355                 360                 365

Phe Pro Ala Ala Ser Pro Tyr Val Leu Ala Cys Gly Gly Thr Arg Leu
370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
                405                 410                 415

Pro Ala Trp Gln Glu His Ala Asn Val Pro Pro Ser Ala Asn Pro Gly
                420                 425                 430

Ala Ser Ser Gly Arg Gly Val Pro Asp Leu Ala Gly Asn Ala Asp Pro
            435                 440                 445

Ala Thr Gly Tyr Glu Val Val Ile Asp Gly Glu Ala Thr Val Ile Gly
450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
                500                 505                 510

Ile Ala Asn Arg Ala Gln Ile Tyr Gln Ala Gly Pro Gly Trp Asp Pro
            515                 520                 525
```

```
Cys Thr Gly Leu Gly Ser Pro Ile Gly Val Arg Leu Leu Gln Ala Leu
            530                 535                 540

Leu Pro Ser Ala Ser Gln Pro Gln Pro Gly Ser Thr Glu Asn Leu Tyr
545                 550                 555                 560

Phe Gln Ser Gly Ala Leu Glu His His His His His
                565                 570

<210> SEQ ID NO 7
<211> LENGTH: 573
<212> TYPE: PRT
<213> ORGANISM: Artificial Sequence
<220> FEATURE:
<223> OTHER INFORMATION: Synthetic

<400> SEQUENCE: 7

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
                20                  25                  30

Gly Pro Val Ala Gly Asp Glu Arg Met Ala Val Thr Val Leu Arg
                35                  40                  45

Arg Gln Arg Ala Gly Glu Leu Ala Ala His Val Glu Arg Gln Ala Ala
    50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
                100                 105                 110

Ala Val Leu Ser Gly Pro Val Asp Ala Ile Asn Arg Ala Phe Gly Val
                115                 120                 125

Glu Leu Arg His Phe Asp His Pro Asp Gly Ser Tyr Arg Ser Tyr Leu
        130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
                180                 185                 190

Thr Ala Tyr Thr Pro Leu Asp Val Ala Gln Ala Tyr Gln Phe Pro Glu
        195                 200                 205

Gly Leu Asp Gly Gln Gly Gln Cys Ile Ala Ile Glu Leu Gly Gly
        210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Ser Gly Pro Asp Gly Glu Val Glu Leu Asp Ile
                260                 265                 270

Glu Val Ala Gly Ala Leu Ala Pro Gly Ala Lys Phe Ala Val Tyr Phe
        275                 280                 285

Ala Pro Asn Thr Asp Ala Gly Phe Leu Asp Ala Ile Thr Thr Ala Ile
                290                 295                 300

His Asp Pro Thr Leu Lys Pro Ser Val Val Ser Ile Ser Trp Gly Gly
305                 310                 315                 320
```

```
Pro Glu Asp Ser Trp Thr Ser Ala Ala Ile Ala Ala Met Asn Arg Ala
            325                 330                 335

Phe Leu Asp Ala Ala Ala Leu Gly Val Thr Val Leu Ala Ala Ala Gly
        340                 345                 350

Asp Ser Gly Ser Thr Gly Gly Glu Gln Asp Gly Leu Tyr His Val Asp
    355                 360                 365

Phe Pro Ala Ala Ser Pro Tyr Val Leu Ala Cys Gly Gly Thr Arg Leu
370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
                405                 410                 415

Pro Ala Trp Gln Glu His Ala Asn Val Pro Pro Ser Ala Asn Pro Gly
            420                 425                 430

Ala Ser Ser Gly Arg Gly Val Pro Asp Leu Ala Gly Asn Ala Asp Pro
        435                 440                 445

Ala Thr Gly Tyr Glu Val Val Ile Asp Gly Glu Ala Thr Val Ile Gly
    450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
        515                 520                 525

Cys Thr Gly Leu Gly Ser Pro Ile Gly Val Arg Leu Leu Gln Ala Leu
530                 535                 540

Leu Pro Ser Ala Ser Gln Pro Gln Pro Gly Ser Thr Glu Asn Leu Tyr
545                 550                 555                 560

Phe Gln Ser Gly Ala Leu Glu His His His His His
                565                 570
```

<210> SEQ ID NO 8
<211> LENGTH: 573
<212> TYPE: PRT
<213> ORGANISM: Artificial Sequence
<220> FEATURE:
<223> OTHER INFORMATION: Synthetic

<400> SEQUENCE: 8

```
Met Ser Asp Met Glu Lys Pro Trp Lys Glu Gly Glu Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Leu Arg
        35                  40                  45

Arg Gln Arg Ala Gly Glu Leu Ala Ala His Val Glu Arg Gln Ala Ala
    50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110
```

```
Ala Val Leu Ser Gly Pro Val Asp Ala Ile Asn Arg Ala Phe Gly Val
            115                 120                 125

Glu Leu Arg His Phe Asp His Pro Asp Gly Ser Tyr Arg Ser Tyr Leu
    130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
    195                 200                 205

Gly Leu Asp Gly Gln Gly Gln Cys Ile Ala Ile Ile Glu Leu Gly Gly
210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Ser Gly Pro Asp Gly Glu Val Glu Leu Asp Ile
            260                 265                 270

Glu Val Ala Gly Ala Leu Ala Pro Gly Ala Lys Phe Ala Val Tyr Phe
    275                 280                 285

Ala Pro Asn Thr Asp Ala Gly Phe Leu Asp Ala Ile Thr Thr Ala Ile
290                 295                 300

His Asp Pro Thr Leu Lys Pro Ser Val Val Ser Ile Ser Trp Gly Gly
305                 310                 315                 320

Pro Glu Asp Ser Trp Thr Ser Ala Ala Ile Ala Ala Met Asn Arg Ala
                325                 330                 335

Phe Leu Asp Ala Ala Ala Leu Gly Val Thr Val Leu Ala Ala Ala Gly
            340                 345                 350

Asp Ser Gly Ser Ala Asp Gly Glu Gln Asp Gly Leu Tyr His Val Asp
    355                 360                 365

Phe Pro Ala Ala Ser Pro Tyr Val Leu Ala Cys Gly Gly Thr Arg Leu
370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
                405                 410                 415

Pro Ala Trp Gln Glu His Ala Asn Val Pro Ser Ala Asn Pro Gly
            420                 425                 430

Ala Ser Ser Gly Arg Gly Val Pro Asp Leu Ala Gly Asn Ala Asp Pro
    435                 440                 445

Ala Thr Gly Tyr Glu Val Val Ile Asp Gly Glu Ala Thr Val Ile Gly
450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
    515                 520                 525

Cys Thr Gly Leu Gly Ser Pro Ile Gly Val Arg Leu Leu Gln Ala Leu
```

```
                 530             535             540
Leu Pro Ser Ala Ser Gln Pro Gln Pro Gly Ser Thr Glu Asn Leu Tyr
545                 550             555                 560

Phe Gln Ser Gly Ala Leu Glu His His His His His His
                565                 570

<210> SEQ ID NO 9
<211> LENGTH: 573
<212> TYPE: PRT
<213> ORGANISM: Artificial Sequence
<220> FEATURE:
<223> OTHER INFORMATION: Synthetic

<400> SEQUENCE: 9

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
                20                  25                  30

Gly Pro Val Ala Gly Asp Glu Arg Met Ala Val Thr Val Val Leu Arg
            35                  40                  45

Arg Gln Arg Ala Gly Glu Leu Ala Ala His Val Glu Arg Gln Ala Ala
        50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Val Asp Ala Ile Asn Arg Ala Phe Gly Val
        115                 120                 125

Glu Leu Arg His Phe Asp His Pro Asp Gly Ser Tyr Arg Ser Tyr Leu
130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
        195                 200                 205

Gly Leu Asp Gly Gln Gly Gln Cys Ile Ala Ile Ile Glu Leu Gly Gly
    210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Ser Gly Pro Asp Gly Glu Val Glu Leu Asp Ile
            260                 265                 270

Glu Val Ala Gly Ala Leu Ala Pro Gly Ala Lys Phe Ala Val Tyr Phe
        275                 280                 285

Ala Pro Asn Thr Ala Ala Gly Phe Leu Asp Ala Ile Thr Thr Ala Ile
    290                 295                 300

His Asp Pro Thr Leu Lys Pro Ser Val Val Ser Ile Ser Trp Gly Gly
305                 310                 315                 320

Pro Glu Asp Ser Trp Thr Ser Ala Ala Ile Ala Ala Met Asn Arg Ala
```

```
                325                 330                 335
Phe Leu Asp Ala Ala Leu Gly Val Thr Val Leu Ala Ala Gly
            340                 345                 350
Asp Ser Gly Ser Thr Asp Gly Glu Gln Asp Gly Leu Tyr His Val Asp
        355                 360                 365
Phe Pro Ala Ala Ser Pro Tyr Val Leu Ala Cys Gly Gly Thr Arg Leu
    370                 375                 380
Val Ala Ser Gly Gly Arg Ile Ala Gln Glu Thr Val Trp Asn Asp Gly
385                 390                 395                 400
Pro Asp Gly Gly Ala Thr Gly Gly Val Ser Arg Ile Phe Pro Leu
            405                 410                 415
Pro Ala Trp Gln Glu His Ala Asn Val Pro Ser Ala Asn Pro Gly
        420                 425                 430
Ala Ser Ser Gly Arg Gly Val Pro Asp Leu Ala Gly Asn Ala Asp Pro
    435                 440                 445
Ala Thr Gly Tyr Glu Val Val Ile Asp Gly Glu Ala Thr Val Ile Gly
450                 455                 460
Gly Thr Ser Ala Val Ala Pro Leu Phe Ala Ala Leu Val Ala Arg Ile
465                 470                 475                 480
Asn Gln Lys Leu Gly Lys Ala Val Gly Tyr Leu Asn Pro Thr Leu Tyr
            485                 490                 495
Gln Leu Pro Ala Asp Val Phe His Asp Ile Thr Glu Gly Asn Asn Asp
        500                 505                 510
Ile Ala Asn Arg Ala Gln Ile Tyr Gln Ala Gly Pro Gly Trp Asp Pro
    515                 520                 525
Cys Thr Gly Leu Gly Ser Pro Ile Gly Val Arg Leu Leu Gln Ala Leu
530                 535                 540
Leu Pro Ser Ala Ser Gln Pro Gln Pro Gly Ser Thr Glu Asn Leu Tyr
545                 550                 555                 560
Phe Gln Ser Gly Ala Leu Glu His His His His His
            565                 570

<210> SEQ ID NO 10
<211> LENGTH: 573
<212> TYPE: PRT
<213> ORGANISM: Artificial Sequence
<220> FEATURE:
<223> OTHER INFORMATION: Synthetic

<400> SEQUENCE: 10

Met Ser Asp Met Glu Lys Pro Trp Lys Glu Gly Glu Glu Ala Arg Ala
1               5                   10                  15
Val Leu Gln Gly His Ala Arg Ala Gln Ala Pro Gln Ala Val Asp Lys
            20                  25                  30
Gly Pro Val Ala Gly Asp Glu Arg Met Ala Val Thr Val Leu Arg
        35                  40                  45
Arg Gln Arg Ala Gly Glu Leu Ala Ala His Val Glu Arg Gln Ala Ala
    50                  55                  60
Ile Ala Pro His Ala Arg Glu His Leu Lys Arg Glu Ala Phe Ala Ala
65                  70                  75                  80
Ser His Gly Ala Ser Leu Asp Asp Phe Ala Glu Leu Arg Arg Phe Ala
            85                  90                  95
Asp Ala His Gly Leu Ala Leu Asp Arg Ala Asn Val Ala Ala Gly Thr
        100                 105                 110
Ala Val Leu Ser Gly Pro Val Asp Ala Ile Asn Arg Ala Phe Gly Val
```

```
            115                 120                 125
Glu Leu Arg His Phe Asp His Pro Asp Gly Ser Tyr Arg Ser Tyr Leu
            130                 135                 140
Gly Glu Val Thr Val Pro Ala Ser Ile Ala Pro Met Ile Glu Ala Val
145                 150                 155                 160
Leu Gly Leu Asp Thr Arg Pro Val Ala Arg Pro His Phe Arg Met Gln
                165                 170                 175
Arg Arg Ala Glu Gly Gly Phe Glu Ala Arg Ser Gln Ala Ala Ala Pro
            180                 185                 190
Thr Ala Tyr Thr Pro Leu Asp Val Ala Gln Ala Tyr Gln Phe Pro Glu
                195                 200                 205
Gly Leu Asp Gly Gln Gly Gln Cys Ile Ala Ile Ile Glu Leu Gly Gly
            210                 215                 220
Gly Tyr Asp Glu Ala Ser Leu Ala Gln Tyr Phe Ala Ser Leu Gly Val
225                 230                 235                 240
Pro Ala Pro Gln Val Val Ser Val Ser Val Asp Gly Ala Ser Asn Gln
                245                 250                 255
Pro Thr Gly Asp Pro Ser Gly Pro Asp Gly Glu Val Glu Leu Asp Ile
            260                 265                 270
Glu Val Ala Gly Ala Leu Ala Pro Gly Ala Lys Phe Ala Val Tyr Phe
            275                 280                 285
Ala Pro Asn Thr Asp Ala Gly Phe Leu Asp Ala Ile Thr Thr Ala Ile
            290                 295                 300
His Asp Pro Thr Leu Lys Pro Ser Val Val Ser Ile Ser Trp Ser Gly
305                 310                 315                 320
Pro Glu Asp Ser Trp Thr Ser Ala Ala Ile Ala Ala Met Asn Arg Ala
                325                 330                 335
Phe Leu Asp Ala Ala Ala Leu Gly Val Thr Val Leu Ala Ala Ala Gly
            340                 345                 350
Asp Ser Gly Ser Thr Asp Gly Glu Gln Asp Gly Leu Tyr His Val Ser
            355                 360                 365
Phe Pro Ala Ala Ser Pro Tyr Val Leu Ala Cys Gly Gly Thr Arg Leu
            370                 375                 380
Val Ala Ser Gly Gly Arg Ile Ala Gln Glu Thr Val Trp Asn Asp Gly
385                 390                 395                 400
Pro Asp Gly Gly Ala Thr Gly Gly Val Ser Arg Ile Phe Pro Leu
                405                 410                 415
Pro Ala Trp Gln Glu His Ala Asn Val Pro Pro Ser Ala Asn Pro Gly
                420                 425                 430
Ala Ser Ser Gly Arg Gly Val Pro Asp Leu Ala Gly Asn Ala Asp Pro
            435                 440                 445
Ala Thr Gly Tyr Glu Val Val Ile Asp Gly Glu Ala Thr Val Ile Gly
            450                 455                 460
Gly Thr Ser Ala Val Ala Pro Leu Phe Ala Ala Leu Val Ala Arg Ile
465                 470                 475                 480
Asn Gln Lys Leu Gly Lys Ala Val Gly Tyr Leu Asn Pro Thr Leu Tyr
                485                 490                 495
Gln Leu Pro Ala Asp Val Phe His Asp Ile Thr Glu Gly Asn Asn Asp
            500                 505                 510
Ile Ala Asn Arg Ala Gln Ile Tyr Gln Ala Gly Pro Gly Trp Asp Pro
            515                 520                 525
Cys Thr Gly Leu Gly Ser Pro Ile Gly Val Arg Leu Leu Gln Ala Leu
530                 535                 540
```

-continued

Leu Pro Ser Ala Ser Gln Pro Gln Pro Gly Ser Thr Glu Asn Leu Tyr
545                 550                 555                 560

Phe Gln Ser Gly Ala Leu Glu His His His His His His
                565                 570

<210> SEQ ID NO 11
<211> LENGTH: 573
<212> TYPE: PRT
<213> ORGANISM: Artificial Sequence
<220> FEATURE:
<223> OTHER INFORMATION: Synthetic

<400> SEQUENCE: 11

Met Ser Asp Met Glu Lys Pro Trp Lys Glu Gly Glu Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Val Leu Arg
        35                  40                  45

Arg Gln Arg Ala Gly Glu Leu Ala Ala His Val Glu Arg Gln Ala Ala
    50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Val Asp Ala Ile Asn Arg Ala Phe Gly Val
        115                 120                 125

Glu Leu Arg His Phe Asp His Pro Asp Gly Ser Tyr Arg Ser Tyr Leu
    130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
        195                 200                 205

Gly Leu Asp Gly Gln Gly Gln Cys Ile Ala Ile Ile Glu Leu Gly Gly
    210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Ser Gly Pro Asp Gly Glu Val Glu Leu Asp Ile
            260                 265                 270

Glu Val Ala Gly Ala Leu Ala Pro Gly Ala Lys Phe Ala Val Tyr Phe
        275                 280                 285

Ala Pro Asn Thr Asp Ala Gly Phe Leu Asp Ala Ile Thr Thr Ala Ile
    290                 295                 300

His Asp Pro Thr Leu Lys Pro Ser Val Val Ser Ile Ser Trp Gly Gly
305                 310                 315                 320

Pro Glu Asp Ser Trp Thr Ser Ala Ala Ile Ala Ala Met Asn Arg Ala
                325                 330                 335

```
Phe Leu Asp Ala Ala Leu Gly Val Thr Val Leu Ala Ala Gly
            340                 345                 350

Asp Ser Gly Ser Thr Gly Gly Glu Gln Asp Gly Leu Tyr His Val His
        355                 360                 365

Phe Pro Ala Ala Ser Pro Tyr Val Leu Ala Cys Gly Gly Thr Arg Leu
    370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
                405                 410                 415

Pro Ala Trp Gln Glu His Ala Asn Val Pro Ser Ala Asn Pro Gly
            420                 425                 430

Ala Ser Ser Gly Arg Gly Val Pro Asp Leu Ala Gly Asn Ala Asp Pro
        435                 440                 445

Ala Thr Gly Tyr Glu Val Val Ile Asp Gly Glu Ala Thr Val Ile Gly
    450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
        500                 505                 510

Ile Ala Asn Arg Ala Gln Ile Tyr Gln Ala Gly Pro Gly Trp Asp Pro
    515                 520                 525

Cys Thr Gly Leu Gly Ser Pro Ile Gly Val Arg Leu Gln Ala Leu
530                 535                 540

Leu Pro Ser Ala Ser Gln Pro Gln Pro Gly Ser Thr Glu Asn Leu Tyr
545                 550                 555                 560

Phe Gln Ser Gly Ala Leu Glu His His His His His
                565                 570

<210> SEQ ID NO 12
<211> LENGTH: 573
<212> TYPE: PRT
<213> ORGANISM: Artificial Sequence
<220> FEATURE:
<223> OTHER INFORMATION: Synthetic

<400> SEQUENCE: 12

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
                20                  25                  30

Gly Pro Val Ala Gly Asp Glu Arg Met Ala Val Thr Val Leu Arg
            35                  40                  45

Arg Gln Arg Ala Gly Glu Leu Ala Ala His Val Glu Arg Gln Ala Ala
        50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Val Asp Ala Ile Asn Arg Ala Phe Gly Val
        115                 120                 125
```

```
Glu Leu Arg His Phe Asp His Pro Asp Gly Ser Tyr Arg Ser Tyr Leu
    130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
        195                 200                 205

Gly Leu Asp Gly Gln Gly Gln Cys Ile Ala Ile Glu Leu Gly Gly
210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Ser Gly Pro Asp Gly Glu Val Glu Leu Asp Ile
                260                 265                 270

Glu Val Ala Gly Ala Leu Ala Pro Gly Ala Lys Phe Ala Val Tyr Phe
            275                 280                 285

Ala Pro Asp Thr Asp Ala Gly Phe Leu Asp Ala Ile Thr Thr Ala Ile
290                 295                 300

His Asp Pro Thr Leu Lys Pro Ser Val Val Ser Ile Ser Trp Gly Gly
305                 310                 315                 320

Pro Glu Asp Ser Trp Thr Ser Ala Ala Ile Ala Ala Met Asn Arg Ala
                325                 330                 335

Phe Leu Asp Ala Ala Leu Gly Val Thr Val Leu Ala Ala Ala Gly
            340                 345                 350

Asp Ser Gly Ser Thr Asp Gly Glu Asp Asp Gly Leu Tyr His Val Asp
        355                 360                 365

Phe Pro Ala Ala Ser Pro Tyr Val Leu Ala Cys Gly Gly Thr Arg Leu
370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
                405                 410                 415

Pro Ala Trp Gln Glu His Ala Asn Val Pro Pro Ser Ala Asn Pro Gly
                420                 425                 430

Ala Ser Ser Gly Arg Gly Val Pro Asp Leu Ala Gly Asn Ala Asp Pro
            435                 440                 445

Ala Thr Gly Tyr Glu Val Val Ile Asp Gly Glu Ala Thr Val Ile Gly
        450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
                500                 505                 510

Ile Ala Asn Arg Ala Gln Ile Tyr Gln Ala Gly Pro Gly Trp Asp Pro
            515                 520                 525

Cys Thr Gly Leu Gly Ser Pro Ile Gly Val Arg Leu Leu Gln Ala Leu
530                 535                 540
```

Leu Pro Ser Ala Ser Gln Pro Gln Pro Gly Ser Thr Glu Asn Leu Tyr
545                 550                 555                 560

Phe Gln Ser Gly Ala Leu Glu His His His His His His
                565                 570

<210> SEQ ID NO 13
<211> LENGTH: 573
<212> TYPE: PRT
<213> ORGANISM: Artificial Sequence
<220> FEATURE:
<223> OTHER INFORMATION: Synthetic

<400> SEQUENCE: 13

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
                20                  25                  30

Gly Pro Val Ala Gly Asp Glu Arg Met Ala Val Thr Val Val Leu Arg
            35                  40                  45

Arg Gln Arg Ala Gly Glu Leu Ala Ala His Val Glu Arg Gln Ala Ala
        50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Val Asp Ala Ile Asn Arg Ala Phe Gly Val
        115                 120                 125

Glu Leu Arg His Phe Asp His Pro Asp Gly Ser Tyr Arg Ser Tyr Leu
    130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
        195                 200                 205

Gly Leu Asp Gly Gln Gly Gln Cys Ile Ala Ile Ile Glu Leu Gly Gly
    210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Ser Gly Pro Asp Gly Glu Val Glu Leu Asp Ile
            260                 265                 270

Glu Val Ala Gly Ala Leu Ala Pro Gly Ala Lys Phe Ala Val Tyr Phe
        275                 280                 285

Ala Pro Asp Thr Asp Ala Gly Phe Leu Asp Ala Ile Thr Thr Ala Ile
    290                 295                 300

His Asp Pro Thr Leu Lys Pro Ser Val Val Ser Ile Ser Trp Gly Gly
305                 310                 315                 320

Pro Glu Asp Ser Trp Thr Ser Ala Ala Ile Ala Ala Met Asn Arg Ala
                325                 330                 335

```
Phe Leu Asp Ala Ala Ala Leu Gly Val Thr Val Leu Ala Ala Ala Gly
                340                 345                 350

Asp Ser Gly Ser Thr Asn Gly Glu Gln Asp Gly Leu Tyr His Val Asp
        355                 360                 365

Phe Pro Ala Ala Ser Pro Tyr Val Leu Ala Cys Gly Gly Thr Arg Leu
    370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Gly Val Ser Arg Ile Phe Pro Leu
                405                 410                 415

Pro Ala Trp Gln Glu His Ala Asn Val Pro Pro Ser Ala Asn Pro Gly
                420                 425                 430

Ala Ser Ser Gly Arg Gly Val Pro Asp Leu Ala Gly Asn Ala Asp Pro
            435                 440                 445

Ala Thr Gly Tyr Glu Val Val Ile Asp Gly Glu Ala Thr Val Ile Gly
        450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
        515                 520                 525

Cys Thr Gly Leu Gly Ser Pro Ile Gly Val Arg Leu Leu Gln Ala Leu
530                 535                 540

Leu Pro Ser Ala Ser Gln Pro Gln Pro Gly Ser Thr Glu Asn Leu Tyr
545                 550                 555                 560

Phe Gln Ser Gly Ala Leu Glu His His His His His
                565                 570

<210> SEQ ID NO 14
<211> LENGTH: 573
<212> TYPE: PRT
<213> ORGANISM: Artificial Sequence
<220> FEATURE:
<223> OTHER INFORMATION: Synthetic

<400> SEQUENCE: 14

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
                20                  25                  30

Gly Pro Val Ala Gly Asp Glu Arg Met Ala Val Thr Val Val Leu Arg
            35                  40                  45

Arg Gln Arg Ala Gly Glu Leu Ala Ala His Val Glu Arg Gln Ala Ala
        50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Val Asp Ala Ile Asn Arg Ala Phe Gly Val
        115                 120                 125
```

-continued

Glu Leu Arg His Phe Asp His Pro Asp Gly Ser Tyr Arg Ser Tyr Leu
130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
            165                 170                 175

Arg Arg Ala Glu Gly Phe Glu Ala Arg Ser Gln Ala Ala Ala Pro
        180                 185                 190

Thr Ala Tyr Thr Pro Leu Asp Val Ala Gln Ala Tyr Gln Phe Pro Glu
            195                 200                 205

Gly Leu Asp Gly Gln Gly Gln Cys Ile Ala Ile Ile Glu Leu Gly Gly
210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Ser Gly Pro Asp Gly Glu Val Glu Leu Asp Ile
            260                 265                 270

Glu Val Ala Gly Ala Leu Ala Pro Gly Ala Lys Phe Ala Val Tyr Phe
    275                 280                 285

Ala Pro Asp Thr Ala Ala Gly Phe Leu Asp Ala Ile Thr Thr Ala Ile
290                 295                 300

His Asp Pro Thr Leu Lys Pro Ser Val Val Ser Ile Ser Trp Gly Gly
305                 310                 315                 320

Pro Glu Asp Ser Trp Thr Ser Ala Ala Ile Ala Ala Met Asn Arg Ala
                325                 330                 335

Phe Leu Asp Ala Ala Leu Gly Val Thr Val Leu Ala Ala Ala Gly
            340                 345                 350

Asp Ser Gly Ser Thr Asp Gly Glu Gln Asp Gly Leu Tyr His Val Asp
            355                 360                 365

Phe Pro Ala Ala Ser Pro Tyr Val Leu Ala Cys Gly Gly Thr Arg Leu
370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
            405                 410                 415

Pro Ala Trp Gln Glu His Ala Asn Val Pro Pro Ser Ala Asn Pro Gly
            420                 425                 430

Ala Ser Ser Gly Arg Gly Val Pro Asp Leu Ala Gly Asn Ala Asp Pro
        435                 440                 445

Ala Thr Gly Tyr Glu Val Val Ile Asp Gly Glu Ala Thr Val Ile Gly
    450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
            515                 520                 525

Cys Thr Gly Leu Gly Ser Pro Ile Gly Val Arg Leu Leu Gln Ala Leu
530                 535                 540

Leu Pro Ser Ala Ser Gln Pro Gln Pro Gly Ser Thr Glu Asn Leu Tyr

```
                545                 550                 555                 560
Phe Gln Ser Gly Ala Leu Glu His His His His His
                    565                 570

<210> SEQ ID NO 15
<211> LENGTH: 573
<212> TYPE: PRT
<213> ORGANISM: Artificial Sequence
<220> FEATURE:
<223> OTHER INFORMATION: Synthetic

<400> SEQUENCE: 15

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
                20                  25                  30

Gly Pro Val Ala Gly Asp Glu Arg Met Ala Val Thr Val Val Leu Arg
            35                  40                  45

Arg Gln Arg Ala Gly Glu Leu Ala Ala His Val Glu Arg Gln Ala Ala
        50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Val Asp Ala Ile Asn Arg Ala Phe Gly Val
        115                 120                 125

Glu Leu Arg His Phe Asp His Pro Asp Gly Ser Tyr Arg Ser Tyr Leu
    130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
        195                 200                 205

Gly Leu Asp Gly Gln Gly Gln Cys Ile Ala Ile Ile Glu Leu Gly Gly
    210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Ser Gly Pro Asp Gly Glu Val Glu Leu Asp Ile
            260                 265                 270

Glu Val Ala Gly Ala Leu Ala Pro Gly Ala Lys Phe Ala Val Tyr Phe
        275                 280                 285

Ala Pro Asp Thr Ala Ala Gly Phe Leu Asp Ala Ile Thr Thr Ala Ile
    290                 295                 300

His Asp Pro Thr Leu Lys Pro Ser Val Val Ser Ile Ser Trp Gly Gly
305                 310                 315                 320

Pro Glu Asp Ser Trp Thr Ser Ala Ala Ile Ala Ala Met Asn Arg Ala
                325                 330                 335

Phe Leu Asp Ala Ala Ala Leu Gly Val Thr Val Leu Ala Ala Ala Gly
```

```
                340                 345                 350
Asp Ser Gly Ser Thr Asn Gly Glu Gln Asp Gly Leu Tyr His Val Asp
            355                 360                 365

Phe Pro Ala Ala Ser Pro Tyr Val Leu Ala Cys Gly Gly Thr Arg Leu
        370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
                405                 410                 415

Pro Ala Trp Gln Glu His Ala Asn Val Pro Ser Ala Asn Pro Gly
            420                 425                 430

Ala Ser Ser Gly Arg Gly Val Pro Asp Leu Ala Gly Asn Ala Asp Pro
            435                 440                 445

Ala Thr Gly Tyr Glu Val Val Ile Asp Gly Ala Thr Val Ile Gly
            450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
                500                 505                 510

Ile Ala Asn Arg Ala Gln Ile Tyr Gln Ala Gly Pro Gly Trp Asp Pro
            515                 520                 525

Cys Thr Gly Leu Gly Ser Pro Ile Gly Val Arg Leu Leu Gln Ala Leu
530                 535                 540

Leu Pro Ser Ala Ser Gln Pro Gln Pro Gly Ser Thr Glu Asn Leu Tyr
545                 550                 555                 560

Phe Gln Ser Gly Ala Leu Glu His His His His His His
                565                 570

<210> SEQ ID NO 16
<211> LENGTH: 573
<212> TYPE: PRT
<213> ORGANISM: Artificial Sequence
<220> FEATURE:
<223> OTHER INFORMATION: Synthetic

<400> SEQUENCE: 16

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Leu Arg
            35                  40                  45

Arg Gln Arg Ala Gly Glu Leu Ala Ala His Val Glu Arg Gln Ala Ala
        50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Val Asp Ala Ile Asn Arg Ala Phe Gly Val
            115                 120                 125

Glu Leu Arg His Phe Asp His Pro Asp Gly Ser Tyr Arg Ser Tyr Leu
```

```
            130                 135                 140
Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
                195                 200                 205

Gly Leu Asp Gly Gln Gly Gln Cys Ile Ala Ile Ile Glu Leu Gly Gly
            210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Ser Gly Pro Asp Gly Glu Val Glu Leu Asp Ile
                260                 265                 270

Glu Val Ala Gly Ala Leu Ala Pro Gly Ala Lys Phe Ala Val Tyr Phe
                275                 280                 285

Ala Pro Asn Thr Asp Ala Gly Phe Leu Asp Ala Ile Thr Thr Ala Ile
                290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
                325                 330                 335

Phe Leu Asp Ala Ala Ala Leu Gly Val Thr Val Leu Ala Ala Ala Gly
                340                 345                 350

Asp Ser Gly Ser Thr Gly Gly Glu Gln Asp Gly Leu Tyr His Val His
                355                 360                 365

Phe Pro Ala Ala Ser Pro Tyr Val Leu Ala Cys Gly Gly Thr Arg Leu
                370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
                405                 410                 415

Pro Ala Trp Gln Glu His Ala Asn Val Pro Ser Ala Asn Pro Gly
                420                 425                 430

Ala Ser Ser Gly Arg Gly Val Pro Asp Leu Ala Gly Asn Ala Asp Pro
                435                 440                 445

Ala Thr Gly Tyr Glu Val Val Ile Asp Gly Glu Ala Thr Val Ile Gly
                450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
                500                 505                 510

Ile Ala Asn Arg Ala Gln Ile Tyr Gln Ala Gly Pro Gly Trp Asp Pro
                515                 520                 525

Cys Thr Gly Leu Gly Ser Pro Ile Gly Val Arg Leu Leu Gln Ala Leu
                530                 535                 540

Leu Pro Ser Ala Ser Gln Pro Gln Pro Gly Ser Thr Glu Asn Leu Tyr
545                 550                 555                 560
```

```
Phe Gln Ser Gly Ala Leu Glu His His His His His
                565                 570

<210> SEQ ID NO 17
<211> LENGTH: 573
<212> TYPE: PRT
<213> ORGANISM: Artificial Sequence
<220> FEATURE:
<223> OTHER INFORMATION: Synthetic

<400> SEQUENCE: 17

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Leu Arg
            35                  40                  45

Arg Gln Arg Ala Gly Glu Leu Ala Ala His Val Glu Arg Gln Ala Ala
    50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Val Asp Ala Ile Asn Arg Ala Phe Gly Val
            115                 120                 125

Glu Leu Arg His Phe Asp His Pro Asp Gly Ser Tyr Arg Ser Tyr Leu
    130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Pro
            180                 185                 190

Thr Ala Tyr Thr Pro Leu Asp Val Ala Gln Ala Tyr Gln Phe Pro Glu
            195                 200                 205

Gly Leu Asp Gly Gln Gly Gln Cys Ile Ala Ile Ile Glu Leu Gly Gly
    210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Ser Gly Pro Asp Gly Glu Val Glu Leu Asp Ile
            260                 265                 270

Glu Val Ala Gly Ala Leu Ala Pro Gly Ala Lys Phe Ala Val Tyr Phe
            275                 280                 285

Ala Pro Asn Thr Asp Ala Gly Phe Leu Asp Ala Ile Thr Thr Ala Ile
    290                 295                 300

His Asp Pro Thr Leu Lys Pro Ser Val Val Ser Ile Ser Trp Gly Gly
305                 310                 315                 320

Pro Glu Asp Ser Trp Thr Ser Ala Ala Ile Ala Ala Met Asn Arg Ala
                325                 330                 335

Phe Leu Asp Ala Ala Ala Leu Gly Val Thr Val Leu Ala Ala Ala Gly
            340                 345                 350
```

-continued

```
Asp Asn Gly Ser Thr Gly Gly Glu Gln Asp Gly Leu Tyr His Val His
            355                 360                 365
Phe Pro Ala Ala Ser Pro Tyr Val Leu Ala Cys Gly Gly Thr Arg Leu
370                 375                 380
Val Ala Ser Gly Gly Arg Ile Ala Gln Glu Thr Val Trp Asn Asp Gly
385                 390                 395                 400
Pro Asp Gly Gly Ala Thr Gly Gly Val Ser Arg Ile Phe Pro Leu
                405                 410                 415
Pro Ala Trp Gln Glu His Ala Asn Val Pro Pro Ser Ala Asn Pro Gly
            420                 425                 430
Ala Ser Ser Gly Arg Gly Val Pro Asp Leu Ala Gly Asn Ala Asp Pro
                435                 440                 445
Ala Thr Gly Tyr Glu Val Val Ile Asp Gly Glu Ala Thr Val Ile Gly
            450                 455                 460
Gly Thr Ser Ala Val Ala Pro Leu Phe Ala Ala Leu Val Ala Arg Ile
465                 470                 475                 480
Asn Gln Lys Leu Gly Lys Ala Val Gly Tyr Leu Asn Pro Thr Leu Tyr
                485                 490                 495
Gln Leu Pro Ala Asp Val Phe His Asp Ile Thr Glu Gly Asn Asn Asp
            500                 505                 510
Ile Ala Asn Arg Ala Gln Ile Tyr Gln Ala Gly Pro Gly Trp Asp Pro
                515                 520                 525
Cys Thr Gly Leu Gly Ser Pro Ile Gly Val Arg Leu Leu Gln Ala Leu
530                 535                 540
Leu Pro Ser Ala Ser Gln Pro Gln Pro Gly Ser Thr Glu Asn Leu Tyr
545                 550                 555                 560
Phe Gln Ser Gly Ala Leu Glu His His His His His His
                565                 570
```

<210> SEQ ID NO 18
<211> LENGTH: 573
<212> TYPE: PRT
<213> ORGANISM: Artificial Sequence
<220> FEATURE:
<223> OTHER INFORMATION: Synthetic

<400> SEQUENCE: 18

```
Met Ser Asp Met Glu Lys Pro Trp Lys Glu Gly Glu Glu Ala Arg Ala
1               5                   10                  15
Val Leu Gln Gly His Ala Arg Ala Gln Ala Pro Gln Ala Val Asp Lys
                20                  25                  30
Gly Pro Val Ala Gly Asp Glu Arg Met Ala Val Thr Val Leu Arg
            35                  40                  45
Arg Gln Arg Ala Gly Glu Leu Ala Ala His Val Glu Arg Gln Ala Ala
    50                  55                  60
Ile Ala Pro His Ala Arg Glu His Leu Lys Arg Glu Ala Phe Ala Ala
65                  70                  75                  80
Ser His Gly Ala Ser Leu Asp Asp Phe Ala Glu Leu Arg Arg Phe Ala
                85                  90                  95
Asp Ala His Gly Leu Ala Leu Asp Arg Ala Asn Val Ala Ala Gly Thr
            100                 105                 110
Ala Val Leu Ser Gly Pro Val Asp Ala Ile Asn Arg Ala Phe Gly Val
        115                 120                 125
Glu Leu Arg His Phe Asp His Pro Asp Gly Ser Tyr Arg Ser Tyr Leu
    130                 135                 140
```

```
Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
            165                 170                 175

Arg Arg Ala Glu Gly Gly Phe Glu Ala Arg Ser Gln Ala Ala Ala Pro
        180                 185                 190

Thr Ala Tyr Thr Pro Leu Asp Val Ala Gln Ala Tyr Gln Phe Pro Glu
    195                 200                 205

Gly Leu Asp Gly Gln Gly Gln Cys Ile Ala Ile Ile Glu Leu Gly Gly
210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Ser Gly Pro Asp Gly Glu Val Glu Leu Asp Ile
            260                 265                 270

Glu Val Ala Gly Ala Leu Ala Pro Gly Ala Lys Phe Ala Val Tyr Phe
        275                 280                 285

Ala Pro Asp Thr Asp Ala Gly Phe Leu Asp Ala Ile Thr Thr Ala Ile
    290                 295                 300

His Asp Pro Thr Leu Lys Pro Ser Val Val Ser Ile Ser Trp Gly Gly
305                 310                 315                 320

Pro Glu Asp Ser Trp Thr Ser Ala Ala Ile Ala Ala Met Asn Arg Ala
                325                 330                 335

Phe Leu Asp Ala Ala Ala Leu Gly Val Thr Val Leu Ala Ala Ala Gly
            340                 345                 350

Asp Ser Gly Ser Thr Gly Gly Glu Asp Asp Gly Leu Tyr His Val Asp
        355                 360                 365

Phe Pro Ala Ala Ser Pro Tyr Val Leu Ala Cys Gly Gly Thr Arg Leu
    370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
                405                 410                 415

Pro Ala Trp Gln Glu His Ala Asn Val Pro Pro Ser Ala Asn Pro Gly
            420                 425                 430

Ala Ser Ser Gly Arg Gly Val Pro Asp Leu Ala Gly Asn Ala Asp Pro
        435                 440                 445

Ala Thr Gly Tyr Glu Val Val Ile Asp Gly Glu Ala Thr Val Ile Gly
    450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
        515                 520                 525

Cys Thr Gly Leu Gly Ser Pro Ile Gly Val Arg Leu Leu Gln Ala Leu
    530                 535                 540

Leu Pro Ser Ala Ser Gln Pro Gln Pro Gly Ser Thr Glu Asn Leu Tyr
545                 550                 555                 560
```

Phe Gln Ser Gly Ala Leu Glu His His His His His
                565                 570

<210> SEQ ID NO 19
<211> LENGTH: 573
<212> TYPE: PRT
<213> ORGANISM: Artificial Sequence
<220> FEATURE:
<223> OTHER INFORMATION: Synthetic

<400> SEQUENCE: 19

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
                20                  25                  30

Gly Pro Val Ala Gly Asp Glu Arg Met Ala Val Thr Val Leu Arg
            35                  40                  45

Arg Gln Arg Ala Gly Glu Leu Ala Ala His Val Glu Arg Gln Ala Ala
        50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Val Asp Ala Ile Asn Arg Ala Phe Gly Val
        115                 120                 125

Glu Leu Arg His Phe Asp His Pro Asp Gly Ser Tyr Arg Ser Tyr Leu
    130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
        195                 200                 205

Gly Leu Asp Gly Gln Gly Gln Cys Ile Ala Ile Ile Glu Leu Gly Gly
    210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Ser Gly Pro Asp Gly Glu Val Glu Leu Asp Ile
            260                 265                 270

Glu Val Ala Gly Ala Leu Ala Pro Gly Ala Lys Phe Ala Val Tyr Phe
        275                 280                 285

Ala Pro Asp Thr Asp Ala Gly Phe Leu Asp Ala Ile Thr Thr Ala Ile
    290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
                325                 330                 335

Phe Leu Asp Ala Ala Ala Leu Gly Val Thr Val Leu Ala Ala Ala Gly
            340                 345                 350

```
Asp Ser Gly Ser Thr Gly Gly Glu Gln Asp Gly Leu Tyr His Val His
        355                 360                 365

Phe Pro Ala Ala Ser Pro Tyr Val Leu Ala Cys Gly Gly Thr Arg Leu
370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
            405                 410                 415

Pro Ala Trp Gln Glu His Ala Asn Val Pro Pro Ser Ala Asn Pro Gly
                420                 425                 430

Ala Ser Ser Gly Arg Gly Val Pro Asp Leu Ala Gly Asn Ala Asp Pro
        435                 440                 445

Ala Thr Gly Tyr Glu Val Val Ile Asp Gly Glu Ala Thr Val Ile Gly
        450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
        515                 520                 525

Cys Thr Gly Leu Gly Ser Pro Ile Gly Val Arg Leu Leu Gln Ala Leu
        530                 535                 540

Leu Pro Ser Ala Ser Gln Pro Gln Pro Gly Ser Thr Glu Asn Leu Tyr
545                 550                 555                 560

Phe Gln Ser Gly Ala Leu Glu His His His His His His
                565                 570

<210> SEQ ID NO 20
<211> LENGTH: 573
<212> TYPE: PRT
<213> ORGANISM: Artificial Sequence
<220> FEATURE:
<223> OTHER INFORMATION: Synthetic

<400> SEQUENCE: 20

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
                20                  25                  30

Gly Pro Val Ala Gly Asp Glu Arg Met Ala Val Thr Val Leu Arg
            35                  40                  45

Arg Gln Arg Ala Gly Glu Leu Ala Ala His Val Glu Arg Gln Ala Ala
50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Val Asp Ala Ile Asn Arg Ala Phe Gly Val
        115                 120                 125

Glu Leu Arg His Phe Asp His Pro Asp Gly Ser Tyr Arg Ser Tyr Leu
        130                 135                 140
```

```
Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
            165                 170                 175

Arg Arg Ala Glu Gly Phe Glu Ala Arg Ser Gln Ala Ala Pro
        180                 185                 190

Thr Ala Tyr Thr Pro Leu Asp Val Ala Gln Ala Tyr Gln Phe Pro Glu
        195                 200                 205

Gly Leu Asp Gly Gln Gly Gln Cys Ile Ala Ile Glu Leu Gly Gly
        210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Ser Gly Pro Asp Gly Glu Val Glu Leu Asp Ile
            260                 265                 270

Glu Val Ala Gly Ala Leu Ala Pro Gly Ala Lys Phe Ala Val Tyr Phe
        275                 280                 285

Ala Pro Asp Thr Ala Ala Gly Phe Leu Asp Ala Ile Thr Thr Ala Ile
290                 295                 300

His Asp Pro Thr Leu Lys Pro Ser Val Val Ser Ile Ser Trp Gly Gly
305                 310                 315                 320

Pro Glu Asp Ser Trp Thr Ser Ala Ala Ile Ala Ala Met Asn Arg Ala
                325                 330                 335

Phe Leu Asp Ala Ala Leu Gly Val Thr Val Leu Ala Ala Ala Gly
            340                 345                 350

Asp Ser Gly Ser Thr Asn Gly Glu Asp Asp Gly Leu Tyr His Val Asp
        355                 360                 365

Phe Pro Ala Ala Ser Pro Tyr Val Leu Ala Cys Gly Gly Thr Arg Leu
        370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
                405                 410                 415

Pro Ala Trp Gln Glu His Ala Asn Val Pro Ser Ala Asn Pro Gly
            420                 425                 430

Ala Ser Ser Gly Arg Gly Val Pro Asp Leu Ala Gly Asn Ala Asp Pro
                435                 440                 445

Ala Thr Gly Tyr Glu Val Val Ile Asp Gly Ala Thr Val Ile Gly
        450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
        515                 520                 525

Cys Thr Gly Leu Gly Ser Pro Ile Gly Val Arg Leu Leu Gln Ala Leu
        530                 535                 540

Leu Pro Ser Ala Ser Gln Pro Gln Pro Gly Ser Thr Glu Asn Leu Tyr
545                 550                 555                 560

Phe Gln Ser Gly Ala Leu Glu His His His His His His
```

```
                  565                 570

<210> SEQ ID NO 21
<211> LENGTH: 573
<212> TYPE: PRT
<213> ORGANISM: Artificial Sequence
<220> FEATURE:
<223> OTHER INFORMATION: Synthetic

<400> SEQUENCE: 21

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
                20                  25                  30

Gly Pro Val Ala Gly Asp Glu Arg Met Ala Val Thr Val Val Leu Arg
            35                  40                  45

Arg Gln Arg Ala Gly Glu Leu Ala Ala His Val Glu Arg Gln Ala Ala
        50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Val Asp Ala Ile Asn Arg Ala Phe Gly Val
        115                 120                 125

Glu Leu Arg His Phe Asp His Pro Asp Gly Ser Tyr Arg Ser Tyr Leu
130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
        195                 200                 205

Gly Leu Asp Gly Gln Gly Gln Cys Ile Ala Ile Ile Glu Leu Gly Gly
    210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Ser Gly Pro Asp Gly Glu Val Glu Leu Asp Ile
            260                 265                 270

Glu Val Ala Gly Ala Leu Ala Pro Gly Ala Lys Phe Ala Val Tyr Phe
        275                 280                 285

Ala Pro Asn Thr Asp Ala Gly Phe Leu Asp Ala Ile Thr Thr Ala Ile
    290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
                325                 330                 335

Phe Leu Asp Ala Ala Ala Leu Gly Val Thr Val Leu Ala Ala Ala Gly
            340                 345                 350

Asp Asn Gly Ser Thr Gly Gly Glu Gln Asp Gly Leu Tyr His Val His
```

```
                355                 360                 365
Phe Pro Ala Ala Ser Pro Tyr Val Leu Ala Cys Gly Gly Thr Arg Leu
    370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Gly Val Ser Arg Ile Phe Pro Leu
                405                 410                 415

Pro Ala Trp Gln Glu His Ala Asn Val Pro Ser Ala Asn Pro Gly
            420                 425                 430

Ala Ser Ser Gly Arg Gly Val Pro Asp Leu Ala Gly Asn Ala Asp Pro
        435                 440                 445

Ala Thr Gly Tyr Glu Val Val Ile Asp Gly Glu Ala Thr Val Ile Gly
    450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
        515                 520                 525

Cys Thr Gly Leu Gly Ser Pro Ile Gly Val Arg Leu Leu Gln Ala Leu
    530                 535                 540

Leu Pro Ser Ala Ser Gln Pro Gln Pro Gly Ser Thr Glu Asn Leu Tyr
545                 550                 555                 560

Phe Gln Ser Gly Ala Leu Glu His His His His His
                565                 570

<210> SEQ ID NO 22
<211> LENGTH: 573
<212> TYPE: PRT
<213> ORGANISM: Artificial Sequence
<220> FEATURE:
<223> OTHER INFORMATION: Synthetic

<400> SEQUENCE: 22

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Leu Arg
        35                  40                  45

Arg Gln Arg Ala Gly Glu Leu Ala Ala His Val Glu Arg Gln Ala Ala
    50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Val Asp Ala Ile Asn Arg Ala Phe Gly Val
        115                 120                 125

Glu Leu Arg His Phe Asp His Pro Asp Gly Ser Tyr Arg Ser Tyr Leu
    130                 135                 140

Gly Glu Val Thr Val Pro Ala Ser Ile Ala Pro Met Ile Glu Ala Val
```

```
            145                 150                 155                 160
Leu Gly Leu Asp Thr Arg Pro Val Ala Arg Pro His Phe Arg Met Gln
                165                 170                 175
Arg Arg Ala Glu Gly Gly Phe Glu Ala Arg Ser Gln Ala Ala Ala Pro
                180                 185                 190
Thr Ala Tyr Thr Pro Leu Asp Val Ala Gln Ala Tyr Gln Phe Pro Glu
                195                 200                 205
Gly Leu Asp Gly Gln Gly Gln Cys Ile Ala Ile Ile Glu Leu Gly Gly
                210                 215                 220
Gly Tyr Asp Glu Ala Ser Leu Ala Gln Tyr Phe Ala Ser Leu Gly Val
225                 230                 235                 240
Pro Ala Pro Gln Val Val Ser Val Ser Val Asp Gly Ala Ser Asn Gln
                245                 250                 255
Pro Thr Gly Asp Pro Ser Gly Pro Asp Gly Glu Val Glu Leu Asp Ile
                260                 265                 270
Glu Val Ala Gly Ala Leu Ala Pro Gly Ala Lys Phe Ala Val Tyr Phe
                275                 280                 285
Ala Pro Asp Thr Ala Ala Gly Phe Leu Asp Ala Ile Thr Thr Ala Ile
                290                 295                 300
His Asp Pro Thr Leu Lys Pro Ser Val Val Ser Ile Ser Trp Gly Gly
305                 310                 315                 320
Pro Glu Asp Ser Trp Thr Ser Ala Ala Ile Ala Ala Met Asn Arg Ala
                325                 330                 335
Phe Leu Asp Ala Ala Ala Leu Gly Val Thr Val Leu Ala Ala Ala Gly
                340                 345                 350
Asp Ser Gly Ser Thr Gly Gly Glu Asp Asp Gly Leu Tyr His Val Asp
                355                 360                 365
Phe Pro Ala Ala Ser Pro Tyr Val Leu Ala Cys Gly Gly Thr Arg Leu
                370                 375                 380
Val Ala Ser Gly Gly Arg Ile Ala Gln Glu Thr Val Trp Asn Asp Gly
385                 390                 395                 400
Pro Asp Gly Gly Ala Thr Gly Gly Val Ser Arg Ile Phe Pro Leu
                405                 410                 415
Pro Ala Trp Gln Glu His Ala Asn Val Pro Pro Ser Ala Asn Pro Gly
                420                 425                 430
Ala Ser Ser Gly Arg Gly Val Pro Asp Leu Ala Gly Asn Ala Asp Pro
                435                 440                 445
Ala Thr Gly Tyr Glu Val Val Ile Asp Gly Glu Ala Thr Val Ile Gly
                450                 455                 460
Gly Thr Ser Ala Val Ala Pro Leu Phe Ala Ala Leu Val Ala Arg Ile
465                 470                 475                 480
Asn Gln Lys Leu Gly Lys Ala Val Gly Tyr Leu Asn Pro Thr Leu Tyr
                485                 490                 495
Gln Leu Pro Ala Asp Val Phe His Asp Ile Thr Glu Gly Asn Asn Asp
                500                 505                 510
Ile Ala Asn Arg Ala Gln Ile Tyr Gln Ala Gly Pro Gly Trp Asp Pro
                515                 520                 525
Cys Thr Gly Leu Gly Ser Pro Ile Gly Val Arg Leu Leu Gln Ala Leu
                530                 535                 540
Leu Pro Ser Ala Ser Gln Pro Gln Pro Gly Ser Thr Glu Asn Leu Tyr
545                 550                 555                 560
Phe Gln Ser Gly Ala Leu Glu His His His His His
                565                 570
```

<210> SEQ ID NO 23
<211> LENGTH: 573
<212> TYPE: PRT
<213> ORGANISM: Artificial Sequence
<220> FEATURE:
<223> OTHER INFORMATION: Synthetic

<400> SEQUENCE: 23

```
Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Val Leu Arg
                35                  40                  45

Arg Gln Arg Ala Gly Glu Leu Ala Ala His Val Glu Arg Gln Ala Ala
        50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Val Asp Ala Ile Asn Arg Ala Phe Gly Val
            115                 120                 125

Glu Leu Arg His Phe Asp His Pro Asp Gly Ser Tyr Arg Ser Tyr Leu
        130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
        195                 200                 205

Gly Leu Asp Gly Gln Gly Gln Cys Ile Ala Ile Ile Glu Leu Gly Gly
    210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Ser Gly Pro Asp Gly Glu Val Glu Leu Asp Ile
            260                 265                 270

Glu Val Ala Gly Ala Leu Ala Pro Gly Ala Lys Phe Ala Val Tyr Phe
        275                 280                 285

Ala Pro Asp Thr Asp Ala Gly Phe Leu Asp Ala Ile Thr Thr Ala Ile
    290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
                325                 330                 335

Phe Leu Asp Ala Ala Leu Gly Val Thr Val Leu Ala Ala Ala Gly
            340                 345                 350

Asp Ser Gly Ser Thr Gly Gly Glu Asp Asp Gly Leu Tyr His Val His
        355                 360                 365
```

```
Phe Pro Ala Ala Ser Pro Tyr Val Leu Ala Cys Gly Gly Thr Arg Leu
    370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
                405                 410                 415

Pro Ala Trp Gln Glu His Ala Asn Val Pro Ser Ala Asn Pro Gly
            420                 425                 430

Ala Ser Ser Gly Arg Gly Val Pro Asp Leu Ala Gly Asn Ala Asp Pro
        435                 440                 445

Ala Thr Gly Tyr Glu Val Val Ile Asp Gly Ala Thr Val Ile Gly
    450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
    515                 520                 525

Cys Thr Gly Leu Gly Ser Pro Ile Gly Val Arg Leu Leu Gln Ala Leu
530                 535                 540

Leu Pro Ser Ala Ser Gln Pro Gln Pro Gly Ser Thr Glu Asn Leu Tyr
545                 550                 555                 560

Phe Gln Ser Gly Ala Leu Glu His His His His His His
                565                 570

<210> SEQ ID NO 24
<211> LENGTH: 573
<212> TYPE: PRT
<213> ORGANISM: Artificial Sequence
<220> FEATURE:
<223> OTHER INFORMATION: Synthetic

<400> SEQUENCE: 24

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Leu Arg
                35                  40                  45

Arg Gln Arg Ala Gly Glu Leu Ala Ala His Val Glu Arg Gln Ala Ala
    50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Val Asp Ala Ile Asn Arg Ala Phe Gly Val
        115                 120                 125

Glu Leu Arg His Phe Asp His Pro Asp Gly Ser Tyr Arg Ser Tyr Leu
    130                 135                 140

Gly Glu Val Thr Val Pro Ala Ser Ile Ala Pro Met Ile Glu Ala Val
145                 150                 155                 160
```

```
Leu Gly Leu Asp Thr Arg Pro Val Ala Arg Pro His Phe Arg Met Gln
            165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
            195                 200                 205

Gly Leu Asp Gly Gln Gly Gln Cys Ile Ala Ile Ile Glu Leu Gly Gly
            210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
            245                 250                 255

Pro Thr Gly Asp Pro Ser Gly Pro Asp Gly Glu Val Glu Leu Asp Ile
            260                 265                 270

Glu Val Ala Gly Ala Leu Ala Pro Gly Ala Lys Phe Ala Val Tyr Phe
            275                 280                 285

Ala Pro Asp Thr Asp Ala Gly Phe Leu Asp Ala Ile Thr Thr Ala Ile
            290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
            325                 330                 335

Phe Leu Asp Ala Ala Ala Leu Gly Val Thr Val Leu Ala Ala Ala Gly
            340                 345                 350

Asp Asn Gly Ser Thr Gly Gly Glu Gln Asp Gly Leu Tyr His Val His
            355                 360                 365

Phe Pro Ala Ala Ser Pro Tyr Val Leu Ala Cys Gly Gly Thr Arg Leu
            370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
            405                 410                 415

Pro Ala Trp Gln Glu His Ala Asn Val Pro Pro Ser Ala Asn Pro Gly
            420                 425                 430

Ala Ser Ser Gly Arg Gly Val Pro Asp Leu Ala Gly Asn Ala Asp Pro
            435                 440                 445

Ala Thr Gly Tyr Glu Val Val Ile Asp Gly Glu Ala Thr Val Ile Gly
            450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
            485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
            515                 520                 525

Cys Thr Gly Leu Gly Ser Pro Ile Gly Val Arg Leu Leu Gln Ala Leu
            530                 535                 540

Leu Pro Ser Ala Ser Gln Pro Gln Pro Gly Ser Thr Glu Asn Leu Tyr
545                 550                 555                 560

Phe Gln Ser Gly Ala Leu Glu His His His His His
            565                 570
```

-continued

<210> SEQ ID NO 25
<211> LENGTH: 573
<212> TYPE: PRT
<213> ORGANISM: Artificial Sequence
<220> FEATURE:
<223> OTHER INFORMATION: Synthetic

<400> SEQUENCE: 25

```
Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Leu Arg
            35                  40                  45

Arg Gln Arg Ala Gly Glu Leu Ala Ala His Val Glu Arg Gln Ala Ala
    50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Val Asp Ala Ile Asn Arg Ala Phe Gly Val
            115                 120                 125

Glu Leu Arg His Phe Asp His Pro Asp Gly Ser Tyr Arg Ser Tyr Leu
            130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
            195                 200                 205

Gly Leu Asp Gly Gln Gly Gln Cys Ile Ala Ile Glu Leu Gly Gly
            210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Ser Gly Pro Asp Gly Glu Val Glu Leu Asp Ile
            260                 265                 270

Glu Val Ala Gly Ala Leu Ala Pro Gly Ala Lys Phe Ala Val Tyr Phe
            275                 280                 285

Ala Pro Asp Thr Ala Ala Gly Phe Leu Asp Ala Ile Thr Thr Ala Ile
            290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
                325                 330                 335

Phe Leu Asp Ala Ala Ala Leu Gly Val Thr Val Leu Ala Ala Ala Gly
            340                 345                 350

Asp Ser Gly Ser Thr Gly Gly Glu Asp Asp Gly Leu Tyr His Val His
            355                 360                 365
```

Phe Pro Ala Ala Ser Pro Tyr Val Leu Ala Cys Gly Gly Thr Arg Leu
370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
                405                 410                 415

Pro Ala Trp Gln Glu His Ala Asn Val Pro Pro Ser Ala Asn Pro Gly
                420                 425                 430

Ala Ser Ser Gly Arg Gly Val Pro Asp Leu Ala Gly Asn Ala Asp Pro
        435                 440                 445

Ala Thr Gly Tyr Glu Val Val Ile Asp Gly Glu Ala Thr Val Ile Gly
450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
                500                 505                 510

Ile Ala Asn Arg Ala Gln Ile Tyr Gln Ala Gly Pro Gly Trp Asp Pro
515                 520                 525

Cys Thr Gly Leu Gly Ser Pro Ile Gly Val Arg Leu Leu Gln Ala Leu
530                 535                 540

Leu Pro Ser Ala Ser Gln Pro Gln Pro Gly Ser Thr Glu Asn Leu Tyr
545                 550                 555                 560

Phe Gln Ser Gly Ala Leu Glu His His His His His His
                565                 570

<210> SEQ ID NO 26
<211> LENGTH: 573
<212> TYPE: PRT
<213> ORGANISM: Artificial Sequence
<220> FEATURE:
<223> OTHER INFORMATION: Synthetic

<400> SEQUENCE: 26

Met Ser Asp Met Glu Lys Pro Trp Lys Glu Gly Glu Glu Ala Arg Ala
1               5                   10                  15

Val Leu Gln Gly His Ala Arg Ala Gln Ala Pro Gln Ala Val Asp Lys
                20                  25                  30

Gly Pro Val Ala Gly Asp Glu Arg Met Ala Val Thr Val Leu Arg
            35                  40                  45

Arg Gln Arg Ala Gly Glu Leu Ala Ala His Val Glu Arg Gln Ala Ala
    50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
                100                 105                 110

Ala Val Leu Ser Gly Pro Val Asp Ala Ile Asn Arg Ala Phe Gly Val
            115                 120                 125

Glu Leu Arg His Phe Asp His Pro Asp Gly Ser Tyr Arg Ser Tyr Leu
    130                 135                 140

Gly Glu Val Thr Val Pro Ala Ser Ile Ala Pro Met Ile Glu Ala Val
145                 150                 155                 160

```
Leu Gly Leu Asp Thr Arg Pro Val Ala Arg Pro His Phe Arg Met Gln
                165                 170                 175
Arg Arg Ala Glu Gly Gly Phe Glu Ala Arg Ser Gln Ala Ala Ala Pro
            180                 185                 190
Thr Ala Tyr Thr Pro Leu Asp Val Ala Gln Ala Tyr Gln Phe Pro Glu
        195                 200                 205
Gly Leu Asp Gly Gln Gly Gln Cys Ile Ala Ile Ile Glu Leu Gly Gly
    210                 215                 220
Gly Tyr Asp Glu Ala Ser Leu Ala Gln Tyr Phe Ala Ser Leu Gly Val
225                 230                 235                 240
Pro Ala Pro Gln Val Val Ser Val Ser Val Asp Gly Ala Ser Asn Gln
                245                 250                 255
Pro Thr Gly Asp Pro Ser Gly Pro Asp Gly Glu Val Glu Leu Asp Ile
            260                 265                 270
Glu Val Ala Gly Ala Leu Ala Pro Gly Ala Lys Phe Ala Val Tyr Phe
        275                 280                 285
Ala Pro Asp Thr Asp Ala Gly Phe Leu Asp Ala Ile Thr Thr Ala Ile
    290                 295                 300
His Asp Pro Thr Leu Lys Pro Ser Val Val Ser Ile Ser Trp Ser Gly
305                 310                 315                 320
Pro Glu Asp Ser Trp Thr Ser Ala Ala Ile Ala Ala Met Asn Arg Ala
                325                 330                 335
Phe Leu Asp Ala Ala Leu Gly Val Thr Val Leu Ala Ala Ala Gly
            340                 345                 350
Asp Asn Gly Ser Thr Gly Gly Glu Asp Gly Leu Tyr His Val His
            355                 360                 365
Phe Pro Ala Ala Ser Pro Tyr Val Leu Ala Cys Gly Gly Thr Arg Leu
    370                 375                 380
Val Ala Ser Gly Gly Arg Ile Ala Gln Glu Thr Val Trp Asn Asp Gly
385                 390                 395                 400
Pro Asp Gly Gly Ala Thr Gly Gly Val Ser Arg Ile Phe Pro Leu
            405                 410                 415
Pro Ala Trp Gln Glu His Ala Asn Val Pro Pro Ser Ala Asn Pro Gly
        420                 425                 430
Ala Ser Ser Gly Arg Gly Val Pro Asp Leu Ala Gly Asn Ala Asp Pro
    435                 440                 445
Ala Thr Gly Tyr Glu Val Val Ile Asp Gly Glu Ala Thr Val Ile Gly
    450                 455                 460
Gly Thr Ser Ala Val Ala Pro Leu Phe Ala Ala Leu Val Ala Arg Ile
465                 470                 475                 480
Asn Gln Lys Leu Gly Lys Ala Val Gly Tyr Leu Asn Pro Thr Leu Tyr
                485                 490                 495
Gln Leu Pro Ala Asp Val Phe His Asp Ile Thr Glu Gly Asn Asn Asp
            500                 505                 510
Ile Ala Asn Arg Ala Gln Ile Tyr Gln Ala Gly Pro Gly Trp Asp Pro
        515                 520                 525
Cys Thr Gly Leu Gly Ser Pro Ile Gly Val Arg Leu Leu Gln Ala Leu
    530                 535                 540
Leu Pro Ser Ala Ser Gln Pro Gln Pro Gly Ser Thr Glu Asn Leu Tyr
545                 550                 555                 560
Phe Gln Ser Gly Ala Leu Glu His His His His His
                565                 570
```

```
<210> SEQ ID NO 27
<211> LENGTH: 573
<212> TYPE: PRT
<213> ORGANISM: Artificial Sequence
<220> FEATURE:
<223> OTHER INFORMATION: Synthetic

<400> SEQUENCE: 27
```

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Val Leu Arg
        35                  40                  45

Arg Gln Arg Ala Gly Glu Leu Ala Ala His Val Glu Arg Gln Ala Ala
    50                  55                  60

Ile Ala Pro His Ala Arg Glu His Leu Lys Arg Glu Ala Phe Ala Ala
65              70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Val Asp Ala Ile Asn Arg Ala Phe Gly Val
        115                 120                 125

Glu Leu Arg His Phe Asp His Pro Asp Gly Ser Tyr Arg Ser Tyr Leu
    130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
        195                 200                 205

Gly Leu Asp Gly Gln Gly Gln Cys Ile Ala Ile Ile Glu Leu Gly Gly
    210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Ser Gly Pro Asp Gly Glu Val Glu Leu Asp Ile
            260                 265                 270

Glu Val Ala Gly Ala Leu Ala Pro Gly Ala Lys Phe Ala Val Tyr Phe
        275                 280                 285

Ala Pro Asp Thr Ala Ala Gly Phe Leu Asp Ala Ile Thr Thr Ala Ile
    290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
                325                 330                 335

Phe Leu Asp Ala Ala Leu Gly Val Thr Val Leu Ala Ala Ala Gly
            340                 345                 350

Asp Asn Gly Ser Thr Gly Gly Glu Asp Asp Gly Leu Tyr His Val His
        355                 360                 365

Phe Pro Ala Ala Ser Pro Tyr Val Leu Ala Cys Gly Gly Thr Arg Leu

```
                370                 375                 380
Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
                405                 410                 415

Pro Ala Trp Gln Glu His Ala Asn Val Pro Ser Ala Asn Pro Gly
                420                 425                 430

Ala Ser Ser Gly Arg Gly Val Pro Asp Leu Ala Gly Asn Ala Asp Pro
                435                 440                 445

Ala Thr Gly Tyr Glu Val Val Ile Asp Gly Glu Ala Thr Val Ile Gly
                450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
                500                 505                 510

Ile Ala Asn Arg Ala Gln Ile Tyr Gln Ala Gly Pro Gly Trp Asp Pro
                515                 520                 525

Cys Thr Gly Leu Gly Ser Pro Ile Gly Val Arg Leu Leu Gln Ala Leu
                530                 535                 540

Leu Pro Ser Ala Ser Gln Pro Gln Pro Gly Ser Thr Glu Asn Leu Tyr
545                 550                 555                 560

Phe Gln Ser Gly Ala Leu Glu His His His His His His
                565                 570

<210> SEQ ID NO 28
<211> LENGTH: 573
<212> TYPE: PRT
<213> ORGANISM: Artificial Sequence
<220> FEATURE:
<223> OTHER INFORMATION: Synthetic

<400> SEQUENCE: 28

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
                20                  25                  30

Gly Pro Val Ala Gly Asp Glu Arg Met Ala Val Thr Val Leu Arg
                35                  40                  45

Arg Gln Arg Ala Gly Glu Leu Ala Ala His Val Glu Arg Gln Ala Ala
                50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
                100                 105                 110

Ala Val Leu Ser Gly Pro Val Asp Ala Ile Asn Arg Ala Phe Gly Val
                115                 120                 125

Glu Leu Arg His Phe Asp His Pro Asp Gly Ser Tyr Arg Ser Tyr Leu
                130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
```

```
                165                 170                 175
Arg Arg Ala Glu Gly Gly Phe Glu Ala Arg Ser Gln Ala Ala Pro
                180                 185                 190

Thr Ala Tyr Thr Pro Leu Asp Val Ala Gln Tyr Gln Phe Pro Glu
                195                 200                 205

Gly Leu Asp Gly Gln Gly Gln Cys Ile Ala Ile Ile Glu Leu Gly Gly
            210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Ser Gly Pro Asp Gly Glu Val Glu Leu Asp Ile
                260                 265                 270

Glu Val Ala Gly Ala Leu Ala Pro Gly Ala Lys Phe Ala Val Tyr Phe
                275                 280                 285

Ala Pro Asp Ser Asp Ala Gly Phe Leu Asp Ala Ile Thr Thr Ala Ile
                290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
                325                 330                 335

Phe Leu Asp Ala Ala Leu Gly Val Thr Val Leu Ala Ala Ala Gly
                340                 345                 350

Asp Ser Gly Ser Thr Gly Gly Glu Gln Asp Gly Leu Tyr His Val His
                355                 360                 365

Phe Pro Ala Ala Ser Pro Tyr Val Leu Ala Cys Gly Gly Thr Arg Leu
                370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
                405                 410                 415

Pro Ala Trp Gln Glu His Ala Asn Val Pro Pro Ser Ala Asn Pro Gly
                420                 425                 430

Ala Ser Ser Gly Arg Gly Val Pro Asp Leu Ala Gly Asn Ala Asp Pro
                435                 440                 445

Ala Thr Gly Tyr Glu Val Val Ile Asp Gly Ala Thr Val Ile Gly
                450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
                500                 505                 510

Ile Ala Asn Arg Ala Gln Ile Tyr Gln Ala Gly Pro Gly Trp Asp Pro
                515                 520                 525

Cys Thr Gly Leu Gly Ser Pro Ile Gly Val Arg Leu Leu Gln Ala Leu
                530                 535                 540

Leu Pro Ser Ala Ser Gln Pro Gln Pro Gly Ser Thr Glu Asn Leu Tyr
545                 550                 555                 560

Phe Gln Ser Gly Ala Leu Glu His His His His His His
                565                 570

<210> SEQ ID NO 29
```

```
<211> LENGTH: 573
<212> TYPE: PRT
<213> ORGANISM: Artificial Sequence
<220> FEATURE:
<223> OTHER INFORMATION: Synthetic

<400> SEQUENCE: 29
```

| | | | | | | | | | | | | | | | |
|---|---|---|---|---|---|---|---|---|---|---|---|---|---|---|---|
| Met | Ser | Asp | Met | Glu | Lys | Pro | Trp | Lys | Glu | Gly | Glu | Ala | Arg | Ala | |
| 1 | | | | 5 | | | | | 10 | | | | | 15 | |
| Val | Leu | Gln | Gly | His | Ala | Arg | Ala | Gln | Ala | Pro | Gln | Ala | Val | Asp | Lys |
| | | | 20 | | | | | 25 | | | | | 30 | | |
| Gly | Pro | Val | Ala | Gly | Asp | Glu | Arg | Met | Ala | Val | Thr | Val | Val | Leu | Arg |
| | | | 35 | | | | | 40 | | | | | 45 | | |
| Arg | Gln | Arg | Ala | Gly | Glu | Leu | Ala | Ala | His | Val | Glu | Arg | Gln | Ala | Ala |
| | 50 | | | | | 55 | | | | | 60 | | | | |
| Ile | Ala | Pro | His | Ala | Arg | Glu | His | Leu | Lys | Arg | Glu | Ala | Phe | Ala | Ala |
| 65 | | | | | 70 | | | | | 75 | | | | | 80 |
| Ser | His | Gly | Ala | Ser | Leu | Asp | Asp | Phe | Ala | Glu | Leu | Arg | Arg | Phe | Ala |
| | | | | 85 | | | | | 90 | | | | | 95 | |
| Asp | Ala | His | Gly | Leu | Ala | Leu | Asp | Arg | Ala | Asn | Val | Ala | Ala | Gly | Thr |
| | | | 100 | | | | | 105 | | | | | 110 | | |
| Ala | Val | Leu | Ser | Gly | Pro | Val | Asp | Ala | Ile | Asn | Arg | Ala | Phe | Gly | Val |
| | | | 115 | | | | | 120 | | | | | 125 | | |
| Glu | Leu | Arg | His | Phe | Asp | His | Pro | Asp | Gly | Ser | Tyr | Arg | Ser | Tyr | Leu |
| | 130 | | | | | 135 | | | | | 140 | | | | |
| Gly | Glu | Val | Thr | Val | Pro | Ala | Ser | Ile | Ala | Pro | Met | Ile | Glu | Ala | Val |
| 145 | | | | | 150 | | | | | 155 | | | | | 160 |
| Leu | Gly | Leu | Asp | Thr | Arg | Pro | Val | Ala | Arg | Pro | His | Phe | Arg | Met | Gln |
| | | | | 165 | | | | | 170 | | | | | 175 | |
| Arg | Arg | Ala | Glu | Gly | Gly | Phe | Glu | Ala | Arg | Ser | Gln | Ala | Ala | Ala | Pro |
| | | | 180 | | | | | 185 | | | | | 190 | | |
| Thr | Ala | Tyr | Thr | Pro | Leu | Asp | Val | Ala | Gln | Ala | Tyr | Gln | Phe | Pro | Glu |
| | | | 195 | | | | | 200 | | | | | 205 | | |
| Gly | Leu | Asp | Gly | Gln | Gly | Gln | Cys | Ile | Ala | Ile | Ile | Glu | Leu | Gly | Gly |
| | 210 | | | | | 215 | | | | | 220 | | | | |
| Gly | Tyr | Asp | Glu | Ala | Ser | Leu | Ala | Gln | Tyr | Phe | Ala | Ser | Leu | Gly | Val |
| 225 | | | | | 230 | | | | | 235 | | | | | 240 |
| Pro | Ala | Pro | Gln | Val | Val | Ser | Val | Ser | Val | Asp | Gly | Ala | Ser | Asn | Gln |
| | | | | 245 | | | | | 250 | | | | | 255 | |
| Pro | Thr | Gly | Asp | Pro | Ser | Gly | Pro | Asp | Gly | Glu | Val | Glu | Leu | Asp | Ile |
| | | | 260 | | | | | 265 | | | | | 270 | | |
| Glu | Val | Ala | Gly | Ala | Leu | Ala | Pro | Gly | Ala | Lys | Phe | Ala | Val | Tyr | Phe |
| | | | 275 | | | | | 280 | | | | | 285 | | |
| Ala | Pro | Asp | Thr | Thr | Ala | Gly | Phe | Leu | Asp | Ala | Ile | Thr | Thr | Ala | Ile |
| | 290 | | | | | 295 | | | | | 300 | | | | |
| His | Asp | Pro | Thr | Leu | Lys | Pro | Ser | Val | Val | Ser | Ile | Ser | Trp | Ser | Gly |
| 305 | | | | | 310 | | | | | 315 | | | | | 320 |
| Pro | Glu | Asp | Ser | Trp | Thr | Ser | Ala | Ala | Ile | Ala | Ala | Met | Asn | Arg | Ala |
| | | | | 325 | | | | | 330 | | | | | 335 | |
| Phe | Leu | Asp | Ala | Ala | Ala | Leu | Gly | Val | Thr | Val | Leu | Ala | Ala | Ala | Gly |
| | | | 340 | | | | | 345 | | | | | 350 | | |
| Asp | Ser | Gly | Ser | Thr | Gly | Gly | Glu | Gln | Asp | Gly | Leu | Tyr | His | Val | His |
| | | | 355 | | | | | 360 | | | | | 365 | | |
| Phe | Pro | Ala | Ala | Ser | Pro | Tyr | Val | Leu | Ala | Cys | Gly | Gly | Thr | Arg | Leu |
| | 370 | | | | | 375 | | | | | 380 | | | | |

```
Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
            405                 410                 415

Pro Ala Trp Gln Glu His Ala Asn Val Pro Pro Ser Ala Asn Pro Gly
            420                 425                 430

Ala Ser Ser Gly Arg Gly Val Pro Asp Leu Ala Gly Asn Ala Asp Pro
            435                 440                 445

Ala Thr Gly Tyr Glu Val Val Ile Asp Gly Glu Ala Thr Val Ile Gly
            450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
            515                 520                 525

Cys Thr Gly Leu Gly Ser Pro Ile Gly Val Arg Leu Leu Gln Ala Leu
530                 535                 540

Leu Pro Ser Ala Ser Gln Pro Gln Pro Gly Ser Thr Glu Asn Leu Tyr
545                 550                 555                 560

Phe Gln Ser Gly Ala Leu Glu His His His His His His
                565                 570

<210> SEQ ID NO 30
<211> LENGTH: 573
<212> TYPE: PRT
<213> ORGANISM: Artificial Sequence
<220> FEATURE:
<223> OTHER INFORMATION: Synthetic

<400> SEQUENCE: 30

Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
                20                  25                  30

Gly Pro Val Ala Gly Asp Glu Arg Met Ala Val Thr Val Leu Arg
            35                  40                  45

Arg Gln Arg Ala Gly Glu Leu Ala Ala His Val Glu Arg Gln Ala Ala
    50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Val Asp Ala Ile Asn Arg Ala Phe Gly Val
        115                 120                 125

Glu Leu Arg His Phe Asp His Pro Asp Gly Ser Tyr Arg Ser Tyr Leu
    130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175
```

```
Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
            195                 200                 205

Gly Leu Asp Gly Gln Gly Gln Cys Ile Ala Ile Ile Glu Leu Gly Gly
            210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                    245                 250                 255

Pro Thr Gly Asp Pro Gly Gly Pro Asp Gly Glu Val Glu Leu Asp Ile
            260                 265                 270

Glu Val Ala Gly Ala Leu Ala Pro Gly Ala Lys Phe Ala Val Tyr Phe
            275                 280                 285

Ala Pro Asp Ser Asp Ala Gly Phe Leu Asp Ala Ile Thr Thr Ala Ile
            290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
                    325                 330                 335

Phe Leu Asp Ala Ala Ala Leu Gly Val Thr Val Leu Ala Ala Ala Gly
            340                 345                 350

Asp Ser Gly Ser Thr Gly Gly Glu Gln Asp Gly Leu Tyr His Val His
            355                 360                 365

Phe Pro Ala Ala Ser Pro Tyr Val Leu Ala Cys Gly Gly Thr Arg Leu
            370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
                    405                 410                 415

Pro Ala Trp Gln Glu His Ala Asn Val Pro Ser Ala Asn Pro Gly
            420                 425                 430

Ala Ser Ser Gly Arg Gly Val Pro Asp Leu Ala Gly Asn Ala Asp Pro
            435                 440                 445

Ala Thr Gly Tyr Glu Val Val Ile Asp Gly Glu Ala Thr Val Ile Gly
            450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                    485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
            515                 520                 525

Cys Thr Gly Leu Gly Ser Pro Ile Gly Val Arg Leu Leu Gln Ala Leu
            530                 535                 540

Leu Pro Ser Ala Ser Gln Pro Gln Pro Gly Ser Thr Glu Asn Leu Tyr
545                 550                 555                 560

Phe Gln Ser Gly Ala Leu Glu His His His His His
                    565                 570

<210> SEQ ID NO 31
<211> LENGTH: 573
```

```
<212> TYPE: PRT
<213> ORGANISM: Artificial Sequence
<220> FEATURE:
<223> OTHER INFORMATION: Synthetic

<400> SEQUENCE: 31
```

| | | | | | | | | | | | | | | |
|---|---|---|---|---|---|---|---|---|---|---|---|---|---|---|
| Met | Ser | Asp | Met | Glu | Lys | Pro | Trp | Lys | Glu | Gly | Glu | Ala | Arg | Ala |
| 1 | | | | 5 | | | | | 10 | | | | | 15 |
| Val | Leu | Gln | Gly | His | Ala | Arg | Ala | Gln | Ala | Pro | Gln | Ala | Val | Asp | Lys |
| | | | 20 | | | | | 25 | | | | | 30 | | |
| Gly | Pro | Val | Ala | Gly | Asp | Glu | Arg | Met | Ala | Val | Thr | Val | Val | Leu | Arg |
| | | | 35 | | | | | 40 | | | | | 45 | | |
| Arg | Gln | Arg | Ala | Gly | Glu | Leu | Ala | Ala | His | Val | Glu | Arg | Gln | Ala | Ala |
| | 50 | | | | | 55 | | | | | 60 | | | | |
| Ile | Ala | Pro | His | Ala | Arg | Glu | His | Leu | Lys | Arg | Glu | Ala | Phe | Ala | Ala |
| 65 | | | | | 70 | | | | | 75 | | | | | 80 |
| Ser | His | Gly | Ala | Ser | Leu | Asp | Asp | Phe | Ala | Glu | Leu | Arg | Arg | Phe | Ala |
| | | | | 85 | | | | | 90 | | | | | 95 | |
| Asp | Ala | His | Gly | Leu | Ala | Leu | Asp | Arg | Ala | Asn | Val | Ala | Ala | Gly | Thr |
| | | | 100 | | | | | 105 | | | | | 110 | | |
| Ala | Val | Leu | Ser | Gly | Pro | Val | Asp | Ala | Ile | Asn | Arg | Ala | Phe | Gly | Val |
| | | | 115 | | | | | 120 | | | | | 125 | | |
| Glu | Leu | Arg | His | Phe | Asp | His | Pro | Asp | Gly | Ser | Tyr | Arg | Ser | Tyr | Leu |
| | 130 | | | | | 135 | | | | | 140 | | | | |
| Gly | Glu | Val | Thr | Val | Pro | Ala | Ser | Ile | Ala | Pro | Met | Ile | Glu | Ala | Val |
| 145 | | | | | 150 | | | | | 155 | | | | | 160 |
| Leu | Gly | Leu | Asp | Thr | Arg | Pro | Val | Ala | Arg | Pro | His | Phe | Arg | Met | Gln |
| | | | | 165 | | | | | 170 | | | | | 175 | |
| Arg | Arg | Ala | Glu | Gly | Gly | Phe | Glu | Ala | Arg | Ser | Gln | Ala | Ala | Ala | Pro |
| | | | 180 | | | | | 185 | | | | | 190 | | |
| Thr | Ala | Tyr | Thr | Pro | Leu | Asp | Val | Ala | Gln | Ala | Tyr | Gln | Phe | Pro | Glu |
| | | | 195 | | | | | 200 | | | | | 205 | | |
| Gly | Leu | Asp | Gly | Gln | Gly | Gln | Cys | Ile | Ala | Ile | Glu | Leu | Gly | Gly |
| | 210 | | | | | 215 | | | | | 220 | | | | |
| Gly | Tyr | Asp | Glu | Ala | Ser | Leu | Ala | Gln | Tyr | Phe | Ala | Ser | Leu | Gly | Val |
| 225 | | | | | 230 | | | | | 235 | | | | | 240 |
| Pro | Ala | Pro | Gln | Val | Val | Ser | Val | Ser | Val | Asp | Gly | Ala | Ser | Asn | Gln |
| | | | | 245 | | | | | 250 | | | | | 255 | |
| Pro | Thr | Gly | Asp | Pro | Lys | Gly | Pro | Asp | Gly | Glu | Val | Glu | Leu | Asp | Ile |
| | | | 260 | | | | | 265 | | | | | 270 | | |
| Glu | Val | Ala | Gly | Ala | Leu | Ala | Pro | Gly | Ala | Lys | Phe | Ala | Val | Tyr | Phe |
| | | | 275 | | | | | 280 | | | | | 285 | | |
| Ala | Pro | Asp | Thr | Asn | Ala | Gly | Phe | Leu | Asp | Ala | Ile | Thr | Thr | Ala | Ile |
| | 290 | | | | | 295 | | | | | 300 | | | | |
| His | Asp | Pro | Thr | Leu | Lys | Pro | Ser | Val | Val | Ser | Ile | Ser | Trp | Ser | Gly |
| 305 | | | | | 310 | | | | | 315 | | | | | 320 |
| Pro | Glu | Asp | Ser | Trp | Thr | Ser | Ala | Ala | Ile | Ala | Ala | Met | Asn | Arg | Ala |
| | | | | 325 | | | | | 330 | | | | | 335 | |
| Phe | Leu | Asp | Ala | Ala | Ala | Leu | Gly | Val | Thr | Val | Leu | Ala | Ala | Ala | Gly |
| | | | 340 | | | | | 345 | | | | | 350 | | |
| Asp | Ser | Gly | Ser | Thr | Gly | Gly | Glu | Gln | Asp | Gly | Leu | Tyr | His | Val | His |
| | | | 355 | | | | | 360 | | | | | 365 | | |
| Phe | Pro | Ala | Ala | Ser | Pro | Tyr | Val | Leu | Ala | Cys | Gly | Gly | Thr | Arg | Leu |
| | 370 | | | | | 375 | | | | | 380 | | | | |

```
Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
            405                 410                 415

Pro Ala Trp Gln Glu His Ala Asn Val Pro Pro Ser Ala Asn Pro Gly
            420                 425                 430

Ala Ser Ser Gly Arg Gly Val Pro Asp Leu Ala Gly Asn Ala Asp Pro
            435                 440                 445

Ala Thr Gly Tyr Glu Val Val Ile Asp Gly Glu Ala Thr Val Ile Gly
        450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
            485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
            515                 520                 525

Cys Thr Gly Leu Gly Ser Pro Ile Gly Val Arg Leu Leu Gln Ala Leu
530                 535                 540

Leu Pro Ser Ala Ser Gln Pro Gln Pro Gly Ser Thr Glu Asn Leu Tyr
545                 550                 555                 560

Phe Gln Ser Gly Ala Leu Glu His His His His His His
            565                 570

<210> SEQ ID NO 32
<211> LENGTH: 573
<212> TYPE: PRT
<213> ORGANISM: Artificial Sequence
<220> FEATURE:
<223> OTHER INFORMATION: Synthetic

<400> SEQUENCE: 32

Met Ser Asp Met Glu Lys Pro Trp Lys Glu Gly Glu Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Leu Arg
        35                  40                  45

Arg Gln Arg Ala Gly Glu Leu Ala Ala His Val Glu Arg Gln Ala Ala
    50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
            85                  90                  95

Asp Ala His Gly Leu Ala Leu Asp Arg Ala Asn Val Ala Ala Gly Thr
            100                 105                 110

Ala Val Leu Ser Gly Pro Asp Asp Ala Ile Asn Arg Ala Phe Gly Val
            115                 120                 125

Glu Leu Arg His Phe Asp His Pro Asp Gly Ser Tyr Arg Ser Tyr Leu
        130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175
```

```
Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
            195                 200                 205

Gly Leu Asp Gly Gln Gly Gln Cys Ile Ala Ile Ile Glu Leu Gly Gly
            210                 215                 220

Gly Tyr Asp Glu Ala Ser Leu Ala Gln Tyr Phe Ala Ser Leu Gly Val
225                 230                 235                 240

Pro Ala Pro Gln Val Ser Val Ser Val Asp Gly Ala Ser Asn Gln
                245                 250                 255

Pro Thr Gly Asp Pro Lys Gly Pro Asp Gly Glu Val Glu Leu Asp Ile
            260                 265                 270

Glu Val Ala Gly Ala Leu Ala Pro Gly Ala Lys Phe Ala Val Tyr Phe
            275                 280                 285

Ala Pro Asp Thr Thr Ala Gly Phe Leu Asp Ala Ile Thr Thr Ala Ile
            290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
                325                 330                 335

Phe Leu Asp Ala Ala Ala Leu Gly Val Thr Val Leu Ala Ala Ala Gly
            340                 345                 350

Asp Ser Gly Ser Thr Gly Gly Glu Gln Asp Gly Leu Tyr His Val His
            355                 360                 365

Phe Pro Ala Ala Ser Pro Tyr Val Leu Ala Cys Gly Gly Thr Arg Leu
            370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
                405                 410                 415

Pro Ala Trp Gln Glu His Ala Asn Val Pro Pro Ser Ala Asn Pro Gly
            420                 425                 430

Ala Ser Ser Gly Arg Gly Val Pro Asp Leu Ala Gly Asn Ala Asp Pro
            435                 440                 445

Ala Thr Gly Tyr Glu Val Val Ile Asp Gly Glu Ala Thr Val Ile Gly
            450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
            515                 520                 525

Cys Thr Gly Leu Gly Ser Pro Ile Gly Val Arg Leu Leu Gln Ala Leu
530                 535                 540

Leu Pro Ser Ala Ser Gln Pro Gln Pro Gly Ser Thr Glu Asn Leu Tyr
545                 550                 555                 560

Phe Gln Ser Gly Ala Leu Glu His His His His His
                565                 570

<210> SEQ ID NO 33
<211> LENGTH: 573
<212> TYPE: PRT
```

<213> ORGANISM: Artificial Sequence
<220> FEATURE:
<223> OTHER INFORMATION: Synthetic

<400> SEQUENCE: 33

```
Met Ser Asp Met Glu Lys Pro Trp Lys Glu Gly Glu Ala Arg Ala
1               5                   10                  15

Val Leu Gln Gly His Ala Arg Ala Gln Ala Pro Gln Ala Val Asp Lys
            20                  25                  30

Gly Pro Val Ala Gly Asp Glu Arg Met Ala Val Thr Val Leu Arg
            35                  40                  45

Arg Gln Arg Ala Gly Glu Leu Ala Ala His Val Glu Arg Gln Ala Ala
50                  55                  60

Ile Ala Pro His Ala Arg Glu His Leu Lys Arg Glu Ala Phe Ala Ala
65                  70                  75                  80

Ser His Gly Ala Ser Leu Asp Asp Phe Ala Glu Leu Arg Arg Phe Ala
                85                  90                  95

Asp Ala His Gly Leu Ala Leu Asp Arg Ala Asn Val Ala Ala Gly Thr
            100                 105                 110

Ala Val Leu Ser Gly Pro Val Asp Ala Ile Asn Arg Ala Phe Gly Val
            115                 120                 125

Glu Leu Arg His Phe Asp His Pro Asp Gly Ser Tyr Arg Ser Tyr Leu
130                 135                 140

Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
                165                 170                 175

Arg Arg Ala Glu Gly Gly Phe Glu Ala Arg Ser Gln Ala Ala Ala Pro
            180                 185                 190

Thr Ala Tyr Thr Pro Leu Asp Val Ala Gln Ala Tyr Gln Phe Pro Glu
            195                 200                 205

Gly Leu Asp Gly Gln Gly Gln Cys Ile Ala Ile Glu Leu Gly Gly
        210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Ser Gly Pro Asp Gly Glu Val Glu Leu Asp Ile
            260                 265                 270

Glu Val Ala Gly Ala Leu Ala Pro Gly Ala Lys Phe Ala Val Tyr Phe
            275                 280                 285

Ala Pro Asn Thr Asp Ala Gly Phe Leu Asp Ala Ile Thr Thr Ala Ile
290                 295                 300

His Asp Pro Thr Leu Lys Pro Ser Val Val Ser Ile Ser Trp Gly Gly
305                 310                 315                 320

Pro Glu Asp Ser Trp Thr Ser Ala Ala Ile Ala Ala Met Asn Arg Ala
                325                 330                 335

Phe Leu Asp Ala Ala Ala Leu Gly Val Thr Val Leu Ala Ala Ala Gly
            340                 345                 350

Asp Ser Gly Ser Thr Asp Gly Glu Gln Asp Gly Leu Tyr His Val Asp
            355                 360                 365

Phe Pro Ala Ala Ser Pro Tyr Val Leu Ala Cys Gly Gly Thr Arg Leu
370                 375                 380

Val Ala Ser Gly Gly Arg Ile Ala Gln Glu Thr Val Trp Asn Asp Gly
```

```
            385                 390                 395                 400

Pro Asp Gly Gly Ala Thr Gly Gly Val Ser Arg Ile Phe Pro Leu
                    405                 410                 415

Pro Ala Trp Gln Glu His Ala Asn Val Pro Ser Ala Asn Pro Gly
                420                 425                 430

Ala Ser Ser Gly Arg Gly Val Pro Asp Leu Ala Gly Asn Ala Asp Pro
                    435                 440                 445

Ala Thr Gly Tyr Glu Val Val Ile Asp Gly Glu Ala Thr Val Ile Gly
                    450                 455                 460

Gly Thr Ser Ala Val Ala Pro Leu Phe Ala Ala Leu Val Ala Arg Ile
    465                 470                 475                 480

Asn Gln Lys Leu Gly Lys Ala Val Gly Tyr Leu Asn Pro Thr Leu Tyr
                    485                 490                 495

Gln Leu Pro Ala Asp Val Phe His Asp Ile Thr Glu Gly Asn Asn Asp
                    500                 505                 510

Ile Ala Asn Arg Ala Gln Ile Tyr Gln Ala Gly Pro Gly Trp Asp Pro
                    515                 520                 525

Cys Thr Gly Leu Gly Ser Pro Ile Gly Val Arg Leu Leu Gln Ala Leu
    530                 535                 540

Leu Pro Ser Ala Ser Gln Pro Gln Pro Gly Ser Thr Glu Asn Leu Tyr
    545                 550                 555                 560

Phe Gln Ser Gly Ala Leu Glu His His His His His His
                    565                 570

<210> SEQ ID NO 34
<211> LENGTH: 6
<212> TYPE: PRT
<213> ORGANISM: Artificial Sequence
<220> FEATURE:
<223> OTHER INFORMATION: Synthetic

<400> SEQUENCE: 34

Pro Gln Pro Gln Leu Pro
1               5

<210> SEQ ID NO 35
<211> LENGTH: 384
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (73)..(73)
<223> OTHER INFORMATION: X can be S, K or G
<220> FEATURE:
<221> NAME/KEY: MISC_FEATURE
<222> LOCATION: (102)..(102)
<223> OTHER INFORMATION: X can be N or D
<220> FEATURE:
<221> NAME/KEY: MISC_FEATURE
<222> LOCATION: (103)..(103)
<223> OTHER INFORMATION: X can be T or S
<220> FEATURE:
<221> NAME/KEY: MISC_FEATURE
<222> LOCATION: (104)..(104)
<223> OTHER INFORMATION: X can be T or S
<220> FEATURE:
<221> NAME/KEY: MISC_FEATURE
<222> LOCATION: (130)..(130)
<223> OTHER INFORMATION: X can be G or S
<220> FEATURE:
<221> NAME/KEY: MISC_FEATURE
<222> LOCATION: (165)..(165)
<223> OTHER INFORMATION: X can be S or N
```

```
<220> FEATURE:
<221> NAME/KEY: MISC_FEATURE
<222> LOCATION: (168)..(168)
<223> OTHER INFORMATION: X can be T or A
<220> FEATURE:
<221> NAME/KEY: MISC_FEATURE
<222> LOCATION: (169)..(169)
<223> OTHER INFORMATION: X can be D, N or G
<220> FEATURE:
<221> NAME/KEY: MISC_FEATURE
<222> LOCATION: (172)..(172)
<223> OTHER INFORMATION: X can be Q or D
<220> FEATURE:
<221> NAME/KEY: MISC_FEATURE
<222> LOCATION: (179)..(179)
<223> OTHER INFORMATION: X can be D, S, or H

<400> SEQUENCE: 35

Ala Ala Pro Thr Ala Tyr Thr Pro Leu Asp Val Ala Gln Ala Tyr Gln
 1               5                  10                  15

Phe Pro Glu Gly Leu Asp Gly Gln Gly Gln Cys Ile Ala Ile Ile Glu
             20                  25                  30

Leu Gly Gly Gly Tyr Asp Glu Ala Ser Leu Ala Gln Tyr Phe Ala Ser
         35                  40                  45

Leu Gly Val Pro Ala Pro Gln Val Val Ser Val Ser Val Asp Gly Ala
     50                  55                  60

Ser Asn Gln Pro Thr Gly Asp Pro Xaa Gly Pro Asp Gly Glu Val Glu
 65                  70                  75                  80

Leu Asp Ile Glu Val Ala Gly Ala Leu Ala Pro Gly Ala Lys Phe Ala
                 85                  90                  95

Val Tyr Phe Ala Pro Xaa Xaa Xaa Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Xaa Gly Pro Glu Asp Ser Trp Thr Ser Ala Ala Ile Ala Ala Met
130                 135                 140

Asn Arg Ala Phe Leu Asp Ala Ala Leu Gly Val Thr Val Leu Ala
145                 150                 155                 160

Ala Ala Gly Asp Xaa Gly Ser Xaa Xaa Gly Glu Xaa Asp Gly Leu Tyr
                165                 170                 175

His Val Xaa Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Val Ser Arg Ile
210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
305                 310                 315                 320
```

```
Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro Gly Ser Thr Glu
        355                 360                 365

Asn Leu Tyr Phe Gln Ser Gly Ala Leu Glu His His His His His His
    370                 375                 380

<210> SEQ ID NO 36
<211> LENGTH: 384
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (73)..(73)
<223> OTHER INFORMATION: X can be S, K or G
<220> FEATURE:
<221> NAME/KEY: MISC_FEATURE
<222> LOCATION: (102)..(102)
<223> OTHER INFORMATION: All mutants with more than 10-fold activity
      have this substitution
<220> FEATURE:
<221> NAME/KEY: MISC_FEATURE
<222> LOCATION: (103)..(103)
<223> OTHER INFORMATION: X can be T or S
<220> FEATURE:
<221> NAME/KEY: MISC_FEATURE
<222> LOCATION: (104)..(104)
<223> OTHER INFORMATION: X can be D, A, T or N
<220> FEATURE:
<221> NAME/KEY: MISC_FEATURE
<222> LOCATION: (130)..(130)
<223> OTHER INFORMATION: X can be G or S
<220> FEATURE:
<221> NAME/KEY: MISC_FEATURE
<222> LOCATION: (165)..(165)
<223> OTHER INFORMATION: X can be S or N
<220> FEATURE:
<221> NAME/KEY: MISC_FEATURE
<222> LOCATION: (168)..(168)
<223> OTHER INFORMATION: X can be T or A
<220> FEATURE:
<221> NAME/KEY: MISC_FEATURE
<222> LOCATION: (169)..(169)
<223> OTHER INFORMATION: X can be D, N, or G
<220> FEATURE:
<221> NAME/KEY: MISC_FEATURE
<222> LOCATION: (172)..(172)
<223> OTHER INFORMATION: X can be Q or D
<220> FEATURE:
<221> NAME/KEY: MISC_FEATURE
<222> LOCATION: (179)..(179)
<223> OTHER INFORMATION: X can be D, S, or H

<400> SEQUENCE: 36

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Xaa Gly Pro Asp Gly Glu Val Glu
65                  70                  75                  80

Leu Asp Ile Glu Val Ala Gly Ala Leu Ala Pro Gly Ala Lys Phe Ala
```

```
                    85                  90                  95
Val Tyr Phe Ala Pro Asp Xaa Xaa Ala Gly Phe Leu Asp Ala Ile Thr
                100                 105                 110

Thr Ala Ile His Asp Pro Thr Leu Lys Pro Ser Val Val Ser Ile Ser
            115                 120                 125

Trp Xaa Gly Pro Glu Asp Ser Trp Thr Ser Ala Ala Ile Ala Ala Met
        130                 135                 140

Asn Arg Ala Phe Leu Asp Ala Ala Leu Gly Val Thr Val Leu Ala
145                 150                 155                 160

Ala Ala Gly Asp Xaa Gly Ser Xaa Xaa Gly Glu Xaa Asp Gly Leu Tyr
                165                 170                 175

His Val Xaa Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Val Ser Arg Ile
210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro Gly Ser Thr Glu
        355                 360                 365

Asn Leu Tyr Phe Gln Ser Gly Ala Leu Glu His His His His His
    370                 375                 380

<210> SEQ ID NO 37
<211> LENGTH: 384
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (73)..(73)
<223> OTHER INFORMATION: X is S, K, or G
<220> FEATURE:
<221> NAME/KEY: MISC_FEATURE
<222> LOCATION: (102)..(102)
<223> OTHER INFORMATION: All mutants with more than 20-fold activity
      increase have this substitution together with 358 substitution
<220> FEATURE:
<221> NAME/KEY: MISC_FEATURE
<222> LOCATION: (103)..(103)
<223> OTHER INFORMATION: X is T or S
<220> FEATURE:
<221> NAME/KEY: MISC_FEATURE
<222> LOCATION: (104)..(104)
```

```
<223> OTHER INFORMATION: X is D, A, T or N
<220> FEATURE:
<221> NAME/KEY: MISC_FEATURE
<222> LOCATION: (130)..(130)
<223> OTHER INFORMATION: X is G or S
<220> FEATURE:
<221> NAME/KEY: MISC_FEATURE
<222> LOCATION: (165)..(165)
<223> OTHER INFORMATION: X is S or N
<220> FEATURE:
<221> NAME/KEY: MISC_FEATURE
<222> LOCATION: (168)..(168)
<223> OTHER INFORMATION: X is T or A
<220> FEATURE:
<221> NAME/KEY: MISC_FEATURE
<222> LOCATION: (169)..(169)
<223> OTHER INFORMATION: X is N or G (most have G at this position)
<220> FEATURE:
<221> NAME/KEY: MISC_FEATURE
<222> LOCATION: (172)..(172)
<223> OTHER INFORMATION: X is Q or D
<220> FEATURE:
<221> NAME/KEY: MISC_FEATURE
<222> LOCATION: (179)..(179)
<223> OTHER INFORMATION: X is D, S, or H

<400> SEQUENCE: 37
```

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
50                  55                  60

Ser Asn Gln Pro Thr Gly Asp Pro Xaa Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Xaa Xaa Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Xaa Gly Pro Glu Asp Ser Trp Thr Ser Ala Ala Ile Ala Ala Met
130                 135                 140

Asn Arg Ala Phe Leu Asp Ala Ala Leu Gly Val Thr Val Leu Ala
145                 150                 155                 160

Ala Ala Gly Asp Xaa Gly Ser Xaa Xaa Gly Glu Xaa Asp Gly Leu Tyr
                165                 170                 175

His Val Xaa Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Gly Val Ser Arg Ile
210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

```
Val Ile Gly Gly Thr Ser Ala Val Ala Pro Leu Phe Ala Ala Leu Val
            275                 280                 285

Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln Pro Gly Ser Thr Glu
            355                 360                 365

Asn Leu Tyr Phe Gln Ser Gly Ala Leu Glu His His His His His His
            370                 375                 380
```

<210> SEQ ID NO 38
<211> LENGTH: 384
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (73)..(73)
<223> OTHER INFORMATION: X is S, K, or G
<220> FEATURE:
<221> NAME/KEY: MISC_FEATURE
<222> LOCATION: (102)..(102)
<223> OTHER INFORMATION: All mutants with more than 50-fold activity
      increase have this substitution together with 319, 358, and 368
      substitutions
<220> FEATURE:
<221> NAME/KEY: MISC_FEATURE
<222> LOCATION: (103)..(103)
<223> OTHER INFORMATION: X is T or S
<220> FEATURE:
<221> NAME/KEY: MISC_FEATURE
<222> LOCATION: (104)..(104)
<223> OTHER INFORMATION: X is D, A, T, or N
<220> FEATURE:
<221> NAME/KEY: MISC_FEATURE
<222> LOCATION: (165)..(165)
<223> OTHER INFORMATION: X is S or N
<220> FEATURE:
<221> NAME/KEY: MISC_FEATURE
<222> LOCATION: (168)..(168)
<223> OTHER INFORMATION: X is T or A
<220> FEATURE:
<221> NAME/KEY: MISC_FEATURE
<222> LOCATION: (172)..(172)
<223> OTHER INFORMATION: X is Q or D

<400> SEQUENCE: 38

```
Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
                20                  25                  30

Leu Gly Gly Gly Tyr Asp Glu Ala Ser Leu Ala Gln Tyr Phe Ala Ser
            35                  40                  45

Leu Gly Val Pro Ala Pro Gln Val Val Ser Val Ser Val Asp Gly Ala
        50                  55                  60

Ser Asn Gln Pro Thr Gly Asp Pro Xaa Gly Pro Asp Gly Glu Val Glu
65                  70                  75                  80

Leu Asp Ile Glu Val Ala Gly Ala Leu Ala Pro Gly Ala Lys Phe Ala
                85                  90                  95
```

```
Val Tyr Phe Ala Pro Asp Xaa Xaa Ala Gly Phe Leu Asp Ala Ile Thr
                100                 105                 110

Thr Ala Ile His Asp Pro Thr Leu Lys Pro Ser Val Val Ser Ile Ser
            115                 120                 125

Trp Ser Gly Pro Glu Asp Ser Trp Thr Ser Ala Ala Ile Ala Ala Met
        130                 135                 140

Asn Arg Ala Phe Leu Asp Ala Ala Leu Gly Val Thr Val Leu Ala
145                 150                 155                 160

Ala Ala Gly Asp Xaa Gly Ser Xaa Gly Gly Glu Xaa Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Val Ser Arg Ile
210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
        290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro Gly Ser Thr Glu
        355                 360                 365

Asn Leu Tyr Phe Gln Ser Gly Ala Leu Glu His His His His His
370                 375                 380

<210> SEQ ID NO 39
<211> LENGTH: 384
<212> TYPE: PRT
<213> ORGANISM: Artificial Sequence
<220> FEATURE:
<223> OTHER INFORMATION: Synthetic

<400> SEQUENCE: 39

Ala Ala Pro Thr Ala Tyr Thr Pro Leu Asp Val Ala Gln Ala Tyr Gln
1               5                   10                  15

Phe Pro Glu Gly Leu Asp Gly Gln Gln Cys Ile Ala Ile Ile Glu
                20                  25                  30

Leu Gly Gly Gly Tyr Asp Glu Ala Ser Leu Ala Gln Tyr Phe Ala Ser
            35                  40                  45

Leu Gly Val Pro Ala Pro Gln Val Val Ser Val Ser Val Asp Gly Ala
        50                  55                  60

Ser Asn Gln Pro Thr Gly Asp Pro Ser Gly Pro Asp Gly Glu Val Glu
65                  70                  75                  80
```

```
Leu Asp Ile Glu Val Ala Gly Ala Leu Ala Pro Gly Ala Lys Phe Ala
                85                  90                  95

Val Tyr Phe Ala Pro Asn Thr Asp Ala Gly Phe Leu Asp Ala Ile Thr
            100                 105                 110

Thr Ala Ile His Asp Pro Thr Leu Lys Pro Ser Val Val Ser Ile Ser
            115                 120                 125

Trp Gly Gly Pro Glu Asp Ser Trp Thr Ser Ala Ala Ile Ala Ala Met
130                 135                 140

Asn Arg Ala Phe Leu Asp Ala Ala Leu Gly Val Thr Val Leu Ala
145                 150                 155                 160

Ala Ala Gly Asp Ser Gly Ser Thr Asn Gly Glu Gln Asp Gly Leu Tyr
            165                 170                 175

His Val Asp Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
            195                 200                 205

Asn Asp Gly Pro Asp Gly Gly Ala Thr Gly Gly Val Ser Arg Ile
210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
            245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
            275                 280                 285

Ala Arg Ile Asn Gln Lys Leu Gly Lys Ala Val Gly Tyr Leu Asn Pro
290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
            325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro Gly Ser Thr Glu
            355                 360                 365

Asn Leu Tyr Phe Gln Ser Gly Ala Leu Glu His His His His His
            370                 375                 380

<210> SEQ ID NO 40
<211> LENGTH: 384
<212> TYPE: PRT
<213> ORGANISM: Artificial Sequence
<220> FEATURE:
<223> OTHER INFORMATION: Synthetic

<400> SEQUENCE: 40

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
            35                  40                  45

Leu Gly Val Pro Ala Pro Gln Val Val Ser Val Ser Val Asp Gly Ala
50                  55                  60
```

```
Ser Asn Gln Pro Thr Gly Asp Pro Ser Gly Pro Asp Gly Glu Val Glu
 65                  70                  75                  80

Leu Asp Ile Glu Val Ala Gly Ala Leu Ala Pro Gly Ala Lys Phe Ala
                 85                  90                  95

Val Tyr Phe Ala Pro Asp Thr Asp Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Gly Gly Pro Glu Asp Ser Trp Thr Ser Ala Ala Ile Ala Ala Met
130                 135                 140

Asn Arg Ala Phe Leu Asp Ala Ala Leu Gly Val Thr Val Leu Ala
145                 150                 155                 160

Ala Ala Gly Asp Ser Gly Ser Thr Asp Gly Glu Gln Asp Gly Leu Tyr
                165                 170                 175

His Val Asp Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Val Ser Arg Ile
210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro Gly Ser Thr Glu
        355                 360                 365

Asn Leu Tyr Phe Gln Ser Gly Ala Leu Glu His His His His
370                 375                 380
```

<210> SEQ ID NO 41
<211> LENGTH: 384
<212> TYPE: PRT
<213> ORGANISM: Artificial Sequence
<220> FEATURE:
<223> OTHER INFORMATION: Synthetic

<400> SEQUENCE: 41

```
Ala Ala Pro Thr Ala Tyr Thr Pro Leu Asp Val Ala Gln Ala Tyr Gln
1               5                  10                  15

Phe Pro Glu Gly Leu Asp Gly Gln Gly Gln Cys Ile Ala Ile Ile Glu
                20                  25                  30

Leu Gly Gly Gly Tyr Asp Glu Ala Ser Leu Ala Gln Tyr Phe Ala Ser
            35                  40                  45
```

Leu Gly Val Pro Ala Pro Gln Val Ser Val Ser Val Asp Gly Ala
 50                  55                  60

Ser Asn Gln Pro Thr Gly Asp Pro Ser Gly Pro Asp Gly Glu Val Glu
 65                  70                  75                  80

Leu Asp Ile Glu Val Ala Gly Ala Leu Ala Pro Gly Ala Lys Phe Ala
                 85                  90                  95

Val Tyr Phe Ala Pro Asn Thr Asp Ala Gly Phe Leu Asp Ala Ile Thr
            100                 105                 110

Thr Ala Ile His Asp Pro Thr Leu Lys Pro Ser Val Ser Ile Ser
        115                 120                 125

Trp Gly Gly Pro Glu Asp Ser Trp Thr Ser Ala Ile Ala Ala Met
130                 135                 140

Asn Arg Ala Phe Leu Asp Ala Ala Leu Gly Val Thr Val Leu Ala
145                 150                 155                 160

Ala Ala Gly Asp Ser Gly Ser Thr Gly Gly Glu Gln Asp Gly Leu Tyr
                165                 170                 175

His Val Asp Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Val Ser Arg Ile
210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro Gly Ser Thr Glu
        355                 360                 365

Asn Leu Tyr Phe Gln Ser Gly Ala Leu Glu His His His His His
370                 375                 380

<210> SEQ ID NO 42
<211> LENGTH: 384
<212> TYPE: PRT
<213> ORGANISM: Artificial Sequence
<220> FEATURE:
<223> OTHER INFORMATION: Synthetic

<400> SEQUENCE: 42

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

```
Leu Gly Gly Gly Tyr Asp Glu Ala Ser Leu Ala Gln Tyr Phe Ala Ser
             35                  40                  45

Leu Gly Val Pro Ala Pro Gln Val Val Ser Val Ser Val Asp Gly Ala
 50                  55                  60

Ser Asn Gln Pro Thr Gly Asp Pro Ser Gly Pro Asp Gly Glu Val Glu
 65                  70                  75                  80

Leu Asp Ile Glu Val Ala Gly Ala Leu Ala Pro Gly Ala Lys Phe Ala
                 85                  90                  95

Val Tyr Phe Ala Pro Asn Thr Asp Ala Gly Phe Leu Asp Ala Ile Thr
                100                 105                 110

Thr Ala Ile His Asp Pro Thr Leu Lys Pro Ser Val Val Ser Ile Ser
            115                 120                 125

Trp Gly Gly Pro Glu Asp Ser Trp Thr Ser Ala Ala Ile Ala Ala Met
        130                 135                 140

Asn Arg Ala Phe Leu Asp Ala Ala Leu Gly Val Thr Val Leu Ala
145                 150                 155                 160

Ala Ala Gly Asp Ser Gly Ser Ala Asp Gly Glu Gln Asp Gly Leu Tyr
                165                 170                 175

His Val Asp Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Val Ser Arg Ile
210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro Gly Ser Thr Glu
        355                 360                 365

Asn Leu Tyr Phe Gln Ser Gly Ala Leu Glu His His His His His
370                 375                 380

<210> SEQ ID NO 43
<211> LENGTH: 384
<212> TYPE: PRT
<213> ORGANISM: Artificial Sequence
<220> FEATURE:
<223> OTHER INFORMATION: Synthetic

<400> SEQUENCE: 43

Ala Ala Pro Thr Ala Tyr Thr Pro Leu Asp Val Ala Gln Ala Tyr Gln
 1               5                  10                  15
```

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Ser Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asn Thr Ala Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Gly Gly Pro Glu Asp Ser Trp Thr Ser Ala Ala Ile Ala Ala Met
    130                 135                 140

Asn Arg Ala Phe Leu Asp Ala Ala Leu Gly Val Thr Val Leu Ala
145                 150                 155                 160

Ala Ala Gly Asp Ser Gly Ser Thr Asp Gly Glu Gln Asp Gly Leu Tyr
                165                 170                 175

His Val Asp Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Ala Thr Gly Gly Val Ser Arg Ile
210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro Gly Ser Thr Glu
        355                 360                 365

Asn Leu Tyr Phe Gln Ser Gly Ala Leu Glu His His His His His
    370                 375                 380

<210> SEQ ID NO 44
<211> LENGTH: 384
<212> TYPE: PRT
<213> ORGANISM: Artificial Sequence
<220> FEATURE:
<223> OTHER INFORMATION: Synthetic

<400> SEQUENCE: 44

```
Ala Ala Pro Thr Ala Tyr Thr Pro Leu Asp Val Ala Gln Ala Tyr Gln
  1               5                  10                  15

Phe Pro Glu Gly Leu Asp Gly Gln Gly Gln Cys Ile Ala Ile Ile Glu
             20                  25                  30

Leu Gly Gly Gly Tyr Asp Glu Ala Ser Leu Ala Gln Tyr Phe Ala Ser
         35                  40                  45

Leu Gly Val Pro Ala Pro Gln Val Val Ser Val Ser Val Asp Gly Ala
 50                  55                  60

Ser Asn Gln Pro Thr Gly Asp Pro Ser Gly Pro Asp Gly Glu Val Glu
 65                  70                  75                  80

Leu Asp Ile Glu Val Ala Gly Ala Leu Ala Pro Gly Ala Lys Phe Ala
                 85                  90                  95

Val Tyr Phe Ala Pro Asn Thr Asp Ala Gly Phe Leu Asp Ala Ile Thr
             100                 105                 110

Thr Ala Ile His Asp Pro Thr Leu Lys Pro Ser Val Ser Ile Ser
         115                 120                 125

Trp Ser Gly Pro Glu Asp Ser Trp Thr Ser Ala Ala Ile Ala Ala Met
130                 135                 140

Asn Arg Ala Phe Leu Asp Ala Ala Ala Leu Gly Val Thr Val Leu Ala
145                 150                 155                 160

Ala Ala Gly Asp Ser Gly Ser Thr Asp Gly Glu Gln Asp Gly Leu Tyr
                 165                 170                 175

His Val Ser Phe Pro Ala Ala Ser Pro Tyr Val Leu Ala Cys Gly Gly
             180                 185                 190

Thr Arg Leu Val Ala Ser Gly Gly Arg Ile Ala Gln Glu Thr Val Trp
         195                 200                 205

Asn Asp Gly Pro Asp Gly Gly Ala Thr Gly Gly Val Ser Arg Ile
210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                 245                 250                 255

Ala Asp Pro Ala Thr Gly Tyr Glu Val Val Ile Asp Gly Glu Ala Thr
             260                 265                 270

Val Ile Gly Gly Thr Ser Ala Val Ala Pro Leu Phe Ala Ala Leu Val
         275                 280                 285

Ala Arg Ile Asn Gln Lys Leu Gly Lys Ala Val Gly Tyr Leu Asn Pro
290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                 325                 330                 335

Trp Asp Pro Cys Thr Gly Leu Gly Ser Pro Ile Gly Val Arg Leu Leu
             340                 345                 350

Gln Ala Leu Leu Pro Ser Ala Ser Gln Pro Pro Gly Ser Thr Glu
         355                 360                 365

Asn Leu Tyr Phe Gln Ser Gly Ala Leu Glu His His His His His
370                 375                 380
```

<210> SEQ ID NO 45
<211> LENGTH: 384
<212> TYPE: PRT
<213> ORGANISM: Artificial Sequence
<220> FEATURE:
<223> OTHER INFORMATION: Synthetic

<400> SEQUENCE: 45

```
Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Ser Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asn Thr Asp Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Gly Gly Pro Glu Asp Ser Trp Thr Ser Ala Ala Ile Ala Ala Met
130                 135                 140

Asn Arg Ala Phe Leu Asp Ala Ala Leu Gly Val Thr Val Leu Ala
145                 150                 155                 160

Ala Ala Gly Asp Ser Gly Ser Thr Gly Gly Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Val Ser Arg Ile
210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro Gly Ser Thr Glu
        355                 360                 365

Asn Leu Tyr Phe Gln Ser Gly Ala Leu Glu His His His His His His
    370                 375                 380

<210> SEQ ID NO 46
<211> LENGTH: 384
<212> TYPE: PRT
```

<213> ORGANISM: Artificial Sequence
<220> FEATURE:
<223> OTHER INFORMATION: Synthetic

<400> SEQUENCE: 46

```
Ala Ala Pro Thr Ala Tyr Thr Pro Leu Asp Val Ala Gln Ala Tyr Gln
1               5                   10                  15

Phe Pro Glu Gly Leu Asp Gly Gln Gly Cys Ile Ala Ile Ile Glu
            20                  25                  30

Leu Gly Gly Gly Tyr Asp Glu Ala Ser Leu Ala Gln Tyr Phe Ala Ser
            35                  40                  45

Leu Gly Val Pro Ala Pro Gln Val Val Ser Val Ser Val Asp Gly Ala
50                  55                  60

Ser Asn Gln Pro Thr Gly Asp Pro Ser Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Asp Ala Gly Phe Leu Asp Ala Ile Thr
                100                 105                 110

Thr Ala Ile His Asp Pro Thr Leu Lys Pro Ser Val Val Ser Ile Ser
            115                 120                 125

Trp Gly Gly Pro Glu Asp Ser Trp Thr Ser Ala Ala Ile Ala Ala Met
130                 135                 140

Asn Arg Ala Phe Leu Asp Ala Ala Leu Gly Val Thr Val Leu Ala
145                 150                 155                 160

Ala Ala Gly Asp Ser Gly Ser Thr Asp Gly Glu Asp Asp Gly Leu Tyr
                165                 170                 175

His Val Asp Phe Pro Ala Ala Ser Pro Tyr Val Leu Ala Cys Gly Gly
                180                 185                 190

Thr Arg Leu Val Ala Ser Gly Gly Arg Ile Ala Gln Glu Thr Val Trp
            195                 200                 205

Asn Asp Gly Pro Asp Gly Gly Ala Thr Gly Gly Val Ser Arg Ile
210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
                260                 265                 270

Val Ile Gly Gly Thr Ser Ala Val Ala Pro Leu Phe Ala Ala Leu Val
            275                 280                 285

Ala Arg Ile Asn Gln Lys Leu Gly Lys Ala Val Gly Tyr Leu Asn Pro
290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln Pro Gly Ser Thr Glu
            355                 360                 365

Asn Leu Tyr Phe Gln Ser Gly Ala Leu Glu His His His His His
            370                 375                 380
```

<210> SEQ ID NO 47
<211> LENGTH: 384
<212> TYPE: PRT
<213> ORGANISM: Artificial Sequence
<220> FEATURE:
<223> OTHER INFORMATION: Synthetic

<400> SEQUENCE: 47

```
Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Ser Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Asp Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Gly Gly Pro Glu Asp Ser Trp Thr Ser Ala Ala Ile Ala Ala Met
    130                 135                 140

Asn Arg Ala Phe Leu Asp Ala Ala Ala Leu Gly Val Thr Val Leu Ala
145                 150                 155                 160

Ala Ala Gly Asp Ser Gly Ser Thr Asn Gly Glu Gln Asp Gly Leu Tyr
                165                 170                 175

His Val Asp Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro Gly Ser Thr Glu
        355                 360                 365

Asn Leu Tyr Phe Gln Ser Gly Ala Leu Glu His His His His His His
```

370 375 380

<210> SEQ ID NO 48
<211> LENGTH: 384
<212> TYPE: PRT
<213> ORGANISM: Artificial Sequence
<220> FEATURE:
<223> OTHER INFORMATION: Synthetic

<400> SEQUENCE: 48

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Ser Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Ala Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Gly Gly Pro Glu Asp Ser Trp Thr Ser Ala Ala Ile Ala Ala Met
    130                 135                 140

Asn Arg Ala Phe Leu Asp Ala Ala Ala Leu Gly Val Thr Val Leu Ala
145                 150                 155                 160

Ala Ala Gly Asp Ser Gly Ser Thr Asp Gly Glu Gln Asp Gly Leu Tyr
                165                 170                 175

His Val Asp Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro Gly Ser Thr Glu 355                 360                 365
Asn Leu Tyr Phe Gln Ser Gly Ala Leu Glu His His His His His His
    370                 375                 380

<210> SEQ ID NO 49
<211> LENGTH: 384
<212> TYPE: PRT
<213> ORGANISM: Artificial Sequence
<220> FEATURE:
<223> OTHER INFORMATION: Synthetic

<400> SEQUENCE: 49

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Ser Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Ala Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Gly Gly Pro Glu Asp Ser Trp Thr Ser Ala Ala Ile Ala Ala Met
    130                 135                 140

Asn Arg Ala Phe Leu Asp Ala Ala Leu Gly Val Thr Val Leu Ala
145                 150                 155                 160

Ala Ala Gly Asp Ser Gly Ser Thr Asn Gly Glu Gln Asp Gly Leu Tyr
                165                 170                 175

His Val Asp Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu

```
            340                 345                 350
Gln Ala Leu Leu Pro Ser Ala Ser Gln Pro Gln Pro Gly Ser Thr Glu
            355                 360                 365

Asn Leu Tyr Phe Gln Ser Gly Ala Leu Glu His His His His His His
        370                 375                 380

<210> SEQ ID NO 50
<211> LENGTH: 384
<212> TYPE: PRT
<213> ORGANISM: Artificial Sequence
<220> FEATURE:
<223> OTHER INFORMATION: Synthetic

<400> SEQUENCE: 50

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Ser Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asn Thr Asp Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
    130                 135                 140

Asn Arg Ala Phe Leu Asp Ala Ala Ala Leu Gly Val Thr Val Leu Ala
145                 150                 155                 160

Ala Ala Gly Asp Ser Gly Ser Thr Gly Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
```

```
                      325                 330                 335
Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro Gly Ser Thr Glu
        355                 360                 365

Asn Leu Tyr Phe Gln Ser Gly Ala Leu Glu His His His His His His
    370                 375                 380

<210> SEQ ID NO 51
<211> LENGTH: 384
<212> TYPE: PRT
<213> ORGANISM: Artificial Sequence
<220> FEATURE:
<223> OTHER INFORMATION: Synthetic

<400> SEQUENCE: 51

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Ser Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asn Thr Asp Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Gly Gly Pro Glu Asp Ser Trp Thr Ser Ala Ala Ile Ala Ala Met
    130                 135                 140

Asn Arg Ala Phe Leu Asp Ala Ala Ala Leu Gly Val Thr Val Leu Ala
145                 150                 155                 160

Ala Ala Gly Asp Asn Gly Ser Thr Gly Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
```

```
            305                 310                 315                 320
Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln Pro Gly Ser Thr Glu
                355                 360                 365

Asn Leu Tyr Phe Gln Ser Gly Ala Leu Glu His His His His His His
                370                 375                 380
```

<210> SEQ ID NO 52
<211> LENGTH: 384
<212> TYPE: PRT
<213> ORGANISM: Artificial Sequence
<220> FEATURE:
<223> OTHER INFORMATION: Synthetic

<400> SEQUENCE: 52

```
Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
                20                  25                  30

Leu Gly Gly Gly Tyr Asp Glu Ala Ser Leu Ala Gln Tyr Phe Ala Ser
                35                  40                  45

Leu Gly Val Pro Ala Pro Gln Val Val Ser Val Ser Val Asp Gly Ala
                50                  55                  60

Ser Asn Gln Pro Thr Gly Asp Pro Ser Gly Pro Asp Gly Glu Val Glu
65              70                  75                  80

Leu Asp Ile Glu Val Ala Gly Ala Leu Ala Pro Gly Ala Lys Phe Ala
                85                  90                  95

Val Tyr Phe Ala Pro Asp Thr Asp Ala Gly Phe Leu Asp Ala Ile Thr
                100                 105                 110

Thr Ala Ile His Asp Pro Thr Leu Lys Pro Ser Val Val Ser Ile Ser
                115                 120                 125

Trp Gly Gly Pro Glu Asp Ser Trp Thr Ser Ala Ala Ile Ala Ala Met
                130                 135                 140

Asn Arg Ala Phe Leu Asp Ala Ala Leu Gly Val Thr Val Leu Ala
145                 150                 155                 160

Ala Ala Gly Asp Ser Gly Ser Thr Gly Gly Glu Asp Asp Gly Leu Tyr
                165                 170                 175

His Val Asp Phe Pro Ala Ala Ser Pro Tyr Val Leu Ala Cys Gly Gly
                180                 185                 190

Thr Arg Leu Val Ala Ser Gly Gly Arg Ile Ala Gln Glu Thr Val Trp
                195                 200                 205

Asn Asp Gly Pro Asp Gly Gly Ala Thr Gly Gly Val Ser Arg Ile
                210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Ile Asp Gly Glu Ala Thr
                260                 265                 270

Val Ile Gly Gly Thr Ser Ala Val Ala Pro Leu Phe Ala Ala Leu Val
                275                 280                 285

Ala Arg Ile Asn Gln Lys Leu Gly Lys Ala Val Gly Tyr Leu Asn Pro
```

```
                    290                 295                 300
Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln Pro Gly Ser Thr Glu
                355                 360                 365

Asn Leu Tyr Phe Gln Ser Gly Ala Leu Glu His His His His His His
                370                 375                 380

<210> SEQ ID NO 53
<211> LENGTH: 384
<212> TYPE: PRT
<213> ORGANISM: Artificial Sequence
<220> FEATURE:
<223> OTHER INFORMATION: Synthetic

<400> SEQUENCE: 53

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
                20                  25                  30

Leu Gly Gly Gly Tyr Asp Glu Ala Ser Leu Ala Gln Tyr Phe Ala Ser
                35                  40                  45

Leu Gly Val Pro Ala Pro Gln Val Val Ser Val Ser Val Asp Gly Ala
50                  55                  60

Ser Asn Gln Pro Thr Gly Asp Pro Ser Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Asp Ala Gly Phe Leu Asp Ala Ile Thr
                100                 105                 110

Thr Ala Ile His Asp Pro Thr Leu Lys Pro Ser Val Val Ser Ile Ser
                115                 120                 125

Trp Ser Gly Pro Glu Asp Ser Trp Thr Ser Ala Ala Ile Ala Ala Met
130                 135                 140

Asn Arg Ala Phe Leu Asp Ala Ala Leu Gly Val Thr Val Leu Ala
145                 150                 155                 160

Ala Ala Gly Asp Ser Gly Ser Thr Gly Gly Glu Gln Asp Gly Leu Tyr
                165                 170                 175

His Val His Phe Pro Ala Ala Ser Pro Tyr Val Leu Ala Cys Gly Gly
                180                 185                 190

Thr Arg Leu Val Ala Ser Gly Gly Arg Ile Ala Gln Glu Thr Val Trp
                195                 200                 205

Asn Asp Gly Pro Asp Gly Ala Thr Gly Gly Val Ser Arg Ile
                210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
                260                 265                 270

Val Ile Gly Gly Thr Ser Ala Val Ala Pro Leu Phe Ala Ala Leu Val
```

```
                275                 280                 285
Ala Arg Ile Asn Gln Lys Leu Gly Lys Ala Val Gly Tyr Leu Asn Pro
        290                 295                 300
Thr Leu Tyr Gln Leu Pro Ala Asp Val Phe His Asp Ile Thr Glu Gly
305                 310                 315                 320
Asn Asn Asp Ile Ala Asn Arg Ala Gln Ile Tyr Gln Ala Gly Pro Gly
                325                 330                 335
Trp Asp Pro Cys Thr Gly Leu Gly Ser Pro Ile Gly Val Arg Leu Leu
        340                 345                 350
Gln Ala Leu Leu Pro Ser Ala Ser Gln Pro Gln Pro Gly Ser Thr Glu
                355                 360                 365
Asn Leu Tyr Phe Gln Ser Gly Ala Leu Glu His His His His His His
        370                 375                 380

<210> SEQ ID NO 54
<211> LENGTH: 384
<212> TYPE: PRT
<213> ORGANISM: Artificial Sequence
<220> FEATURE:
<223> OTHER INFORMATION: Synthetic

<400> SEQUENCE: 54

Ala Ala Pro Thr Ala Tyr Thr Pro Leu Asp Val Ala Gln Ala Tyr Gln
1               5                   10                  15
Phe Pro Glu Gly Leu Asp Gly Gln Gly Cys Ile Ala Ile Ile Glu
                20                  25                  30
Leu Gly Gly Gly Tyr Asp Glu Ala Ser Leu Ala Gln Tyr Phe Ala Ser
            35                  40                  45
Leu Gly Val Pro Ala Pro Gln Val Val Ser Val Ser Val Asp Gly Ala
        50                  55                  60
Ser Asn Gln Pro Thr Gly Asp Pro Ser Gly Pro Asp Gly Glu Val Glu
65                  70                  75                  80
Leu Asp Ile Glu Val Ala Gly Ala Leu Ala Pro Gly Ala Lys Phe Ala
                85                  90                  95
Val Tyr Phe Ala Pro Asp Thr Ala Ala Gly Phe Leu Asp Ala Ile Thr
                100                 105                 110
Thr Ala Ile His Asp Pro Thr Leu Lys Pro Ser Val Val Ser Ile Ser
            115                 120                 125
Trp Gly Gly Pro Glu Asp Ser Trp Thr Ser Ala Ala Ile Ala Ala Met
        130                 135                 140
Asn Arg Ala Phe Leu Asp Ala Ala Ala Leu Gly Val Thr Val Leu Ala
145                 150                 155                 160
Ala Ala Gly Asp Ser Gly Ser Thr Asn Gly Glu Asp Asp Gly Leu Tyr
                165                 170                 175
His Val Asp Phe Pro Ala Ala Ser Pro Tyr Val Leu Ala Cys Gly Gly
                180                 185                 190
Thr Arg Leu Val Ala Ser Gly Gly Arg Ile Ala Gln Glu Thr Val Trp
            195                 200                 205
Asn Asp Gly Pro Asp Gly Gly Ala Thr Gly Gly Gly Val Ser Arg Ile
        210                 215                 220
Phe Pro Leu Pro Ala Trp Gln Glu His Ala Asn Val Pro Pro Ser Ala
225                 230                 235                 240
Asn Pro Gly Ala Ser Ser Gly Arg Gly Val Pro Asp Leu Ala Gly Asn
                245                 250                 255
Ala Asp Pro Ala Thr Gly Tyr Glu Val Val Ile Asp Gly Glu Ala Thr
```

```
            260                 265                 270
Val Ile Gly Gly Thr Ser Ala Val Ala Pro Leu Phe Ala Ala Leu Val
            275                 280                 285

Ala Arg Ile Asn Gln Lys Leu Gly Lys Ala Val Gly Tyr Leu Asn Pro
        290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro Gly Ser Thr Glu
        355                 360                 365

Asn Leu Tyr Phe Gln Ser Gly Ala Leu Glu His His His His His His
        370                 375                 380

<210> SEQ ID NO 55
<211> LENGTH: 384
<212> TYPE: PRT
<213> ORGANISM: Artificial Sequence
<220> FEATURE:
<223> OTHER INFORMATION: Synthetic

<400> SEQUENCE: 55

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Ser Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asn Thr Asp Ala Gly Phe Leu Asp Ala Ile Thr
            100                 105                 110

Thr Ala Ile His Asp Pro Thr Leu Lys Pro Ser Val Ser Ile Ser
        115                 120                 125

Trp Ser Gly Pro Glu Asp Ser Trp Thr Ser Ala Ile Ala Ala Met
130                 135                 140

Asn Arg Ala Phe Leu Asp Ala Ala Ala Leu Gly Val Thr Val Leu Ala
145                 150                 155                 160

Ala Ala Gly Asp Asn Gly Ser Thr Gly Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
```

```
            245                 250                 255
Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
            275                 280                 285

Ala Arg Ile Asn Gln Lys Leu Gly Lys Ala Val Gly Tyr Leu Asn Pro
        290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro Gly Ser Thr Glu
            355                 360                 365

Asn Leu Tyr Phe Gln Ser Gly Ala Leu Glu His His His His His His
        370                 375                 380
```

<210> SEQ ID NO 56
<211> LENGTH: 384
<212> TYPE: PRT
<213> ORGANISM: Artificial Sequence
<220> FEATURE:
<223> OTHER INFORMATION: Synthetic

<400> SEQUENCE: 56

```
Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
        35                  40                  45

Leu Gly Val Pro Ala Pro Gln Val Val Ser Val Ser Val Asp Gly Ala
    50                  55                  60

Ser Asn Gln Pro Thr Gly Asp Pro Ser Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Ala Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Gly Gly Pro Glu Asp Ser Trp Thr Ser Ala Ala Ile Ala Ala Met
    130                 135                 140

Asn Arg Ala Phe Leu Asp Ala Ala Leu Gly Val Thr Val Leu Ala
145                 150                 155                 160

Ala Ala Gly Asp Ser Gly Ser Thr Gly Gly Glu Asp Asp Gly Leu Tyr
                165                 170                 175

His Val Asp Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Val Ser Arg Ile
    210                 215                 220

Phe Pro Leu Pro Ala Trp Gln Glu His Ala Asn Val Pro Pro Ser Ala
```

```
                225                 230                 235                 240
Asn Pro Gly Ala Ser Ser Gly Arg Gly Val Pro Asp Leu Ala Gly Asn
            245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
            275                 280                 285

Ala Arg Ile Asn Gln Lys Leu Gly Lys Ala Val Gly Tyr Leu Asn Pro
            290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln Pro Gly Ser Thr Glu
                355                 360                 365

Asn Leu Tyr Phe Gln Ser Gly Ala Leu Glu His His His His His His
                370                 375                 380

<210> SEQ ID NO 57
<211> LENGTH: 384
<212> TYPE: PRT
<213> ORGANISM: Artificial Sequence
<220> FEATURE:
<223> OTHER INFORMATION: Synthetic

<400> SEQUENCE: 57

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
            35                  40                  45

Leu Gly Val Pro Ala Pro Gln Val Val Ser Val Ser Val Asp Gly Ala
        50                  55                  60

Ser Asn Gln Pro Thr Gly Asp Pro Ser Gly Pro Asp Gly Glu Val Glu
65              70                  75                  80

Leu Asp Ile Glu Val Ala Gly Ala Leu Ala Pro Gly Ala Lys Phe Ala
            85                  90                  95

Val Tyr Phe Ala Pro Thr Asp Ala Gly Phe Leu Asp Ala Ile Thr Thr
            100                 105                 110

Thr Ala Ile His Asp Pro Thr Leu Lys Pro Ser Val Val Ser Ile Ser
            115                 120                 125

Trp Ser Gly Pro Glu Asp Ser Trp Thr Ser Ala Ala Ile Ala Ala Met
        130                 135                 140

Asn Arg Ala Phe Leu Asp Ala Ala Ala Leu Gly Val Thr Val Leu Ala
145                 150                 155                 160

Ala Ala Gly Asp Ser Gly Ser Thr Gly Gly Glu Asp Asp Gly Leu Tyr
                165                 170                 175

His Val His Phe Pro Ala Ala Ser Pro Tyr Val Leu Ala Cys Gly Gly
                180                 185                 190

Thr Arg Leu Val Ala Ser Gly Gly Arg Ile Ala Gln Glu Thr Val Trp
                195                 200                 205

Asn Asp Gly Pro Asp Gly Gly Ala Thr Gly Gly Gly Val Ser Arg Ile
```

```
                    210                 215                 220
Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
                260                 265                 270

Val Ile Gly Gly Thr Ser Ala Val Ala Pro Leu Phe Ala Ala Leu Val
                275                 280                 285

Ala Arg Ile Asn Gln Lys Leu Gly Lys Ala Val Gly Tyr Leu Asn Pro
                290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln Pro Gly Ser Thr Glu
                355                 360                 365

Asn Leu Tyr Phe Gln Ser Gly Ala Leu Glu His His His His His His
                370                 375                 380

<210> SEQ ID NO 58
<211> LENGTH: 384
<212> TYPE: PRT
<213> ORGANISM: Artificial Sequence
<220> FEATURE:
<223> OTHER INFORMATION: Synthetic

<400> SEQUENCE: 58

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
                20                  25                  30

Leu Gly Gly Gly Tyr Asp Glu Ala Ser Leu Ala Gln Tyr Phe Ala Ser
            35                  40                  45

Leu Gly Val Pro Ala Pro Gln Val Val Ser Val Ser Val Asp Gly Ala
50                  55                  60

Ser Asn Gln Pro Thr Gly Asp Pro Ser Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Asp Ala Gly Phe Leu Asp Ala Ile Thr
                100                 105                 110

Thr Ala Ile His Asp Pro Thr Leu Lys Pro Ser Val Val Ser Ile Ser
            115                 120                 125

Trp Ser Gly Pro Glu Asp Ser Trp Thr Ser Ala Ala Ile Ala Ala Met
130                 135                 140

Asn Arg Ala Phe Leu Asp Ala Ala Leu Gly Val Thr Val Leu Ala
145                 150                 155                 160

Ala Ala Gly Asp Asn Gly Ser Thr Gly Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
```

```
            195                 200                 205
Asn Asp Gly Pro Asp Gly Ala Thr Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro Gly Ser Thr Glu
        355                 360                 365

Asn Leu Tyr Phe Gln Ser Gly Ala Leu Glu His His His His His His
    370                 375                 380
```

<210> SEQ ID NO 59
<211> LENGTH: 384
<212> TYPE: PRT
<213> ORGANISM: Artificial Sequence
<220> FEATURE:
<223> OTHER INFORMATION: Synthetic

<400> SEQUENCE: 59

```
Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
                20                  25                  30

Leu Gly Gly Gly Tyr Asp Glu Ala Ser Leu Ala Gln Tyr Phe Ala Ser
            35                  40                  45

Leu Gly Val Pro Ala Pro Gln Val Val Ser Val Ser Val Asp Gly Ala
        50                  55                  60

Ser Asn Gln Pro Thr Gly Asp Pro Ser Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Ala Ala Gly Phe Leu Asp Ala Ile Thr
            100                 105                 110

Thr Ala Ile His Asp Pro Thr Leu Lys Pro Ser Val Val Ser Ile Ser
        115                 120                 125

Trp Ser Gly Pro Glu Asp Ser Trp Thr Ser Ala Ala Ile Ala Ala Met
130                 135                 140

Asn Arg Ala Phe Leu Asp Ala Ala Leu Gly Val Thr Val Leu Ala
145                 150                 155                 160

Ala Ala Gly Asp Ser Gly Ser Thr Gly Gly Glu Asp Asp Gly Leu Tyr
                165                 170                 175

His Val His Phe Pro Ala Ala Ser Pro Tyr Val Leu Ala Cys Gly Gly
```

```
                180             185             190
Thr Arg Leu Val Ala Ser Gly Gly Arg Ile Ala Gln Glu Thr Val Trp
        195                 200                 205
Asn Asp Gly Pro Asp Gly Gly Ala Thr Gly Gly Val Ser Arg Ile
    210                 215                 220
Phe Pro Leu Pro Ala Trp Gln Glu His Ala Asn Val Pro Pro Ser Ala
225                 230                 235                 240
Asn Pro Gly Ala Ser Ser Gly Arg Gly Val Pro Asp Leu Ala Gly Asn
            245                 250                 255
Ala Asp Pro Ala Thr Gly Tyr Glu Val Val Ile Asp Gly Glu Ala Thr
        260                 265                 270
Val Ile Gly Gly Thr Ser Ala Val Ala Pro Leu Phe Ala Ala Leu Val
        275                 280                 285
Ala Arg Ile Asn Gln Lys Leu Gly Lys Ala Val Gly Tyr Leu Asn Pro
        290                 295                 300
Thr Leu Tyr Gln Leu Pro Ala Asp Val Phe His Asp Ile Thr Glu Gly
305                 310                 315                 320
Asn Asn Asp Ile Ala Asn Arg Ala Gln Ile Tyr Gln Ala Gly Pro Gly
            325                 330                 335
Trp Asp Pro Cys Thr Gly Leu Gly Ser Pro Ile Gly Val Arg Leu Leu
            340                 345                 350
Gln Ala Leu Leu Pro Ser Ala Ser Gln Pro Gln Pro Gly Ser Thr Glu
        355                 360                 365
Asn Leu Tyr Phe Gln Ser Gly Ala Leu Glu His His His His His His
        370                 375                 380

<210> SEQ ID NO 60
<211> LENGTH: 384
<212> TYPE: PRT
<213> ORGANISM: Artificial Sequence
<220> FEATURE:
<223> OTHER INFORMATION: Synthetic

<400> SEQUENCE: 60

Ala Ala Pro Thr Ala Tyr Thr Pro Leu Asp Val Ala Gln Ala Tyr Gln
1               5                   10                  15
Phe Pro Glu Gly Leu Asp Gly Gln Gly Gln Cys Ile Ala Ile Ile Glu
            20                  25                  30
Leu Gly Gly Gly Tyr Asp Glu Ala Ser Leu Ala Gln Tyr Phe Ala Ser
            35                  40                  45
Leu Gly Val Pro Ala Pro Gln Val Val Ser Val Ser Val Asp Gly Ala
        50                  55                  60
Ser Asn Gln Pro Thr Gly Asp Pro Ser Gly Pro Asp Gly Glu Val Glu
65                  70                  75                  80
Leu Asp Ile Glu Val Ala Gly Ala Leu Ala Pro Gly Ala Lys Phe Ala
                85                  90                  95
Val Tyr Phe Ala Pro Asp Thr Asp Ala Gly Phe Leu Asp Ala Ile Thr
            100                 105                 110
Thr Ala Ile His Asp Pro Thr Leu Lys Pro Ser Val Val Ser Ile Ser
            115                 120                 125
Trp Ser Gly Pro Glu Asp Ser Trp Thr Ser Ala Ala Ile Ala Ala Met
        130                 135                 140
Asn Arg Ala Phe Leu Asp Ala Ala Ala Leu Gly Val Thr Val Leu Ala
145                 150                 155                 160
Ala Ala Gly Asp Asn Gly Ser Thr Gly Gly Glu Asp Asp Gly Leu Tyr
```

```
                    165                 170                 175
His Val His Phe Pro Ala Ala Ser Pro Tyr Val Leu Ala Cys Gly Gly
                180                 185                 190

Thr Arg Leu Val Ala Ser Gly Gly Arg Ile Ala Gln Glu Thr Val Trp
            195                 200                 205

Asn Asp Gly Pro Asp Gly Gly Ala Thr Gly Gly Val Ser Arg Ile
    210                 215                 220

Phe Pro Leu Pro Ala Trp Gln Glu His Ala Asn Val Pro Pro Ser Ala
225                 230                 235                 240

Asn Pro Gly Ala Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
                260                 265                 270

Val Ile Gly Gly Thr Ser Ala Val Ala Pro Leu Phe Ala Ala Leu Val
            275                 280                 285

Ala Arg Ile Asn Gln Lys Leu Gly Lys Ala Val Gly Tyr Leu Asn Pro
        290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln Pro Gly Ser Thr Glu
                355                 360                 365

Asn Leu Tyr Phe Gln Ser Gly Ala Leu Glu His His His His His His
                370                 375                 380

<210> SEQ ID NO 61
<211> LENGTH: 384
<212> TYPE: PRT
<213> ORGANISM: Artificial Sequence
<220> FEATURE:
<223> OTHER INFORMATION: Synthetic

<400> SEQUENCE: 61

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
                20                  25                  30

Leu Gly Gly Gly Tyr Asp Glu Ala Ser Leu Ala Gln Tyr Phe Ala Ser
            35                  40                  45

Leu Gly Val Pro Ala Pro Gln Val Val Ser Val Ser Val Asp Gly Ala
        50                  55                  60

Ser Asn Gln Pro Thr Gly Asp Pro Ser Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Ala Ala Gly Phe Leu Asp Ala Ile Thr
                100                 105                 110

Thr Ala Ile His Asp Pro Thr Leu Lys Pro Ser Val Val Ser Ile Ser
            115                 120                 125

Trp Ser Gly Pro Glu Asp Ser Trp Thr Ser Ala Ile Ala Ala Met
        130                 135                 140

Asn Arg Ala Phe Leu Asp Ala Ala Ala Leu Gly Val Thr Val Leu Ala
```

```
                145                 150                 155                 160
Ala Ala Gly Asp Asn Gly Ser Thr Gly Gly Glu Asp Gly Leu Tyr
                165                 170                 175

His Val His Phe Pro Ala Ala Ser Pro Tyr Val Leu Ala Cys Gly Gly
                180                 185                 190

Thr Arg Leu Val Ala Ser Gly Arg Ile Ala Gln Glu Thr Val Trp
                195                 200                 205

Asn Asp Gly Pro Asp Gly Ala Thr Gly Gly Val Ser Arg Ile
                210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
                260                 265                 270

Val Ile Gly Gly Thr Ser Ala Val Ala Pro Leu Phe Ala Ala Leu Val
                275                 280                 285

Ala Arg Ile Asn Gln Lys Leu Gly Lys Ala Val Gly Tyr Leu Asn Pro
                290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln Pro Gly Ser Thr Glu
                355                 360                 365

Asn Leu Tyr Phe Gln Ser Gly Ala Leu Glu His His His His His His
                370                 375                 380

<210> SEQ ID NO 62
<211> LENGTH: 384
<212> TYPE: PRT
<213> ORGANISM: Artificial Sequence
<220> FEATURE:
<223> OTHER INFORMATION: Synthetic

<400> SEQUENCE: 62

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
                20                  25                  30

Leu Gly Gly Gly Tyr Asp Glu Ala Ser Leu Ala Gln Tyr Phe Ala Ser
                35                  40                  45

Leu Gly Val Pro Ala Pro Gln Val Val Ser Val Ser Val Asp Gly Ala
                50                  55                  60

Ser Asn Gln Pro Thr Gly Asp Pro Ser Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Ser Asp Ala Gly Phe Leu Asp Ala Ile Thr
                100                 105                 110

Thr Ala Ile His Asp Pro Thr Leu Lys Pro Ser Val Val Ser Ile Ser
                115                 120                 125

Trp Ser Gly Pro Glu Asp Ser Trp Thr Ser Ala Ala Ile Ala Ala Met
```

```
            130                 135                 140
Asn Arg Ala Phe Leu Asp Ala Ala Leu Gly Val Thr Val Leu Ala
145                 150                 155                 160

Ala Ala Gly Asp Ser Gly Ser Thr Gly Gly Glu Gln Asp Gly Leu Tyr
                    165                 170                 175

His Val His Phe Pro Ala Ala Ser Pro Tyr Val Leu Ala Cys Gly Gly
                180                 185                 190

Thr Arg Leu Val Ala Ser Gly Gly Arg Ile Ala Gln Glu Thr Val Trp
                195                 200                 205

Asn Asp Gly Pro Asp Gly Gly Ala Thr Gly Gly Gly Val Ser Arg Ile
            210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
                260                 265                 270

Val Ile Gly Gly Thr Ser Ala Val Ala Pro Leu Phe Ala Ala Leu Val
                275                 280                 285

Ala Arg Ile Asn Gln Lys Leu Gly Lys Ala Val Gly Tyr Leu Asn Pro
                290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln Pro Gly Ser Thr Glu
                355                 360                 365

Asn Leu Tyr Phe Gln Ser Gly Ala Leu Glu His His His His His His
                370                 375                 380

<210> SEQ ID NO 63
<211> LENGTH: 384
<212> TYPE: PRT
<213> ORGANISM: Artificial Sequence
<220> FEATURE:
<223> OTHER INFORMATION: Synthetic

<400> SEQUENCE: 63

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
                20                  25                  30

Leu Gly Gly Gly Tyr Asp Glu Ala Ser Leu Ala Gln Tyr Phe Ala Ser
                35                  40                  45

Leu Gly Val Pro Ala Pro Gln Val Val Ser Val Ser Val Asp Gly Ala
                50                  55                  60

Ser Asn Gln Pro Thr Gly Asp Pro Ser Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Thr Thr Ala Gly Phe Leu Asp Ala Ile Thr
                100                 105                 110

Thr Ala Ile His Asp Pro Thr Leu Lys Pro Ser Val Val Ser Ile Ser
```

```
                115                 120                 125
Trp Ser Gly Pro Glu Asp Ser Trp Thr Ser Ala Ala Ile Ala Ala Met
    130                 135                 140

Asn Arg Ala Phe Leu Asp Ala Ala Ala Leu Gly Val Thr Val Leu Ala
145                 150                 155                 160

Ala Ala Gly Asp Ser Gly Ser Thr Gly Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
        195                 200                 205

Asn Asp Gly Pro Asp Gly Gly Ala Thr Gly Gly Val Ser Arg Ile
210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
            260                 265                 270

Val Ile Gly Gly Thr Ser Ala Val Ala Pro Leu Phe Ala Ala Leu Val
        275                 280                 285

Ala Arg Ile Asn Gln Lys Leu Gly Lys Ala Val Gly Tyr Leu Asn Pro
    290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
            340                 345                 350

Gln Ala Leu Leu Pro Ser Ala Ser Gln Pro Gln Pro Gly Ser Thr Glu
        355                 360                 365

Asn Leu Tyr Phe Gln Ser Gly Ala Leu Glu His His His His His His
    370                 375                 380

<210> SEQ ID NO 64
<211> LENGTH: 384
<212> TYPE: PRT
<213> ORGANISM: Artificial Sequence
<220> FEATURE:
<223> OTHER INFORMATION: Synthetic

<400> SEQUENCE: 64

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
                20                  25                  30

Leu Gly Gly Gly Tyr Asp Glu Ala Ser Leu Ala Gln Tyr Phe Ala Ser
            35                  40                  45

Leu Gly Val Pro Ala Pro Gln Val Val Ser Val Ser Val Asp Gly Ala
        50                  55                  60

Ser Asn Gln Pro Thr Gly Asp Pro Gly Gly Pro Asp Gly Glu Val Glu
65                  70                  75                  80

Leu Asp Ile Glu Val Ala Gly Ala Leu Ala Pro Gly Ala Lys Phe Ala
                85                  90                  95

Val Tyr Phe Ala Pro Asp Ser Asp Ala Gly Phe Leu Asp Ala Ile Thr
```

```
                100             105             110
Thr Ala Ile His Asp Pro Thr Leu Lys Pro Ser Val Val Ser Ile Ser
            115                 120                 125
Trp Ser Gly Pro Glu Asp Ser Trp Thr Ser Ala Ala Ile Ala Ala Met
    130                 135                 140
Asn Arg Ala Phe Leu Asp Ala Ala Leu Gly Val Thr Val Leu Ala
145                 150                 155                 160
Ala Ala Gly Asp Ser Gly Ser Thr Gly Gly Glu Gln Asp Gly Leu Tyr
                165                 170                 175
His Val His Phe Pro Ala Ala Ser Pro Tyr Val Leu Ala Cys Gly Gly
            180                 185                 190
Thr Arg Leu Val Ala Ser Gly Gly Arg Ile Ala Gln Glu Thr Val Trp
            195                 200                 205
Asn Asp Gly Pro Asp Gly Gly Ala Thr Gly Gly Val Ser Arg Ile
210                 215                 220
Phe Pro Leu Pro Ala Trp Gln Glu His Ala Asn Val Pro Ser Ala
225                 230                 235                 240
Asn Pro Gly Ala Ser Ser Gly Arg Gly Val Pro Asp Leu Ala Gly Asn
                245                 250                 255
Ala Asp Pro Ala Thr Gly Tyr Glu Val Val Ile Asp Gly Glu Ala Thr
            260                 265                 270
Val Ile Gly Gly Thr Ser Ala Val Ala Pro Leu Phe Ala Ala Leu Val
            275                 280                 285
Ala Arg Ile Asn Gln Lys Leu Gly Lys Ala Val Gly Tyr Leu Asn Pro
            290                 295                 300
Thr Leu Tyr Gln Leu Pro Ala Asp Val Phe His Asp Ile Thr Glu Gly
305                 310                 315                 320
Asn Asn Asp Ile Ala Asn Arg Ala Gln Ile Tyr Gln Ala Gly Pro Gly
                325                 330                 335
Trp Asp Pro Cys Thr Gly Leu Gly Ser Pro Ile Gly Val Arg Leu Leu
            340                 345                 350
Gln Ala Leu Leu Pro Ser Ala Ser Gln Pro Gln Pro Gly Ser Thr Glu
            355                 360                 365
Asn Leu Tyr Phe Gln Ser Gly Ala Leu Glu His His His His His
            370                 375                 380

<210> SEQ ID NO 65
<211> LENGTH: 384
<212> TYPE: PRT
<213> ORGANISM: Artificial Sequence
<220> FEATURE:
<223> OTHER INFORMATION: Synthetic

<400> SEQUENCE: 65

Ala Ala Pro Thr Ala Tyr Thr Pro Leu Asp Val Ala Gln Ala Tyr Gln
1               5                   10                  15
Phe Pro Glu Gly Leu Asp Gly Gln Gly Gln Cys Ile Ala Ile Ile Glu
                20                  25                  30
Leu Gly Gly Gly Tyr Asp Glu Ala Ser Leu Ala Gln Tyr Phe Ala Ser
            35                  40                  45
Leu Gly Val Pro Ala Pro Gln Val Val Ser Val Ser Val Asp Gly Ala
            50                  55                  60
Ser Asn Gln Pro Thr Gly Asp Pro Lys Gly Pro Asp Gly Glu Val Glu
65                  70                  75                  80
Leu Asp Ile Glu Val Ala Gly Ala Leu Ala Pro Gly Ala Lys Phe Ala
```

```
            85                  90                  95
Val Tyr Phe Ala Pro Asp Thr Asn Ala Gly Phe Leu Asp Ala Ile Thr
            100                 105                 110

Thr Ala Ile His Asp Pro Thr Leu Lys Pro Ser Val Val Ser Ile Ser
            115                 120                 125

Trp Ser Gly Pro Glu Asp Ser Trp Thr Ser Ala Ala Ile Ala Ala Met
            130                 135                 140

Asn Arg Ala Phe Leu Asp Ala Ala Leu Gly Val Thr Val Leu Ala
145                 150                 155                 160

Ala Ala Gly Asp Ser Gly Ser Thr Gly Glu Gln Asp Gly Leu Tyr
                165                 170                 175

His Val His Phe Pro Ala Ala Ser Pro Tyr Val Leu Ala Cys Gly Gly
            180                 185                 190

Thr Arg Leu Val Ala Ser Gly Gly Arg Ile Ala Gln Glu Thr Val Trp
            195                 200                 205

Asn Asp Gly Pro Asp Gly Gly Ala Thr Gly Gly Val Ser Arg Ile
            210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
                260                 265                 270

Val Ile Gly Gly Thr Ser Ala Val Ala Pro Leu Phe Ala Ala Leu Val
            275                 280                 285

Ala Arg Ile Asn Gln Lys Leu Gly Lys Ala Val Gly Tyr Leu Asn Pro
290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln Pro Gly Ser Thr Glu
            355                 360                 365

Asn Leu Tyr Phe Gln Ser Gly Ala Leu Glu His His His His His
            370                 375                 380

<210> SEQ ID NO 66
<211> LENGTH: 384
<212> TYPE: PRT
<213> ORGANISM: Artificial Sequence
<220> FEATURE:
<223> OTHER INFORMATION: Synthetic

<400> SEQUENCE: 66

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
            20                  25                  30

Leu Gly Gly Gly Tyr Asp Glu Ala Ser Leu Ala Gln Tyr Phe Ala Ser
            35                  40                  45

Leu Gly Val Pro Ala Pro Gln Val Val Ser Val Ser Val Asp Gly Ala
            50                  55                  60

Ser Asn Gln Pro Thr Gly Asp Pro Lys Gly Pro Asp Gly Glu Val Glu
```

```
                65                  70                  75                  80
Leu Asp Ile Glu Val Ala Gly Ala Leu Ala Pro Gly Ala Lys Phe Ala
                    85                  90                  95

Val Tyr Phe Ala Pro Asp Thr Thr Ala Gly Phe Leu Asp Ala Ile Thr
                100                 105                 110

Thr Ala Ile His Asp Pro Thr Leu Lys Pro Ser Val Ser Ile Ser
                115                 120                 125

Trp Ser Gly Pro Glu Asp Ser Trp Thr Ser Ala Ala Ile Ala Ala Met
                130                 135                 140

Asn Arg Ala Phe Leu Asp Ala Ala Leu Gly Val Thr Val Leu Ala
145                 150                 155                 160

Ala Ala Gly Asp Ser Gly Ser Thr Gly Gly Glu Gln Asp Gly Leu Tyr
                165                 170                 175

His Val His Phe Pro Ala Ala Ser Pro Tyr Val Leu Ala Cys Gly Gly
                180                 185                 190

Thr Arg Leu Val Ala Ser Gly Gly Arg Ile Ala Gln Glu Thr Val Trp
                195                 200                 205

Asn Asp Gly Pro Asp Gly Gly Ala Thr Gly Gly Gly Val Ser Arg Ile
210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
                260                 265                 270

Val Ile Gly Gly Thr Ser Ala Val Ala Pro Leu Phe Ala Ala Leu Val
                275                 280                 285

Ala Arg Ile Asn Gln Lys Leu Gly Lys Ala Val Gly Tyr Leu Asn Pro
                290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gln Pro Gln Pro Gly Ser Thr Glu
                355                 360                 365

Asn Leu Tyr Phe Gln Ser Gly Ala Leu Glu His His His His His
370                 375                 380

<210> SEQ ID NO 67
<211> LENGTH: 384
<212> TYPE: PRT
<213> ORGANISM: Artificial Sequence
<220> FEATURE:
<223> OTHER INFORMATION: Synthetic

<400> SEQUENCE: 67

Ala Ala Pro Thr Ala Tyr Thr Pro Leu Asp Val Ala Gln Ala Tyr Gln
1               5                   10                  15

Phe Pro Glu Gly Leu Asp Gly Gln Gly Gln Cys Ile Ala Ile Ile Glu
                20                  25                  30

Leu Gly Gly Gly Tyr Asp Glu Ala Ser Leu Ala Gln Tyr Phe Ala Ser
                35                  40                  45

Leu Gly Val Pro Ala Pro Gln Val Val Ser Val Ser Val Asp Gly Ala
```

-continued

```
                50                  55                  60
Ser Asn Gln Pro Thr Gly Asp Pro Ser Gly Pro Asp Gly Glu Val Glu
 65                  70                  75                  80

Leu Asp Ile Glu Val Ala Gly Ala Leu Ala Pro Gly Ala Lys Phe Ala
                 85                  90                  95

Val Tyr Phe Ala Pro Asn Thr Asp Ala Gly Phe Leu Asp Ala Ile Thr
                100                 105                 110

Thr Ala Ile His Asp Pro Thr Leu Lys Pro Ser Val Val Ser Ile Ser
                115                 120                 125

Trp Gly Gly Pro Glu Asp Ser Trp Thr Ser Ala Ala Ile Ala Ala Met
                130                 135                 140

Asn Arg Ala Phe Leu Asp Ala Ala Leu Gly Val Thr Val Leu Ala
145                 150                 155                 160

Ala Ala Gly Asp Ser Gly Ser Thr Asp Gly Glu Gln Asp Gly Leu Tyr
                165                 170                 175

His Val Asp Phe Pro Ala Ala Ser Pro Tyr Val Leu Ala Cys Gly Gly
                180                 185                 190

Thr Arg Leu Val Ala Ser Gly Gly Arg Ile Ala Gln Glu Thr Val Trp
                195                 200                 205

Asn Asp Gly Pro Asp Gly Gly Ala Thr Gly Gly Val Ser Arg Ile
210                 215                 220

Phe Pro Leu Pro Ala Trp Gln Glu His Ala Asn Val Pro Pro Ser Ala
225                 230                 235                 240

Asn Pro Gly Ala Ser Ser Gly Arg Gly Val Pro Asp Leu Ala Gly Asn
                245                 250                 255

Ala Asp Pro Ala Thr Gly Tyr Glu Val Val Ile Asp Gly Glu Ala Thr
                260                 265                 270

Val Ile Gly Gly Thr Ser Ala Val Ala Pro Leu Phe Ala Ala Leu Val
                275                 280                 285

Ala Arg Ile Asn Gln Lys Leu Gly Lys Ala Val Gly Tyr Leu Asn Pro
                290                 295                 300

Thr Leu Tyr Gln Leu Pro Ala Asp Val Phe His Asp Ile Thr Glu Gly
305                 310                 315                 320

Asn Asn Asp Ile Ala Asn Arg Ala Gln Ile Tyr Gln Ala Gly Pro Gly
                325                 330                 335

Trp Asp Pro Cys Thr Gly Leu Gly Ser Pro Ile Gly Val Arg Leu Leu
                340                 345                 350

Gln Ala Leu Leu Pro Ser Ala Ser Gly Pro Gln Pro Gly Ser Thr Glu
                355                 360                 365

Asn Leu Tyr Phe Gln Ser Gly Ala Leu Glu His His His His His His
                370                 375                 380
```

<210> SEQ ID NO 68
<211> LENGTH: 4
<212> TYPE: PRT
<213> ORGANISM: Artificial Sequence
<220> FEATURE:
<223> OTHER INFORMATION: Synthetic

<400> SEQUENCE: 68

Pro Gln Leu Pro
1

<210> SEQ ID NO 69
<211> LENGTH: 6
<212> TYPE: PRT

```
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-terminal QXL520
<220> FEATURE:
<221> NAME/KEY: MISC_FEATURE
<222> LOCATION: (6)..(6)
<223> OTHER INFORMATION: C-terminal K(5-FAM)

<400> SEQUENCE: 69

Pro Gln Pro Gln Leu Pro
1               5

<210> SEQ ID NO 70
<211> LENGTH: 12
<212> TYPE: PRT
<213> ORGANISM: Artificial Sequence
<220> FEATURE:
<223> OTHER INFORMATION: Synthetic

<400> SEQUENCE: 70

Gln Leu Gln Pro Phe Pro Gln Pro Gln Leu Pro Tyr
1               5                   10

<210> SEQ ID NO 71
<211> LENGTH: 290
<212> TYPE: PRT
<213> ORGANISM: Artificial Sequence
<220> FEATURE:
<223> OTHER INFORMATION: Synthetic

<400> SEQUENCE: 71

Met Val Arg Val Pro Val Pro Gln Leu Gln Pro Gln Asn Pro Ser Gln
1               5                   10                  15

Gln Gln Pro Gln Glu Gln Val Pro Leu Val Gln Gln Gln Gln Phe Pro
            20                  25                  30

Gly Gln Gln Gln Pro Phe Pro Pro Gln Gln Pro Tyr Pro Gln Pro Gln
        35                  40                  45

Pro Phe Pro Ser Gln Gln Phe Tyr Leu Gln Leu Gln Pro Phe Pro Gln
    50                  55                  60

Pro Gln Leu Pro Tyr Pro Gln Pro Gln Leu Pro Tyr Pro Gln Pro Gln
65                  70                  75                  80

Leu Pro Tyr Pro Gln Pro Gln Phe Arg Pro Gln Gln Pro Tyr Pro
                85                  90                  95

Gln Ser Gln Pro Gln Tyr Ser Gln Pro Gln Gln Pro Ile Ser Gln Gln
            100                 105                 110

Gln Gln Gln Gln Gln Gln Gln Gln Gln Lys Gln Gln Gln Gln
        115                 120                 125

Gln Gln Gln Ile Leu Gln Gln Ile Leu Gln Gln Leu Ile Pro Cys
        130                 135                 140

Arg Asp Val Val Leu Gln His Ser Ile Ala Tyr Gly Ser Ser Gln
145                 150                 155                 160

Val Leu Gln Gln Ser Thr Tyr Gly Leu Val Gln Gln Leu Cys Cys Gln
                165                 170                 175

Gln Leu Trp Gln Ile Pro Glu Gln Ser Arg Cys Gln Ala Ile His Asn
            180                 185                 190

Val Val His Ala Ile Ile Leu His Gln Gln Gln Gln Gln Gln Gln
        195                 200                 205
```

```
Gln Gln Gln Gln Pro Leu Ser Gln Val Ser Phe Gln Gln Pro Gln Gln
    210                 215                 220
Gln Tyr Pro Ser Gly Gln Gly Ser Phe Gln Pro Ser Gln Gln Asn Pro
225                 230                 235                 240
Gln Ala Gln Gly Ser Val Gln Pro Gln Gln Leu Pro Gln Phe Glu Glu
                245                 250                 255
Ile Arg Asn Leu Ala Leu Glu Thr Leu Pro Ala Met Cys Asn Val Tyr
            260                 265                 270
Ile Pro Pro Tyr Cys Thr Ile Ala Pro Val Gly Ile Phe Gly Thr Asn
        275                 280                 285
Tyr Arg
    290

<210> SEQ ID NO 72
<211> LENGTH: 33
<212> TYPE: PRT
<213> ORGANISM: Artificial Sequence
<220> FEATURE:
<223> OTHER INFORMATION: Synthetic

<400> SEQUENCE: 72

Leu Gln Leu Gln Pro Phe Pro Gln Pro Gln Leu Pro Tyr Pro Gln Pro
1               5                   10                  15
Gln Leu Pro Tyr Pro Gln Pro Gln Leu Pro Tyr Pro Gln Pro Gln Pro
            20                  25                  30
Phe

<210> SEQ ID NO 73
<211> LENGTH: 26
<212> TYPE: PRT
<213> ORGANISM: Artificial Sequence
<220> FEATURE:
<223> OTHER INFORMATION: Synthetic

<400> SEQUENCE: 73

Phe Leu Gln Pro Gln Gln Pro Phe Pro Gln Gln Pro Gln Gln Pro Tyr
1               5                   10                  15
Pro Gln Gln Pro Gln Gln Pro Phe Pro Gln
            20                  25

<210> SEQ ID NO 74
<211> LENGTH: 512
<212> TYPE: PRT
<213> ORGANISM: Artificial Sequence
<220> FEATURE:
<223> OTHER INFORMATION: Synthetic

<400> SEQUENCE: 74

Met Ala Pro Ser Asp Val Glu Ile Val Asp Pro Val Ala Pro Glu Glu
1               5                   10                  15
Arg Ile Thr Val Thr Val Leu Leu Arg Arg Arg Ser Ser Ile Pro Asp
            20                  25                  30
Gln Leu Ile Glu Gly Pro Asp Thr Leu Ser Arg Ala Glu Leu Ala Asp
        35                  40                  45
Arg His Gly Ala Asp Pro Ala Asp Val Glu Ala Val Arg Val Ala Met
    50                  55                  60
Ser Gly Ala Gly Leu Thr Val Val Gly Thr Asp Leu Pro Ser Arg Arg
65                  70                  75                  80
Val Thr Val Ala Gly Thr Ala Glu Ala Leu Met Arg Thr Phe Gly Ala
                85                  90                  95
```

```
Glu Leu Gln Ile Val Arg Asp Ala Ser Gly Phe Gln His Arg Ala Arg
            100                 105                 110

Ser Gly Glu Leu Arg Ile Pro Ala Ala Leu Asp Gly Ile Val Ile Ala
        115                 120                 125

Val Leu Gly Leu Asp Asn Arg Pro Gln Ala Glu Ala Arg Phe Arg Ala
130                 135                 140

Ser Gln Pro Glu Ala Ala Arg Ser Phe Arg Pro Asp Ala Leu Gly Arg
145                 150                 155                 160

Val Tyr Arg Phe Pro Ala Asn Thr Asp Gly Thr Gln Thr Ile Ala
                165                 170                 175

Ile Val Glu Leu Gly Gly Gly Phe Arg Gln Ser Glu Leu Asp Thr Tyr
            180                 185                 190

Phe Gly Gly Leu Gly Ile Pro Ala Pro Gln Val Leu Ala Val Gly Val
        195                 200                 205

Asp Gly Gly Gln Asn Leu Pro Ser Gly Asp Ala Gly Ser Ala Asp Gly
    210                 215                 220

Glu Val Leu Leu Asp Ile Glu Val Ala Gly Ala Leu Ala Pro Gly Ala
225                 230                 235                 240

Arg Gln Val Val Tyr Phe Ala Pro Asn Thr Asp Arg Gly Phe Val Asp
                245                 250                 255

Ala Val Thr Thr Ala Val His Ala Asp Pro Thr Pro Ala Ala Val Ser
            260                 265                 270

Ile Ser Trp Gly Ala Pro Glu Asp Lys Trp Thr Ala Gln Ala Arg Arg
        275                 280                 285

Ala Phe Asp Ala Ala Leu Ala Asp Ala Ala Leu Gly Val Thr Val
    290                 295                 300

Thr Ala Ala Gly Asp Arg Gly Ser Ala Asp Gly Glu Gly Gly Gly
305                 310                 315                 320

Gly Leu His Thr Asp Phe Pro Ala Ser Ser Pro His Leu Leu Ala Cys
                325                 330                 335

Gly Gly Thr Lys Leu Ala Val Ala Asp Gly Gly Thr Val Ala Ser Glu
            340                 345                 350

Thr Val Trp Asn Gly Gly Glu Arg Gly Gly Ala Thr Gly Gly Gly Val
        355                 360                 365

Ser Val Ala Phe Gly Leu Pro Ala Tyr Gln Arg Asn Ala Gly Val Asp
    370                 375                 380

Lys Arg Arg Lys Thr Gly Lys Pro Gly Arg Gly Val Pro Asp Val Ala
385                 390                 395                 400

Ala Val Ala Asp Pro Ala Thr Gly Tyr Glu Val Leu Val Asp Gly Glu
                405                 410                 415

Gln Leu Val Phe Gly Gly Thr Ser Ala Val Ala Pro Leu Trp Ala Ala
            420                 425                 430

Leu Val Ala Arg Leu Thr Gln Ala Leu Gly Arg Pro Leu Gly Leu Leu
        435                 440                 445

Asn Thr Ala Leu Tyr Asp Gly Ala Gln Pro Gly Arg Thr Gln Pro Gly
    450                 455                 460

Phe Arg Asp Val Thr Glu Gly Asp Asn Asp Ile Ser Gly Lys His Gly
465                 470                 475                 480

Pro Tyr Pro Ala Arg Ala Gly Trp Asp Ala Cys Thr Gly Leu Gly Val
                485                 490                 495

Pro Asp Gly Glu Ala Leu Leu Ala Leu Arg Lys Pro Gly Lys Glu
            500                 505                 510
```

```
<210> SEQ ID NO 75
<211> LENGTH: 523
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (106)..(106)
<223> OTHER INFORMATION: Xaa is V or D
<220> FEATURE:
<221> NAME/KEY: MISC_FEATURE
<222> LOCATION: (246)..(246)
<223> OTHER INFORMATION: Xaa is N, S, K or G
<220> FEATURE:
<221> NAME/KEY: MISC_FEATURE
<222> LOCATION: (275)..(275)
<223> OTHER INFORMATION: Xaa is N or D
<220> FEATURE:
<221> NAME/KEY: MISC_FEATURE
<222> LOCATION: (276)..(276)
<223> OTHER INFORMATION: Xaa is T or S
<220> FEATURE:
<221> NAME/KEY: MISC_FEATURE
<222> LOCATION: (277)..(277)
<223> OTHER INFORMATION: Xaa is D, A, T or N
<220> FEATURE:
<221> NAME/KEY: MISC_FEATURE
<222> LOCATION: (303)..(303)
<223> OTHER INFORMATION: Xaa is G or S
<220> FEATURE:
<221> NAME/KEY: MISC_FEATURE
<222> LOCATION: (338)..(338)
<223> OTHER INFORMATION: Xaa is N or S
<220> FEATURE:
<221> NAME/KEY: MISC_FEATURE
<222> LOCATION: (341)..(341)
<223> OTHER INFORMATION: Xaa is G, T or A
<220> FEATURE:
<221> NAME/KEY: MISC_FEATURE
<222> LOCATION: (342)..(342)
<223> OTHER INFORMATION: Xaa is D, G or N
<220> FEATURE:
<221> NAME/KEY: MISC_FEATURE
<222> LOCATION: (345)..(345)
<223> OTHER INFORMATION: Xaa is D, G or Q
<220> FEATURE:
<221> NAME/KEY: MISC_FEATURE
<222> LOCATION: (352)..(352)
<223> OTHER INFORMATION: Xaa is D, S or H

<400> SEQUENCE: 75

Met Ala Asn His Pro Leu Asn Gly Ser Glu Arg Glu Cys Leu Lys Asp
1               5                   10                  15

Ala Gln Pro Ile Gly Lys Ala Asp Pro Asn Glu Arg Leu Glu Val Thr
            20                  25                  30

Met Leu Val Arg Arg Arg Ser His Asp Ala Phe Glu Lys His Ile Ser
        35                  40                  45

Ala Leu Ala Ala Gln Gly Ala Ser Ala Lys His Ile Asp His Asp Glu
    50                  55                  60

Phe Thr Lys His Phe Gly Ala Asp Ser Ala Asp Leu Ala Ala Val His
65                  70                  75                  80

Ala Phe Ala Gln Lys His Gly Leu Ser Val Val Glu Ser His Glu Ala
                85                  90                  95

Arg Arg Ala Val Val Leu Ser Gly Thr Xaa Ala Gln Phe Asp Ala Ala
            100                 105                 110

Phe Gly Val Ser Leu Gln Gln Tyr Glu His Asp Gly Thr Tyr Arg
        115                 120                 125

Gly Arg Thr Gly Pro Ile His Leu Pro Asp Glu Leu Asn Gly Val Val
```

```
            130                 135                 140
Asp Ala Val Met Gly Leu Asp Asn Arg Pro Gln Ala Arg Pro Ser Phe
145                 150                 155                 160

Arg Thr Arg Ala Gln Gly Asn Val Arg Trp Thr Ala Arg Ala Ala Gly
                165                 170                 175

Ala Ser Thr Phe Thr Pro Val Gln Leu Ala Ser Leu Tyr Asp Phe Pro
            180                 185                 190

Gln Gly Asp Gly Gln Asn Gln Cys Ile Gly Ile Ile Glu Leu Gly Gly
        195                 200                 205

Gly Tyr Arg Pro Ala Asp Leu Lys Thr Tyr Phe Ala Ser Leu Asn Met
    210                 215                 220

Lys Ala Pro Ser Val Thr Ala Val Ser Val Asp His Gly Arg Asn His
225                 230                 235                 240

Pro Thr Gly Asp Pro Xaa Gly Pro Asp Gly Glu Val Met Leu Asp Ile
                245                 250                 255

Glu Val Ala Gly Ala Val Ala Pro Gly Ala Lys Ile Val Val Tyr Phe
                260                 265                 270

Ala Pro Xaa Xaa Xaa Ala Gly Phe Ile Asp Ala Ile Gly Thr Ala Ile
            275                 280                 285

His Asp Thr Lys Asn Lys Pro Ser Val Ile Ser Ile Ser Trp Xaa Gly
        290                 295                 300

Pro Glu Ser Ala Trp Thr Gln Gln Ala Met Asn Ala Phe Asp Gln Ala
305                 310                 315                 320

Phe Gln Ser Ala Ala Ala Leu Gly Val Thr Ile Cys Ala Ala Ser Gly
                325                 330                 335

Asp Xaa Gly Ser Xaa Xaa Gly Val Xaa Asp Gly Ala Asp His Val Xaa
            340                 345                 350

Phe Pro Ala Ser Ser Pro Tyr Ala Leu Gly Cys Gly Gly Thr Ser Leu
        355                 360                 365

Gln Ala Ser Gly Asn Gly Ile Ala Ser Glu Thr Val Trp Asn Asp Gly
    370                 375                 380

Ala Asn Gly Gly Ala Thr Gly Gly Gly Val Ser Ser Phe Phe Ala Leu
385                 390                 395                 400

Pro Ala Trp Gln Glu Gly Leu Arg Val Thr Arg Ala Gly Gly Ala His
                405                 410                 415

Ser Pro Leu Ala Met Arg Gly Val Pro Asp Val Ala Gly Asn Ala Asp
                420                 425                 430

Pro Val Thr Gly Tyr Glu Val Arg Val Asp Gly His Asp Met Val Ile
            435                 440                 445

Gly Gly Thr Ser Ala Val Ala Pro Leu Trp Ala Gly Leu Ile Ala Arg
        450                 455                 460

Ile Asn Ala Ile Lys Gly Ala Pro Val Gly Tyr Ile Asn Pro His Leu
465                 470                 475                 480

Tyr Lys Asp Pro Leu Ala Leu Val Asp Ile Thr Lys Gly Asn Asn Asp
                485                 490                 495

Asp Phe His Ala Thr Ala Gly Trp Asp Ala Cys Thr Gly Leu Gly Arg
            500                 505                 510

Pro Asp Gly Lys Lys Val Lys Asp Ala Val Ser
        515                 520

<210> SEQ ID NO 76
<211> LENGTH: 554
<212> TYPE: PRT
<213> ORGANISM: Artificial Sequence
```

```
<220> FEATURE:
<223> OTHER INFORMATION: Synthetic
<220> FEATURE:
<221> NAME/KEY: MISC_FEATURE
<222> LOCATION: (120)..(120)
<223> OTHER INFORMATION: Xaa is V or D
<220> FEATURE:
<221> NAME/KEY: MISC_FEATURE
<222> LOCATION: (259)..(259)
<223> OTHER INFORMATION: Xaa is N, S, K or G
<220> FEATURE:
<221> NAME/KEY: MISC_FEATURE
<222> LOCATION: (288)..(288)
<223> OTHER INFORMATION: Xaa is N or D
<220> FEATURE:
<221> NAME/KEY: MISC_FEATURE
<222> LOCATION: (289)..(289)
<223> OTHER INFORMATION: Xaa is S or T
<220> FEATURE:
<221> NAME/KEY: MISC_FEATURE
<222> LOCATION: (290)..(290)
<223> OTHER INFORMATION: Xaa is D, A, T, or N
<220> FEATURE:
<221> NAME/KEY: MISC_FEATURE
<222> LOCATION: (316)..(316)
<223> OTHER INFORMATION: Xaa is G or S
<220> FEATURE:
<221> NAME/KEY: MISC_FEATURE
<222> LOCATION: (351)..(351)
<223> OTHER INFORMATION: Xaa is D, S or N
<220> FEATURE:
<221> NAME/KEY: MISC_FEATURE
<222> LOCATION: (354)..(354)
<223> OTHER INFORMATION: Xaa is T or A
<220> FEATURE:
<221> NAME/KEY: MISC_FEATURE
<222> LOCATION: (355)..(355)
<223> OTHER INFORMATION: Xaa is D, N, or G
<220> FEATURE:
<221> NAME/KEY: MISC_FEATURE
<222> LOCATION: (358)..(358)
<223> OTHER INFORMATION: Xaa is Q or D
<220> FEATURE:
<221> NAME/KEY: MISC_FEATURE
<222> LOCATION: (365)..(365)
<223> OTHER INFORMATION: Xaa is D, S or H

<400> SEQUENCE: 76

Met Asn His Asp His Ser Pro Thr Gly Gly Glu Leu Ser Asn Trp Val
1               5                   10                  15

Arg Val Pro Gly Ser Glu Arg Ala Ala Val Gln Gly Ser Arg Lys Val
                20                  25                  30

Gly Pro Ala Asp Pro Asn Glu Gln Met Ser Val Thr Val Val Arg
            35                  40                  45

Arg Pro Ala Ala Asp Thr Ala Val Thr Ser Met Ile Glu Lys Val Gly
    50                  55                  60

Ala Gln Pro Leu Ser Glu Arg Arg His Leu Thr Arg Glu Glu Phe Ala
65                  70                  75                  80

Ser Thr His Gly Ala Asn Pro Ala Asp Leu Ser Lys Val Glu Lys Phe
                85                  90                  95

Ala His Glu His Asn Leu Gln Val Lys Glu Val Asn Ala Ala Ala Gly
            100                 105                 110

Thr Met Val Leu Ser Gly Thr Xaa Thr Ser Phe Ser Lys Ala Phe Gly
        115                 120                 125

Val Glu Leu Ser Thr Tyr Glu His Pro Asp Phe Thr Tyr Arg Gly Arg
    130                 135                 140

Ile Gly His Val His Ile Pro Asp Tyr Leu Ala Asp Thr Ile Gln Ser
145                 150                 155                 160
```

Val Leu Gly Leu Asp Asn Arg Pro Gln Ala Ser Pro Arg Phe Arg Val
            165                 170                 175

Leu Lys Glu Glu Gly Gly Val Thr Thr Ala His Ala Gly Arg Thr Ser
        180                 185                 190

Tyr Thr Pro Leu Glu Val Ala Ala Leu Tyr Asn Phe Pro Ser Ile His
            195                 200                 205

Cys Lys Asp Gln Cys Ile Gly Ile Leu Glu Leu Gly Gly Tyr Arg
        210                 215                 220

Pro Ala Asp Leu Gln Thr Tyr Phe Asn Gly Leu Gly Ile Pro Gln Pro
225                 230                 235                 240

Asn Ile Thr Asp Val Ser Val Gly Gly Ala Ala Asn Arg Pro Thr Gly
                245                 250                 255

Asp Pro Xaa Gly Pro Asp Gly Glu Val Val Leu Asp Ile Glu Val Ala
            260                 265                 270

Ala Ala Val Thr Pro Gly Ala Lys Ile Ala Val Tyr Phe Ala Asp Xaa
            275                 280                 285

Xaa Xaa Asp Gly Phe Leu Asn Ala Ile Thr Thr Ala Ile His Asp Thr
        290                 295                 300

Arg Asn Lys Pro Ser Val Ile Ser Ile Ser Trp Xaa Lys Ala Glu Ile
305                 310                 315                 320

Gly Trp Thr Pro Gln Ala Ile Asn Ala Met Asn Gln Ala Phe Arg Asp
            325                 330                 335

Ala Ala Ala Leu Gly Val Thr Ile Cys Cys Ala Ser Gly Asp Xaa Gly
            340                 345                 350

Ser Xaa Xaa Arg Val Xaa Asp Gly Arg Tyr His Val Xaa Phe Pro Ala
        355                 360                 365

Ser Ser Pro Tyr Val Leu Ala Cys Gly Gly Thr Arg Leu Glu Ser Ser
        370                 375                 380

Gly Ser Thr Ile Thr Gln Glu Val Val Trp Asn Glu Gly Ala Leu Gly
385                 390                 395                 400

Gly Gly Ala Thr Gly Gly Gly Val Ser Asp Val Phe Asp Arg Pro Asn
            405                 410                 415

Trp Gln Ala Asn Ala Asn Val Pro Thr Ser Ala Asn Pro Glu Arg Arg
            420                 425                 430

Ile Gly Arg Gly Val Pro Asp Trp Ala Gly Asn Ala Asp Pro Ala Thr
        435                 440                 445

Gly Tyr Gln Ile Leu Val Asp Gly Thr Arg Ala Val Ile Gly Gly Thr
        450                 455                 460

Ser Ala Val Ala Pro Leu Phe Ala Gly Leu Ile Ala Ile Ile Asn Gln
465                 470                 475                 480

Lys Leu Gly His Ser Val Gly Phe Ile Asn Pro Ile Leu Tyr Asn Leu
            485                 490                 495

Ser Ala Gln His Asn Val Phe His Asp Ile Thr Ser Gly Asn Asn Asp
            500                 505                 510

Met Ser Gly Gln Asn Gly Pro Tyr Glu Ala Gln Pro Gly Trp Asp Ala
        515                 520                 525

Cys Thr Gly Leu Gly Ser Pro Asp Gly Thr Lys Leu Met Asn Ala Ile
        530                 535                 540

Ser Glu Ala His Arg Leu Val Ser Val Gly
545                 550

<210> SEQ ID NO 77
<211> LENGTH: 507
<212> TYPE: PRT

<213> ORGANISM: Artificial Sequence
<220> FEATURE:
<223> OTHER INFORMATION: Synthetic

<400> SEQUENCE: 77

```
Met Ala Pro Glu Glu Arg Arg Thr Leu Pro Gly Ser Ala Met Pro Arg
1               5                   10                  15

Pro Ala Gly Ala Gln Val Leu Gly Gln Ile Pro Asp Asp Glu Arg Val
            20                  25                  30

Glu Val Thr Val Val Leu Gln Pro Arg Ala Pro Leu Pro Glu Pro Gly
        35                  40                  45

Pro Thr Pro Met Ser Arg Ala Glu Leu Ala Asp Leu Arg Ser Pro Pro
    50                  55                  60

Glu Gly Ala Leu Glu Ala Ile Ala Arg Tyr Val Ala Gly Gln Gly Leu
65                  70                  75                  80

Glu Val Ile Ala Ala Asp Ala Pro Arg Arg Ile Val Leu Ala Gly
                85                  90                  95

Ser Ala Ala Arg Ile Ala Ala Leu Phe Gly Ile Ser Phe Val Arg Leu
                100                 105                 110

Gln Leu Glu Gly Arg Arg Tyr Arg Thr Tyr Glu Gly Glu Ile Ser Leu
            115                 120                 125

Pro Ala Glu Leu Ala Pro Leu Val Val Ala Val Leu Gly Leu Asp Thr
    130                 135                 140

Arg Pro Phe Ala Arg Ser His Arg Arg Pro Ala Val Ala Pro Asn Ala
145                 150                 155                 160

Pro Thr Thr Ala Pro Thr Val Ala Arg Ala Tyr Asp Phe Pro Thr Ala
                165                 170                 175

Tyr Asp Gly Arg Gly Thr Thr Ile Gly Phe Ile Glu Leu Gly Gly Gly
            180                 185                 190

Phe Gln Glu Ser Asp Leu Val Arg Tyr Cys Glu Gly Leu Gly Leu Ser
    195                 200                 205

Thr Pro Gln Val Ser Val Val Gly Val Asp Gly Ala Arg Asn Ala Pro
    210                 215                 220

Thr Gly Asp Pro Asn Gly Pro Asp Ala Glu Val Met Leu Asp Leu Glu
225                 230                 235                 240

Val Ala Thr Gly Val Ala Asn Gly Ala Asp Leu Val Leu Tyr Met Ala
                245                 250                 255

Ala Asn Thr Asp Ala Ala Phe Tyr Ser Ala Ile Ala Thr Ala Leu Arg
            260                 265                 270

Asp Ala Thr His Ala Pro Val Ala Ile Ser Ile Ser Trp Gly Ala Pro
        275                 280                 285

Glu Glu Ser Tyr Pro Ala Thr Thr Ile Ala Ala Phe Glu Ser Val Leu
    290                 295                 300

Glu Glu Ala Val His Val Gly Val Thr Val Leu Val Ala Ala Gly Asp
305                 310                 315                 320

Gln Gly Ser Thr Asp Gly Val Asp Asp Gly Arg Ala His Val Asp Tyr
                325                 330                 335

Pro Ala Ala Ser Pro Tyr Val Leu Ala Cys Gly Gly Thr Arg Leu Asp
            340                 345                 350

Leu Asp Gly Thr Thr Ile Val Ala Glu Thr Val Trp Asn Asp Leu Pro
        355                 360                 365

Asn Gly Gly Ala Thr Gly Gly Ile Ser Ala Leu Phe Pro Val Pro
    370                 375                 380

Ser Trp Gln Ala Gly Ile Ala Met Pro Pro Ser Ala Asn Pro Gly Ala
```

```
                385                 390                 395                 400
Gly Pro Gly Arg Gly Val Pro Asp Val Ala Gly Asn Ala Asp Pro Asp
                    405                 410                 415

Thr Gly Tyr Arg Ile Val Val Asp Gly Val Ala Thr Val Gly Gly
                420                 425                 430

Thr Ser Ala Val Ala Pro Leu Trp Ala Gly Leu Val Ala Arg Cys His
                435                 440                 445

Gln Ala Gly Ala Arg Gly Phe Trp Asn Pro Leu Leu Tyr Ala Ala
450                 455                 460

Arg Gly Ser Ser Ala Phe His Glu Ile Thr Val Gly Ser Asn Gly Ala
465                 470                 475                 480

Tyr Asp Ala Gly Pro Ile Trp Asn Ala Cys Cys Gly Leu Gly Ser Pro
                    485                 490                 495

Asn Gly Thr Ala Ile Leu Gln Thr Leu Arg Ala
                500                 505

<210> SEQ ID NO 78
<211> LENGTH: 507
<212> TYPE: PRT
<213> ORGANISM: Artificial Sequence
<220> FEATURE:
<223> OTHER INFORMATION: Synthetic

<400> SEQUENCE: 78

Met Ala Pro Glu Glu Arg Arg Thr Leu Pro Gly Ser Ala Met Pro Arg
1               5                   10                  15

Pro Ala Gly Ala Gln Val Leu Gly Gln Ile Pro Asp Asp Glu Arg Val
                20                  25                  30

Glu Val Thr Val Val Leu Gln Pro Arg Ala Pro Leu Pro Glu Pro Gly
            35                  40                  45

Pro Thr Pro Met Ser Arg Ala Glu Leu Ala Asp Leu Arg Ser Pro Pro
    50                  55                  60

Glu Gly Ala Leu Glu Ala Ile Ala Arg Tyr Val Ala Gly Gln Gly Leu
65                  70                  75                  80

Glu Val Ile Ala Ala Asp Ala Pro Arg Arg Ile Val Leu Ala Gly
                85                  90                  95

Ser Ala Ala Arg Ile Ala Ala Leu Phe Gly Ile Ser Phe Val Arg Leu
                100                 105                 110

Gln Leu Glu Gly Arg Arg Tyr Arg Thr Tyr Glu Gly Glu Ile Ser Leu
            115                 120                 125

Pro Ala Glu Leu Ala Pro Leu Val Val Ala Val Leu Gly Leu Asp Thr
    130                 135                 140

Arg Pro Phe Ala Arg Ser His Arg Arg Pro Ala Val Ala Pro Asn Ala
145                 150                 155                 160

Pro Thr Thr Ala Pro Thr Val Arg Ala Tyr Asp Phe Pro Thr Ala
                165                 170                 175

Tyr Asp Gly Arg Gly Thr Thr Ile Gly Phe Ile Glu Leu Gly Gly Gly
                180                 185                 190

Phe Gln Glu Ser Asp Leu Val Arg Tyr Cys Glu Gly Leu Gly Leu Ser
            195                 200                 205

Thr Pro Gln Val Ser Val Gly Val Asp Gly Ala Arg Asn Ala Pro
    210                 215                 220

Thr Gly Asp Pro Asn Gly Pro Asp Ala Glu Val Met Leu Asp Leu Glu
225                 230                 235                 240

Val Ala Thr Gly Val Ala Asn Gly Ala Asp Leu Val Leu Tyr Met Ala
```

```
                245                 250                 255
Ala Asn Thr Asp Ala Ala Phe Tyr Ser Ala Ile Ala Thr Ala Leu Arg
            260                 265                 270

Asp Ala Thr His Ala Pro Val Ala Ile Ser Ile Ser Trp Ser Ala Pro
        275                 280                 285

Glu Glu Ser Tyr Pro Ala Thr Thr Ile Ala Ala Phe Glu Ser Val Leu
    290                 295                 300

Glu Glu Ala Val His Val Gly Val Thr Val Leu Val Ala Ala Gly Asp
305                 310                 315                 320

Gln Gly Ser Thr Gly Gly Val Asp Asp Gly Arg Ala His Val His Tyr
                325                 330                 335

Pro Ala Ala Ser Pro Tyr Val Leu Ala Cys Gly Gly Thr Arg Leu Asp
            340                 345                 350

Leu Asp Gly Thr Thr Ile Val Ala Glu Thr Val Trp Asn Asp Leu Pro
        355                 360                 365

Asn Gly Gly Ala Thr Gly Gly Ile Ser Ala Leu Phe Pro Val Pro
    370                 375                 380

Ser Trp Gln Ala Gly Ile Ala Met Pro Ser Ala Asn Pro Gly Ala
385                 390                 395                 400

Gly Pro Gly Arg Gly Val Pro Asp Val Ala Gly Asn Ala Asp Pro Asp
                405                 410                 415

Thr Gly Tyr Arg Ile Val Val Asp Gly Val Ala Thr Val Val Gly Gly
            420                 425                 430

Thr Ser Ala Val Ala Pro Leu Trp Ala Gly Leu Val Ala Arg Cys His
        435                 440                 445

Gln Ala Gly Ala Arg Gly Gly Phe Trp Asn Pro Leu Leu Tyr Ala Ala
    450                 455                 460

Arg Gly Ser Ser Ala Phe His Glu Ile Thr Val Gly Ser Asn Gly Ala
465                 470                 475                 480

Tyr Asp Ala Gly Pro Ile Trp Asn Ala Cys Cys Gly Leu Gly Ser Pro
                485                 490                 495

Asn Gly Thr Ala Ile Leu Gln Thr Leu Arg Ala
            500                 505

<210> SEQ ID NO 79
<211> LENGTH: 532
<212> TYPE: PRT
<213> ORGANISM: Artificial Sequence
<220> FEATURE:
<223> OTHER INFORMATION: Synthetic

<400> SEQUENCE: 79

Met Thr Lys Gln Pro Val Ser Gly Ser Ser Asp Lys Ile His Pro Asp
1               5                   10                  15

Asp Ala Lys Cys Ile Gly Asp Cys Asp Pro Ser Glu Gln Ile Glu Val
            20                  25                  30

Ile Val Met Leu Arg Arg Lys Asp Glu Ala Gly Phe Arg Gln Met Met
        35                  40                  45

Ser Arg Ile Asp Ala Gly Glu Ala Pro Gly Gln Ala Val Ser Arg Glu
    50                  55                  60

Glu Phe Asp Arg Arg Phe Thr Ala Ser Asp Glu Asp Ile Asp Lys Val
65                  70                  75                  80

Lys Ala Phe Ala Lys Gln Tyr Gly Leu Ser Val Glu Arg Ala Glu Thr
                85                  90                  95

Glu Thr Arg Ser Val Val Leu Lys Gly Thr Ile Glu Gln Phe Gln Lys
```

```
              100                 105                 110
Ala Phe Asp Val Lys Leu Glu Arg Phe Gln His His Asn Ile Gly Glu
              115                 120                 125
Tyr Arg Gly Arg Thr Gly Pro Val Asn Val Pro Asp Glu Met His Asp
              130                 135                 140
Ala Val Thr Ala Val Leu Gly Leu Asp Ser Lys Pro Gln Ala Arg Pro
145               150                 155                 160
His Phe Arg Phe Arg Pro Pro Phe Lys Pro Leu Arg Gly Ala Ala Pro
              165                 170                 175
Ala Ser Phe Ser Pro Val Asp Leu Ala Lys Leu Tyr Asp Phe Pro Asp
              180                 185                 190
Gly Asp Gly Ala Gly Gln Cys Ile Ala Ile Ile Glu Leu Gly Gly Gly
              195                 200                 205
Tyr Arg Asp Ser Asp Leu Ser Ala Tyr Phe Ser Lys Leu Gly Val Lys
              210                 215                 220
Ala Pro Thr Val Val Pro Val Gly Val Asp Gly Gly Lys Asn Ala Pro
225               230                 235                 240
Thr Gly Asn Pro Asn Gly Pro Asp Gly Glu Val Thr Leu Asp Ile Glu
                  245                 250                 255
Ile Ala Gly Ala Ile Ala Pro Gly Ala Arg Ile Ala Val Tyr Phe Ala
                  260                 265                 270
Pro Asn Ser Asp Ala Gly Phe Val Asp Ala Val Asn Arg Ala Leu His
              275                 280                 285
Asp Ala Ala Asn Lys Pro Ser Val Ile Ser Ile Ser Trp Gly Gly Pro
              290                 295                 300
Glu Ser Asn Trp Ser Pro Gln Ser Met Ser Ala Phe Asn Asp Val Leu
305               310                 315                 320
Gln Ser Ala Ala Ala Leu Gly Val Thr Val Cys Ala Ala Ser Gly Asp
                  325                 330                 335
Gly Gly Ser Ala Asp Gly Val Gly Asp Gly Ala Asp His Val Asp Phe
                  340                 345                 350
Pro Ala Ser Ser Pro Tyr Val Leu Gly Cys Gly Gly Thr Ser Leu Ala
                  355                 360                 365
Ala Ser Gly Ala Gly Ile Ala Lys Glu Val Val Trp Asn Asp Gly Asp
              370                 375                 380
Gln Gly Gly Ala Gly Gly Gly Val Ser Gly Thr Phe Ala Leu Pro
385                   390                 395                 400
Val Trp Gln Lys Gly Leu Ser Val Thr Arg Asn Gly Lys His Ile Ala
                  405                 410                 415
Leu Ala Lys Arg Gly Val Pro Asp Val Ala Gly Asp Ala Ser Pro Gln
              420                 425                 430
Thr Gly Tyr Glu Val Leu Ile Asp Gly Glu Asp Thr Val Val Gly Gly
              435                 440                 445
Thr Ser Ala Val Ala Pro Leu Trp Ala Ala Leu Ile Ala Arg Ile Asn
              450                 455                 460
Ala Ile Asp Ala Ser Pro Ala Gly Phe Val Asn Pro Lys Leu Tyr Lys
465               470                 475                 480
Ala Lys Thr Ala Phe Arg Asp Ile Thr Glu Gly Asn Asn Gly Ser Phe
                  485                 490                 495
Ser Ala Ala Ala Gly Trp Asp Ala Cys Thr Gly Met Gly Ser Pro Asp
                  500                 505                 510
Gly Gly Lys Ile Ala Ala Ala Leu Lys Pro Ala Lys Pro Ser Gln Ser
              515                 520                 525
```

Ala Gly Gln Gln
    530

<210> SEQ ID NO 80
<211> LENGTH: 544
<212> TYPE: PRT
<213> ORGANISM: Artificial Sequence
<220> FEATURE:
<223> OTHER INFORMATION: Synthetic

<400> SEQUENCE: 80

Met Gly Arg Leu Gln Gly Ser Tyr Arg Pro Ser Leu Gly Thr Pro Val
1               5                   10                  15

Gly Pro Val Pro Asp Asp Gln Pro Ile Asp Val Thr Val Val Leu Arg
            20                  25                  30

Pro Thr Ala Ala Asp Asp Phe Arg Ala Asp Pro Asp Asp Val Ala Ala
        35                  40                  45

Val Arg Ala Phe Ala Gly Arg Ala Gly Leu Asp Val Ala Glu Val Asp
    50                  55                  60

Glu Pro Ala Arg Thr Val Arg Leu Arg Gly Pro Ala Ala Ala Ala Arg
65                  70                  75                  80

Thr Ala Phe Asp Thr Pro Leu Ala Leu Tyr Asp Ser Gly Gly Arg Ala
                85                  90                  95

Ile Arg Gly Arg Glu Gly Asp Leu Gly Leu Pro Asp Glu Leu Asp Asp
            100                 105                 110

Arg Val Val Ala Val Leu Gly Leu Asp Glu Arg Pro Ala Ala Arg Pro
        115                 120                 125

Arg Phe Gln Pro Ala Ala Ser Ala Arg Gln Gly Leu Thr Ala Leu Gln
    130                 135                 140

Val Ala Arg Ala Tyr Asp Phe Pro Ala Ala Thr Gly Glu Gly Gln Thr
145                 150                 155                 160

Ile Ala Ile Ile Glu Leu Gly Gly Gly Phe Gly Gln Ala Asp Leu Asp
                165                 170                 175

Thr Tyr Phe Gly Gly Leu Asp Leu Pro Thr Pro Ala Val Ser Ala Val
            180                 185                 190

Gly Val Gln Gly Ala Ala Asn Val Pro Gly Gly Asp Pro Asp Gly Ala
        195                 200                 205

Asp Gly Glu Val Leu Leu Asp Ile Glu Val Ala Gly Ala Val Ala Pro
    210                 215                 220

Gly Ala Ala Gln Val Val Tyr Phe Ala Pro Asn Thr Asp Ala Gly Phe
225                 230                 235                 240

Leu Ala Ala Ile Asn Ala Ala Ala Ala Thr Pro Arg Pro Ala Ala
                245                 250                 255

Ile Ser Ile Ser Trp Gly Gly Pro Glu Ser Ser Trp Thr Ala Gln Ala
            260                 265                 270

Met Arg Ala Tyr Asp Gln Ala Phe Ala Ala Arg Ala Ala Gly Ile
    275                 280                 285

Thr Val Leu Ala Ala Ala Gly Asp Ala Gly Asp Asp Ala Thr Asp
290                 295                 300

Arg Leu Val Ala Asp Phe Pro Ala Gly Ser Pro Asn Val Ile Ala Cys
305                 310                 315                 320

Gly Gly Thr Lys Leu Thr Leu Asp Ala Gly Ala Arg Ala Ser Glu
                325                 330                 335

Val Val Trp Asn Glu Ala Ala Asp Ser Ala Thr Gly Gly Gly Tyr Ser
            340                 345                 350

```
Ala Thr Phe Thr Arg Pro Ala Trp Gln Pro Ala Ala Val Gly Arg Tyr
        355                 360                 365

Arg Gly Leu Pro Asp Ile Ser Gly Asn Ala Asp Pro Gln Thr Gly Tyr
    370                 375                 380

Arg Val Val Val Asp Gly Gln Pro Thr Val Val Gly Gly Thr Ser Ala
385                 390                 395                 400

Val Ala Pro Leu Leu Ala Gly Leu Val Ala Arg Leu Ala Gln Leu Thr
                405                 410                 415

Gly Ala Pro Val Ala Asp Leu Ala Ala Val Ala Tyr Ala Asn Pro Ala
            420                 425                 430

Ala Phe Thr Asp Ile Thr Ala Gly Asp Asn Gln Gly Tyr Pro Ala Arg
        435                 440                 445

Ser Gly Trp Asp Pro Ala Ser Gly Leu Gly Ser Pro Val Gly Thr Lys
    450                 455                 460

Leu Leu Thr Ala Val Gly Gly Pro Thr Pro Pro Thr Thr Pro Pro
465                 470                 475                 480

Pro Thr Thr Pro Pro Thr Thr Pro Pro Thr Ile Pro Pro Pro
                485                 490                 495

Thr Thr Pro Pro Thr Gln Thr Val Asp Ala Ala Asp Arg Ala Leu Trp
            500                 505                 510

Ser Ala Val Ala Thr Trp Ala Gly Gly Thr His Thr Gly Ala Asn Ala
        515                 520                 525

Arg Ala Ala Lys Ala Val Arg Ala Trp Ala Gln Ala Lys Ser Leu Ala
    530                 535                 540
```

<210> SEQ ID NO 81
<211> LENGTH: 523
<212> TYPE: PRT
<213> ORGANISM: Artificial Sequence
<220> FEATURE:
<223> OTHER INFORMATION: Synthetic

<400> SEQUENCE: 81

```
Met Thr Gln Pro Arg Tyr Thr Pro Leu Pro Gly Ser Glu Arg Glu Ala
1               5                   10                  15

Pro Leu Leu Ala Ala Arg Ser Asn Ala Thr Ala Ala Arg Ala Ser Arg
            20                  25                  30

Ala Gln Thr Ala Ser Ala Thr Val Val Leu Arg Arg Ser Glu Leu
        35                  40                  45

Pro Glu Ala Leu Val Leu Asp Gln Gln Phe Ile Ser Ser Asp Glu Leu
    50                  55                  60

Ala Ala Arg Tyr Gly Ala Asp Pro Val Asp Ile Glu Lys Val Arg Ser
65                  70                  75                  80

Val Leu Glu Arg Phe Lys Val Ser Val Val Glu Val Asp Ala Ala Ser
                85                  90                  95

Arg Arg Val Lys Val Glu Gly Ala Val Ala Asp Ile Glu Arg Ala Phe
            100                 105                 110

Asn Ile Ala Leu His Ser Ala Ser Gly Thr Asp Pro His Ser Gly Arg
        115                 120                 125

Gly Phe Glu Tyr Arg Tyr Arg Thr Gly Val Leu Ser Val Pro Ala Glu
    130                 135                 140

Leu Gly Gly Ile Val Thr Ala Val Leu Gly Leu Asp Asn Arg Gln
145                 150                 155                 160

Ala Glu Thr Arg Leu Arg Val Val Pro Ala Ala Leu Gly Ser Ser
                165                 170                 175
```

Tyr Thr Pro Val Gln Leu Gly Glu Ile Tyr Asn Phe Pro Gln Asp Ala
                180                 185                 190

Thr Gly Ala Gly Gln Arg Ile Ala Ile Glu Leu Gly Gly Gly Tyr
    195                 200                 205

Thr Pro Ala Gly Leu Arg Arg Tyr Phe Ala Ser Leu Gly Val Val Pro
210                 215                 220

Pro Lys Val Ala Ala Val Ser Val Asp Gly Ala Gln Asn Ala Pro Gly
225                 230                 235                 240

Pro Asp Pro Gly Ala Asp Gly Glu Val Gln Leu Val Glu Val Ala
                245                 250                 255

Gly Ala Leu Ala Pro Gly Ala His Val Leu Val Tyr Phe Ala Pro Asn
                260                 265                 270

Thr Asp Gln Gly Phe Leu Asp Ala Val Ser Gln Ala Ala His Ala Thr
                275                 280                 285

Pro Pro Pro Thr Ala Ile Ser Ile Ser Trp Gly Ala Ser Glu Asp Ser
                290                 295                 300

Trp Thr Ala Ser Ala Arg Asp Ala Leu Asn Gln Ala Leu Arg Asp Ala
305                 310                 315                 320

Ala Ala Leu Gly Val Thr Val Thr Ala Ala Gly Asp Ser Gly Ser
                325                 330                 335

Ser Asp Gly Val Pro Asp Arg Arg Ala His Val Asp Phe Pro Ala Ser
                340                 345                 350

Ser Pro Tyr Val Leu Ala Thr Gly Gly Thr Ser Leu Arg Ala Asp Pro
                355                 360                 365

Ala Thr Gly Val Val Gln Ser Glu Thr Val Trp Asn Asp Ser Gln Gly
                370                 375                 380

Ser Thr Gly Gly Gly Val Ser Asp Val Phe Pro Arg Pro Ala Trp Gln
385                 390                 395                 400

Ala His Val Asp Val Pro His Ala Gly Arg Gly Val Pro Asp Val Ser
                405                 410                 415

Ala Val Ala Asp Pro Ala Thr Gly Tyr Gln Val Leu Val Asp Asn Gln
                420                 425                 430

Pro Ala Val Ile Gly Gly Thr Ser Ala Val Ala Pro Leu Trp Ala Ala
                435                 440                 445

Leu Val Ala Arg Leu Ala Glu Ser Leu Gly Arg Pro Leu Gly Leu Leu
450                 455                 460

Gln Pro Leu Val Tyr Pro Arg Thr Pro Gly Ser Thr Ala Tyr Pro Gly
465                 470                 475                 480

Phe Arg Asp Ile Thr Ile Gly Asn Asn Gly Ala Tyr Lys Ala Gly Lys
                485                 490                 495

Gly Trp Asp Ala Ala Thr Gly Leu Gly Val Pro Asp Gly Thr Glu Leu
                500                 505                 510

Leu Ala His Leu Arg Gly Leu Asn Gly Ser Glu
                515                 520

<210> SEQ ID NO 82
<211> LENGTH: 537
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (106)..(106)
<223> OTHER INFORMATION: Xaa is I, V or D
<220> FEATURE:

```
<221> NAME/KEY: MISC_FEATURE
<222> LOCATION: (244)..(244)
<223> OTHER INFORMATION: Xaa is N, S, K, or G
<220> FEATURE:
<221> NAME/KEY: MISC_FEATURE
<222> LOCATION: (273)..(273)
<223> OTHER INFORMATION: Xaa is N or D
<220> FEATURE:
<221> NAME/KEY: MISC_FEATURE
<222> LOCATION: (274)..(274)
<223> OTHER INFORMATION: Xaa is S or T
<220> FEATURE:
<221> NAME/KEY: MISC_FEATURE
<222> LOCATION: (275)..(275)
<223> OTHER INFORMATION: Xaa is D, A, T or N
<220> FEATURE:
<221> NAME/KEY: MISC_FEATURE
<222> LOCATION: (301)..(301)
<223> OTHER INFORMATION: Xaa is G or S
<220> FEATURE:
<221> NAME/KEY: MISC_FEATURE
<222> LOCATION: (340)..(340)
<223> OTHER INFORMATION: Xaa is D, N, or G
<220> FEATURE:
<221> NAME/KEY: MISC_FEATURE
<222> LOCATION: (350)..(350)
<223> OTHER INFORMATION: Xaa is D, S, or H

<400> SEQUENCE: 82

Met Ala Arg His Leu His Ala Gly Ser Glu Pro Lys Val Ile Thr Glu
1               5                   10                  15

Ser Lys Cys Ile Gly Ala Cys Asp Pro Ala Glu Arg Ile His Val Thr
            20                  25                  30

Val Met Leu Arg Arg Glu Gly Glu Gln Ala Leu Asp Ala Leu Val Asp
        35                  40                  45

Lys Leu Ala Ser Gly Asp Pro Ala Ala Lys Pro Val Ser Arg Glu Asp
    50                  55                  60

Phe Ala Lys Arg Phe Gly Ala Arg Ala Asp Asp Ile Gln His Thr Glu
65                  70                  75                  80

Ala Phe Ala Lys Arg His Gln Leu Thr Val Glu Arg Val Asp Pro Val
                85                  90                  95

Gln Ser Val Val Glu Leu Ala Gly Thr Xaa Ala Gln Phe Glu Asn Ala
            100                 105                 110

Phe Gly Val Lys Leu Glu Lys Tyr Glu His His Ala Ile Gly Ser Phe
        115                 120                 125

Arg Ala Arg Thr Gly Ala Ile Ala Leu Pro Asp Glu Leu His Asp Ala
    130                 135                 140

Val Thr Ala Val Leu Gly Leu Asp Thr Arg Pro Gln Ala His Pro His
145                 150                 155                 160

Phe Arg Phe Arg Pro Pro Phe Gln Pro Ala Arg Ser Gly Ala Gly Thr
                165                 170                 175

Ser Tyr Thr Pro Leu Gln Leu Ala Ser Ile Tyr Asn Phe Pro Glu Gly
            180                 185                 190

Asp Gly Ala Gly Gln Cys Ile Ala Leu Val Glu Leu Gly Gly Gly Tyr
        195                 200                 205

Arg Ala Ala Asp Ile Arg Gln Tyr Phe Glu Gln Leu Gly Val Lys Pro
    210                 215                 220

Pro Lys Leu Val Asp Val Ser Val Asn Gly Arg Asn Ala Pro Thr
225                 230                 235                 240

Asp Asp Pro Xaa Gly Pro Asp Gly Glu Val Ala Leu Asp Ile Glu Val
                245                 250                 255

Ala Gly Ala Ile Ala Pro Gly Ala Thr Ile Ala Val Tyr Phe Ala Gly
```

```
                260             265             270
Xaa Xaa Xaa Ala Gly Phe Ile Gln Ser Val Asn Gln Ala Ile His Asp
        275             280             285
Ser Thr Asn Arg Pro Ser Val Val Ser Ile Ser Trp Xaa Gly Pro Glu
    290             295             300
Ala Ser Trp Thr Gln Gln Ser Ile Thr Ala Phe Asn Asn Val Leu Lys
305             310             315             320
Thr Ala Ala Ser Leu Gly Val Thr Val Cys Ala Ala Ser Gly Asp Ser
                325             330             335
Gly Ser Ser Xaa Gly Leu Gln Asp Gly Ser Asn His Val Xaa Phe Pro
        340             345             350
Ala Ser Ser Pro Tyr Val Leu Ala Cys Gly Gly Thr Thr Leu Asp Ala
    355             360             365
Gln Ala Gly Gln Gly Ile Arg Arg Glu Val Val Trp Asn Asp Glu Ala
370             375             380
Ala Ser Gly Gly Ala Gly Gly Gly Val Ser Ala Val Phe Pro Ala
385             390             395             400
Pro Ser Tyr Gln Lys Gly Leu Ser Ala Lys Ala Thr Gly Gly Ser
                405             410             415
Thr Pro Leu Ser Gln Arg Gly Val Pro Asp Val Ala Gly Asp Ala Ser
        420             425             430
Pro Thr Thr Gly Tyr Ile Ile Ser Ile Ala Gly Thr Thr Ala Val Leu
    435             440             445
Gly Gly Thr Ser Ala Val Ala Pro Leu Trp Ala Ala Leu Ile Ala Arg
450             455             460
Ile Asn Ala Asn Gly Lys Ser Pro Val Gly Trp Ala Asn Pro Lys Leu
465             470             475             480
Tyr Ala Gln Pro Gly Ala Phe His Asp Ile Thr Gln Gly Asn Asn Gly
                485             490             495
Ala Phe Ala Ala Ser Glu Gly Trp Asp Ala Cys Thr Gly Leu Gly Ser
        500             505             510
Pro Asp Gly Ala Lys Val Ala Ala Leu Gln Gly Ala Ser Gly Gly
    515             520             525
Ser Gln Gln Gly Arg Ala Thr Gly Ala
    530             535
```

<210> SEQ ID NO 83
<211> LENGTH: 519
<212> TYPE: PRT
<213> ORGANISM: Artificial Sequence
<220> FEATURE:
<223> OTHER INFORMATION: Synthetic

<400> SEQUENCE: 83

```
Met Thr Lys His Pro Leu Pro Gly Ser Glu Arg Val Leu Ala Pro Gly
1               5               10              15
Ser Lys Val Val Ala Gln Cys Asp Pro Ser Glu Thr Ile Glu Val Val
            20              25              30
Val Val Leu Arg Arg Lys Asn Glu Gln Gln Phe Ala Gln Met Met Lys
        35              40              45
Thr Ile Glu Ala Gly Ala Ala Gly Ala Arg Pro Leu Thr Arg Glu Glu
    50              55              60
Leu Glu Gln Arg Phe Gly Ala Leu Pro Glu Asp Ile Ala Lys Leu Lys
65              70              75              80
Ala Phe Ala Ala Gln His Gly Leu Ser Val Val Arg Glu Asp Ala Ser
```

-continued

```
                85                  90                  95
Ala Arg Thr Val Val Leu Ser Gly Arg Ile Glu Gln Phe Gln Gln Ala
            100                 105                 110

Phe Asp Val Gln Leu Gln His Tyr Glu His Gln Ser Met Gly Arg Phe
            115                 120                 125

Arg Gly Arg Thr Gly Ala Ile Ser Val Pro Asp Glu Leu His Gly Val
        130                 135                 140

Val Thr Ala Val Leu Gly Leu Asp Asp Arg Pro Gln Ala Arg Pro His
145                 150                 155                 160

Phe Arg Ile Arg Pro Pro Phe Gln Pro Ala Arg Ala Gln Ser Ala Ser
                165                 170                 175

Ser Phe Thr Pro Leu Gln Leu Ala Ser Leu Tyr Arg Phe Pro Gln Gly
            180                 185                 190

Asp Gly Ser Gly Gln Cys Ile Gly Ile Val Glu Leu Gly Gly Gly Tyr
            195                 200                 205

Arg Thr Ala Asp Leu Asp Ser Tyr Phe Ser Ser Leu Gly Val Gly Ser
        210                 215                 220

Pro Lys Val Val Ala Val Gly Val Asp Gln Ser Gly Asn Gln Pro Thr
225                 230                 235                 240

Gly Asp Pro Asn Gly Pro Asp Gly Glu Val Thr Leu Asp Ile Glu Ile
                245                 250                 255

Ala Gly Ala Leu Ala Pro Ala Ala Thr Ile Ala Val Tyr Phe Thr Thr
            260                 265                 270

Asn Ser Asp Ala Gly Phe Ile Asp Ala Val Ser Gln Ala Val His Asp
            275                 280                 285

Arg Thr Asn Gln Pro Ser Val Ile Ser Ile Ser Trp Gly Ala Pro Glu
        290                 295                 300

Ser Met Trp Thr Ala Gln Ser Met Lys Ala Leu Asn Asp Val Leu Gln
305                 310                 315                 320

Ser Ala Ala Ile Gly Val Thr Val Cys Ala Ala Ser Gly Asp Ser
                325                 330                 335

Gly Ser Ser Asp Gly Val Gly Asp Gly Arg Asp His Val Asp Phe Pro
            340                 345                 350

Ala Ser Ser Pro Tyr Val Leu Ala Cys Gly Gly Thr Ser Leu Gln Gly
            355                 360                 365

Ser Gly Arg Thr Val Ala His Glu Val Val Trp Asn Asp Gly Ser Asn
        370                 375                 380

Gly Gly Ala Thr Gly Gly Val Ser Gly Ala Phe Pro Val Pro Ala
385                 390                 395                 400

Trp Gln Glu Gly Leu Ser Thr Ser Ala Ala Gln Gly Gly Gln Arg Ala
                405                 410                 415

Leu Thr Gly Arg Gly Val Pro Asp Val Ala Gly Asp Ala Ser Pro Leu
            420                 425                 430

Thr Gly Tyr Asp Val Ile Val Asp Gly Asn Asn Thr Val Ile Gly Gly
            435                 440                 445

Thr Ser Ala Val Ala Pro Leu Trp Ala Ala Leu Ile Ala Arg Ile Asn
        450                 455                 460

Gly Ala Lys Gly Ala Pro Val Gly Phe Val Asn Pro Lys Leu Tyr Lys
465                 470                 475                 480

Ala Ser Ala Cys Asn Asp Ile Thr Gln Gly Asn Asn Gly Ser Tyr Ala
                485                 490                 495

Ala Thr Thr Gly Trp Asp Ala Cys Thr Gly Leu Gly Ser Pro Asp Gly
            500                 505                 510
```

Val Lys Val Ala Ala Ala Leu
        515

<210> SEQ ID NO 84
<211> LENGTH: 512
<212> TYPE: PRT
<213> ORGANISM: Artificial Sequence
<220> FEATURE:
<223> OTHER INFORMATION: Synthetic

<400> SEQUENCE: 84

Met Ser Pro Ile Ala Ser Arg Arg Ser Ala Leu Pro Leu Ser Glu Arg
1               5                   10                  15

Pro Ala Pro Glu Asn Ala Arg Ala Leu Ala Ala Val Glu Pro Asp Arg
            20                  25                  30

Thr Met Thr Val Ser Val Leu Val Arg Arg Lys Lys Pro Leu Val Leu
        35                  40                  45

Ala Asp Leu Glu Gly Lys Lys Leu Thr His Arg Glu Phe Glu Arg Arg
50                  55                  60

Tyr Gly Ala Ser Glu Lys Asp Phe Ala Thr Ile Ala Lys Phe Ala Ala
65                  70                  75                  80

Gly His Gly Leu Ala Val Asp His His Ala Ser Ser Leu Ala Arg Arg
                85                  90                  95

Thr Val Val Leu Arg Gly Thr Arg Gln Met Gln Gln Ala Phe Gly
            100                 105                 110

Val Thr Leu His Asp Tyr Glu Asp Ser Glu Thr Gln Gln Arg Tyr His
        115                 120                 125

Ser Phe Thr Gly Ala Ile Thr Val Pro Ala Ala His Ala Arg Ile Ile
130                 135                 140

Glu Ser Val Leu Gly Leu Asp Ala Arg Pro Ile Ala Lys Pro His Phe
145                 150                 155                 160

Arg Val Arg Lys Arg Ser Ala Ala Thr Gly Ala Val Ser Phe Asn
                165                 170                 175

Pro Pro Gln Val Ala Ser Leu Tyr Ser Phe Pro Thr Gly Val Asp Gly
            180                 185                 190

Ser Gly Glu Thr Ile Gly Ile Leu Glu Leu Gly Gly Tyr Glu Thr
        195                 200                 205

Ser Asp Ile Gln Gln Tyr Phe Ser Gly Leu Gly Ile Gln Pro Pro Thr
210                 215                 220

Val Val Ala Val Ser Val Asp Gly Ala Val Asn Ala Pro Gly Asn Pro
225                 230                 235                 240

Asn Gly Ala Asp Gly Glu Val Ala Leu Asp Ile Gln Val Ala Gly Ser
            245                 250                 255

Ile Ala Pro Gly Ala Lys Leu Ala Val Tyr Phe Ala Pro Asn Thr Glu
        260                 265                 270

Gln Gly Phe Val Asp Ala Ile Thr Thr Ala Val His Asp Thr Ala Asn
        275                 280                 285

Lys Pro Ser Val Leu Ser Ile Ser Trp Gly Gly Pro Glu Ser Ser Trp
290                 295                 300

Pro Gln Ala Ala Ala Gln Ser Leu Asn Asn Ala Cys Glu Ser Ala Ala
305                 310                 315                 320

Ala Leu Gly Val Thr Ile Thr Val Ala Ser Gly Asp Asn Gly Ser Thr
            325                 330                 335

Asp Gly Val Gln Asp Gly Gln Asn His Val Asp Phe Pro Ala Ser Ser
        340                 345                 350

```
Pro Tyr Val Leu Ala Cys Gly Gly Thr Tyr Leu Ala Ala Val Asn Asn
            355                 360                 365

Gly Val Pro Gln Glu Ser Val Trp Asp Asp Leu Ala Ser Gly Gly Gly
    370                 375                 380

Ala Thr Gly Gly Val Ser Ala Leu Phe Pro Leu Pro Ala Trp Gln
385                 390                 395                 400

Thr Gly Ala Asn Val Pro Gly Gly Ser Met Arg Gly Val Pro Asp Val
                405                 410                 415

Ala Gly Asp Ala Ser Pro Glu Ser Gly Tyr Asn Val Leu Val Asp Gly
            420                 425                 430

Gln Pro Gln Val Val Gly Gly Thr Ser Ala Val Ala Pro Leu Trp Ala
            435                 440                 445

Ala Leu Ile Ala Leu Val Asn Gln Gln Lys Gly Glu Ala Ala Gly Phe
            450                 455                 460

Val Asn Ala Ala Leu Tyr Gln Asn Pro Ser Ala Phe His Asp Ile Thr
465                 470                 475                 480

Gln Gly Ser Asn Gly Ala Tyr Ala Ala Pro Gly Trp Asp Pro Cys
                485                 490                 495

Thr Gly Leu Gly Ser Pro Met Gly Thr Ala Ile Ala Lys Ile Leu Ala
            500                 505                 510
```

<210> SEQ ID NO 85
<211> LENGTH: 531
<212> TYPE: PRT
<213> ORGANISM: Artificial Sequence
<220> FEATURE:
<223> OTHER INFORMATION: Synthetic

<400> SEQUENCE: 85

```
Met Ser Ala Phe Asp Gln Leu Val Pro Leu Pro Gly Ser Glu Lys Thr
1               5                   10                  15

Val Pro Asp Ala Ala Pro Ser Gln Thr Leu Asp Pro Asn Glu Val Leu
            20                  25                  30

Thr Val Thr Ile Arg Ile Arg Arg Lys Arg Thr Leu Ala Ser Leu Val
        35                  40                  45

Ser Thr Thr Ala Pro Val Thr Glu Val Val Ser Arg Ser Glu Tyr Ala
    50                  55                  60

Ser Arg Phe Gly Ala Asp Pro Ala Ile Val Lys Gln Val Glu Ala Phe
65                  70                  75                  80

Ala Ser Ala Tyr Asp Leu Ser Leu Val Glu Gln Ser Leu Ala Arg Arg
                85                  90                  95

Ser Val Leu Leu Arg Gly Thr Val Ala Gln Met Glu Gln Ala Phe Gly
            100                 105                 110

Val Ser Leu Ala Asn Tyr Gln Leu Ala Asp Gly Thr Val Phe Arg Gly
        115                 120                 125

Arg Thr Gly Val Val Asn Val Pro Ser Glu Leu Val Glu His Ile Glu
    130                 135                 140

Gly Val Phe Gly Leu Asp Asn Arg Pro Gln Ala Arg Ala His Phe Gln
145                 150                 155                 160

Val Tyr Lys Pro Glu Lys Gly Thr Lys Val Ala Pro Arg Ala Gly Gly
                165                 170                 175

Ile Ser Tyr Thr Pro Pro Gln Leu Ala Arg Leu Tyr Asn Phe Pro Thr
            180                 185                 190

Gly Val Thr Gly Lys Gly Gln Cys Ile Ala Ile Ile Glu Leu Gly Gly
        195                 200                 205
```

Gly Phe Arg Thr Ala Asp Ile Lys Thr Tyr Phe Gly Gly Leu Gly Leu
            210                 215                 220

Lys Pro Pro Thr Val Val Ala Val Ser Val Asp Gly Gly His Asn Ala
225                 230                 235                 240

Pro Ser Thr Ala Asp Ser Ala Asp Gly Glu Val Met Leu Asp Ile Asp
                245                 250                 255

Val Ala Gly Gly Val Ala Pro Gly Ala Lys Ile Val Val Tyr Phe Ala
            260                 265                 270

Pro Asn Thr Asp Gln Gly Phe Leu Asp Ala Ile Thr Thr Ala Met His
        275                 280                 285

Asp Thr Lys Asn Lys Pro Ser Val Ile Ser Ile Ser Trp Gly Ala Ala
    290                 295                 300

Glu Ser Asn Trp Thr Pro Gln Ala Leu Thr Ser Phe Asn Gln Ala Phe
305                 310                 315                 320

Gln Ala Ala Ala Leu Gly Ile Thr Val Cys Ala Ala Ala Gly Asp
                325                 330                 335

Thr Gly Ser Asp Asp Ser Val Gly Asp Gly Lys Ala His Val Asp Phe
                340                 345                 350

Pro Ala Ser Ser Pro Phe Val Leu Ala Cys Gly Gly Thr Lys Leu Thr
            355                 360                 365

Ala Thr Asp Asn Val Ile Ala Ser Glu Val Val Trp His Glu Ser Lys
        370                 375                 380

Thr Ser Ala Thr Gly Gly Val Ser Asp Val Phe Asp Leu Pro Asp
385                 390                 395                 400

Tyr Gln Gln Lys Ser His Val Pro Pro Ser Val Asn Asp Lys Thr Arg
                405                 410                 415

Ile Gly Arg Gly Val Pro Asp Val Ala Ala Val Ala Asp Pro Val Thr
            420                 425                 430

Gly Tyr Ala Val Arg Val Asp Gly Ser Asn Leu Val Phe Gly Gly Thr
        435                 440                 445

Ser Ala Val Ala Pro Leu Met Ala Gly Leu Ile Ala Leu Ile Asn Gln
    450                 455                 460

Gln Arg Gly Lys Ala Val Gly Phe Ile His Pro Leu Ile Tyr Ala Asn
465                 470                 475                 480

Pro Ser Ala Phe Arg Asp Ile Thr Gln Gly Asn Asn Thr Thr Thr Thr
                485                 490                 495

Gly Asn Lys Gly Tyr Ala Ala Thr Thr Gly Trp Asp Ala Cys Thr Gly
            500                 505                 510

Leu Gly Val Ala Asp Gly Lys Lys Leu Ala Ser Val Leu Thr Ala Thr
        515                 520                 525

Pro Val Ala
    530

<210> SEQ ID NO 86
<211> LENGTH: 567
<212> TYPE: PRT
<213> ORGANISM: Artificial Sequence
<220> FEATURE:
<223> OTHER INFORMATION: Synthetic

<400> SEQUENCE: 86

Met Ala Ala Thr Pro Arg Phe Ala Ser Gln Pro Arg Val Thr Leu Pro
1               5                   10                  15

Gly Ser Gln Lys His Pro Leu Thr Thr Asp Thr Glu Val Pro Pro Pro
            20                  25                  30

```
Ala Pro Val Lys Ala Ala Thr Lys Leu Ser Ala Thr Pro Phe Thr
         35                  40                  45
Val Thr Val Ile Val Lys Arg Lys Asn Pro Leu Asn Leu Lys Gln Val
 50                  55                  60
Leu Lys Pro Ala Gly Arg Leu Thr His Ala Ala Phe Ala Lys Ala His
 65                  70                  75                  80
Gly Pro Ser Pro Asp Gly Val Lys Leu Val Lys Ala Phe Ala Lys Glu
                 85                  90                  95
Phe Gly Leu Thr Val Ala Pro Ala Pro Gly Gln Gly Arg Arg Ala Leu
                100                 105                 110
Tyr Leu Thr Gly Thr Ala Ala Met Gln Thr Ala Phe Gly Val Thr
            115                 120                 125
Phe Ala Thr Lys Ile Met Glu Gly Thr Lys Tyr Arg Val Arg Glu Gly
            130                 135                 140
Asp Ile Cys Leu Pro Lys Glu Leu Ile Gly His Val Asp Ala Val Leu
145                 150                 155                 160
Gly Leu Asp Asn Arg Pro Gln Ala Lys Pro His Phe Arg His His Lys
                165                 170                 175
Pro Ala Ala Thr Ser Val Ser Tyr Thr Pro Val Gln Val Gly Gln Leu
            180                 185                 190
Tyr Gly Phe Pro Ser Gly Ala Lys Ala Thr Gly Gln Thr Ile Gly Leu
            195                 200                 205
Ile Glu Leu Gly Gly Gly Phe Arg Ala Ala Asp Ile Thr Ala Tyr Phe
    210                 215                 220
Lys Thr Leu Gly Gln Thr Ala Pro Lys Val Thr Ala Val Leu Val Asp
225                 230                 235                 240
Lys Ala Lys Asn Thr Pro Thr Thr Ser Ser Ala Asp Gly Glu Val
                245                 250                 255
Met Leu Asp Ile Glu Val Ala Ala Val Ala Pro Gly Ala Asn Ile
            260                 265                 270
Ala Val Tyr Phe Ala Pro Asn Thr Asp Gln Gly Phe Ile Asp Ala Ile
        275                 280                 285
Ser Gln Ala Val His Asp Thr Val Asn Lys Pro Ser Val Ile Ser Ile
    290                 295                 300
Ser Trp Gly Gly Pro Glu Ser Thr Trp Thr Ala Gln Ser Leu Ala Ala
305                 310                 315                 320
Leu Asp Ala Ala Cys Gln Ser Ala Ala Leu Gly Ile Thr Ile Thr
                325                 330                 335
Val Ala Ala Gly Asp Asp Gly Ser Thr Asp Gly Val Lys Gly Thr Val
                340                 345                 350
Asn His Val Asp Phe Pro Ala Ser Ser Pro His Val Leu Gly Cys Gly
            355                 360                 365
Gly Thr Lys Leu Leu Gly Ser Gly Thr Thr Ile Thr Ser Glu Val Val
    370                 375                 380
Trp Asn Glu Leu Thr Ala Asn Glu Gly Ala Thr Gly Gly Gly Val Ser
385                 390                 395                 400
Asn Val Phe Pro Leu Pro Thr Trp Gln Ala Lys Ser Asn Val Pro Lys
                405                 410                 415
Pro Thr Val Ala Ala Gly Gly Arg Gly Val Pro Asp Val Ser Gly Asn
            420                 425                 430
Ala Asp Pro Ser Thr Gly Tyr Thr Val Arg Val Asp Gly Ser Thr Phe
            435                 440                 445
```

```
Pro Ile Gly Gly Thr Ser Ala Val Ala Pro Leu Trp Ala Gly Leu Ile
450                 455                 460

Ala Leu Cys Asn Ala Gln Asn Lys Thr Thr Ala Gly Phe Ile Asn Pro
465                 470                 475                 480

Ala Leu Tyr Ala Ala Ala Ala Lys Ser Phe Arg Asp Ile Thr Ser
            485                 490                 495

Gly Asn Asn Gly Gly Phe Lys Ala Gly Pro Gly Trp Asp Ala Cys Thr
                500                 505                 510

Gly Leu Gly Ser Pro Ile Gly Thr Ala Ile Ala Lys Thr Leu Ala Pro
            515                 520                 525

Ala Thr Lys Ser Thr Ser Lys Thr Ala Val Lys Asn Ala Pro Glu Ile
530                 535                 540

Arg Phe Arg Pro His Lys Lys Ala Pro Thr Lys Thr Ala Ala Lys Thr
545                 550                 555                 560

Pro Ala Leu Arg Arg Leu Lys
            565
```

```
<210> SEQ ID NO 87
<211> LENGTH: 543
<212> TYPE: PRT
<213> ORGANISM: Artificial Sequence
<220> FEATURE:
<223> OTHER INFORMATION: Synthetic

<400> SEQUENCE: 87

Met Pro Thr Ser Ser Arg Phe Ala Ser Gln Ser Arg Val Pro Leu Pro
1               5                   10                  15

Gly Ser Glu Arg Lys Pro Phe Val Pro Ala Gly Ala Pro Lys Ala Ala
            20                  25                  30

Lys Thr Pro Lys Val Ser Thr Ala Val Lys Thr Val Pro Ala Thr Gly
            35                  40                  45

Arg Ile Arg Val Ser Leu Ile Val Pro Pro Lys Gln Pro Leu Asp Thr
    50                  55                  60

Lys Arg Leu Gly Lys Leu Asp Ala Arg Leu Ser Arg Ala Gln Phe Ala
65                  70                  75                  80

Ala Arg His Gly Ala Asp Pro Ala Ser Val Arg Leu Val Lys Ala Phe
                85                  90                  95

Ala Lys Glu Phe Gly Leu Thr Val Glu Pro Ile Thr Gln Pro Gly Arg
            100                 105                 110

Cys Thr Val Gln Leu Ser Gly Thr Cys Ala Ala Met Arg Lys Ala Phe
        115                 120                 125

Ala Ile Ser Leu Val Glu His Thr Thr Glu Gln Gly Lys Phe Arg Leu
    130                 135                 140

Arg Glu Gly Glu Ile Ser Leu Pro Ala Glu Leu Glu Gly His Val Leu
145                 150                 155                 160

Ala Val Leu Gly Leu Asp Asn Arg Pro Gln Ala Lys Pro His Phe Arg
                165                 170                 175

Ile Ala Lys Pro Arg Ala Thr Asn Val Ser Tyr Thr Pro Val Gln Val
            180                 185                 190

Ala Gln Met Tyr Gly Phe Pro Ala Gly Ala Thr Ala Thr Gly Gln Thr
        195                 200                 205

Ile Gly Ile Ile Glu Leu Gly Gly Gly Tyr Arg Ala Ala Asp Leu Thr
    210                 215                 220

Ala Tyr Phe Lys Thr Leu Gly Leu Pro Ala Pro Thr Val Thr Ala Val
225                 230                 235                 240
```

```
Pro Ile Asp Gly Gly Lys Asn Thr Pro Gly Asn Ala Asn Gly Ala Asp
            245                 250                 255
Gly Glu Val Met Leu Asp Ile Glu Val Cys Ala Ala Val Ala Gln Gly
        260                 265                 270
Ala Lys Ile Ala Val Tyr Phe Thr Thr Asn Thr Asp Gln Gly Phe Ile
        275                 280                 285
Asp Ala Ile Thr Thr Ala Val His Asp Ser Thr Asn Lys Pro Ser Val
        290                 295                 300
Ile Ser Ile Ser Trp Gly Gly Pro Glu Ser Ser Trp Thr Glu Gln Ser
305                 310                 315                 320
Met Thr Ala Leu Asp Ala Ala Cys Gln Ala Ala Ala Val Gly Val
            325                 330                 335
Thr Ile Thr Val Ala Ala Gly Asp Asn Gly Ser Ser Asp Gly Ala Ser
            340                 345                 350
Gly Asp Asn Val Asp Phe Pro Ala Ser Ser Pro His Val Leu Ala Cys
        355                 360                 365
Gly Gly Thr Lys Leu Val Gly Ser Gly Ser Thr Ile Thr Ser Glu Val
        370                 375                 380
Val Trp Asp Glu Thr Ser Asn Asp Glu Gly Ala Thr Gly Gly Val
385                 390                 395                 400
Ser Thr Val Phe Ala Leu Pro Thr Trp Gln Lys Asn Ala Asn Val Pro
            405                 410                 415
Ser Pro Thr Thr Ser Ala Gly Gly Arg Gly Val Pro Asp Val Ser Gly
            420                 425                 430
Asp Ala Asp Pro Ser Thr Gly Tyr Thr Ile Arg Val Asp Ser Glu Thr
        435                 440                 445
Thr Val Ile Gly Gly Thr Ser Ala Val Ala Pro Leu Trp Ala Gly Leu
450                 455                 460
Ile Ala Leu Ala Asn Ala Gln Asn Lys Val Ala Ala Gly Phe Val Asn
465                 470                 475                 480
Pro Ala Leu Tyr Ala Ala Gly Ala Lys Lys Ala Phe Arg Asp Ile Thr
            485                 490                 495
Gln Gly Asn Asn Gly Ser Phe Ser Ala Gly Pro Gly Trp Asp Ala Cys
        500                 505                 510
Thr Gly Leu Gly Ser Pro Val Gly Asn Leu Val Ile Gln Ala Val Ala
        515                 520                 525
Pro Lys Ser Thr Thr Thr Lys Lys Ala Lys Lys Gly Lys Thr Lys
        530                 535                 540

<210> SEQ ID NO 88
<211> LENGTH: 378
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (111)..(111)
<223> OTHER INFORMATION: Xaa is N, S, G or K
<220> FEATURE:
<221> NAME/KEY: MISC_FEATURE
<222> LOCATION: (139)..(139)
<223> OTHER INFORMATION: Xaa is N or D
<220> FEATURE:
<221> NAME/KEY: MISC_FEATURE
<222> LOCATION: (140)..(140)
<223> OTHER INFORMATION: Xaa is N, T or S
<220> FEATURE:
<221> NAME/KEY: MISC_FEATURE
<222> LOCATION: (141)..(141)
```

<223> OTHER INFORMATION: Xaa is E, T, D, A, or N
<220> FEATURE:
<221> NAME/KEY: MISC_FEATURE
<222> LOCATION: (164)..(164)
<223> OTHER INFORMATION: Xaa is G or S
<220> FEATURE:
<221> NAME/KEY: MISC_FEATURE
<222> LOCATION: (203)..(203)
<223> OTHER INFORMATION: Xaa is D, N or G
<220> FEATURE:
<221> NAME/KEY: MISC_FEATURE
<222> LOCATION: (211)..(211)
<223> OTHER INFORMATION: Xaa is D, S or H

<400> SEQUENCE: 88

```
Met His Ser Tyr Leu Lys Gln Gln Ser His Met Gln Ser Tyr Leu Glu
1               5                   10                  15

Gln Glu Asn His Met Arg Ser Tyr Leu Glu Met Arg Lys Lys Pro Tyr
            20                  25                  30

Phe Asp Asp Leu Ala Asn Ile Arg Pro Gly Gly Leu Thr Pro Ala Gln
        35                  40                  45

Val Cys Gln Ala Tyr Gln Phe Ala Lys Val Gln Pro Val Arg Pro Val
    50                  55                  60

Lys Leu Gly Ile Val Ser Leu Ala Gly Gln Tyr Leu Ser Ser Asp Met
65                  70                  75                  80

Ser Lys Ala Phe Thr Gly Tyr Gly Leu Pro Thr Pro Val Val Ser Thr
                85                  90                  95

Ala Gly Ser Gln Val Leu Gly Asp Leu Trp Ser Asn Val Glu Xaa Met
            100                 105                 110

Met Asp Ile Glu Ile Ala Gly Ala Trp Ala Tyr Ala Thr Gly Thr
        115                 120                 125

Ala Ala Thr Leu Leu Met Gln Phe Glu Pro Xaa Xaa Xaa Thr Gly Ile
    130                 135                 140

Pro Asn Ala Ile Asn Ala Leu Val Ala Ala Gly Cys Glu Val Ile Ser
145                 150                 155                 160

Ile Ser Trp Xaa Ala Pro Ala Asn Leu Gln Thr Met Glu Ala Ile Thr
                165                 170                 175

Ala Arg Lys Glu Ala Cys Lys Gln Ala Ala Val Gln Asn Val His Val
            180                 185                 190

Phe Ala Ala Ser Gly Asp Glu Ser Leu Asn Xaa Gly Thr Asn Ser Arg
        195                 200                 205

Thr Pro Xaa Asp Pro Cys Cys Asp Pro Asn Val Trp Gly Val Gly Gly
    210                 215                 220

Thr Arg Leu Val Leu Gln Ala Asp Gly Ser Ile Ala Gln Glu Ser Ala
225                 230                 235                 240

Trp Gly Asp Gly Asn Ala Ala Asp Lys Gly Gly Gly Gly Phe Asp
                245                 250                 255

Ser Arg Glu Pro Leu Pro Asp Tyr Gln Val Gly Val Val His Ser Glu
            260                 265                 270

His Arg Gly Ser Pro Asp Ser Ser Ala Asn Ala Asp Pro Gly Thr Gly
        275                 280                 285

Tyr Ala Ile Val Ala Asn Gly Gln Trp Leu Ile Gly Gly Gly Thr Ser
    290                 295                 300

Ala Ser Ala Pro Leu Thr Ala Gly Tyr Val Ala Ala Ile Leu Ser Thr
305                 310                 315                 320

Leu Pro Gly Pro Ile Ser Gln Ser Val Leu Gln Arg Lys Leu Tyr Thr
                325                 330                 335
```

```
Ala His Lys Thr Ala Phe Arg Asp Ile Leu Leu Gly Ser Asn Gly Ala
            340                 345                 350

Pro Ala Arg Pro Gly Trp Glu Glu Ala Thr Gly Leu Gly Ser Ile Asn
            355                 360                 365

Gly Pro Gly Leu Ala Ala Ala Leu Gln Ser
        370                 375

<210> SEQ ID NO 89
<211> LENGTH: 523
<212> TYPE: PRT
<213> ORGANISM: Artificial Sequence
<220> FEATURE:
<223> OTHER INFORMATION: Synthetic

<400> SEQUENCE: 89

Met Ala Asn His Pro Leu Asn Gly Ser Glu Arg Glu Cys Leu Lys Asp
1               5                   10                  15

Ala Gln Pro Ile Gly Lys Ala Asp Pro Asn Glu Arg Leu Glu Val Thr
            20                  25                  30

Met Leu Val Arg Arg Ser His Asp Ala Phe Glu Lys His Ile Ser
        35                  40                  45

Ala Leu Ala Ala Gln Gly Ala Ser Ala Lys His Ile Asp His Asp Glu
    50                  55                  60

Phe Thr Lys His Phe Gly Ala Asp Ser Ala Asp Leu Ala Ala Val His
65                  70                  75                  80

Ala Phe Ala Gln Lys His Gly Leu Ser Val Val Glu Ser His Glu Ala
                85                  90                  95

Arg Arg Ala Val Val Leu Ser Gly Thr Val Ala Gln Phe Asp Ala Ala
            100                 105                 110

Phe Gly Val Ser Leu Gln Gln Tyr Glu His Asp Gly Gly Thr Tyr Arg
        115                 120                 125

Gly Arg Thr Gly Pro Ile His Leu Pro Asp Glu Leu Asn Gly Val Val
    130                 135                 140

Asp Ala Val Met Gly Leu Asp Asn Arg Pro Gln Ala Arg Pro Ser Phe
145                 150                 155                 160

Arg Thr Arg Ala Gln Gly Asn Val Arg Trp Thr Ala Arg Ala Ala Gly
                165                 170                 175

Ala Ser Thr Phe Thr Pro Val Gln Leu Ala Ser Leu Tyr Asp Phe Pro
            180                 185                 190

Gln Gly Asp Gly Gln Asn Gln Cys Ile Gly Ile Glu Leu Gly Gly
        195                 200                 205

Gly Tyr Arg Pro Ala Asp Leu Lys Thr Tyr Phe Ala Ser Leu Asn Met
    210                 215                 220

Lys Ala Pro Ser Val Thr Ala Val Ser Val Asp His Gly Arg Asn His
225                 230                 235                 240

Pro Thr Gly Asp Pro Asn Gly Pro Asp Gly Glu Val Met Leu Asp Ile
                245                 250                 255

Glu Val Ala Gly Ala Val Ala Pro Gly Ala Lys Ile Val Val Tyr Phe
            260                 265                 270

Ala Pro Asn Thr Asp Ala Gly Phe Ile Asp Ala Ile Gly Thr Ala Ile
        275                 280                 285

His Asp Thr Lys Asn Lys Pro Ser Val Ile Ser Ile Ser Trp Ser Gly
    290                 295                 300

Pro Glu Ser Ala Trp Thr Gln Gln Ala Met Asn Ala Phe Asp Gln Ala
305                 310                 315                 320
```

```
Phe Gln Ser Ala Ala Ala Leu Gly Val Thr Ile Cys Ala Ala Ser Gly
                325                 330                 335
Asp Asn Gly Ser Gly Gly Val Gly Asp Gly Ala Asp His Val His
            340                 345                 350
Phe Pro Ala Ser Ser Pro Tyr Ala Leu Gly Cys Gly Gly Thr Ser Leu
                355                 360                 365
Gln Ala Ser Gly Asn Gly Ile Ala Ser Glu Thr Val Trp Asn Asp Gly
            370                 375                 380
Ala Asn Gly Gly Ala Thr Gly Gly Gly Val Ser Ser Phe Phe Ala Leu
385                 390                 395                 400
Pro Ala Trp Gln Glu Gly Leu Arg Val Thr Arg Ala Gly Gly Ala His
                405                 410                 415
Ser Pro Leu Ala Met Arg Gly Val Pro Asp Val Ala Gly Asn Ala Asp
                420                 425                 430
Pro Val Thr Gly Tyr Glu Val Arg Val Asp Gly His Asp Met Val Ile
                435                 440                 445
Gly Gly Thr Ser Ala Val Ala Pro Leu Trp Ala Gly Leu Ile Ala Arg
            450                 455                 460
Ile Asn Ala Ile Lys Gly Ala Pro Val Gly Tyr Ile Asn Pro His Leu
465                 470                 475                 480
Tyr Lys Asp Pro Leu Ala Leu Val Asp Ile Thr Lys Gly Asn Asn Asp
                485                 490                 495
Asp Phe His Ala Thr Ala Gly Trp Asp Ala Cys Thr Gly Leu Gly Arg
                500                 505                 510
Pro Asp Gly Lys Lys Val Lys Asp Ala Val Ser
                515                 520

<210> SEQ ID NO 90
<211> LENGTH: 567
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (554)..(567)
<223> OTHER INFORMATION: Amino acids are optionally absent.

<400> SEQUENCE: 90

Met Ser Asp Met Glu Lys Pro Trp Lys Glu Gly Glu Glu Ala Arg Ala
1               5                   10                  15
Val Leu Gln Gly His Ala Arg Ala Gln Ala Pro Gln Ala Val Asp Lys
                20                  25                  30
Gly Pro Val Ala Gly Asp Glu Arg Met Ala Val Thr Val Leu Arg
                35                  40                  45
Arg Gln Arg Ala Gly Glu Leu Ala Ala His Val Glu Arg Gln Ala Ala
        50                  55                  60
Ile Ala Pro His Ala Arg Glu His Leu Lys Arg Glu Ala Phe Ala Ala
65                  70                  75                  80
Ser His Gly Ala Ser Leu Asp Asp Phe Ala Glu Leu Arg Arg Phe Ala
                85                  90                  95
Asp Ala His Gly Leu Ala Leu Asp Arg Ala Asn Val Ala Ala Gly Thr
                100                 105                 110
Ala Val Leu Ser Gly Pro Asp Asp Ala Ile Asn Arg Ala Phe Gly Val
                115                 120                 125
Glu Leu Arg His Phe Asp His Pro Asp Gly Ser Tyr Arg Ser Tyr Leu
                130                 135                 140
```

-continued

```
Gly Glu Val Thr Val Pro Ala Ser Ile Ala Pro Met Ile Glu Ala Val
145                 150                 155                 160

Leu Gly Leu Asp Thr Arg Pro Val Ala Arg Pro His Phe Arg Met Gln
            165                 170                 175

Arg Arg Ala Glu Gly Gly Phe Glu Ala Arg Ser Gln Ala Ala Ala Pro
        180                 185                 190

Thr Ala Tyr Thr Pro Leu Asp Val Ala Gln Ala Tyr Gln Phe Pro Glu
    195                 200                 205

Gly Leu Asp Gly Gln Gly Gln Cys Ile Ala Ile Ile Glu Leu Gly Gly
210                 215                 220

Gly Tyr Asp Glu Ala Ser Leu Ala Gln Tyr Phe Ala Ser Leu Gly Val
225                 230                 235                 240

Pro Ala Pro Gln Val Val Ser Val Ser Val Asp Gly Ala Ser Asn Gln
                245                 250                 255

Pro Thr Gly Asp Pro Lys Gly Pro Asp Gly Glu Val Glu Leu Asp Ile
            260                 265                 270

Glu Val Ala Gly Ala Leu Ala Pro Gly Ala Lys Phe Ala Val Tyr Phe
        275                 280                 285

Ala Pro Asp Thr Thr Ala Gly Phe Leu Asp Ala Ile Thr Thr Ala Ile
    290                 295                 300

His Asp Pro Thr Leu Lys Pro Ser Val Val Ser Ile Ser Trp Ser Gly
305                 310                 315                 320

Pro Glu Asp Ser Trp Thr Ser Ala Ala Ile Ala Ala Met Asn Arg Ala
                325                 330                 335

Phe Leu Asp Ala Ala Ala Leu Gly Val Thr Val Leu Ala Ala Ala Gly
            340                 345                 350

Asp Ser Gly Ser Thr Gly Gly Glu Gln Asp Gly Leu Tyr His Val His
        355                 360                 365

Phe Pro Ala Ala Ser Pro Tyr Val Leu Ala Cys Gly Gly Thr Arg Leu
    370                 375                 380

Val Ala Ser Gly Gly Arg Ile Ala Gln Glu Thr Val Trp Asn Asp Gly
385                 390                 395                 400

Pro Asp Gly Gly Ala Thr Gly Gly Val Ser Arg Ile Phe Pro Leu
                405                 410                 415

Pro Ala Trp Gln Glu His Ala Asn Val Pro Pro Ser Ala Asn Pro Gly
            420                 425                 430

Ala Ser Ser Gly Arg Gly Val Pro Asp Leu Ala Gly Asn Ala Asp Pro
        435                 440                 445

Ala Thr Gly Tyr Glu Val Val Ile Asp Gly Glu Ala Thr Val Ile Gly
    450                 455                 460

Gly Thr Ser Ala Val Ala Pro Leu Phe Ala Ala Leu Val Ala Arg Ile
465                 470                 475                 480

Asn Gln Lys Leu Gly Lys Ala Val Gly Tyr Leu Asn Pro Thr Leu Tyr
                485                 490                 495

Gln Leu Pro Ala Asp Val Phe His Asp Ile Thr Glu Gly Asn Asn Asp
            500                 505                 510

Ile Ala Asn Arg Ala Gln Ile Tyr Gln Ala Gly Pro Gly Trp Asp Pro
        515                 520                 525

Cys Thr Gly Leu Gly Ser Pro Ile Gly Val Arg Leu Leu Gln Ala Leu
    530                 535                 540

Leu Pro Ser Ala Ser Gln Pro Gln Pro Gly Ser Thr Glu Asn Leu Tyr
545                 550                 555                 560
```

```
Phe Gln Ser Gly Ala Leu Glu
            565

<210> SEQ ID NO 91
<211> LENGTH: 6
<212> TYPE: PRT
<213> ORGANISM: Artificial Sequence
<220> FEATURE:
<223> OTHER INFORMATION: Synthetic

<400> SEQUENCE: 91

Gln Pro Gln Leu Pro Tyr
1               5

<210> SEQ ID NO 92
<211> LENGTH: 9
<212> TYPE: PRT
<213> ORGANISM: Artificial Sequence
<220> FEATURE:
<223> OTHER INFORMATION: Synthetic

<400> SEQUENCE: 92

Ile Gln Pro Gln Gln Pro Ala Gln Leu
1               5

<210> SEQ ID NO 93
<211> LENGTH: 14
<212> TYPE: PRT
<213> ORGANISM: Artificial Sequence
<220> FEATURE:
<223> OTHER INFORMATION: Synthetic

<400> SEQUENCE: 93

Pro Gln Pro Gln Leu Pro Tyr Ser Gln Pro Gln Pro Phe Arg
1               5                   10

<210> SEQ ID NO 94
<211> LENGTH: 20
<212> TYPE: PRT
<213> ORGANISM: Artificial Sequence
<220> FEATURE:
<223> OTHER INFORMATION: Synthetic

<400> SEQUENCE: 94

Leu Gln Leu Gln Pro Phe Pro Gln Pro Gln Leu Pro Tyr Pro Gln Pro
1               5                   10                  15

Gln Leu Pro Tyr
            20

<210> SEQ ID NO 95
<211> LENGTH: 539
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (116)..(116)
<223> OTHER INFORMATION: Xaa is I, V or D
<220> FEATURE:
<221> NAME/KEY: MISC_FEATURE
<222> LOCATION: (255)..(255)
<223> OTHER INFORMATION: Xaa is N, S, K, or G
<220> FEATURE:
<221> NAME/KEY: MISC_FEATURE
<222> LOCATION: (284)..(284)
<223> OTHER INFORMATION: Xaa is N or D
<220> FEATURE:
<221> NAME/KEY: MISC_FEATURE
```

```
<222> LOCATION: (285)..(285)
<223> OTHER INFORMATION: Xaa is S or T
<220> FEATURE:
<221> NAME/KEY: MISC_FEATURE
<222> LOCATION: (286)..(286)
<223> OTHER INFORMATION: Xaa is D, A, T, or N
<220> FEATURE:
<221> NAME/KEY: MISC_FEATURE
<222> LOCATION: (312)..(312)
<223> OTHER INFORMATION: Xaa is G or S
<220> FEATURE:
<221> NAME/KEY: MISC_FEATURE
<222> LOCATION: (347)..(347)
<223> OTHER INFORMATION: Xaa is S or N
<220> FEATURE:
<221> NAME/KEY: MISC_FEATURE
<222> LOCATION: (350)..(350)
<223> OTHER INFORMATION: Xaa is G, T or A
<220> FEATURE:
<221> NAME/KEY: MISC_FEATURE
<222> LOCATION: (351)..(351)
<223> OTHER INFORMATION: Xaa is D, N or G
<220> FEATURE:
<221> NAME/KEY: MISC_FEATURE
<222> LOCATION: (354)..(354)
<223> OTHER INFORMATION: Xaa is Q or D
<220> FEATURE:
<221> NAME/KEY: MISC_FEATURE
<222> LOCATION: (361)..(361)
<223> OTHER INFORMATION: Xaa is D, S or H

<400> SEQUENCE: 95

Met Gln Arg Gly Thr Lys Glu Gly Leu Asn Met Ala Arg His Leu Gln
1               5                   10                  15

Ala Asp Arg Glu Pro Arg Ile Val Pro Glu Ser Lys Cys Leu Gly Gln
            20                  25                  30

Cys Asp Pro Ala Glu Arg Ile His Val Thr Ile Met Leu Arg Arg Gln
        35                  40                  45

Glu Gly Gln Leu Asp Ala Leu Val His Gln Leu Ala Thr Gly Asp
    50                  55                  60

Ala Arg Ala Lys Pro Val Ser Arg Asp Ala Phe Ala Gln Arg Phe Ser
65                  70                  75                  80

Ala Asn Pro Asp Asp Ile Arg Lys Thr Glu Asp Phe Ala His Arg His
                85                  90                  95

Gln Leu Thr Val Asp Arg Val Asp Pro Val Glu Ser Val Val Val Leu
            100                 105                 110

Ser Gly Thr Xaa Ala Gln Phe Glu Ala Ala Phe Ser Val Lys Leu Glu
        115                 120                 125

Arg Phe Glu His Arg Ser Ile Gly Gln Tyr Arg Gly Arg Ser Gly Pro
    130                 135                 140

Ile Val Leu Pro Asp Asp Ile Gly Asp Ala Val Thr Ala Val Leu Gly
145                 150                 155                 160

Leu Asp Ser Arg Pro Gln Ala Arg Pro His Phe Arg Phe Arg Pro Pro
                165                 170                 175

Phe Lys Pro Ala Arg Gly Ala Ala Ala Val Thr Phe Thr Pro Ile Gln
            180                 185                 190

Leu Ala Ser Leu Tyr Asp Phe Pro Ala Gly Asp Gly Ala Gly Gln Cys
        195                 200                 205

Ile Ala Ile Ile Glu Leu Gly Gly Gly Tyr Arg Ala Ala Asp Ile Gln
    210                 215                 220

Gln Tyr Phe Arg Gly Leu Gly Ile Thr Thr Pro Pro Lys Leu Val Asp
225                 230                 235                 240

Val Asn Val Gly Thr Gly Arg Asn Ala Pro Thr Gly Glu Pro Xaa Gly
```

```
                245                 250                 255
Pro Asp Gly Glu Val Ala Leu Asp Ile Glu Ile Ala Gly Ala Ile Ala
            260                 265                 270
Pro Ala Ala Lys Ile Ala Val Tyr Phe Ala Pro Xaa Xaa Xaa Ala Gly
        275                 280                 285
Phe Ile Gln Ala Val Asn Ala Ala Val Thr Asp Lys Thr Asn Gln Pro
    290                 295                 300
Ser Val Ile Ser Ile Ser Trp Xaa Gly Pro Glu Ala Ile Trp Gln Ala
305                 310                 315                 320
Gln Ser Ala Gln Ala Phe Asn Arg Val Leu Gln Ala Ala Ala Ala Gln
            325                 330                 335
Gly Ile Thr Val Cys Ala Ala Ser Gly Asp Xaa Gly Ser Xaa Xaa Gly
        340                 345                 350
Leu Xaa Asp Gly Ala Asp His Val Xaa Phe Pro Ala Ser Ser Pro Tyr
    355                 360                 365
Val Leu Gly Cys Gly Gly Thr Gln Leu Asp Ala Leu Pro Gly Gln Gly
    370                 375                 380
Ile Arg Ser Glu Val Thr Trp Asn Asp Glu Ala Ser Gly Gly Gly Ala
385                 390                 395                 400
Gly Gly Gly Gly Val Ser Ala Leu Phe Asp Leu Pro Ala Trp Gln Gln
            405                 410                 415
Gly Leu Lys Val Ala Arg Ala Asp Gly Thr Thr Thr Pro Leu Ala Lys
        420                 425                 430
Arg Gly Val Pro Asp Val Ala Gly Asp Ala Ser Pro Gln Thr Gly Tyr
    435                 440                 445
Glu Val Ser Val Ala Gly Thr Pro Ala Val Met Gly Gly Thr Ser Ala
    450                 455                 460
Val Ala Pro Leu Trp Ala Ala Leu Ile Ala Arg Ile Asn Ala Ala Asn
465                 470                 475                 480
Gly Ala Ser Ala Gly Trp Ile Asn Pro Val Leu Tyr Lys His Pro Gly
            485                 490                 495
Ala Leu Arg Asp Ile Thr Lys Gly Ser Asn Gly Thr Tyr Ala Ala Ala
        500                 505                 510
Ser Gly Trp Asp Ala Cys Thr Gly Leu Gly Ser Pro Asn Gly Ala Gln
    515                 520                 525
Leu Ala Thr Ile Leu Ala Arg Lys Pro Ser Ser
    530                 535

<210> SEQ ID NO 96
<211> LENGTH: 512
<212> TYPE: PRT
<213> ORGANISM: Artificial Sequence
<220> FEATURE:
<223> OTHER INFORMATION: Synthetic

<400> SEQUENCE: 96

Met Ala Pro Ser Asp Val Glu Ile Val Asp Pro Val Ala Pro Glu Glu
1               5                   10                  15
Arg Ile Thr Val Thr Val Leu Leu Arg Arg Arg Ser Ser Ile Pro Asp
            20                  25                  30
Gln Leu Ile Glu Gly Pro Asp Thr Leu Ser Arg Ala Glu Leu Ala Asp
        35                  40                  45
Arg His Gly Ala Asp Pro Ala Asp Val Glu Ala Val Arg Val Ala Met
    50                  55                  60
Ser Gly Ala Gly Leu Thr Val Val Gly Thr Asp Leu Pro Ser Arg Arg
```

```
                65                  70                  75                  80
Val Thr Val Ala Gly Thr Ala Glu Ala Leu Met Arg Thr Phe Gly Ala
                    85                  90                  95
Glu Leu Gln Ile Val Arg Asp Ala Ser Gly Phe Gln His Arg Ala Arg
                    100                 105                 110
Ser Gly Glu Leu Arg Ile Pro Ala Ala Leu Asp Gly Ile Val Ile Ala
                    115                 120                 125
Val Leu Gly Leu Asp Asn Arg Pro Gln Ala Glu Ala Arg Phe Arg Ala
130                 135                 140
Ser Gln Pro Glu Ala Ala Arg Ser Phe Arg Pro Asp Ala Leu Gly Arg
145                 150                 155                 160
Val Tyr Arg Phe Pro Ala Asn Thr Asp Gly Thr Gln Thr Ile Ala
                    165                 170                 175
Ile Val Glu Leu Gly Gly Gly Phe Arg Gln Ser Glu Leu Asp Thr Tyr
                    180                 185                 190
Phe Gly Gly Leu Gly Ile Pro Ala Pro Gln Val Leu Ala Val Gly Val
                    195                 200                 205
Asp Gly Gly Gln Asn Leu Pro Ser Gly Asp Ala Gly Ser Ala Asp Gly
                    210                 215                 220
Glu Val Leu Leu Asp Ile Glu Val Ala Gly Ala Leu Ala Pro Gly Ala
225                 230                 235                 240
Arg Gln Val Val Tyr Phe Ala Pro Asn Thr Asp Arg Gly Phe Val Asp
                    245                 250                 255
Ala Val Thr Thr Ala Val His Ala Asp Pro Thr Pro Ala Ala Val Ser
                    260                 265                 270
Ile Ser Trp Gly Ala Pro Glu Asp Lys Trp Thr Ala Gln Ala Arg Arg
                    275                 280                 285
Ala Phe Asp Ala Ala Leu Ala Asp Ala Ala Leu Gly Val Thr Val
                    290                 295                 300
Thr Ala Ala Ala Gly Asp Arg Gly Ser Ala Asp Gly Glu Gly Gly
305                 310                 315                 320
Gly Leu His Thr Asp Phe Pro Ala Ser Ser Pro His Leu Leu Ala Cys
                    325                 330                 335
Gly Gly Thr Lys Leu Ala Val Ala Asp Gly Gly Thr Val Ala Ser Glu
                    340                 345                 350
Thr Val Trp Asn Gly Gly Glu Arg Gly Gly Ala Thr Gly Gly Gly Val
                    355                 360                 365
Ser Val Ala Phe Gly Leu Pro Ala Tyr Gln Arg Asn Ala Gly Val Asp
370                 375                 380
Lys Arg Arg Lys Thr Gly Lys Pro Gly Arg Gly Val Pro Asp Val Ala
385                 390                 395                 400
Ala Val Ala Asp Pro Ala Thr Gly Tyr Glu Val Leu Val Asp Gly Glu
                    405                 410                 415
Gln Leu Val Phe Gly Gly Thr Ser Ala Val Ala Pro Leu Trp Ala Ala
                    420                 425                 430
Leu Val Ala Arg Leu Thr Gln Ala Leu Gly Arg Pro Leu Gly Leu Leu
                    435                 440                 445
Asn Thr Ala Leu Tyr Asp Gly Ala Gln Pro Gly Arg Thr Gln Pro Gly
                    450                 455                 460
Phe Arg Asp Val Thr Glu Gly Asp Asn Asp Ile Ser Gly Lys His Gly
465                 470                 475                 480
Pro Tyr Pro Ala Arg Ala Gly Trp Asp Ala Cys Thr Gly Leu Gly Val
                    485                 490                 495
```

```
Pro Asp Gly Glu Ala Leu Leu Ala Ala Leu Arg Lys Pro Gly Lys Glu
            500                 505                 510

<210> SEQ ID NO 97
<211> LENGTH: 539
<212> TYPE: PRT
<213> ORGANISM: Artificial Sequence
<220> FEATURE:
<223> OTHER INFORMATION: Synthetic

<400> SEQUENCE: 97

Met Gln Arg Gly Thr Lys Glu Gly Leu Asn Met Ala Arg His Leu Gln
1               5                   10                  15

Ala Asp Arg Glu Pro Arg Ile Val Pro Glu Ser Lys Cys Leu Gly Gln
            20                  25                  30

Cys Asp Pro Ala Glu Arg Ile His Val Thr Ile Met Leu Arg Arg Gln
        35                  40                  45

Glu Glu Gly Gln Leu Asp Ala Leu Val His Gln Leu Ala Thr Gly Asp
    50                  55                  60

Ala Arg Ala Lys Pro Val Ser Arg Asp Ala Phe Ala Gln Arg Phe Ser
65                  70                  75                  80

Ala Asn Pro Asp Asp Ile Arg Lys Thr Glu Asp Phe Ala His Arg His
                85                  90                  95

Gln Leu Thr Val Asp Arg Val Asp Pro Val Glu Ser Val Val Val Leu
            100                 105                 110

Ser Gly Thr Ile Ala Gln Phe Glu Ala Phe Ser Val Lys Leu Glu
        115                 120                 125

Arg Phe Glu His Arg Ser Ile Gly Gln Tyr Arg Gly Arg Ser Gly Pro
    130                 135                 140

Ile Val Leu Pro Asp Asp Ile Gly Asp Ala Val Thr Ala Val Leu Gly
145                 150                 155                 160

Leu Asp Ser Arg Pro Gln Ala Arg Pro His Phe Arg Phe Arg Pro Pro
                165                 170                 175

Phe Lys Pro Ala Arg Gly Ala Ala Ala Val Thr Phe Thr Pro Ile Gln
            180                 185                 190

Leu Ala Ser Leu Tyr Asp Phe Pro Ala Gly Asp Gly Ala Gly Gln Cys
        195                 200                 205

Ile Ala Ile Ile Glu Leu Gly Gly Gly Tyr Arg Ala Ala Asp Ile Gln
    210                 215                 220

Gln Tyr Phe Arg Gly Leu Gly Ile Thr Thr Pro Pro Lys Leu Val Asp
225                 230                 235                 240

Val Asn Val Gly Thr Gly Arg Asn Ala Pro Thr Gly Glu Pro Asn Gly
                245                 250                 255

Pro Asp Gly Glu Val Ala Leu Asp Ile Glu Ile Ala Gly Ala Ile Ala
            260                 265                 270

Pro Ala Ala Lys Ile Ala Val Tyr Phe Ala Pro Asn Ser Asp Ala Gly
        275                 280                 285

Phe Ile Gln Ala Val Asn Ala Ala Val Thr Asp Lys Thr Asn Gln Pro
    290                 295                 300

Ser Val Ile Ser Ile Ser Trp Gly Gly Pro Glu Ala Ile Trp Gln Ala
305                 310                 315                 320

Gln Ser Ala Gln Ala Phe Asn Arg Val Leu Gln Ala Ala Ala Gln
                325                 330                 335

Gly Ile Thr Val Cys Ala Ala Ser Gly Asp Ser Gly Ser Gly Asp Gly
            340                 345                 350
```

```
Leu Gln Asp Gly Ala Asp His Val Asp Phe Pro Ala Ser Ser Pro Tyr
            355                 360                 365

Val Leu Gly Cys Gly Gly Thr Gln Leu Asp Ala Leu Pro Gly Gln Gly
    370                 375                 380

Ile Arg Ser Glu Val Thr Trp Asn Asp Glu Ala Ser Gly Gly Gly Ala
385                 390                 395                 400

Gly Gly Gly Gly Val Ser Ala Leu Phe Asp Leu Pro Ala Trp Gln Gln
                405                 410                 415

Gly Leu Lys Val Ala Arg Ala Asp Gly Thr Thr Pro Leu Ala Lys
            420                 425                 430

Arg Gly Val Pro Asp Val Ala Gly Asp Ala Ser Pro Thr Gly Tyr
                435                 440                 445

Glu Val Ser Val Ala Gly Thr Pro Ala Val Met Gly Gly Thr Ser Ala
    450                 455                 460

Val Ala Pro Leu Trp Ala Ala Leu Ile Ala Arg Ile Asn Ala Ala Asn
465                 470                 475                 480

Gly Ala Ser Ala Gly Trp Ile Asn Pro Val Leu Tyr Lys His Pro Gly
                485                 490                 495

Ala Leu Arg Asp Ile Thr Lys Gly Ser Asn Gly Thr Tyr Ala Ala Ala
                500                 505                 510

Ser Gly Trp Asp Ala Cys Thr Gly Leu Gly Ser Pro Asn Gly Ala Gln
            515                 520                 525

Leu Ala Thr Ile Leu Ala Arg Lys Pro Ser Ser
            530                 535

<210> SEQ ID NO 98
<211> LENGTH: 523
<212> TYPE: PRT
<213> ORGANISM: Artificial Sequence
<220> FEATURE:
<223> OTHER INFORMATION: Synthetic

<400> SEQUENCE: 98

Met Ala Asn His Pro Leu Asn Gly Ser Glu Arg Glu Cys Leu Lys Asp
1               5                   10                  15

Ala Gln Pro Ile Gly Lys Ala Asp Pro Asn Glu Arg Leu Glu Val Thr
            20                  25                  30

Met Leu Val Arg Arg Ser His Asp Ala Phe Glu Lys His Ile Ser
        35                  40                  45

Ala Leu Ala Ala Gln Gly Ala Ser Ala Lys His Ile Asp His Asp Glu
    50                  55                  60

Phe Thr Lys His Phe Gly Ala Asp Ser Ala Asp Leu Ala Ala Val His
65                  70                  75                  80

Ala Phe Ala Gln Lys His Gly Leu Ser Val Val Glu Ser His Glu Ala
                85                  90                  95

Arg Arg Ala Val Val Leu Ser Gly Thr Val Ala Gln Phe Asp Ala Ala
            100                 105                 110

Phe Gly Val Ser Leu Gln Gln Tyr Glu His Asp Gly Thr Tyr Arg
        115                 120                 125

Gly Arg Thr Gly Pro Ile His Leu Pro Asp Glu Leu Asn Gly Val Val
    130                 135                 140

Asp Ala Val Met Gly Leu Asp Asn Arg Pro Gln Ala Arg Pro Ser Phe
145                 150                 155                 160

Arg Thr Arg Ala Gln Gly Asn Val Arg Trp Thr Ala Arg Ala Ala Gly
                165                 170                 175
```

```
Ala Ser Thr Phe Thr Pro Val Gln Leu Ala Ser Leu Tyr Asp Phe Pro
            180                 185                 190

Gln Gly Asp Gly Gln Asn Gln Cys Ile Gly Ile Ile Glu Leu Gly Gly
        195                 200                 205

Gly Tyr Arg Pro Ala Asp Leu Lys Thr Tyr Phe Ala Ser Leu Asn Met
    210                 215                 220

Lys Ala Pro Ser Val Thr Ala Val Ser Val Asp His Gly Arg Asn His
225                 230                 235                 240

Pro Thr Gly Asp Pro Asn Gly Pro Asp Gly Glu Val Met Leu Asp Ile
                245                 250                 255

Glu Val Ala Gly Ala Val Ala Pro Gly Ala Lys Ile Val Val Tyr Phe
                260                 265                 270

Ala Pro Asn Thr Asp Ala Gly Phe Ile Asp Ala Ile Gly Thr Ala Ile
            275                 280                 285

His Asp Thr Lys Asn Lys Pro Ser Val Ile Ser Ile Ser Trp Gly Gly
        290                 295                 300

Pro Glu Ser Ala Trp Thr Gln Gln Ala Met Asn Ala Phe Asp Gln Ala
305                 310                 315                 320

Phe Gln Ser Ala Ala Ala Leu Gly Val Thr Ile Cys Ala Ala Ser Gly
                325                 330                 335

Asp Asn Gly Ser Gly Asp Gly Val Gly Asp Gly Ala Asp His Val Asp
            340                 345                 350

Phe Pro Ala Ser Ser Pro Tyr Ala Leu Gly Cys Gly Gly Thr Ser Leu
        355                 360                 365

Gln Ala Ser Gly Asn Gly Ile Ala Ser Glu Thr Val Trp Asn Asp Gly
    370                 375                 380

Ala Asn Gly Gly Ala Thr Gly Gly Val Ser Ser Phe Phe Ala Leu
385                 390                 395                 400

Pro Ala Trp Gln Glu Gly Leu Arg Val Thr Arg Ala Gly Gly Ala His
                405                 410                 415

Ser Pro Leu Ala Met Arg Gly Val Pro Asp Val Ala Gly Asn Ala Asp
            420                 425                 430

Pro Val Thr Gly Tyr Glu Val Arg Val Asp Gly His Asp Met Val Ile
        435                 440                 445

Gly Gly Thr Ser Ala Val Ala Pro Leu Trp Ala Gly Leu Ile Ala Arg
    450                 455                 460

Ile Asn Ala Ile Lys Gly Ala Pro Val Gly Tyr Ile Asn Pro His Leu
465                 470                 475                 480

Tyr Lys Asp Pro Leu Ala Leu Val Asp Ile Thr Lys Gly Asn Asn Asp
                485                 490                 495

Asp Phe His Ala Thr Ala Gly Trp Asp Ala Cys Thr Gly Leu Gly Arg
            500                 505                 510

Pro Asp Gly Lys Lys Val Lys Asp Ala Val Ser
        515                 520

<210> SEQ ID NO 99
<211> LENGTH: 367
<212> TYPE: PRT
<213> ORGANISM: Artificial Sequence
<220> FEATURE:
<223> OTHER INFORMATION: Synthetic

<400> SEQUENCE: 99

Ala Gly Arg Thr Ser Tyr Thr Pro Leu Glu Val Ala Ala Leu Tyr Asn
1               5                   10                  15
```

```
Phe Pro Ser Ile His Cys Lys Asp Gln Cys Ile Gly Ile Leu Glu Leu
            20                  25                  30

Gly Gly Gly Tyr Arg Pro Ala Asp Leu Gln Thr Tyr Phe Asn Gly Leu
        35                  40                  45

Gly Ile Pro Gln Pro Asn Ile Thr Asp Val Ser Val Gly Gly Ala Ala
 50                  55                  60

Asn Arg Pro Thr Gly Asp Pro Asn Gly Pro Asp Gly Glu Val Val Leu
 65                  70                  75                  80

Asp Ile Glu Val Ala Ala Ala Val Thr Pro Gly Ala Lys Ile Ala Val
                 85                  90                  95

Tyr Phe Ala Asp Asn Ser Asp Asp Gly Phe Leu Asn Ala Ile Thr Thr
                100                 105                 110

Ala Ile His Asp Thr Arg Asn Lys Pro Ser Val Ile Ser Ile Ser Trp
        115                 120                 125

Gly Lys Ala Glu Ile Gly Trp Thr Pro Gln Ala Ile Asn Ala Met Asn
130                 135                 140

Gln Ala Phe Arg Asp Ala Ala Leu Gly Val Thr Ile Cys Cys Ala
145                 150                 155                 160

Ser Gly Asp Asp Gly Ser Thr Asp Arg Val Gln Asp Gly Arg Tyr His
                165                 170                 175

Val Asp Phe Pro Ala Ser Ser Pro Tyr Val Leu Ala Cys Gly Gly Thr
                180                 185                 190

Arg Leu Glu Ser Ser Gly Ser Thr Ile Thr Gln Glu Val Val Trp Asn
            195                 200                 205

Glu Gly Ala Leu Gly Gly Gly Ala Thr Gly Gly Val Ser Asp Val
210                 215                 220

Phe Asp Arg Pro Asn Trp Gln Ala Asn Ala Asn Val Pro Thr Ser Ala
225                 230                 235                 240

Asn Pro Glu Arg Arg Ile Gly Arg Gly Val Pro Asp Trp Ala Gly Asn
                245                 250                 255

Ala Asp Pro Ala Thr Gly Tyr Gln Ile Leu Val Asp Gly Thr Arg Ala
                260                 265                 270

Val Ile Gly Gly Thr Ser Ala Val Ala Pro Leu Phe Ala Gly Leu Ile
            275                 280                 285

Ala Ile Ile Asn Gln Lys Leu Gly His Ser Val Gly Phe Ile Asn Pro
290                 295                 300

Ile Leu Tyr Asn Leu Ser Ala Gln His Asn Val Phe His Asp Ile Thr
305                 310                 315                 320

Ser Gly Asn Asn Asp Met Ser Gly Gln Asn Gly Pro Tyr Glu Ala Gln
                325                 330                 335

Pro Gly Trp Asp Ala Cys Thr Gly Leu Gly Ser Pro Gly Thr Lys
            340                 345                 350

Leu Met Asn Ala Ile Ser Glu Ala His Arg Leu Val Ser Val Gly
        355                 360                 365

<210> SEQ ID NO 100
<211> LENGTH: 507
<212> TYPE: PRT
<213> ORGANISM: Artificial Sequence
<220> FEATURE:
<223> OTHER INFORMATION: Synthetic

<400> SEQUENCE: 100

Met Ala Pro Glu Glu Arg Arg Thr Leu Pro Gly Ser Ala Met Pro Arg
1               5                   10                  15
```

-continued

Pro Ala Gly Ala Gln Val Leu Gly Gln Ile Pro Asp Asp Glu Arg Val
        20                  25                  30

Glu Val Thr Val Val Leu Gln Pro Arg Ala Pro Leu Pro Glu Pro Gly
            35                  40                  45

Pro Thr Pro Met Ser Arg Ala Glu Leu Ala Asp Leu Arg Ser Pro Pro
        50                  55                  60

Glu Gly Ala Leu Glu Ala Ile Ala Arg Tyr Val Ala Gly Gln Gly Leu
65                  70                  75                  80

Glu Val Ile Ala Ala Asp Ala Pro Arg Arg Ile Val Leu Ala Gly
                85                  90                  95

Ser Ala Ala Arg Ile Ala Ala Leu Phe Gly Ile Ser Phe Val Arg Leu
            100                 105                 110

Gln Leu Glu Gly Arg Arg Tyr Arg Thr Tyr Glu Gly Glu Ile Ser Leu
            115                 120                 125

Pro Ala Glu Leu Ala Pro Leu Val Ala Val Leu Gly Leu Asp Thr
        130                 135                 140

Arg Pro Phe Ala Arg Ser His Arg Arg Pro Ala Val Ala Pro Asn Ala
145                 150                 155                 160

Pro Thr Thr Ala Pro Thr Val Ala Arg Ala Tyr Asp Phe Pro Thr Ala
            165                 170                 175

Tyr Asp Gly Arg Gly Thr Thr Ile Gly Phe Ile Glu Leu Gly Gly Gly
            180                 185                 190

Phe Gln Glu Ser Asp Leu Val Arg Tyr Cys Glu Gly Leu Gly Leu Ser
            195                 200                 205

Thr Pro Gln Val Ser Val Val Gly Val Asp Gly Ala Arg Asn Ala Pro
210                 215                 220

Thr Gly Asp Pro Asn Gly Pro Asp Ala Glu Val Met Leu Asp Leu Glu
225                 230                 235                 240

Val Ala Thr Gly Val Ala Asn Gly Ala Asp Leu Val Leu Tyr Met Ala
            245                 250                 255

Ala Asn Thr Asp Ala Ala Phe Tyr Ser Ala Ile Ala Thr Ala Leu Arg
            260                 265                 270

Asp Ala Thr His Ala Pro Val Ala Ile Ser Ile Ser Trp Gly Ala Pro
            275                 280                 285

Glu Glu Ser Tyr Pro Ala Thr Thr Ile Ala Ala Phe Glu Ser Val Leu
        290                 295                 300

Glu Glu Ala Val His Val Gly Val Thr Val Leu Val Ala Ala Gly Asp
305                 310                 315                 320

Gln Gly Ser Thr Asp Gly Val Asp Asp Gly Arg Ala His Val Asp Tyr
            325                 330                 335

Pro Ala Ser Pro Tyr Val Leu Ala Cys Gly Gly Thr Arg Leu Asp
        340                 345                 350

Leu Asp Gly Thr Thr Ile Val Ala Glu Thr Val Trp Asn Asp Leu Pro
        355                 360                 365

Asn Gly Gly Ala Thr Gly Gly Ile Ser Ala Leu Phe Pro Val Pro
        370                 375                 380

Ser Trp Gln Ala Gly Ile Ala Met Pro Pro Ser Ala Asn Pro Gly Ala
385                 390                 395                 400

Gly Pro Gly Arg Gly Val Pro Asp Val Ala Gly Asn Ala Asp Pro Asp
                405                 410                 415

Thr Gly Tyr Arg Ile Val Val Asp Gly Val Ala Thr Val Gly Gly
            420                 425                 430

```
Thr Ser Ala Val Ala Pro Leu Trp Ala Gly Leu Val Ala Arg Cys His
        435                 440                 445

Gln Ala Gly Ala Arg Gly Gly Phe Trp Asn Pro Leu Leu Tyr Ala Ala
    450                 455                 460

Arg Gly Ser Ser Ala Phe His Glu Ile Thr Val Gly Ser Asn Gly Ala
465                 470                 475                 480

Tyr Asp Ala Gly Pro Ile Trp Asn Ala Cys Cys Gly Leu Gly Ser Pro
                485                 490                 495

Asn Gly Thr Ala Ile Leu Gln Thr Leu Arg Ala
            500                 505

<210> SEQ ID NO 101
<211> LENGTH: 507
<212> TYPE: PRT
<213> ORGANISM: Artificial Sequence
<220> FEATURE:
<223> OTHER INFORMATION: Synthetic

<400> SEQUENCE: 101

Met Ala Pro Glu Glu Arg Arg Thr Leu Pro Gly Ser Ala Met Pro Arg
1               5                   10                  15

Pro Ala Gly Ala Gln Val Leu Gly Gln Ile Pro Asp Asp Glu Arg Val
            20                  25                  30

Glu Val Thr Val Val Leu Gln Pro Arg Ala Pro Leu Pro Glu Pro Gly
        35                  40                  45

Pro Thr Pro Met Ser Arg Ala Glu Leu Ala Asp Leu Arg Ser Pro Pro
    50                  55                  60

Glu Gly Ala Leu Glu Ala Ile Ala Arg Tyr Val Ala Gly Gln Gly Leu
65                  70                  75                  80

Glu Val Ile Ala Ala Asp Ala Pro Arg Arg Ile Val Leu Ala Gly
                85                  90                  95

Ser Ala Ala Arg Ile Ala Ala Leu Phe Gly Ile Ser Phe Val Arg Leu
                100                 105                 110

Gln Leu Glu Gly Arg Arg Tyr Arg Thr Tyr Glu Gly Glu Ile Ser Leu
            115                 120                 125

Pro Ala Glu Leu Ala Pro Leu Val Val Ala Val Leu Gly Leu Asp Thr
        130                 135                 140

Arg Pro Phe Ala Arg Ser His Arg Arg Pro Ala Val Ala Pro Asn Ala
145                 150                 155                 160

Pro Thr Thr Ala Pro Thr Val Arg Ala Tyr Asp Phe Pro Thr Ala
                165                 170                 175

Tyr Asp Gly Arg Gly Thr Thr Ile Gly Phe Ile Glu Leu Gly Gly Gly
                180                 185                 190

Phe Gln Glu Ser Asp Leu Val Arg Tyr Cys Glu Gly Leu Gly Leu Ser
            195                 200                 205

Thr Pro Gln Val Ser Val Val Gly Val Asp Gly Ala Arg Asn Ala Pro
    210                 215                 220

Thr Gly Asp Pro Asn Gly Pro Asp Ala Glu Val Met Leu Asp Leu Glu
225                 230                 235                 240

Val Ala Thr Gly Val Ala Asn Gly Ala Asp Leu Val Leu Tyr Met Ala
                245                 250                 255

Ala Asn Thr Asp Ala Ala Phe Tyr Ser Ala Ile Ala Thr Ala Leu Arg
            260                 265                 270

Asp Ala Thr His Ala Pro Val Ala Ile Ser Ile Ser Trp Ser Ala Pro
        275                 280                 285
```

```
Glu Glu Ser Tyr Pro Ala Thr Thr Ile Ala Ala Phe Glu Ser Val Leu
    290                 295                 300

Glu Glu Ala Val His Val Gly Val Thr Val Leu Val Ala Ala Gly Asp
305                 310                 315                 320

Gln Gly Ser Thr Gly Gly Val Asp Asp Gly Arg Ala His Val His Tyr
                325                 330                 335

Pro Ala Ala Ser Pro Tyr Val Leu Ala Cys Gly Gly Thr Arg Leu Asp
                340                 345                 350

Leu Asp Gly Thr Thr Ile Val Ala Glu Thr Val Trp Asn Asp Leu Pro
                355                 360                 365

Asn Gly Gly Ala Thr Gly Gly Ile Ser Ala Leu Phe Pro Val Pro
    370                 375                 380

Ser Trp Gln Ala Gly Ile Ala Met Pro Pro Ser Ala Asn Pro Gly Ala
385                 390                 395                 400

Gly Pro Gly Arg Gly Val Pro Asp Val Ala Gly Asn Ala Asp Pro Asp
                405                 410                 415

Thr Gly Tyr Arg Ile Val Val Asp Gly Val Ala Thr Val Gly Gly
                420                 425                 430

Thr Ser Ala Val Ala Pro Leu Trp Ala Gly Leu Val Ala Arg Cys His
                435                 440                 445

Gln Ala Gly Ala Arg Gly Gly Phe Trp Asn Pro Leu Leu Tyr Ala Ala
    450                 455                 460

Arg Gly Ser Ser Ala Phe His Glu Ile Thr Val Gly Ser Asn Gly Ala
465                 470                 475                 480

Tyr Asp Ala Gly Pro Ile Trp Asn Ala Cys Cys Gly Leu Gly Ser Pro
                485                 490                 495

Asn Gly Thr Ala Ile Leu Gln Thr Leu Arg Ala
                500                 505

<210> SEQ ID NO 102
<211> LENGTH: 532
<212> TYPE: PRT
<213> ORGANISM: Artificial Sequence
<220> FEATURE:
<223> OTHER INFORMATION: Synthetic

<400> SEQUENCE: 102

Met Thr Lys Gln Pro Val Ser Gly Ser Ser Asp Lys Ile His Pro Asp
1               5                   10                  15

Asp Ala Lys Cys Ile Gly Asp Cys Asp Pro Ser Glu Gln Ile Glu Val
                20                  25                  30

Ile Val Met Leu Arg Arg Lys Asp Glu Ala Gly Phe Arg Gln Met Met
            35                  40                  45

Ser Arg Ile Asp Ala Gly Glu Ala Pro Gly Gln Ala Val Ser Arg Glu
    50                  55                  60

Glu Phe Asp Arg Arg Phe Thr Ala Ser Asp Glu Asp Ile Asp Lys Val
65                  70                  75                  80

Lys Ala Phe Ala Lys Gln Tyr Gly Leu Ser Val Glu Arg Ala Glu Thr
                85                  90                  95

Glu Thr Arg Ser Val Val Leu Lys Gly Thr Ile Glu Gln Phe Gln Lys
                100                 105                 110

Ala Phe Asp Val Lys Leu Glu Arg Phe Gln His His Asn Ile Gly Glu
            115                 120                 125

Tyr Arg Gly Arg Thr Gly Pro Val Asn Val Pro Asp Glu Met His Asp
    130                 135                 140
```

Ala Val Thr Ala Val Leu Gly Leu Asp Ser Lys Pro Gln Ala Arg Pro
145                 150                 155                 160

His Phe Arg Phe Arg Pro Pro Phe Lys Pro Leu Arg Gly Ala Ala Pro
            165                 170                 175

Ala Ser Phe Ser Pro Val Asp Leu Ala Lys Leu Tyr Asp Phe Pro Asp
            180                 185                 190

Gly Asp Gly Ala Gly Gln Cys Ile Ala Ile Glu Leu Gly Gly Gly
        195                 200                 205

Tyr Arg Asp Ser Asp Leu Ser Ala Tyr Phe Ser Lys Leu Gly Val Lys
    210                 215                 220

Ala Pro Thr Val Val Pro Val Gly Val Asp Gly Gly Lys Asn Ala Pro
225                 230                 235                 240

Thr Gly Asn Pro Asn Gly Pro Asp Gly Glu Val Thr Leu Asp Ile Glu
            245                 250                 255

Ile Ala Gly Ala Ile Ala Pro Gly Ala Arg Ile Ala Val Tyr Phe Ala
            260                 265                 270

Pro Asn Ser Asp Ala Gly Phe Val Asp Ala Val Asn Arg Ala Leu His
        275                 280                 285

Asp Ala Ala Asn Lys Pro Ser Val Ile Ser Ile Ser Trp Gly Gly Pro
290                 295                 300

Glu Ser Asn Trp Ser Pro Gln Ser Met Ser Ala Phe Asn Asp Val Leu
305                 310                 315                 320

Gln Ser Ala Ala Leu Gly Val Thr Val Cys Ala Ala Ser Gly Asp
            325                 330                 335

Gly Gly Ser Ala Asp Gly Val Gly Asp Gly Ala Asp His Val Asp Phe
        340                 345                 350

Pro Ala Ser Ser Pro Tyr Val Leu Gly Cys Gly Gly Thr Ser Leu Ala
        355                 360                 365

Ala Ser Gly Ala Gly Ile Ala Lys Glu Val Val Trp Asn Asp Gly Asp
    370                 375                 380

Gln Gly Gly Ala Gly Gly Gly Val Ser Gly Thr Phe Ala Leu Pro
385                 390                 395                 400

Val Trp Gln Lys Gly Leu Ser Val Thr Arg Asn Gly Lys His Ile Ala
            405                 410                 415

Leu Ala Lys Arg Gly Val Pro Asp Val Ala Gly Asp Ala Ser Pro Gln
            420                 425                 430

Thr Gly Tyr Glu Val Leu Ile Asp Gly Glu Asp Thr Val Val Gly Gly
        435                 440                 445

Thr Ser Ala Val Ala Pro Leu Trp Ala Ala Leu Ile Ala Arg Ile Asn
450                 455                 460

Ala Ile Asp Ala Ser Pro Ala Gly Phe Val Asn Pro Lys Leu Tyr Lys
465                 470                 475                 480

Ala Lys Thr Ala Phe Arg Asp Ile Thr Glu Gly Asn Asn Gly Ser Phe
            485                 490                 495

Ser Ala Ala Ala Gly Trp Asp Ala Cys Thr Gly Met Gly Ser Pro Asp
        500                 505                 510

Gly Gly Lys Ile Ala Ala Ala Leu Lys Pro Ala Lys Pro Ser Gln Ser
        515                 520                 525

Ala Gly Gln Gln
    530

<210> SEQ ID NO 103
<211> LENGTH: 544
<212> TYPE: PRT

<213> ORGANISM: Artificial Sequence
<220> FEATURE:
<223> OTHER INFORMATION: Synthetic

<400> SEQUENCE: 103

```
Met Gly Arg Leu Gln Gly Ser Tyr Arg Pro Ser Leu Gly Thr Pro Val
1               5                   10                  15

Gly Pro Val Pro Asp Asp Gln Pro Ile Asp Val Thr Val Val Leu Arg
            20                  25                  30

Pro Thr Ala Ala Asp Asp Phe Arg Ala Asp Pro Asp Val Ala Ala
        35                  40                  45

Val Arg Ala Phe Ala Gly Arg Ala Gly Leu Asp Val Ala Glu Val Asp
    50                  55                  60

Glu Pro Ala Arg Thr Val Arg Leu Arg Gly Pro Ala Ala Ala Arg
65                  70                  75                  80

Thr Ala Phe Asp Thr Pro Leu Ala Leu Tyr Asp Ser Gly Gly Arg Ala
                85                  90                  95

Ile Arg Gly Arg Glu Gly Asp Leu Gly Leu Pro Asp Glu Leu Asp Asp
            100                 105                 110

Arg Val Val Ala Val Leu Gly Leu Asp Glu Arg Pro Ala Ala Arg Pro
        115                 120                 125

Arg Phe Gln Pro Ala Ala Ser Ala Arg Gln Gly Leu Thr Ala Leu Gln
130                 135                 140

Val Ala Arg Ala Tyr Asp Phe Pro Ala Ala Thr Gly Glu Gly Gln Thr
145                 150                 155                 160

Ile Ala Ile Ile Glu Leu Gly Gly Gly Phe Gly Gln Ala Asp Leu Asp
                165                 170                 175

Thr Tyr Phe Gly Gly Leu Asp Leu Pro Thr Pro Ala Val Ser Ala Val
            180                 185                 190

Gly Val Gln Gly Ala Ala Asn Val Pro Gly Gly Asp Pro Asp Gly Ala
        195                 200                 205

Asp Gly Glu Val Leu Leu Asp Ile Glu Val Ala Gly Ala Val Ala Pro
    210                 215                 220

Gly Ala Ala Gln Val Val Tyr Phe Ala Pro Asn Thr Asp Ala Gly Phe
225                 230                 235                 240

Leu Ala Ala Ile Asn Ala Ala Ala Ala Thr Pro Arg Pro Ala Ala
                245                 250                 255

Ile Ser Ile Ser Trp Gly Gly Pro Glu Ser Ser Trp Thr Ala Gln Ala
            260                 265                 270

Met Arg Ala Tyr Asp Gln Ala Phe Ala Ala Arg Ala Ala Gly Ile
        275                 280                 285

Thr Val Leu Ala Ala Ala Gly Asp Ala Gly Ala Asp Asp Ala Thr Asp
    290                 295                 300

Arg Leu Val Ala Asp Phe Pro Ala Gly Ser Pro Asn Val Ile Ala Cys
305                 310                 315                 320

Gly Gly Thr Lys Leu Thr Leu Asp Ala Ala Gly Ala Arg Ala Ser Glu
                325                 330                 335

Val Val Trp Asn Glu Ala Ala Asp Ser Ala Thr Gly Gly Tyr Ser
            340                 345                 350

Ala Thr Phe Thr Arg Pro Ala Trp Gln Pro Ala Ala Val Gly Arg Tyr
        355                 360                 365

Arg Gly Leu Pro Asp Ile Ser Gly Asn Ala Asp Pro Gln Thr Gly Tyr
    370                 375                 380

Arg Val Val Val Asp Gly Gln Pro Thr Val Val Gly Gly Thr Ser Ala
```

```
                385                 390                 395                 400
Val Ala Pro Leu Leu Ala Gly Leu Val Ala Arg Leu Ala Gln Leu Thr
                405                 410                 415

Gly Ala Pro Val Ala Asp Leu Ala Ala Val Ala Tyr Ala Asn Pro Ala
                420                 425                 430

Ala Phe Thr Asp Ile Thr Ala Gly Asp Asn Gln Gly Tyr Pro Ala Arg
                435                 440                 445

Ser Gly Trp Asp Pro Ala Ser Gly Leu Gly Ser Pro Val Gly Thr Lys
                450                 455                 460

Leu Leu Thr Ala Val Gly Gly Pro Thr Pro Pro Thr Thr Pro Pro
465                 470                 475                 480

Pro Thr Thr Pro Pro Pro Thr Pro Pro Pro Thr Ile Pro Pro Pro
                485                 490                 495

Thr Thr Pro Pro Thr Gln Thr Val Asp Ala Ala Asp Arg Ala Leu Trp
                500                 505                 510

Ser Ala Val Ala Thr Trp Ala Gly Gly Thr His Thr Gly Ala Asn Ala
                515                 520                 525

Arg Ala Ala Lys Ala Val Arg Ala Trp Ala Gln Ala Lys Ser Leu Ala
                530                 535                 540

<210> SEQ ID NO 104
<211> LENGTH: 523
<212> TYPE: PRT
<213> ORGANISM: Artificial Sequence
<220> FEATURE:
<223> OTHER INFORMATION: Synthetic

<400> SEQUENCE: 104

Met Thr Gln Pro Arg Tyr Thr Pro Leu Pro Gly Ser Glu Arg Glu Ala
1               5                   10                  15

Pro Leu Leu Ala Ala Arg Ser Asn Ala Thr Ala Ala Arg Ala Ser Arg
                20                  25                  30

Ala Gln Thr Ala Ser Ala Thr Val Val Leu Arg Arg Ser Glu Leu
                35                  40                  45

Pro Glu Ala Leu Val Leu Asp Gln Gln Phe Ile Ser Ser Asp Glu Leu
50                  55                  60

Ala Ala Arg Tyr Gly Ala Asp Pro Val Asp Ile Glu Lys Val Arg Ser
65                  70                  75                  80

Val Leu Glu Arg Phe Lys Val Ser Val Glu Val Asp Ala Ala Ser
                85                  90                  95

Arg Arg Val Lys Val Glu Gly Ala Val Ala Asp Ile Glu Arg Ala Phe
                100                 105                 110

Asn Ile Ala Leu His Ser Ala Ser Gly Thr Asp Pro His Ser Gly Arg
                115                 120                 125

Gly Phe Glu Tyr Arg Tyr Arg Thr Gly Val Leu Ser Val Pro Ala Glu
                130                 135                 140

Leu Gly Gly Ile Val Thr Ala Val Leu Gly Leu Asp Asn Arg Arg Gln
145                 150                 155                 160

Ala Glu Thr Arg Leu Arg Val Val Pro Ala Ala Leu Gly Ser Ser
                165                 170                 175

Tyr Thr Pro Val Gln Leu Gly Glu Ile Tyr Asn Phe Pro Gln Asp Ala
                180                 185                 190

Thr Gly Ala Gly Gln Arg Ile Ala Ile Glu Leu Gly Gly Gly Tyr
                195                 200                 205

Thr Pro Ala Gly Leu Arg Arg Tyr Phe Ala Ser Leu Gly Val Val Pro
```

210                 215                 220
Pro Lys Val Ala Val Ser Val Asp Gly Ala Gln Asn Ala Pro Gly
225                 230                 235                 240

Pro Asp Pro Gly Ala Asp Gly Glu Val Gln Leu Asp Val Glu Val Ala
                    245                 250                 255

Gly Ala Leu Ala Pro Gly Ala His Val Leu Val Tyr Phe Ala Pro Asn
                    260                 265                 270

Thr Asp Gln Gly Phe Leu Asp Ala Val Ser Gln Ala Ala His Ala Thr
                275                 280                 285

Pro Pro Pro Thr Ala Ile Ser Ile Ser Trp Gly Ala Ser Glu Asp Ser
290                 295                 300

Trp Thr Ala Ser Ala Arg Asp Ala Leu Asn Gln Ala Leu Arg Asp Ala
305                 310                 315                 320

Ala Ala Leu Gly Val Thr Val Thr Ala Ala Gly Asp Ser Gly Ser
                    325                 330                 335

Ser Asp Gly Val Pro Asp Arg Arg Ala His Val Asp Phe Pro Ala Ser
                340                 345                 350

Ser Pro Tyr Val Leu Ala Thr Gly Gly Thr Ser Leu Arg Ala Asp Pro
                355                 360                 365

Ala Thr Gly Val Val Gln Ser Glu Thr Val Trp Asn Asp Ser Gln Gly
                370                 375                 380

Ser Thr Gly Gly Val Ser Asp Val Phe Pro Arg Pro Ala Trp Gln
385                 390                 395                 400

Ala His Val Asp Val Pro His Ala Gly Arg Gly Val Pro Asp Val Ser
                    405                 410                 415

Ala Val Ala Asp Pro Ala Thr Gly Tyr Gln Val Leu Val Asp Asn Gln
                420                 425                 430

Pro Ala Val Ile Gly Gly Thr Ser Ala Val Ala Pro Leu Trp Ala Ala
                435                 440                 445

Leu Val Ala Arg Leu Ala Glu Ser Leu Gly Arg Pro Leu Gly Leu Leu
                450                 455                 460

Gln Pro Leu Val Tyr Pro Arg Thr Pro Gly Ser Thr Ala Tyr Pro Gly
465                 470                 475                 480

Phe Arg Asp Ile Thr Ile Gly Asn Asn Gly Ala Tyr Lys Ala Gly Lys
                    485                 490                 495

Gly Trp Asp Ala Ala Thr Gly Leu Gly Val Pro Asp Gly Thr Glu Leu
                500                 505                 510

Leu Ala His Leu Arg Gly Leu Asn Gly Ser Glu
                515                 520

<210> SEQ ID NO 105
<211> LENGTH: 537
<212> TYPE: PRT
<213> ORGANISM: Artificial Sequence
<220> FEATURE:
<223> OTHER INFORMATION: Synthetic

<400> SEQUENCE: 105

Met Ala Arg His Leu His Ala Gly Ser Glu Pro Lys Val Ile Thr Glu
1               5                   10                  15

Ser Lys Cys Ile Gly Ala Cys Asp Pro Ala Glu Arg Ile His Val Thr
                20                  25                  30

Val Met Leu Arg Arg Glu Gly Glu Gln Ala Leu Asp Ala Leu Val Asp
            35                  40                  45

Lys Leu Ala Ser Gly Asp Pro Ala Ala Lys Pro Val Ser Arg Glu Asp

```
              50                  55                  60
    Phe Ala Lys Arg Phe Gly Ala Arg Ala Asp Asp Ile Gln His Thr Glu
    65                  70                  75                  80

Ala Phe Ala Lys Arg His Gln Leu Thr Val Glu Arg Val Asp Pro Val
                        85                  90                  95

Gln Ser Val Val Glu Leu Ala Gly Thr Ile Ala Gln Phe Glu Asn Ala
                    100                 105                 110

Phe Gly Val Lys Leu Glu Lys Tyr Glu His His Ala Ile Gly Ser Phe
                115                 120                 125

Arg Ala Arg Thr Gly Ala Ile Ala Leu Pro Asp Glu Leu His Asp Ala
            130                 135                 140

Val Thr Ala Val Leu Gly Leu Asp Thr Arg Pro Gln Ala His Pro His
    145                 150                 155                 160

Phe Arg Phe Arg Pro Pro Phe Gln Pro Ala Arg Ser Gly Ala Gly Thr
                    165                 170                 175

Ser Tyr Thr Pro Leu Gln Leu Ala Ser Ile Tyr Asn Phe Pro Glu Gly
                180                 185                 190

Asp Gly Ala Gly Gln Cys Ile Ala Leu Val Glu Leu Gly Gly Gly Tyr
                195                 200                 205

Arg Ala Ala Asp Ile Arg Gln Tyr Phe Glu Gln Leu Gly Val Lys Pro
            210                 215                 220

Pro Lys Leu Val Asp Val Ser Val Asn Gly Gly Arg Asn Ala Pro Thr
    225                 230                 235                 240

Asp Asp Pro Asn Gly Pro Asp Gly Glu Val Ala Leu Asp Ile Glu Val
                    245                 250                 255

Ala Gly Ala Ile Ala Pro Gly Ala Thr Ile Ala Val Tyr Phe Ala Gly
                260                 265                 270

Asn Ser Asp Ala Gly Phe Ile Gln Ser Val Asn Gln Ala Ile His Asp
                275                 280                 285

Ser Thr Asn Arg Pro Ser Val Val Ser Ile Ser Trp Gly Gly Pro Glu
            290                 295                 300

Ala Ser Trp Thr Gln Gln Ser Ile Thr Ala Phe Asn Asn Val Leu Lys
    305                 310                 315                 320

Thr Ala Ala Ser Leu Gly Val Thr Val Cys Ala Ala Ser Gly Asp Ser
                    325                 330                 335

Gly Ser Ser Asp Gly Leu Gln Asp Gly Ser Asn His Val Asp Phe Pro
                340                 345                 350

Ala Ser Ser Pro Tyr Val Leu Ala Cys Gly Gly Thr Thr Leu Asp Ala
                355                 360                 365

Gln Ala Gly Gln Gly Ile Arg Arg Glu Val Val Trp Asn Asp Glu Ala
            370                 375                 380

Ala Ser Gly Gly Ala Gly Gly Gly Val Ser Ala Val Phe Pro Ala
    385                 390                 395                 400

Pro Ser Tyr Gln Lys Gly Leu Ser Ala Lys Ala Thr Gly Gly Gly Ser
                    405                 410                 415

Thr Pro Leu Ser Gln Arg Gly Val Pro Asp Val Ala Gly Asp Ala Ser
                420                 425                 430

Pro Thr Thr Gly Tyr Ile Ile Ser Ile Ala Gly Thr Thr Ala Val Leu
                435                 440                 445

Gly Gly Thr Ser Ala Val Ala Pro Leu Trp Ala Ala Leu Ile Ala Arg
            450                 455                 460

Ile Asn Ala Asn Gly Lys Ser Pro Val Gly Trp Ala Asn Pro Lys Leu
    465                 470                 475                 480
```

```
Tyr Ala Gln Pro Gly Ala Phe His Asp Ile Thr Gln Gly Asn Asn Gly
                485                 490                 495

Ala Phe Ala Ala Ser Glu Gly Trp Asp Ala Cys Thr Gly Leu Gly Ser
                500                 505                 510

Pro Asp Gly Ala Lys Val Ala Ala Leu Gln Gly Ala Ser Gly Gly
                515                 520                 525

Ser Gln Gln Gly Arg Ala Thr Gly Ala
    530                 535

<210> SEQ ID NO 106
<211> LENGTH: 520
<212> TYPE: PRT
<213> ORGANISM: Artificial Sequence
<220> FEATURE:
<223> OTHER INFORMATION: Synthetic

<400> SEQUENCE: 106

His Met Thr Lys His Pro Leu Pro Gly Ser Glu Arg Val Leu Ala Pro
1               5                   10                  15

Gly Ser Lys Val Val Ala Gln Cys Asp Pro Ser Glu Thr Ile Glu Val
                20                  25                  30

Val Val Leu Arg Arg Lys Asn Glu Gln Gln Phe Ala Gln Met Met
            35                  40                  45

Lys Thr Ile Glu Ala Gly Ala Gly Ala Arg Pro Leu Thr Arg Glu
    50                  55                  60

Glu Leu Glu Gln Arg Phe Gly Ala Leu Pro Glu Asp Ile Ala Lys Leu
65              70                  75                  80

Lys Ala Phe Ala Ala Gln His Gly Leu Ser Val Val Arg Glu Asp Ala
                85                  90                  95

Ser Ala Arg Thr Val Val Leu Ser Gly Arg Ile Glu Gln Phe Gln Gln
                100                 105                 110

Ala Phe Asp Val Gln Leu Gln His Tyr Glu His Gln Ser Met Gly Arg
            115                 120                 125

Phe Arg Gly Arg Thr Gly Ala Ile Ser Val Pro Asp Glu Leu His Gly
    130                 135                 140

Val Val Thr Ala Val Leu Gly Leu Asp Asp Arg Pro Gln Ala Arg Pro
145                 150                 155                 160

His Phe Arg Ile Arg Pro Pro Phe Gln Pro Ala Arg Ala Gln Ser Ala
                165                 170                 175

Ser Ser Phe Thr Pro Leu Gln Leu Ala Ser Leu Tyr Arg Phe Pro Gln
                180                 185                 190

Gly Asp Gly Ser Gly Gln Cys Ile Gly Ile Val Glu Leu Gly Gly Gly
            195                 200                 205

Tyr Arg Thr Ala Asp Leu Asp Ser Tyr Phe Ser Ser Leu Gly Val Gly
    210                 215                 220

Ser Pro Lys Val Val Ala Val Gly Val Asp Gln Ser Gly Asn Gln Pro
225                 230                 235                 240

Thr Gly Asp Pro Asn Gly Pro Asp Gly Glu Val Thr Leu Asp Ile Glu
                245                 250                 255

Ile Ala Gly Ala Leu Ala Pro Ala Thr Ile Ala Val Tyr Phe Thr
                260                 265                 270

Thr Asn Ser Asp Ala Gly Phe Ile Asp Ala Val Ser Gln Ala Val His
            275                 280                 285

Asp Arg Thr Asn Gln Pro Ser Val Ile Ser Ile Ser Trp Gly Ala Pro
    290                 295                 300
```

```
Glu Ser Met Trp Thr Ala Gln Ser Met Lys Ala Leu Asn Asp Val Leu
305                 310                 315                 320

Gln Ser Ala Ala Ala Ile Gly Val Thr Val Cys Ala Ala Ser Gly Asp
                325                 330                 335

Ser Gly Ser Ser Asp Gly Val Gly Asp Gly Arg Asp His Val Asp Phe
            340                 345                 350

Pro Ala Ser Ser Pro Tyr Val Leu Ala Cys Gly Gly Thr Ser Leu Gln
            355                 360                 365

Gly Ser Gly Arg Thr Val Ala His Glu Val Val Trp Asn Asp Gly Ser
        370                 375                 380

Asn Gly Gly Ala Thr Gly Gly Gly Val Ser Gly Ala Phe Pro Val Pro
385                 390                 395                 400

Ala Trp Gln Glu Gly Leu Ser Thr Ser Ala Ala Gln Gly Gly Gln Arg
                405                 410                 415

Ala Leu Thr Gly Arg Gly Val Pro Asp Val Ala Gly Asp Ala Ser Pro
            420                 425                 430

Leu Thr Gly Tyr Asp Val Ile Val Asp Gly Asn Asn Thr Val Ile Gly
        435                 440                 445

Gly Thr Ser Ala Val Ala Pro Leu Trp Ala Ala Leu Ile Ala Arg Ile
    450                 455                 460

Asn Gly Ala Lys Gly Ala Pro Val Gly Phe Val Asn Pro Lys Leu Tyr
465                 470                 475                 480

Lys Ala Ser Ala Cys Asn Asp Ile Thr Gln Gly Asn Asn Gly Ser Tyr
                485                 490                 495

Ala Ala Thr Thr Gly Trp Asp Ala Cys Thr Gly Leu Gly Ser Pro Asp
            500                 505                 510

Gly Val Lys Val Ala Ala Ala Leu
        515                 520

<210> SEQ ID NO 107
<211> LENGTH: 512
<212> TYPE: PRT
<213> ORGANISM: Artificial Sequence
<220> FEATURE:
<223> OTHER INFORMATION: Synthetic

<400> SEQUENCE: 107

Met Ser Pro Ile Ala Ser Arg Arg Ser Ala Leu Pro Leu Ser Glu Arg
1               5                   10                  15

Pro Ala Pro Glu Asn Ala Arg Ala Leu Ala Ala Val Glu Pro Asp Arg
                20                  25                  30

Thr Met Thr Val Ser Val Leu Val Arg Arg Lys Lys Pro Leu Val Leu
            35                  40                  45

Ala Asp Leu Glu Gly Lys Lys Leu Thr His Arg Glu Phe Glu Arg Arg
        50                  55                  60

Tyr Gly Ala Ser Glu Lys Asp Phe Ala Thr Ile Ala Lys Phe Ala Ala
65                  70                  75                  80

Gly His Gly Leu Ala Val Asp His His Ala Ser Ser Leu Ala Arg Arg
                85                  90                  95

Thr Val Val Leu Arg Gly Thr Ala Arg Gln Met Gln Gln Ala Phe Gly
            100                 105                 110

Val Thr Leu His Asp Tyr Glu Asp Ser Glu Thr Gln Gln Arg Tyr His
        115                 120                 125

Ser Phe Thr Gly Ala Ile Thr Val Pro Ala Ala His Ala Arg Ile Ile
    130                 135                 140
```

```
Glu Ser Val Leu Gly Leu Asp Ala Arg Pro Ile Ala Lys Pro His Phe
145                 150                 155                 160

Arg Val Arg Lys Arg Ser Ala Ala Thr Gly Ala Val Ser Phe Asn
        165                 170                 175

Pro Pro Gln Val Ala Ser Leu Tyr Ser Phe Pro Thr Gly Val Asp Gly
            180                 185                 190

Ser Gly Glu Thr Ile Gly Ile Leu Glu Leu Gly Gly Gly Tyr Glu Thr
        195                 200                 205

Ser Asp Ile Gln Gln Tyr Phe Ser Gly Leu Gly Ile Gln Pro Pro Thr
        210                 215                 220

Val Val Ala Val Ser Val Asp Gly Ala Val Asn Ala Pro Gly Asn Pro
225                 230                 235                 240

Asn Gly Ala Asp Gly Glu Val Ala Leu Asp Ile Gln Val Ala Gly Ser
            245                 250                 255

Ile Ala Pro Gly Ala Lys Leu Ala Val Tyr Phe Ala Pro Asn Thr Glu
            260                 265                 270

Gln Gly Phe Val Asp Ala Ile Thr Thr Ala Val His Asp Thr Ala Asn
        275                 280                 285

Lys Pro Ser Val Leu Ser Ile Ser Trp Gly Pro Glu Ser Ser Trp
290                 295                 300

Pro Gln Ala Ala Ala Gln Ser Leu Asn Asn Ala Cys Glu Ser Ala Ala
305                 310                 315                 320

Ala Leu Gly Val Thr Ile Thr Val Ala Ser Gly Asp Asn Gly Ser Thr
            325                 330                 335

Asp Gly Val Gln Asp Gly Gln Asn His Val Asp Phe Pro Ala Ser Ser
        340                 345                 350

Pro Tyr Val Leu Ala Cys Gly Gly Thr Tyr Leu Ala Ala Val Asn Asn
        355                 360                 365

Gly Val Pro Gln Glu Ser Val Trp Asp Asp Leu Ala Ser Gly Gly Gly
        370                 375                 380

Ala Thr Gly Gly Gly Val Ser Ala Leu Phe Pro Leu Pro Ala Trp Gln
385                 390                 395                 400

Thr Gly Ala Asn Val Pro Gly Gly Ser Met Arg Gly Val Pro Asp Val
            405                 410                 415

Ala Gly Asp Ala Ser Pro Glu Ser Gly Tyr Asn Val Leu Val Asp Gly
        420                 425                 430

Gln Pro Gln Val Val Gly Gly Thr Ser Ala Val Ala Pro Leu Trp Ala
        435                 440                 445

Ala Leu Ile Ala Leu Val Asn Gln Gln Lys Gly Glu Ala Ala Gly Phe
        450                 455                 460

Val Asn Ala Ala Leu Tyr Gln Asn Pro Ser Ala Phe His Asp Ile Thr
465                 470                 475                 480

Gln Gly Ser Asn Gly Ala Tyr Ala Ala Ala Pro Gly Trp Asp Pro Cys
            485                 490                 495

Thr Gly Leu Gly Ser Pro Met Gly Thr Ala Ile Ala Lys Ile Leu Ala
            500                 505                 510
```

<210> SEQ ID NO 108
<211> LENGTH: 531
<212> TYPE: PRT
<213> ORGANISM: Artificial Sequence
<220> FEATURE:
<223> OTHER INFORMATION: Synthetic

<400> SEQUENCE: 108

-continued

```
Met Ser Ala Phe Asp Gln Leu Val Pro Leu Pro Gly Ser Glu Lys Thr
1               5                   10                  15

Val Pro Asp Ala Ala Pro Ser Gln Thr Leu Asp Pro Asn Glu Val Leu
            20                  25                  30

Thr Val Thr Ile Arg Ile Arg Arg Lys Arg Thr Leu Ala Ser Leu Val
        35                  40                  45

Ser Thr Thr Ala Pro Val Thr Glu Val Val Ser Arg Ser Glu Tyr Ala
50                  55                  60

Ser Arg Phe Gly Ala Asp Pro Ala Ile Val Lys Gln Val Glu Ala Phe
65                  70                  75                  80

Ala Ser Ala Tyr Asp Leu Ser Leu Val Glu Gln Ser Leu Ala Arg Arg
            85                  90                  95

Ser Val Leu Leu Arg Gly Thr Val Ala Gln Met Glu Gln Ala Phe Gly
        100                 105                 110

Val Ser Leu Ala Asn Tyr Gln Leu Ala Asp Gly Thr Val Phe Arg Gly
    115                 120                 125

Arg Thr Gly Val Val Asn Val Pro Ser Glu Leu Val Glu His Ile Glu
130                 135                 140

Gly Val Phe Gly Leu Asp Asn Arg Pro Gln Ala Arg Ala His Phe Gln
145                 150                 155                 160

Val Tyr Lys Pro Glu Lys Gly Thr Lys Val Ala Pro Arg Ala Gly Gly
            165                 170                 175

Ile Ser Tyr Thr Pro Pro Gln Leu Ala Arg Leu Tyr Asn Phe Pro Thr
        180                 185                 190

Gly Val Thr Gly Lys Gly Gln Cys Ile Ala Ile Glu Leu Gly Gly
    195                 200                 205

Gly Phe Arg Thr Ala Asp Ile Lys Thr Tyr Phe Gly Gly Leu Gly Leu
210                 215                 220

Lys Pro Pro Thr Val Val Ala Val Ser Val Asp Gly Gly His Asn Ala
225                 230                 235                 240

Pro Ser Thr Ala Asp Ser Ala Asp Gly Glu Val Met Leu Asp Ile Asp
            245                 250                 255

Val Ala Gly Gly Val Ala Pro Gly Ala Lys Ile Val Val Tyr Phe Ala
        260                 265                 270

Pro Asn Thr Asp Gln Gly Phe Leu Asp Ala Ile Thr Thr Ala Met His
    275                 280                 285

Asp Thr Lys Asn Lys Pro Ser Val Ile Ser Ile Ser Trp Gly Ala Ala
290                 295                 300

Glu Ser Asn Trp Thr Pro Gln Ala Leu Thr Ser Phe Asn Gln Ala Phe
305                 310                 315                 320

Gln Ala Ala Ala Leu Gly Ile Thr Val Cys Ala Ala Ala Gly Asp
            325                 330                 335

Thr Gly Ser Asp Asp Ser Val Gly Asp Gly Lys Ala His Val Asp Phe
        340                 345                 350

Pro Ala Ser Ser Pro Phe Val Leu Ala Cys Gly Gly Thr Lys Leu Thr
    355                 360                 365

Ala Thr Asp Asn Val Ile Ala Ser Glu Val Val Trp His Glu Ser Lys
370                 375                 380

Thr Ser Ala Thr Gly Gly Val Ser Asp Val Phe Asp Leu Pro Asp
385                 390                 395                 400

Tyr Gln Gln Lys Ser His Val Pro Pro Ser Val Asn Asp Lys Thr Arg
            405                 410                 415
```

```
Ile Gly Arg Gly Val Pro Asp Val Ala Val Ala Asp Pro Val Thr
            420                 425                 430

Gly Tyr Ala Val Arg Val Asp Gly Ser Asn Leu Val Phe Gly Gly Thr
        435                 440                 445

Ser Ala Val Ala Pro Leu Met Ala Gly Leu Ile Ala Leu Ile Asn Gln
450                 455                 460

Gln Arg Gly Lys Ala Val Gly Phe Ile His Pro Leu Ile Tyr Ala Asn
465                 470                 475                 480

Pro Ser Ala Phe Arg Asp Ile Thr Gln Gly Asn Asn Thr Thr Thr Thr
                485                 490                 495

Gly Asn Lys Gly Tyr Ala Ala Thr Thr Gly Trp Asp Ala Cys Thr Gly
            500                 505                 510

Leu Gly Val Ala Asp Gly Lys Lys Leu Ala Ser Val Leu Thr Ala Thr
        515                 520                 525

Pro Val Ala
    530

<210> SEQ ID NO 109
<211> LENGTH: 567
<212> TYPE: PRT
<213> ORGANISM: Artificial Sequence
<220> FEATURE:
<223> OTHER INFORMATION: Synthetic

<400> SEQUENCE: 109

Met Ala Ala Thr Pro Arg Phe Ala Ser Gln Pro Arg Val Thr Leu Pro
1               5                   10                  15

Gly Ser Gln Lys His Pro Leu Thr Thr Asp Thr Glu Val Pro Pro Pro
            20                  25                  30

Ala Pro Val Lys Ala Ala Thr Lys Leu Ser Ala Thr Pro Phe Thr
        35                  40                  45

Val Thr Val Ile Val Lys Arg Lys Asn Pro Leu Asn Leu Lys Gln Val
50                  55                  60

Leu Lys Pro Ala Gly Arg Leu Thr His Ala Ala Phe Ala Lys Ala His
65                  70                  75                  80

Gly Pro Ser Pro Asp Gly Val Lys Leu Val Lys Ala Phe Ala Lys Glu
                85                  90                  95

Phe Gly Leu Thr Val Ala Pro Ala Pro Gly Gln Gly Arg Arg Ala Leu
            100                 105                 110

Tyr Leu Thr Gly Thr Ala Ala Met Gln Thr Ala Phe Gly Val Thr
        115                 120                 125

Phe Ala Thr Lys Ile Met Glu Gly Thr Lys Tyr Arg Val Arg Glu Gly
130                 135                 140

Asp Ile Cys Leu Pro Lys Glu Leu Ile Gly His Val Asp Ala Val Leu
145                 150                 155                 160

Gly Leu Asp Asn Arg Pro Gln Ala Lys Pro His Phe Arg His His Lys
                165                 170                 175

Pro Ala Ala Thr Ser Val Ser Tyr Thr Pro Val Gln Val Gly Gln Leu
            180                 185                 190

Tyr Gly Phe Pro Ser Gly Ala Lys Ala Thr Gly Gln Thr Ile Gly Leu
        195                 200                 205

Ile Glu Leu Gly Gly Gly Phe Arg Ala Ala Asp Ile Thr Ala Tyr Phe
210                 215                 220

Lys Thr Leu Gly Gln Thr Ala Pro Lys Val Thr Ala Val Leu Val Asp
225                 230                 235                 240
```

Lys Ala Lys Asn Thr Pro Thr Thr Ser Ser Ser Ala Asp Gly Glu Val
            245                 250                 255

Met Leu Asp Ile Glu Val Ala Ala Val Ala Pro Gly Ala Asn Ile
        260                 265                 270

Ala Val Tyr Phe Ala Pro Asn Thr Asp Gln Gly Phe Ile Asp Ala Ile
            275                 280                 285

Ser Gln Ala Val His Asp Thr Val Asn Lys Pro Ser Val Ile Ser Ile
290                 295                 300

Ser Trp Gly Gly Pro Glu Ser Thr Trp Thr Ala Gln Ser Leu Ala Ala
305                 310                 315                 320

Leu Asp Ala Ala Cys Gln Ser Ala Ala Leu Gly Ile Thr Ile Thr
                325                 330                 335

Val Ala Ala Gly Asp Asp Gly Ser Thr Asp Gly Val Lys Gly Thr Val
                340                 345                 350

Asn His Val Asp Phe Pro Ala Ser Ser Pro His Val Leu Gly Cys Gly
            355                 360                 365

Gly Thr Lys Leu Leu Gly Ser Gly Thr Thr Ile Thr Ser Glu Val Val
        370                 375                 380

Trp Asn Glu Leu Thr Ala Asn Glu Gly Ala Thr Gly Gly Gly Val Ser
385                 390                 395                 400

Asn Val Phe Pro Leu Pro Thr Trp Gln Ala Lys Ser Asn Val Pro Lys
                405                 410                 415

Pro Thr Val Ala Ala Gly Gly Arg Gly Val Pro Asp Val Ser Gly Asn
                420                 425                 430

Ala Asp Pro Ser Thr Gly Tyr Thr Val Arg Val Asp Gly Ser Thr Phe
            435                 440                 445

Pro Ile Gly Gly Thr Ser Ala Val Ala Pro Leu Trp Ala Gly Leu Ile
450                 455                 460

Ala Leu Cys Asn Ala Gln Asn Lys Thr Thr Ala Gly Phe Ile Asn Pro
465                 470                 475                 480

Ala Leu Tyr Ala Ala Ala Ala Lys Ser Phe Arg Asp Ile Thr Ser
                485                 490                 495

Gly Asn Asn Gly Gly Phe Lys Ala Gly Pro Gly Trp Asp Ala Cys Thr
            500                 505                 510

Gly Leu Gly Ser Pro Ile Gly Thr Ala Ile Ala Lys Thr Leu Ala Pro
        515                 520                 525

Ala Thr Lys Ser Thr Ser Lys Thr Ala Val Lys Asn Ala Pro Glu Ile
    530                 535                 540

Arg Phe Arg Pro His Lys Lys Ala Pro Thr Lys Thr Ala Ala Lys Thr
545                 550                 555                 560

Pro Ala Leu Arg Arg Leu Lys
                565

<210> SEQ ID NO 110
<211> LENGTH: 543
<212> TYPE: PRT
<213> ORGANISM: Artificial Sequence
<220> FEATURE:
<223> OTHER INFORMATION: Synthetic

<400> SEQUENCE: 110

Met Pro Thr Ser Ser Arg Phe Ala Ser Gln Ser Arg Val Pro Leu Pro
1               5                   10                  15

Gly Ser Glu Arg Lys Pro Phe Val Pro Ala Gly Pro Lys Ala Ala
            20                  25                  30

-continued

Lys Thr Pro Lys Val Ser Thr Ala Val Lys Thr Val Pro Ala Thr Gly
             35                  40                  45
Arg Ile Arg Val Ser Leu Ile Val Pro Pro Lys Gln Pro Leu Asp Thr
 50                  55                  60
Lys Arg Leu Gly Lys Leu Asp Ala Arg Leu Ser Arg Ala Gln Phe Ala
 65                  70                  75                  80
Ala Arg His Gly Ala Asp Pro Ala Ser Val Arg Leu Val Lys Ala Phe
                 85                  90                  95
Ala Lys Glu Phe Gly Leu Thr Val Glu Pro Ile Thr Gln Pro Gly Arg
                100                 105                 110
Cys Thr Val Gln Leu Ser Gly Thr Cys Ala Ala Met Arg Lys Ala Phe
                115                 120                 125
Ala Ile Ser Leu Val Glu His Thr Thr Glu Gln Gly Lys Phe Arg Leu
130                 135                 140
Arg Glu Gly Glu Ile Ser Leu Pro Ala Glu Leu Glu Gly His Val Leu
145                 150                 155                 160
Ala Val Leu Gly Leu Asp Asn Arg Pro Gln Ala Lys Pro His Phe Arg
                165                 170                 175
Ile Ala Lys Pro Arg Ala Thr Asn Val Ser Tyr Thr Pro Val Gln Val
                180                 185                 190
Ala Gln Met Tyr Gly Phe Pro Ala Gly Ala Thr Ala Thr Gly Gln Thr
            195                 200                 205
Ile Gly Ile Ile Glu Leu Gly Gly Tyr Arg Ala Ala Asp Leu Thr
            210                 215                 220
Ala Tyr Phe Lys Thr Leu Gly Leu Pro Ala Pro Thr Val Thr Ala Val
225                 230                 235                 240
Pro Ile Asp Gly Gly Lys Asn Thr Pro Gly Asn Ala Asn Gly Ala Asp
                245                 250                 255
Gly Glu Val Met Leu Asp Ile Glu Val Cys Ala Ala Val Ala Gln Gly
                260                 265                 270
Ala Lys Ile Ala Val Tyr Phe Thr Thr Asn Thr Asp Gln Gly Phe Ile
            275                 280                 285
Asp Ala Ile Thr Thr Ala Val His Asp Ser Thr Asn Lys Pro Ser Val
290                 295                 300
Ile Ser Ile Ser Trp Gly Gly Pro Glu Ser Ser Trp Thr Glu Gln Ser
305                 310                 315                 320
Met Thr Ala Leu Asp Ala Ala Cys Gln Ala Ala Ala Val Gly Val
                325                 330                 335
Thr Ile Thr Val Ala Ala Gly Asp Asn Gly Ser Ser Asp Gly Ala Ser
            340                 345                 350
Gly Asp Asn Val Asp Phe Pro Ala Ser Ser Pro His Val Leu Ala Cys
            355                 360                 365
Gly Gly Thr Lys Leu Val Gly Ser Gly Ser Thr Ile Thr Ser Glu Val
        370                 375                 380
Val Trp Asp Glu Thr Ser Asn Asp Glu Gly Ala Thr Gly Gly Val
385                 390                 395                 400
Ser Thr Val Phe Ala Leu Pro Thr Trp Gln Lys Asn Ala Asn Val Pro
                405                 410                 415
Ser Pro Thr Thr Ser Ala Gly Gly Arg Gly Val Pro Asp Val Ser Gly
            420                 425                 430
Asp Ala Asp Pro Ser Thr Gly Tyr Thr Ile Arg Val Asp Ser Glu Thr
        435                 440                 445
Thr Val Ile Gly Gly Thr Ser Ala Val Ala Pro Leu Trp Ala Gly Leu

```
                450                 455                 460
Ile Ala Leu Ala Asn Ala Gln Asn Lys Val Ala Ala Gly Phe Val Asn
465                 470                 475                 480

Pro Ala Leu Tyr Ala Ala Gly Ala Lys Lys Ala Phe Arg Asp Ile Thr
                485                 490                 495

Gln Gly Asn Asn Gly Ser Phe Ser Ala Gly Pro Gly Trp Asp Ala Cys
                500                 505                 510

Thr Gly Leu Gly Ser Pro Val Gly Asn Leu Val Ile Gln Ala Val Ala
            515                 520                 525

Pro Lys Ser Thr Thr Thr Lys Lys Ala Lys Lys Gly Lys Thr Lys
            530                 535                 540

<210> SEQ ID NO 111
<211> LENGTH: 378
<212> TYPE: PRT
<213> ORGANISM: Artificial Sequence
<220> FEATURE:
<223> OTHER INFORMATION: Synthetic

<400> SEQUENCE: 111

Met His Ser Tyr Leu Lys Gln Gln Ser His Met Gln Ser Tyr Leu Glu
1               5                   10                  15

Gln Glu Asn His Met Arg Ser Tyr Leu Glu Met Arg Lys Lys Pro Tyr
                20                  25                  30

Phe Asp Asp Leu Ala Asn Ile Arg Pro Gly Gly Leu Thr Pro Ala Gln
            35                  40                  45

Val Cys Gln Ala Tyr Gln Phe Ala Lys Val Gln Pro Val Arg Pro Val
50                  55                  60

Lys Leu Gly Ile Val Ser Leu Ala Gly Gln Tyr Leu Ser Ser Asp Met
65                  70                  75                  80

Ser Lys Ala Phe Thr Gly Tyr Gly Leu Pro Thr Pro Val Val Ser Thr
                85                  90                  95

Ala Gly Ser Gln Val Leu Gly Asp Leu Trp Ser Asn Val Glu Asn Met
            100                 105                 110

Met Asp Ile Glu Ile Ala Gly Ala Ala Trp Ala Tyr Ala Thr Gly Thr
        115                 120                 125

Ala Ala Thr Leu Leu Met Gln Phe Glu Pro Asn Asn Glu Thr Gly Ile
    130                 135                 140

Pro Asn Ala Ile Asn Ala Leu Val Ala Ala Gly Cys Glu Val Ile Ser
145                 150                 155                 160

Ile Ser Trp Gly Ala Pro Ala Asn Leu Gln Thr Met Glu Ala Ile Thr
                165                 170                 175

Ala Arg Lys Glu Ala Cys Lys Gln Ala Ala Val Gln Asn Val His Val
            180                 185                 190

Phe Ala Ala Ser Gly Asp Glu Ser Leu Asn Asp Gly Thr Asn Ser Arg
        195                 200                 205

Thr Pro Asp Asp Pro Cys Cys Asp Pro Asn Val Trp Gly Val Gly Gly
    210                 215                 220

Thr Arg Leu Val Leu Gln Ala Asp Gly Ser Ile Ala Gln Glu Ser Ala
225                 230                 235                 240

Trp Gly Asp Gly Asn Ala Ala Asp Lys Gly Gly Gly Gly Phe Asp
                245                 250                 255

Ser Arg Glu Pro Leu Pro Asp Tyr Gln Val Gly Val Val His Ser Glu
            260                 265                 270

His Arg Gly Ser Pro Asp Ser Ser Ala Asn Ala Asp Pro Gly Thr Gly
```

```
                275                 280                 285
Tyr Ala Ile Val Ala Asn Gly Gln Trp Leu Ile Gly Gly Thr Ser
290                 295                 300
Ala Ser Ala Pro Leu Thr Ala Gly Tyr Val Ala Ala Ile Leu Ser Thr
305                 310                 315                 320
Leu Pro Gly Pro Ile Ser Gln Ser Val Leu Gln Arg Lys Leu Tyr Thr
                325                 330                 335
Ala His Lys Thr Ala Phe Arg Asp Ile Leu Leu Gly Ser Asn Gly Ala
            340                 345                 350
Pro Ala Arg Pro Gly Trp Glu Glu Ala Thr Gly Leu Gly Ser Ile Asn
        355                 360                 365
Gly Pro Gly Leu Ala Ala Ala Leu Gln Ser
370                 375

<210> SEQ ID NO 112
<211> LENGTH: 523
<212> TYPE: PRT
<213> ORGANISM: Artificial Sequence
<220> FEATURE:
<223> OTHER INFORMATION: Synthetic

<400> SEQUENCE: 112

Met Ala Asn His Pro Leu Asn Gly Ser Glu Arg Glu Cys Leu Lys Asp
1               5                   10                  15
Ala Gln Pro Ile Gly Lys Ala Asp Pro Asn Glu Arg Leu Glu Val Thr
            20                  25                  30
Met Leu Val Arg Arg Arg Ser His Asp Ala Phe Glu Lys His Ile Ser
        35                  40                  45
Ala Leu Ala Ala Gln Gly Ala Ser Ala Lys His Ile Asp His Asp Glu
    50                  55                  60
Phe Thr Lys His Phe Gly Ala Asp Ser Ala Asp Leu Ala Ala Val His
65                  70                  75                  80
Ala Phe Ala Gln Lys His Gly Leu Ser Val Val Glu Ser His Glu Ala
                85                  90                  95
Arg Arg Ala Val Val Leu Ser Gly Thr Val Ala Gln Phe Asp Ala Ala
            100                 105                 110
Phe Gly Val Ser Leu Gln Gln Tyr Glu His Asp Gly Thr Tyr Arg
        115                 120                 125
Gly Arg Thr Gly Pro Ile His Leu Pro Asp Glu Leu Asn Gly Val Val
    130                 135                 140
Asp Ala Val Met Gly Leu Asp Asn Arg Pro Gln Ala Arg Pro Ser Phe
145                 150                 155                 160
Arg Thr Arg Ala Gln Gly Asn Val Arg Trp Thr Ala Arg Ala Ala Gly
                165                 170                 175
Ala Ser Thr Phe Thr Pro Val Gln Leu Ala Ser Leu Tyr Asp Phe Pro
            180                 185                 190
Gln Gly Asp Gly Gln Asn Gln Cys Ile Gly Ile Glu Leu Gly Gly
        195                 200                 205
Gly Tyr Arg Pro Ala Asp Leu Lys Thr Tyr Phe Ala Ser Leu Asn Met
    210                 215                 220
Lys Ala Pro Ser Val Thr Ala Val Ser Val Asp His Gly Arg Asn His
225                 230                 235                 240
Pro Thr Gly Asp Pro Asn Gly Pro Asp Gly Glu Val Met Leu Asp Ile
                245                 250                 255
Glu Val Ala Gly Ala Val Ala Pro Gly Ala Lys Ile Val Val Tyr Phe
```

-continued

```
              260                 265                 270
Ala Pro Asn Thr Asp Ala Gly Phe Ile Asp Ala Ile Gly Thr Ala Ile
            275                 280                 285

His Asp Thr Lys Asn Lys Pro Ser Val Ile Ser Ile Ser Trp Ser Gly
    290                 295                 300

Pro Glu Ser Ala Trp Thr Gln Gln Ala Met Asn Ala Phe Asp Gln Ala
305             310                 315                     320

Phe Gln Ser Ala Ala Ala Leu Gly Val Thr Ile Cys Ala Ala Ser Gly
                325                 330                 335

Asp Asn Gly Ser Gly Gly Val Gly Asp Gly Ala Asp His Val His
            340                 345                 350

Phe Pro Ala Ser Ser Pro Tyr Ala Leu Gly Cys Gly Gly Thr Ser Leu
        355                 360                 365

Gln Ala Ser Gly Asn Gly Ile Ala Ser Glu Thr Val Trp Asn Asp Gly
        370                 375                 380

Ala Asn Gly Gly Ala Thr Gly Gly Gly Val Ser Ser Phe Phe Ala Leu
385                 390                 395                 400

Pro Ala Trp Gln Glu Gly Leu Arg Val Thr Arg Ala Gly Gly Ala His
                405                 410                 415

Ser Pro Leu Ala Met Arg Gly Val Pro Asp Val Ala Gly Asn Ala Asp
            420                 425                 430

Pro Val Thr Gly Tyr Glu Val Arg Val Asp Gly His Asp Met Val Ile
            435                 440                 445

Gly Gly Thr Ser Ala Val Ala Pro Leu Trp Ala Gly Leu Ile Ala Arg
    450                 455                 460

Ile Asn Ala Ile Lys Gly Ala Pro Val Gly Tyr Ile Asn Pro His Leu
465                 470                 475                 480

Tyr Lys Asp Pro Leu Ala Leu Val Asp Ile Thr Lys Gly Asn Asn Asp
            485                 490                 495

Asp Phe His Ala Thr Ala Gly Trp Asp Ala Cys Thr Gly Leu Gly Arg
            500                 505                 510

Pro Asp Gly Lys Lys Val Lys Asp Ala Val Ser
            515                 520
```

COMPOSITIONS AND METHODS FOR TREATING CELIAC SPRUE DISEASE

RELATED APPLICATIONS

This application is a Continuation of U.S. application Ser. No. 14/911,630, filed Feb. 11, 2016, which is a national phase of International Application No. PCT/US2014/050835, filed Aug. 13, 2014, which claims priority to U.S. Provisional Application No. 61/865,787, filed Aug. 14, 2013, the disclosures of which are hereby incorporated by reference in their entirety.

FEDERAL FUNDING STATEMENT

This invention was made with government support under HR0011-08-1-0085 awarded by the Defense Advanced Research Projects Agency. The government has certain rights in the invention.

BACKGROUND

Celiac sprue is a highly prevalent disease in which dietary proteins found in wheat, barley, and rye products known as 'glutens' evoke an immune response in the small intestine of genetically predisposed individuals. The resulting inflammation can lead to the degradation of the villi of the small intestine, impeding the absorption of nutrients. Symptoms can appear in early childhood or later in life, and range widely in severity, from diarrhea, fatigue and weight loss to abdominal distension, anemia, and neurological symptoms. There are currently no effective therapies for this lifelong disease except the total elimination of glutens from the diet. Although celiac sprue remains largely underdiagnosed, its'prevalence in the U.S. and Europe is estimated at 0.5-1.0% of the population. The identification of suitable naturally-occurring enzymes as oral therapeutics for celiac disease is difficult due to the stringent physical and chemical requirements to specifically and efficiently degrade gluten-derived peptides in the harsh and highly acidic environment of the human digestive tract.

SUMMARY OF THE INVENTION

In one aspect, the invention provides methods for treating celiac sprue, comprising administering to a subject with celiac sprue an amount effective to treat the celiac sprue of one or more polypeptides comprising or consisting of the amino acid sequence of a polypeptide selected from the group consisting of SEQ ID NOS: 75, 74, 76-89, 95, 97-98, 102-111, or processed versions thereof. In one embodiment, the one or more polypeptides comprise one or more polypeptides comprising or consisting of the amino acid sequence of a polypeptide selected from the group consisting of SEQ ID NOs: 75, 74, 77, 78, 82, 88, 98, 105, 111, or processed versions thereof. In a further embodiment, the one or more polypeptides comprise a polypeptide with the amino acid sequence of SEQ ID NO: 89.

In another aspect, the invention provides isolated polypeptides selected from the group consisting of the following polypeptides, or processed versions thereof:

(a) SEQ ID NO: 95, wherein one, two, three, four, five, six, seven, eight, nine, ten, or all eleven of the following are true: (i) AA residue 116 is V or D; (ii) AA residue 255 is S, K, or G; (iii) AA residue 284 is D; (iv) AA residue 285 is T; (v) AA residue 286 is A, T, or N; (vi) AA residue 312 is S; (vii) AA residue 347 is N; (viii) AA residue 350 is T or A; (ix) AA residue 351 is N or G; (x) AA residue 354 is D; and (xi) AA residue 361 is S or H;

(b) SEQ ID NO: 75, wherein one, two, three, four, five, six, seven, eight, nine ten, or all eleven of the following are true: (i) AA residue 106 is D; (ii) AA residue 246 is S, K or G; (iii) AA residue 275 is D; (iv) AA residue 276 is S; (v) AA residue 277 is A, T, or N; (vi) AA residue 303 is S; (vii) AA residue 338 is S; (viii) AA residue 341 is T or A; (ix) AA residue 342 is N or G; (x) AA residue 345 is Q or D; and (xi) AA residue 352 is S or H;

(c) SEQ ID NO: 76, wherein one, two, three, four, five, six, seven, eight, nine, ten, or all eleven of the following are true: (i) AA residue 120 is D; (ii) AA residue 259 is S, K, or G; (iii) AA residue 288 is D; (iv) AA residue 289 is T; (v) AA residue 290 is A, T, or N; (vi) AA residue 316 is S; (vii) AA residue 351 is S or N; (viii) AA residue 354 is A; (ix) AA residue 355 is N or G; (x) AA residue 358 is D; and (xi) AA residue 365 is S or H;

(d) SEQ ID NO: 78;

(e) SEQ ID NO: 79, wherein one, two, three, four, five, six, seven, eight, nine, ten, or all eleven of the following are true: (i) AA residue 107 is V or D; (ii) AA residue 245 is S, K, or G; (iii) AA residue 274 is D; (iv) AA residue 275 is T; (v) AA residue 276 is A, T, or N; (vi) AA residue 302 is S; (vii) AA residue 337 is S or N; (viii) AA residue 340 is T or A; (ix) AA residue 341 is N or G; (x) AA residue 344 is Q or D; and (xi) AA residue 351 is S or H;

(f) SEQ ID NO: 80, wherein one, two, three, four, five, six, seven, eight, nine, ten, or all eleven of the following are true: (i) AA residue 76 is V or D; (ii) AA residue 206 is S, K, or G; (iii) AA residue 235 is D; (iv) AA residue 236 is S; (v) AA residue 237 is A, T, or N; (vi) AA residue 262 is S; (vii) AA residue 297 is S or N; (viii) AA residue 300 is T or A; (ix) AA residue 301 is N or G; (x) AA residue 302 is Q or D; and (xi) AA residue 309 is S or H;

(g) SEQ ID NO: 81, wherein one, two, three, four, five, six, seven, eight, nine, ten, or all eleven of the following are true: (i) AA residue 105 is D; (ii) AA residue 244 is S or K; (iii) AA residue 272 is D; (iv) AA residue 273 is S; (v) AA residue 274 is A, T, or N; (vi) AA residue 299 is S; (vii) AA residue 334 is N; (viii) AA residue 337 is T or A; (ix) AA residue 338 is N or G; (x) AA residue 341 is Q or D; and (xi) AA residue 348 is S or H;

(h) SEQ ID NO: 82, wherein one, two, three, four, five, six, seven, eight, nine, ten, or all eleven of the following are true: (i) AA residue 106 is V or D; (ii) AA residue 244 is S, K, or G; (iii) AA residue 273 is D; (iv) AA residue 274 is T; (v) AA residue 275 is A, T, or N; (vi) AA residue 301 is S; (vii) AA residue 336 is N; (viii) AA residue 339 is T or A; (ix) AA residue 340 is N or G; (x) AA residue 343 is D; and (viii) AA residue 350 is S or H;

(i) SEQ ID NO: 83, wherein one, two, three, four, five, six, seven, eight, nine, ten, or all eleven of the following are true: (i) AA residue 107 is V or D; (ii) AA residue 245 is S, K, or G; (iii) AA residue 274 is D; (iv) AA residue 275 is T; (v) AA residue 276 is A, T, or N; (vi) AA residue 302 is S; (vii) AA residue 337 is N; (viii) AA residue 340 is T or A; (ix) AA residue 341 is N or G; (x) AA residue 344 is Q or D; and (xi) AA residue 351 is S or H;

(j) SEQ ID NO: 84, wherein one, two, three, four, five, six, seven, eight, nine, ten, or all eleven of the following are true: (i) AA residue 104 is V or D; (ii) AA residue 241 is S, K, or G; (iii) AA residue 270 is D; (iv) AA residue 271 is S; (v) AA residue 272 is D, A, T, or N; (vi) AA residue 398 is S; (vii) AA residue 33 is S; (viii) AA residue 336 is A; (ix) AA residue 337 is N or G; (x) AA residue 340 is D; and (xi) AA residue 347 is S or H;

(k) SEQ ID NO: 85, wherein one, two, three, four, five, six, seven, eight, nine, ten, or all eleven of the following are true: (i) AA residue 104 is D; (ii) AA residue 245 is S, K, or G; (iii) AA residue 274 is D; (iv) AA residue 275 is S; (v) AA residue 276 is A, T, or N; (vi) AA residue 302 is S; (vii) AA residue 337 is S or N; (viii) AA residue 340 is T or A; (ix) AA residue 341 is N or G; (x) AA residue 344 is Q or D; and (xi) AA residue 351 is S or H;

(l) SEQ ID NO: 86, wherein one, two, three, four, five, six, seven, eight, nine, ten, or all eleven of the following are true: (i) AA residue 118 is V or D; (ii) AA residue 250 K, or G; (iii) AA residue 279 is D; (iv) AA residue 280 is S; (v) AA residue 281 is A, T, or N; (vi) AA residue 307 is S; (vii) AA residue 342 is S or N; (viii) AA residue 345 is A; (ix) AA residue 346 is N or G; (x) AA residue 349 is Q or D; and (xi) AA residue 356 is S or H;

(m) SEQ ID NO: 87, wherein one, two, three, four, five, six, seven, eight, nine, ten, or all eleven of the following are true: (i) AA residue 121 is V or D; (ii) AA residue 253 is S, K, or G; (iii) AA residue 282 is D; (iv) AA residue 283 is S; (v) AA residue 284 is A, T, or N; (vi) AA residue 310 is S; (vii) AA residue 345 is S; (viii) AA residue 348 is T or A; (ix) AA residue 349 is N or G; (x) AA residue 352 is Q or D; and (xi) AA residue 357 is S or H;

(n) SEQ ID NO: 88, wherein one, two, three, four, five, six, seven, eight, nine, or all ten of the following are true: (i) AA residue 111 is S, K, or G; (ii) AA residue 139 is D; (iii) AA residue 140 is T or S; (iv) AA residue 141 is D, A, T, or N; (v) AA residue 164 is S; (vi) AA residue 199 is S or N; (vii) AA residue 202 is T or A; (viii) AA residue 203 is N or G; (ix) AA residue 204 is Q or D; and (x) AA residue 211 is S or H; and (o) SEQ ID NO: 89.

In other aspects, the invention provides nucleic acids encoding the polypeptides of the invention, nucleic acid expression vectors comprising the isolated nucleic acids of the invention, and recombinant host cells comprising the nucleic acid expression vectors of the invention. of In a still further aspect, the invention provides compositions, comprising (a) one or more polypeptides comprising the amino acid sequence of a polypeptide selected from the group consisting of SEQ ID NOs: 74-89, 95, 97-99, and 102-111, or processed versions thereof; and (b) one or more further polypeptides comprising an amino acid sequence selected from the group consisting of:

(A) an amino acid sequence at least 75% identical to the amino acid sequence of SEQ ID NO: 35, wherein
  (i) the polypeptide degrades a PQPQLP (SEQ ID NO: 34) peptide at pH 4; and
  (ii) residue 278 is Ser, residue 78 is Glu, and residue 82 is Asp (B) an an amino acid sequence at least 75% identical to the amino acid sequence of SEQ ID NO: 1, wherein
  (i) the polypeptide degrades a PQPQLP (SEQ ID NO: 34) peptide at pH 4; and
  (ii) residue 467 is Ser, residue 267 is Glu, and residue 271 is Asp.

In a further aspect, the invention provides pharmaceutical compositions, comprising the isolated polypeptides, nucleic acids, expression vectors, host cells, or compositions of the invention, together with a pharmaceutically acceptable carrier.

DETAILED DESCRIPTION

Figure 1:
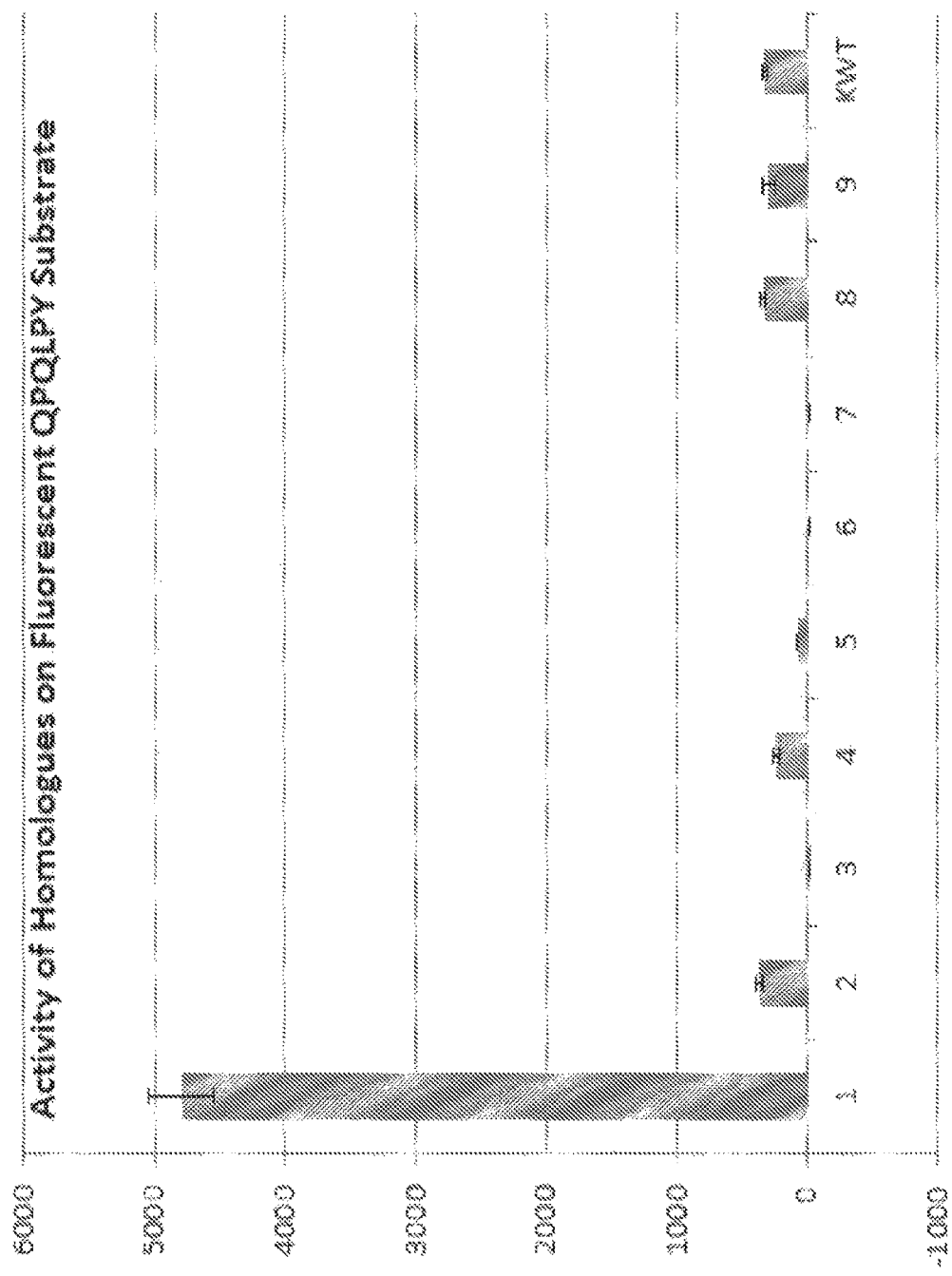
FIG. 1 is a graph showing the activity of various polypeptides to break down a fluorescent analogue of gliadin that was conjugated to a fluorophore and a quencher. X-axis: specific homologue number. KWT=Kumamolisin-As. Y axis: arbitrary enzyme units.

All references cited are herein incorporated by reference in their entirety. Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutsheer, ed., (1990) Academic Press, Inc.); *PCR Protocols: A Guide to Methods and Applications* (Innis, et al. 1990. Academic Press, San Diego, Calif.), *Culture of Animal Cells; A Manual of Basic Technique*, 2$^{nd}$ Ed. (R. I. Freshney, 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog (Ambion, Austin, Tex.).

As used herein, the singular forms "a", "an"and "the" include plural referents unless the context clearly dictates otherwise. "And" as used herein is interchangeably used with "or" unless expressly stated otherwise.

As used herein, amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile, I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

All embodiments of any aspect of the invention can be used in combination, unless the context clearly dictates otherwise.

In a first aspect, the present invention provides methods for treating celiac sprue, comprising administering to a subject with celiac sprue an amount effective to treat the celiac sprue of one or more polypeptides comprising or consisting of the amino acid sequence of a polypeptide selected from the group consisting of the following, or processed versions thereof:

Homologue 1
(SEQ ID NO: 74)
MAPSDVEIVDPVAPEERITVTLLRRRSSIPDQLIEGPDTLSRAELADRHGA

DPADVEAVRVAMSGAGLTVVGTDLPSRRVTVAGTAEALMRTFGAELQIVRD

ASGFQHRARSGELRIPAALDGIVIAVLGLDNRPQAERFRASQPEAARSFRP

DALGRVYRFPANTDGTGQTIAIVELGGGFRQSELDTYFGGLGIPAPQVLAV

GVDGGQNLPSGDAGSADGEVLLDIEVAGALAPGARQVVYFAPNRDRGFVDA

VTTAVHADPTPAAVSISWGAPEDKWTAQARRAFDAALADAAALGVTVTAAA

GDRGSADGEGGGGLHTDFPASSPHLLACGGTKLAVADGGTVASETVWNGGE

RGGATGGGVSVAFGLPAYQRNAGVDKRRKTGKPGRGVPDVAAVADPATGYE

VLDGEQLVFGGTSAVAPLWAALVARLTQALGRPLGLLNTALYDGAQPGRTQ

PGFRDVTEGDNDISGKHGYPARAGQDACTGLGVPDGEALLAALRKPGKE;

Homologue 2
(SEQ ID NO: 95)
MQRGTKEGLNMARHLQADREPRIVPESKCLGQCDPAERIHVTIMLRRQEEG

QLDALVHQLATGDARAKPVSRDAFAQRFSANPDDIRKTEDFAHQLTVDRVD

PVESVVVLSGT(I/V/D)AQFEAAFSVKLERFEHRSIGQYRGRSGPIVLPD

DIGDAVTAVLGLDSRPQARPHFRFRPPFKPARGAAAVTFTPIQLASLYDFP

AGDGAGQCIAIIELGGGYRAADIQQYFRGLGITTPPKLVDVNVGTGRNAPT

GEP(N/S/K/G)GPDGEVALDIEIAGAIPAAKIAVYFAP(N/D)(S/T)

(D/A/T/N)AGFIQAVNAAVTDKTNQPSVISISW(G/S)GPEAIWQAQSAQ

AFNRVLQAAAAQGITVCAASGD(S/N)GS(G/T/A)(D/N/G)GL(Q/D)D

GADHV(D/S/H)FPASSPYVLGCGGTQLDALPGQGIRSEVTWNDEASGGGA

GGGGVSALFDLPAWQQGLKVARADGTTTPLAKRGVPDVAGDASPQTGYEVS

VAGTPAVMGGTSAVAPLWAALIARINAANGASAGWINPVLYKHPGALRDIT

KGSNGTYAAASGWDACTGLSPNGAQLATILARKPSS;

Homologue 4
(SEQ ID NO: 75)
MANHPLNGSERECLKDAQPIGKADPNERLEVTMLVRRSHDAFEKHISALA

AQGASAKHIDHDEFTKHFGADSADLAAVHAFAQKHGLSVVESHEARRAVVL

SGT(V/D)AQFDAAFGVSLQQYEHDGGTYRGRTGPIHLPDELNGVVDAVMG

LDNRPQARPSFRTRAQGNVRWTARAAGASTFTPVQLASLYDFPQGDGQNQC

IGIIELGGGYRPADLKTYFASLNMKAPSVTAVSVDHGRNHPTGDP(N/S/

K/G)GPDGEVMLDIEVAGAVAPGAKIVVYFAP(N/D)(T/S)(D/A/T/N)

AGFIDAIGTAIHDTKNKPSVISISW(G/S)GPESAWTQQAMNAFDQAFQSA

AALGVTICAASGD(N/S)GS(G/T/A)(D/N/G)GV(G/Q/D)DGADHV (D/S/H)FPASSPYALGCGGTSLQASGNGIASETVWNDGANGGATGGGVSS

FFALPAWQEGLRVTRAGGAHSPLAMRGVPDVAGNADPVTGYEVRVDGHDMV

IGGTSAVAPLWAGLIARINAIKGAPVGYINPHLYKDPLALVDITKGNNDDF

HATAGWDACTGLGRPDGKKVKDAVS;

Homologue 5
(SEQ ID NO: 76)
MNHDHSPTGGELSNWVRVPGSERAAVQGSRKVGPADPNEQMSVTVVVRRPA

ADTAVTSMIEKVGAQPLSERRHLREEFASTHGANPADLSKVEKFAHEHNLQ

VKEVNAAAGTMVLSGT(V/D)TSFSKAFGVELSTYEHPDFTYRGRIGHVHI

PDYLADTIQSVLGLDNRPQASPRFRVLKEEGGVTTAHAGRTSYTPLEVAAL

YNFPSIHCKDQCIGILELGGGYRPADLQTYFNGLGIPQPNITDVSVGGAAN

RPTGDP(N/S/K/G)GPDGEVVLDIEVAAAVTPGAKIAVYFAD(N/D)(S/

T)(D/A/T/N)DGFLNAITTAIHDTRNKPSVISISW(G/S)KAEIGWTPQA

INAMNQAFRDAAALGVTICCASGD(D/S/N)GS(T/A)(D//N/G)RV(Q/

D)DGRYHV(D/S/H)FPASSPYVLACGGTRLESSGSTITQEVVWNEGALGG

GATGGGVSDVFDRPNWQANANVPTSANPERRIGRGVPDWAGNADPATGYQI

LVDGTRAVIGGTSAVAPLFAGLIAIINQKLGHSVGFINPILYNLSAQHNVF

HDITSGNNDMSGQNGPYEAQPGQDACTGLGSPDGTKLMNAISEAHRLVSV

G;

Homologue 6
(SEQ ID NO: 77)
MAPEERRTLPGSAMPRPAGAQVLGQIPDDERVEVTVVLQPRAPLPEPGPT

PMSRAELADLRSPPEGALEAIARYVAGQGLEVIAADAPRRRIVLAGSAAR

IAALFGISFVRLQLEGRRYRTYEGEISLPAELAPLVVAVLGLDTRPFARS

HRRPAVAPNAPTTAPTVARAYDFPTAYDGRGTTIGFIELGGGFQESDLVR

YCEGLGLSTPQVSVVGVDGARNAPTGDPNGPDAEVMLDLEVATGVANGAD

LVLYMAANTDAAFYSAIATALRDATHAPVAISISWGAPEESYPATTIAAF

ESVLEEAVHVGVTVLVAAGDQGSTDGVDDGRAHVDYPAASPYVLACGGTR

LDLDGTTIVAETVWNDLPNGGATGGGISALFPVPSWQAGIAMPPSANPGA

GPGRGVPDVAGNADPDTGYRIVVDGVATVVGGTSAVAPLWAGLVARCHQA

GARGGFWNPLLYAARGSSAFHEITVGSNGAYDAGPIWNACCGLGSPNGTA

ILQTLRA;

Homologue 6 mutant:
(SEQ ID NO: 78)
MAPEERRTLPGSAMPRPAGAQVLGQIPDDERVEVTVVLQPRAPLPEPGPT

PMSRAELADLRSPPEGALEAIARYVAGQGLEVIAADAPRRRIVLAGSAAR

IAALFGISFVRLQLEGRRYRTYEGEISLPAELAPLVVAVLGLDTRPFARS

HRRPAVAPNAPTTAPTVARAYDFPTAYDGRGTTIGFIELGGGFQESDLVR

YCEGLGLSTPQVSVVGVDGARNAPTGDPNGPDAEVMLDLEVATGVANGAD

LVLYMAANTDAAFYSAIATALRDATHAPVAISISWSAPEESYPATTIAAF

ESVLEEAVHVGVTVLVAAGDQGSTGVDDGRAHVHYPAASPYVLACGGTR

LDLGTTIVAETVWNDLPNGGATGGGISALFPVPSWQAGIAMPPSANPGAG

PGRGVPDVAGNADPDTGYRIVVDGVATVVGGTSAVAPLWAGLVARCHQAG

ARGGFWNPLLYAARGSSAFHEITVGSNGAYDAGPIWNACCGLGSPNGTAI

LQTLRA;

Homologue 9

(SEQ ID NO: 79)
MTKQPVSGSSDKIHPDDAKCIGDCDPSEQIEVIVMLRRKDEAGFRQMMSR
IDAGEAPGQAVSREEFDRRFTASDEDIDKVKAFAKQYGLSVERAETETRS
VVLKGT(I/V/D)EQFQKAFDVKLERFQHHNIGEYRGRTGPVNVPDEMHD
AVTAVLGLDSKPQARPHFRFRPPFKPLRGAAPASFSPVDLAKLYDFPDGD
GAGQCIAIIELGGGYRDSDLSAYFSKLGVKAPTVVPVGVDGGKNAPTGNP
(N/S/K/G)GPDGEVTLDIEIAGAIAPGARIAVYFAP(N/D)(S/T)(D/
A/T/N)AGFVDAVNRALHDAANKPSVSISW(G/S)GPESNWSPQSMSAF
NDVLQSAAALGVTVCAASGD(G/S/N)GS(A/T)(D/N/G)GV(G/Q/D)
DGADHV(D/S/H)FPASSPYVLGCGGTSLAASGAGIAKEVVWNDGDQGGA
GGGGVSGTFALPVWQKGLSVTRNGKHIALAKRGVPDVAGDASPQTGYEVL
IDGEDTVVGGTSAVAPLWAALIARINAIDASPAGFVNPKLYKAKTAFRDI
TEGNNGSFSAAAGWDACTGMGSPDGGKIAAALKPAKPSQSAGQQ;

Homologue 10

(SEQ ID NO: 80)
MGRLQGSYRPSLGTPVGPVPDDQPIDVTVVLRPTAADDFRADPDDVAAVR
AFAGRAGLDVAEVDEPARTVRLRGP(A/V/D)AAARTAFDTPLALYDSGG
RAIRGREGDLGLPDELDDRVVAVLGLDERPAARPRFQPAASARQGLTALQ
VARAYDFPAATGEGQTIAIIELGGGFGQADLDTYFGGLDLPTPAVSAVGV
QGAANVPGGDP(/S/K/G)DGADGEVLLDIEVAGAVAPGAAQVVYFAP
(N/D)(T/S)(D/A/T/N)AGFLAAINAAAAATPRPAAISISWG(G/S)P
ESSWTAQAMRAYDQAFAAARAAGITVLAAAGD(A/S/N)GA(D/T/A)
(D/S/N/G)(A/Q/D)(TDRLVA(D/S/H)FPAGSPNVIACGGTKLTLDA
AGARASEVVWNEAADSATGGGYSATFTRPAWQPAAVGRYRGLPDISGNAD
PQTGYRVVVDGQPTVVGGTSAVAPLLAGLVARLAQLTGAPVADLAAVAYA
NPAAFTDITAGDNQGYPARSGWDPASGLGSPVGTKLLTAVGGPTPPPTTP
PPTTPPPTTPPPTIPPPTTPPTQTVDAADRALWSAVATWAGGTHTGANAR
AAKAVRAWAQAKSLA;

Homologue 12

(SEQ ID NO: 81)
MTQPRYTPLPGSEREAPLLAARSNATAARASRAQTASATVVLRRRSELPE
ALVLDQQFISSDELAARYGADPVDIEKVRSVLERFKVSVVEVDAASRRVK
VEGA(V/D)ADIERAFNIALHSASGTDPHSGRGFEYRYRTGVLSVPAELG
GIVTAVLGLDNRRQAETRLRVVPAAALGSSYTPVQLGEIYNFPQDATGAG
QRIAIIELGGGYTPAGLRRYFASLGVVPPKVAAVSVDGAQNAPGPDP(G/
S/K/G)ADGEVQLDVEVAGALAPGAHVLVYFAP(N/D)(T/S)(D/A/T/
N)QGFLDAVSQAAHATPPPTAISISW(G/S)ASEDSWTASARDALNQALR
DAAALGVTVTAAAGD(S/N)GS(S/T/A)(D/N/G)GV(P/Q/D)DRRAH
V(D/S/H)FPASSPYVLATGGTSLRADPATGVVQSETVWNDSQGSTGGGV
SDVFPRPAWQAHVDVPHAGRGVPDVSAVADPATGYQVLVDNQPAVIGGTS
AVAPLWAALVARLAESLGRPLGLLQPLVYPRTPGSTAYPGFRDITIGNNG
AYKAGKGWDAATGLGVPDGTELLAHLRGLNGSE;

Homologue 13

(SEQ ID NO: 82)
MARHLHAGSEPKVITESKCIGACDPAERIHVTVMLRREGEQALDALVDKL
ASGDPAAKPVSREDFAKRFGARADDIQHTEAFAKRHQLTVERVDPVQSVV
ELAGT(I/V/D)AQFENAFGVKLEKYEHHAIGSFRARTGAIALPDELHDA
VTAVLGLDTRPQAHPHFRFRPPFQPARSGAGTSYTPLQLASIYNFPEGDG
AGQCIALVELGGGYRAADIRQYFEQLGVKPPKLVDVSVNGGRNAPTDDP
(N/S/K/G)GPDGEVALDIEVAGAIAPGATIAVYFAG(N/D)(S/T)(D/
A/T/N)AGFIQSVNQAIHDSTNRPSVVSISW(G/S)GPEASWTQQSITAF
NNVLKTAASLGVTVCAASGD(S//N)GS(S/T/A)(D/N/G)GL(Q/D)D
GSNHV(D/S/H)FPASSPYVLACGGTTLDAQAGQGIRREVVWNDEAASGG
AGGGGVSAVFPAPSYQKGLSAKATGGGSTPLSQRGVPDVAGDASPTTGYI
ISIAGTTAVLGGTSAVAPLWAALIARINANGKSPVGWANPKLYAQPGAFH
DITQGNNGAFAASEGWDACTGLGSPDGAKVAAALQASGGSQQGRATGA;

Homologue 14

(SEQ ID NO: 83)
MTKHPLPGSERVLAPGSKVVAQCDPSETIEVVVVLRRKNEQQFAQMMKTI
EAGAAGARPLTREELEQRFGALPEDIAKLKAFAAQHGLSVVREDASARTV
VLSGR(I/V/D)EQFQQAFDVQLQHYEHQSMGRFRGRTGAISVPDELHGV
VTAVLGLDDRPQARPHFRIRPPFQPARAQSASSFTPLQLASLYRFPQGDG
SGQCIGIVELGGGYRTADLDSYFSSLGVGSPKVVAVGVDQSGNQPTGDP
(N/S/K/G)GPDGEVTLDIEIAGALAPAATIAVYFTT(N/D)(S/T)(D/
A/T/N)AGFIDAVSQAVHDRTNQPSVISISW(G/S)APESMWTAQSMKAL
NDVLQSAAAIGVTVCAASGD(S/N)GS(S/T/A)(D/N/G)GV(G/Q/D)
DGRDHV(D/S/H)FPASSPYVLACGGTSLQGSGRTVAHEVVWNDGSNGGA
TGGGVSGAFPVPAWQEGLSTSAAQGGQRALTGRGVPDVAGDASPLTGYDV
IVDGNNTVIGGTSAVAPLWAALIARINGAKGAPVGFVNPKLYKASACNDI
TQGNNGSYAATTGWDACTGLGSPDGVKVAAAL;

Homologue 15

(SEQ ID NO: 84)
MSPIASRRSALPLSERPAPENARALAAVEPDRTMTVSVLVRRKKPLVLAD
LEGKKLTHREFERRYGASEKDFATIAKFAAGHGLAVDHHASSLARRTVVL
RGT(A/V/D)RGMQQAFGVTLHDYEDSETQQRYHSFTGAITVPAAHARII
ESVLGLDARPIAKPHFRVRKRSAAATGAVSFNPPQVASLYSFPTGVDGSG
ETIGILELGGGYETSDIQQYFSGLGIQPPTVVAVSVDGAVNAPGNP(N/
S/K/G)GADEVALDIQVAGSIAPGAKLAVYFAP(N/D)(T/S)(E/D/A/
T/N)QGFVDAITTAVHDTANKPSVLSISW(G/S)GPESSWPQAAAQSLNN
ACESAAALGVTITVASGD(N/S)GS(T/A)(D/N/G)GV(Q/D)DGQNHV

```
(D/S/H)FPASSPYVLACGGTYLAAVNNGVPQESVWDDLASGGGATGGGV

SALFPLPAWQTGANVPGGSMRGVPDVAGDASPEGSYNVLVDGQPQVVGGT

SAVAPLWAALIALVNQQKGEAAGFVNAALYQNPSAFHDITQGSNGAYAAA

PGWDPCTGLGSPMGTAIAKILA;

Homologue 16
                                          (SEQ ID NO: 85)
MSAFDQLVPLPGSEKTVPDAAPSQTLDPNEVLTVTIRIRRKRTLASLVST

TAPVTEVVSRSEYASRFGADPAIVKQVEAFASAYDLSLVEQSLARRSVLL

RGT(V/D)AQMEQAFGVSLANYQLADGTVFRGRTGVVNVPSELVEHIEGV

FGLDNRPQARAHFQVYKPEKGTKVAPRAGGISYTPPQLARLYNFPTGVTG

KGQCIAIIELGGGFRTADIKTYFGGLGLKPPTVVAVSVDGGHNAPSTA (D/S/K/G)SADGEVMLDIDVAGGVAPGAKIVVYFAP(N/D)(T/S)(D/

A/T/N)QGFLDAITTAMHDTKNKPSVISISW(G/S)AAESNWTPQALTSF

NQAFQAAAALGITVCAAAGD(T/S/N)GS(D/T/A)(D/N/G)SV(G/Q/

D)DGKAHV(D/S/H)FPASSPFVLACGGTKLTATDNVIASEVVWHESKTS

ATGGGVSDVFDLPDYQQKSHVPPSVNDKTRIGRGVPDVAAVADPVTGYAV

RVDGSNLVFGGTSAVAPLMAGLIALINQQRGKAVGFIHPLIYANPSAFRD

ITQGNNTTTTGNKGYAATTGWDACTGLGVADGKKLASVLTATPVA;

Homologue 17
                                          (SEQ ID NO: 86)
MAATPRFASQPRVTLPGSQKHPLTTDTEVPPPAPVKAAATKLSATPFTVT

VIVKRKNPLNLKQVLKPAGRLTHAAFAKAHGPSPDGVKLVKAFAKEFGLT

VAPAPGQGRRALYLTGT(A/V/D)AAMQTAFGVTFATKIMEGTKYRVREG

DICLPKELIGHVDAVLGLDNRPQAKPHFRHHKPAATSVSYTPVQVGQLYG

FPSGAKATGQTIGLIELGGGFRAADITAYFKTLGQTAPKVTAVLVDKAKN

TPTTS(S/K/G)SADGEVMLDIEVAAAVAPGANIAVYFAP(N/D)(T/S)

(D/A/T/N)QGFIDAISQAVHDTVNKPSVISISW(G/S)GPESTWTAQSL

AALDAACQSAAALGITTTVAAGD(D/S/N)GS(T/A)(D/N/G)GV(K/

Q/D)GTVNHV(D/S/H)FPASSPHVLGCGGTKLLGSGTTITSEVVWNELT

ANEGATGGGVSNVFPLPTWQAKSNVPKPTVAAGGRGVPDVSGNADPSTGY

TVRVDGSTFPIGGTSAVAPLWAGLIALCNAQNKTTAGFINPALYAAAAAK

SFRDITSGNNGGFKAGPGWDACTGLGSPIGTAIAKTLAPATKSTSKTAVK

NAPEIRFRPHKKAPTKTAAKTPALRRLK;

Homologue 19
                                          (SEQ ID NO: 87)
MPTSSRFASQSRVPLPGSERKPFVPAGAPKAAKTPKVSTAVKTVPATGRI

RVSLIVPPKQPLDTKRLGKLDARLSRAQFAARHGADPASVRLVKAFAKEF

GLTVEPITQPGRCTVQLSGT(C/V/D)AAMRKAFAISLVEHTTEQGKFRL

REGEISLPAELEGHVLAVLGLDNRPQAKPHFRIAKPRATNVSYTPVQVAQ

MYGFPAGATATGQTIGIIELGGGYRAADLTAYFKTLGLPAPTVTAVPIDG

GKNTPGNA(N/S/K/G)GADGEVMLDIEVCAAVAQGAKIAVYFTT(N/D)

(T/S)(D/A/T/N)QGFIDAITTAVHDSTNKPSVISISW(G//S)GPESS

WTEQSMTALDAACQAAAAVGVTTTVAAGD(N/S)GS(S/T/S)(D/N/G)

GA(S/Q/D)GDNV(D/S/H)FPASSPHVLACGGTKLVGSGSTITSEVVWD

ETSNDEGATGGGVSTVFALPTWQKNANVPSPTTSAGGRGVPDVSGDADPS

TGYTIRVDSETTVIGGTSAVAPLWAGLIALANAQNKVAAGFVNPALYAAG

AKKAFRDITQGNNGSFSAGPGWDACTGLGSPVGNLVIAQAVAPKSTTTKK

AKKGKTK;
and

Homologue 26
                                          (SEQ ID NO: 88)
MHSYLKQQSHMQSYLEQENHMRSYLEMRKKPYFDDLANIRPGGLTPAQVC

QAYQFAKVQPVRPVKLGIVSLAGQYLSSDMSKAFTGYGLPTPVVSTAGSQ

VLGDLWSNVE(N/S/K/G)MMDIEIAGAAWAYATGTAATLLMQFEP(N/

D)(N/T/S)(E/D/A/T/N)TGIPNAINALVAAGCEVISISW(G/S)APA

NLQTMEAITARKEACKQAAVQNVHVFAASGD(E/S/N)SL(N/T/A)(D/

N/G)(G/Q/D)TNSRTP(D/S/H)DPCCDPNVWGVGGTRLVLQADGSIAQ

ESAWGDGNAADKGGGGGFDSREPLPDYQVGVVHSEHRGSPDSSANADPGT

GYAIVANGQWLIGGGTSASAPLTAGYVAAILSTLPGPISQSVLQRKLYTA

HKTAFRDILLGSNGAPARPGWEEATGLGSINGPGLAAALQS.
```

The polypeptides disclosed herein are Kumamolisin homologue polypeptides and modified versions thereof that have been identified as having similar, improved, or complementary activity compared to Kumamolisin-As in hydrolyzing proline (P)- and glutamine (Q)-rich components of gluten known as 'gliadins' believed responsible for the bulk of the immune response in most celiac sprue patients. Numerous other Kumamolisin homologues tested by the inventors possessed little or no such gliadin hydrolyzing activity. Thus, the polypeptides disclosed herein can be used to treat celiac sprue. The amino acid sequences disclosed herein are for the preprocessed version of the polypeptides, which may hydrolyze their substrates in a processed form. Thus, use of the processed versions of the polypeptides are covered herein. As will be understood by those of skill in the art, the exact processing of the polypeptides may differ from one cell type or set of conditions to another. In one embodiment, the processed forms of the homologues are devoid of the residues shown in Table 1 below, which is a comparison of the residues of Kummamoslisin and the homologues disclosed herein that are present in the pre-processed form but not in the processed form.

TABLE 1

| | Pre-Protein |
| --- | --- |
| Kumamolisin | 1-189 |
| Hom 1 | 1-148 |
| Hom 2 | 1-182 |
| Hom 4 | 1-174 |
| Hom 5 | 1-187 |
| Hom 6 | 1-157 |
| Hom 9 | 1-173 |
| Hom 10 | 1-135 |
| Hom 12 | 1-171 |

TABLE 1-continued

| | Pre-Protein |
|---|---|
| Hom 13 | 1-172 |
| Hom 14 | 1-173 |
| Hom 15 | 1-169 |
| Hom 16 | 1-173 |
| Hom 17 | 1-178 |
| Hom 19 | 1-181 |
| Hom 26 | 1-42 |

In one embodiment, the one or more polypeptides are selected from the group consisting of the following, or processed versions thereof Homologue 1 (NCBI YP_005536585)
(SEQ ID NO: 74)
MAPSDVEIVDPVAPEERITVTVLLRRRSSIPDQLIEGPDTLSRAELADRH

GADPADVEAVRVAMSGAGLTVVGTDLPSRRVTVAGTAEALMRTFGAELQI

VRDASGFQHRARSGELRIPAALDGIVIAVLGLDNRPQAEARFRASQPEAA

RSFRPDALGRVYRFPANTDGTGQTIAIVELGGGFRQSELDTYFGGLGIPA

PQVLAWGVDGGQNLPSGDAGSADGEVLLDIEVAGALAPGARQVVYFAPNT

DRGFVDAVTTAVHADPTPAAVSISWGAPEDKWTAQARRAFDAALADAAAL

GVTVTAAAGDRGSADGEGGGGLHTDFPASSPHLLACGGTKLAVADGGTVA

SETVWNGGERGGATGGGVSVAFGLPAYQRNAGVDKRRKTGKPGRGVPDVA

AVADPATGYEVLVDGEQLVFGGTSAVAPLWAALVARLTQALGRPLGLLNT

ALYDGAQPGRTQPGFRDVTEGDNDISGKHGPYPARAGWDACTGLGVPDGE

ALLAALRKPGKE;

Homologue 2 (NCBI ZP_04943175)
(SEQ ID NO: 97)
MQRGTKEGLNMARHLQADREPRIVPESKCLGQCDPAERIHVTIMLRRQEE

GQLDALVHQLATGDARAKPVSRDAFAQRFSANPDDIRKTEDFAHRHQLTV

DRVDPVESVVVLSGTIAQFEAAFSVKLERFEHRSIGQYRGRSGPIVLPDD

IGDAVTAVLGLDSRPQARPHFRFRPPFKPARGAAAVTFTPIQLASLYDFP

AGDGAGQCIAIIELGGGYRAADIQQYFRGLGITTPPKLVDVNVGTGRNAP

TGEPNGPDGEVALDIEIAGAIAPAAKIAVYFAPNSDAGFIQAVNAAVTDK

TNQPSVSISWGGPEAIWQAQSAWAFNRVLQAAAAQGITVCAASGDSGSG

DGLQDGADHVDFPASSPYVLGCGGTQLDALPGQGIRSEVTWNDEASGGGA

GGGGVSALFDLPAWQQGLKVARADGTTTPLAKRGVPDVAGDASPQTGYEV

SVAGTPAVMGGTSAVAPLWAALIARINAANGASAGWINPVLYKHPGALRD

ITKGSNGTYAAASGWDACTGLGSPNGAQLATILARKPSS;

Homologue 4 (NCBI ZP_10028298)
(SEQ ID NO: 98)
MANHPLNGSERECLKDAQPIGKADPNERLEVTMLVRRRSHDAFEKHISAL

AAQGASAKHIDHDEFTKHFGADSADLAAVHAFAQKHGLSVVESHEARRAV

VLSGTVAQFDAAFGVSLQQYEHDGGTYRGRTGPIHLPDELNGVVDAVMGL

DNRPQARPSFRTRAQGNVRWTARAAGASTFTPVQLASLYDFPQGDGQNQC

IGIIELGGGYRPADLKTYFASLNMKAPSVTAVSVDHGRNHPTGDPNGPDG

EVMLDIEVAGAVAPGAKIVVYFAPNTDAGFIDAIGTAIHDTKNKPSVISI

SWGGPESAWTQQAMNAFDQAFQSAAALGVTICAASGDNGSGDGVGDGADH

VDFPASSPYALGCGGTSLQASGNGIASETVWNDGANGGATGGGVSSFALP

AWQEGLRVTRAGGAHSPLAMRGVPDVAGNADPVTGYEVRVDGHDMVIGGT

SAVAPLWAGLIARINAIKGAPVGYINPHLYDKPLALVDITKGNNDDFHAT

AGWDACTGLGRPDGKKVKDAVS;

Homologue 5 (NCBI ZP_09078202)
(SEQ ID NO: 99)
AGRTSYTPLEVAALYNFPSIHCKDQCIGILELGGGYRPADLQTYFNGLGI

PQPNITDVSVGGAANRPTGDPNGPDGEVVLDIEVAAAVTPGAKIAVYFAD

NSDDGFLNAITTAIHDTRNKPSVISISWGKAEIGWTPQAINAMNQAFRDA

AALGVTICCASGDDGSTDRVQDGRYHVDFPASSPYVLACGGTRLESSGST

ITQEVVWNEGALGGGATGGGVSDVFDRPNWQANANVPTSANPERRIGRGV

PDWAGNADPATGYQILVDGTRAVIGGTSAVAPLFAGLIAIINQKLGHSVG

FINPILYNLSAQHNVFHDITSGNNDMSGQNGPYEAQPGWDACTGLGSPDG

TKLMNAISEAHRLVSVG;

Homologue 6 (NCBI YP_003109679)
(SEQ ID NO: 77)
MAPEERRTLPGSAMPRPAGAQVLGQIPDDERVEVTVVLQPRAPLPEPGPT

PMSRAELADLRSPPEGALEAIARYVAGQGLEVIAADAPRRRIVLAGSAAR

IAALFGISFVRLQLEGRRYRTYEGEISLPAELAPLVVAVLGLDTRPFARS

HRRPAVAPNAPTTAPTVARAYDFPTAYDGRGTTIGFIELGGGFQESDLVR

YCEGLGLSTPQVSVVGVDGARNAPTGDPNGPDAEVMLDLEVATGVANGAD

LVLYMAANTDAAFYSAIATALRDATHAPVAISISWGAPEESYPATTIAAF

ESVLEEAVHVGVTVLVAAGDQGSTDGVDDGRAHVDYPAASPYVLACGGTR

LDLDGTTIVAETVWNDLPNGGATGGGISALFPVPSWQAGIAMPPSANPGA

GPGRGVPDVAGNADPDTGYRIVVDGVATVVGGTSAVAPLWAGLVARCHQA

GARGGFWNPLLYAARGSSAFHEITVGSNGAYDAGPIWNACCGLGSPNGTA

ILQTLRA;

Homologue #6 mutant:
(SEQ ID NO: 78)
MAPEERRTLPGSAMPRPAGAQVLGQIPDDERVEVTVVLQPRAPLPEPGPT

PMSRAELADLRSPPEGALEAIARYVAGQGLEVIAADAPRRRIVLAGSAAR

IAALFGISFVRLQLEGRRYRTYEGEISLPAELAPLVVAVLGLDTRPFARS

HRRPAVAPNAPTTAPTVARAYDFPTAYDGRGTTIGFIELGGGFQESDLVR

YCEGLGLSTPQVSVVGVDGARNAPTGDPNGPDAEVMLDLEVATGVANGAD

LVLYMAANTDAAFYSAIATALRDATHAPVAISISWSAPEESYPATTIAAF

ESVLEEAVHVGVTVLVAAGDQGSTGGVDDGRAHVHYPAASPYVLACGGTR

LDLDGTTIVAETVWNDLPNGGATGGGISALFPVPSWQAGIAMPPSANPGA

-continued
GPGRGVPDVAGNADPDTGYRIVVDGVATVVGGTSAVAPLWAGLVARCHQA
GARGGFWNPLLYAARGSSAFHEITVGSNGAYDAGPIWNACCGLGSPNGTA
ILQTLRA;

Homologue 9 (NCBI YP_005042475)
(SEQ ID NO: 102)
MTKQPVSGSSDKIHPDDAKCIGDCDPSEQIEVIVMLRRKDEAGFRQMMSR
IDAGEAPGQAVSREEFDRRFTASDEDIDKVKAFAKQYGLSVERAETETRS
VVLKGTIEQFQKAFDVKLERFQHHNIGEYRGRTGPVNVPDEMHDAVTAVL
GLDSKPQARPHFRPPFKPLRGAAPASFSPVDLAKLYDFPDGDGAGQCIAI
IELGGGYRDSDLSAYFSKLGVKAPTVVPVGVDGGKNAPTGNPNGPDGEVT
LDIEIAGAIAPGARIAVYFAPNSDAGFVDAVNRALHDAANKPSVISISWG
GPESNWSPQSMSAFNDVLQSAAALGVTVCAASGDGGSADGVGDGADHVDF
PASSPYVLGCGGTSLAASGAGIAKEVVWNDGDQGGAGGGGVSGTFALPVW
QKGLSVTRNGKHIALAKRGVPDVAGDASPQTGYEVLIDGEDTVVGGTSAV
APLWAALIARINAIDASPAGFVNPKLYKAKTAFRDITEGNNGSFSAAAGW
DACTGMGSPDGGKIAAALKPAKPSQSAGQQ;

Homologue 10 (NCBI YP_711059)
(SEQ ID NO: 103)
MGRLQGSYRPSLGTPVGPVPDDQPIDVTVVLRPTAADDFRADPDDVAAVR
AFAGRAGLDVAEVDEPARTVRLRGPAAAARTAFDTPLALYDSGGRAIRGR
EGDLGLPDELDDRVVAVLGLDERPAARPRFQPAASARQGLTALQVARAYD
FPAATGEGQTIAIIELGGGFGQADLDTYFGGLDLPTPAVSAVGVQGAANV
PGGDPDGADGEVLLDIEVAGAVAPGAAQVVYFAPNTDAGFLAAINAAAAA
TPRPAAISISWGGPESSWTAQAMRAYDQAFAAARAAGITVLAAAGDAGAD
DATDRLVADFPAGSPNVIACGGTKLTLDAAGARASEVVWNEAADSATGGG
YSATFTRPAWQPAAVGRYRGLPDISGNAPDPQTGYRVVVDGQPTVVGGTSA
VAPLLAGLVARLAQLTGAPVADLAAVAYANPAAFTDITAGDNQGYPARSG
WDPASGLGSPVGTKLLTAVGGPTPPPTTPPPTTPPPTTPPPTIPPPTTPP
TQTVDAADRALWSAVATWAGGTHTGANARAAKAVRAWAQAKSLA;

Homologue 12 (NCBI YP_003658449)
(SEQ ID NO: 104)
MTQPRYTPLPGSEREAPLLAARSNATAARASRAQTASATVVLRRRSELPE
ALVLDQQFISSDELAARYGADPVDIEKVRSVLERFKVSVVEVDAASRRVK
VEGAVADIERAFNIALHSASGTDPHSGRGFEYRYRTGVLSVPAELGGIVT
AVLGLDNRRQAETRLRVVPAAALGSSYTPVQLGEIYNFPQDATGAGQRIA
IIELGGGYTPAGLRRYFASLGVVPPKVAAVSVDGAQNAPGPDPGADGEVQ
LDVEVAGALAPGAHVLVYFAPNTDQGFLDAVSQAAHATPPPTAISISWGA
SEDSWTASARDALNQALRDAAALGVTVTAAAGDSGSSDGVPDRRAHVDFP
ASSPYVLATGGTSLRADPATGVVQSETVWNDSQGSTGGGVSDVFPRPAWQ
AHVDVPHAGRGVPDVSAVADPATGYQVLVDNQPAVIGGTSAVAPLWAALV -continued
ARLAESLGRPLGLLQPLVYPRTPGSTAYPGFRDITIGNNGAYKAGKGWDA
ATGLGVPDGTELLAHLRGLNGSE;

Homologue 13 (NCBI YP_004348568)
(SEQ ID NO: 105)
MARHLHAGSEPKVITESKCIGACDPEARIHVTVMLRREGEQALDALVDKL
ASGDPAAKPVSREDFAKRFGARADDIQHTEAFAKRHQLTVERVDPVQSVV
ELAGTIAQFENAFGVKLEKYEHHAIGSFRARTGAIALPDELHDAVTAVLG
LDTRPQAHPHFRFRPPFQPARSGAGTSYTPLQLASIYNFPEGDGAGQCIA
LVELGGGYRAADIRQYFEQLGVKPPKLVDVSVNGGRNAPTDDPNGPDGEV
ALDIEVAGAIAPGATIAVYFAGNSDAGFIQSVNQAIHDSTNRPSVVSISW
GGPEASWTQQSITAFNNVLKTAASLGVTVCAASGDSGSSDGLQDGSNHVD
FPASSPYVLACGGTTLDAQAGQGIRREVVWNDEAASGGAGGGGVSAVFPA
PSYQKGLSAKATGGGSTPLSQRGVPDVAGDASPTTGYIISIAGTTAVLGG
TSAVAPLWAALIARINANGKSPVGWANPKLYAQPGAFHDITQGNNGAFAA
SEGWDACTGLGSPDGAKVAAALQGASGGSQQGRATGA;

Homologue 14 (NCBI YP_001861188)
(SEQ ID NO: 106)
HMTKHPLPGSERVLAPGSKVVAQCDPSETIEVVVVLRRKNEQQFAQMMKT
IEAGAAGARPLTREELEQRFGALPEDIAKLKAFAAQHGLSVVREDASART
VVLSGRIEQFQQAFDVQLQHYEHQSMGRFRGRTGAISVPDELHGVVTAVL
GLDDRPQARPHFRIRPPFQPARAQSASSFTPLQLASLYRFPQGDGSGQCI
GIVELGGGYRTADLDSYFSSLGVGSPKVVAVGVDQSGNQPTGDPNGPDGE
VTLDIEIAGALAPAATIAVYFTTNSDAGFIDAVSQAVHDRTNQPSVISIS
WGAPESMWTAQSMKALNDVLQSAAAIGVTVCAASGDSGSSDGVGDGRDHV
DFPASSPYVLACGGTSLQGSGRTVAHEVVWNDGSNGGATGGGVSGAFPVP
AWQEGLSTSAAQGGQRALTGRGVPDVAGDASPLTGYDVIVDGNNTVIGGT
SAVAPLWAALIARINGAKGAPVGFVNPKLYKASACNDITQGNNGSYAATT
GWDACTGLGSPDGVKVAAAL;

Homologue 15 (NCBI YP_002754884)
(SEQ ID NO: 107)
MSPIASRRSALPLSERPAPENARALAAVEPDRTMTVSVLVRRKKPLVLAD
LEGKKLTHREFERRYGASEKDFATIAKFAAGHGLAVDHHASSLARRTVVL
RGTARQMQQAFGVTLHDYEDSETQQRYHSFTGAITVPAAHARIIESVLGL
DARPIAKPHFRVRKRSAAATGAVSFNPPQVASLYSFPTGVDGSGETIGIL
ELGGGYETSDIQQYFSGLGIQPPTVVAVSVDGAVNAPGNPNGADGEVALD
IQVAGSIAPGAKLAVYFAPNTEQGFVDAITTAVHDTANKPSVLSISWGGP
ESSWPQAAAQSLNNACESAAALGVTITVASGDNGSTDGVQDGQNHVDFPA -continued
SSPYVLACGGTYLAAVNNGVPQESVWDDLASGGGATGGGVSALFPLPAWQ

TGANVPGGSMRGVPDVAGDASPESGYNVLVDGQPQVVGGTSAVAPLWAAL

IALVNQQKGEAAGFVNAALYQNPSAFHDITQGSNGAYAAAPGWDPCTGLG

SPMGTAIAKILA;

Homologue 16 (NCBI YP_003387700)
(SEQ ID NO: 108)
MSAFDQLVPLPGSEKTVPDAAPSQTLDPNEVLTVTIRIRRKRTLASLVST

TAPVTEVVSRSEYASRFGADPAIVKQVEAFASAYDLSLVEQSLARRSVLL

RGTVAQMEQAFGVSLANYQLADGTVFRGRTGVVNVPSELVEHIEGVFGLD

NEPQARAHFQVYKPEKGTKVAPRAGGISYTPPQLARLYNFPTGVTGKGQC

IAIIELGGGFRTADIKTYFGGLGLKPPTVVAVSVDGGHNAPSTADSADGE

VMLDIDVAGGVAPGAKIVVYFAPNTDQGFLDAITTAMHDTKNKPSVISIS

WGAAESNWTPQALTSFNQAFQAAAALGITVCAAAGDTGSDDSVGDGKAHV

DFPASSPFVLACGGTKLTATDNVIASEVVWHESKTSATGGVSDVFDLPD

YQQKSHVPPSVNDKTRIGRGVPDVAAVADPVTGYAVRVDGSNLVFGGTSA

VAPLMAGLIALINQQRGKAVGFIHPLIYANPSAFRDITQGNNTTTTGNKG

YAATTGWDACTGLGVADGKKLASVLTATPVA;

Homologue 17 (NCBI YP_004216463)
(SEQ ID NO: 109)
MAATPRFASQPRVTLPGSQKHPLTTDTEVPPPAPVKAAATKLSATPFTVT

VIVKRKNPLNLKQVLKPAGRLTHAAFAKAHGPSPDGVKLVKAFAKEFGLT

VAPAPGQGRRALYLTGTAAAMQTAFGVTFATKIMEGTKYRVREGDICLPK

ELIGHVDAVLGLDNRPQAKPHFRHHKPAATSVSYTPVQVGQLYGFPSGAK

ATGQTIGLIELGGGFRAADITAYFKTLGQTAPKVTAVLVDKAKNTPTTSS

SADGEVMLDIEVAAAVAPGANIAVYFAPNTDQGFIDAISQAVHDTVNKPS

VISISWGGPESTWTAQSLAALDAACQSAAALGITITVAAGDDGSTDGVKG

TVNHVDFPASSPHVLGCGGTKLLGSGTTITSEVVWNELTANEGATGGGVS

NVFPLPTWQAKSNVPKPTVAAGGRGVPDVSGNADPSTGYTVRVDGSTFPI

GGTSAVAPLWAGLIALCNAQNKTTAGFINPALYAAAAAKSFRDITSGNNG

GFKAGPGWDACTGLGSPIGTAIAKTLAPATKSTSKTAVKNAPEIRFRPHK

KAPTKTAAKTPALRRLK;

Homologue 19 (NCBI YP_005056054)
(SEQ ID NO: 110)
MPTSSRFASQSRVPLPGSERKPFVPAGAPKAAKTPKVSTAVKTVPATGRI

RVSLIVPPKQPLDTKRLGKLDARLSRAQFAARHGADPASVRLVKAFAKEF

GLTVEPITQPGRCTVQLSGTCAAMRKAFAISLVEHTTEQGKFRLREGEIS

LPAELEGHVLAVLGLDNRPQAKPHFRIAKPRATNVSYTPVQVAQMYGFPA

GATATGQTIGIIELGGGYRAADLTAYFKTLGLPAPTVTAVPIDGGKNTPG

NANGADGEVMLDIEVCAAVAQGAKIAVYFTTNTDQGFIDAITTAVHDSTN

KPSVISISWGGPESSWTEQSMTALDAACQAAAAVGVTITVAAGDNGSSDG

-continued
ASGDNVDFPASSPHVLACGGTKLVGSGSTITSEVVWDETSNDEGATGGGV

STVFALPTWQKNANVPSPTTSAGGRGVPDVSGDADPSTGYTIRVDSETTV

IGGTSAVAPLWAGLIALANAQNKVAAGFVNPALYAAGAKKAFRDITQGNN

GSFSAGPGWDACTGLGSPVGNLVIQAVAPKSTTTKKAKKGKTK;
and

Homologue 26 (NCBI YP_004030750)
(SEQ ID NO: 111)
MHSYLKQQSHMQSYLEQENHMRSYLEMRKKPYFDDLANIRPGGLTPAQVC

QAYQFAKVQPVRPVKLGIVSLAGQYLSSDMSKAFTGYGLPTPVVSTAGSQ

VLGDLWSNVENMMDIEIAGAAWAYATGTAATLLMQFEPNNETGIPNAINA

LAVAAGCEVISISWGAPANLQTMEAITARKEACKQAAVQNVHVFAASGDE

SLNDGTNSRTPDDPCCDPNVWGVGGTRLVLQADGSIAQESAWGDGNAADK

GGGGGFDSREPLPDYQVGVVHSEHRGSPDSSANADPGTGYAIVANGQWLI

GGGTSASAPLTAGYVAAILSTLPGPISQSVLQRKLYTAHKTAFRDILLGS

NGAPARPGWEEATGLGSINGPGLAAALQS.

In one embodiment, the one or more polypeptides comprise one or more polypeptides comprising or consisting of the amino acid sequence of a polypeptide selected from the group consisting of SEQ ID NOs: 74, 75, 77, 78, 82, 88, 98, 105, 111, or processed versions thereof. In a further embodiment, the one or more polypeptides comprise a polypeptide that comprises or consists of the amino acid sequence:

Homologue 4 mutant
(SEQ ID NO: 89)
MANHPLNGSERECLKDAQPIGKADPNERLEVTMLVRRRSHDAFEKHISAL

AAQGASAKHIDHDEFTKHFGADSADLAAVHAFAQKHGLSVVESHEARRAV

VLSGTVAQFDAAFGVSLQQYEHDGGTYRGRTGPIHLPDELNGVVDAVMGL

DNRPQARPSFRTAQGNVRWTARAAGASTFTPVQLASLYDFPQGDGQNQCI

GIIELGGGYRPADLKTYFASLNMKAPSVTAVSVDHGRNHPTGDPNGPDGE

VMLDIEVAGAVAPGAKIVVYFAPNTDAGFIDAIGTAIHDTKNKPSVISIS

WSGPESAWTQQAMNAFDQAFQSAAALGVTICAASGDNGSGGGVGDGADHV

HFPASSPYALGCGGTSLQASGNGIASETVWNDGANGGATGGGVSSFFALP

AWQEGLRVTRAGGAHSPLAMRGVPDVAGNADPVTGYEVRVDGHDMVIGGT

SAVAPLWAGLIARINAIKGAPVGYINPHLYKDPLALVDITKGNNDDFHAT

AGWDACTGLGRPDGKKVKDAVS, or a processed version thereof.

The methods may comprise administration of the one or more polypeptides together with any other suitable active agent to treat celiac sprue. In various non-limiting embodiments, the methods further comprise administering to the subject an amount of one or more further polypeptides comprising an amino acid sequence selected from the group consisting of:

(A) an amino acid sequence at least 75%, 80%, 85%, 90%, 95%, or 100% identical to the amino acid sequence of SEQ ID NO: 35, wherein
  (i) the polypeptide degrades a PQPQLP (SEQ ID NO: 34) peptide at pH 4; and
  (ii) residue 278 is Ser, residue 78 is Glu, and residue 82 is Asp (B) an an amino acid sequence at least 75%, 80%, 85%, 90%, 95%, or 100% identical to the amino acid sequence of SEQ ID NO: 1, wherein
(i) the polypeptide degrades a PQPQLP (SEQ ID NO: 34) peptide at pH 4; and
(ii) residue 467 is Ser, residue 267 is Glu, and residue 271 is Asp.

The one or more further polypeptides have been disclosed for use in treating celiac sprue (see WO2013/023151). The further polypeptides are either the processed version of Kumamolisin-As (SEQ ID NO: 67) or the preprocessed version of Kumamolisin-As (SEQ ID NO: 33), or modified versions thereof, which are known as a member of the sedolisin family of serine-carboxyl peptidases, and utilizes the key catalytic triad $Ser^{278}$-$Glu^{78}$-$Asp^{82}$ in its processed form to hydrolyze its substrate ($Ser^{467}$-$Glu^{267}$-$Asp^{271}$ in the pre-processed form) Its maximal activity is at pH ~4.0. While the native substrate for Kumamolisin-As is unknown, it has been previously shown to degrade collagen under acidic conditions. In addition, this enzyme has been shown to be thermostable, with an ideal temperature at 60° C., but still showing significant activity at 37° C.

The further polypeptides may comprise one or more amino acid changes from SEQ ID NO: 67 (wild type processed Kumamolisin-As) at one or more residues selected from the group consisting of residues 73, 102, 103, 104, 130, 165, 168, 169, 172, and 179 (numbering based on the wild type processed Kumamolisin-As amino acid sequence). In non-limiting embodiments, the one or more changes relative to the wild type processed Kumamolisin-As amino acid sequence (SEQ ID NO: 67) may be selected from the group consisting of:

| Wild type Residue# | AA change |
| --- | --- |
| S73 | K, G |
| N102 | D |
| T103 | S |
| D104 | A, T, N |
| G130 | S |
| S165 | N |
| T168 | A |
| D169 | N, G |
| Q172 | D |
| D179 | S, H |

In various further non-limiting embodiments, the one or more changes relative to the wild type processed Kumamolisin-As amino acid sequence may include at least N102D. In another embodiment the one or more changes relative to the wild type Kumamolisin-As amino acid sequence may include at least N102D and D169N or D169G. In another embodiment the one or more changes relative to the wild type Kumamolisin-As amino acid sequence may include at least N102D, D169G, and D179H. In another embodiment the one or more changes relative to the wild type Kumamolisin-As amino acid sequence may include at least S73K, D104T, N102D, G130S, D169G, and D179H.

The further polypeptides may comprise one or more amino acid changes from SEQ ID NO: 33 (wild type pre-processed Kumamolisin-As) at one or more residues selected from the group consisting of residues 119, 262, 291, 291, 293, 319, 354, 357, 358, 361, and 368 (numbering based on the wild type pre-processed Kumamolisin-As amino acid sequence). In non-limiting embodiments, the one or more changes relative to the wild type Kumamolisin-As amino acid sequence may be selected from the group consisting of:

| Wild type Residue# | AA change |
| --- | --- |
| V119 | D |
| S262 | K, G |
| N291 | D |
| T292 | S |
| D293 | A, T, N |
| G319 | S |
| S354 | N |
| T357 | A |
| D358 | N, G |
| Q361 | D |
| D368 | S, H |

In various further non-limiting embodiments, the one or more changes relative to the wild type Kumamolisin-As amino acid sequence may include at least N291D. In another embodiment the one or more changes relative to the wild type Kumamolisin-As amino acid sequence may include at least N291D and 358N or 358G. In another embodiment the one or more changes relative to the wild type Kumamolisin-As amino acid sequence may include at least N291D, 358G, and 368H. In another embodiment the one or more changes relative to the wild type Kumamolisin-As amino acid sequence may include at least V119D, S262K, D293T, N291D, G319S, D358G, and D368H.

As used herein, "at least 75% identical" means that the polypeptide differs in its full length amino acid sequence by 25% or less (including any amino acid substitutions, deletions, additions, or insertions) from the polypeptide defined by SEQ ID NO: 1 or 35.

In various further embodiments, the one or more further polypeptides comprise or consist of an amino acid sequence at least 75% identical to any one of SEQ ID NOS: 2-33 or 36-67, or, alternatively, 2-32 or 36-66. They polypeptides represented by these SEQ ID NOS are specific examples of polypeptides with improved protease activity at pH 4 against the oligopeptide PQPQLP (SEQ ID NO: 34) (a substrate representative of gliadin) compared to wild type Kumamolisin-As. In various preferred embodiment, the one or more further polypeptides comprise or consist of an amino acid sequence at least 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence according to any one of SEQ ID NOS: 36-66. In a further embodiment the one or more polypeptides comprise or consist of an amino acid sequence according to any one of SEQ ID NOS: 2-33 or 36-67 or, alternatively, 2-32 or 36-66.

In one embodiment, the one or more further polypeptide comprises or consists of a polypeptide comprising the amino acid sequence shown below (KumaMax™):

(SEQ ID NO: 90)
MSDMEKPWKEGEEARAVLQGHARAQAPQAVDKGPVAGDERMAVTVVLRRQ

RAGELAAHVERQAAIAPHAREHLKREAFAASHGASLDDFAELRRFADAHG

LALDRANVAAGTAVLSGPDDAINRAFGVELRHFDHPDGSYRSYLGEVTVP

ASIAPMIEAVLGLDTRPVARPHFRMQRRAEGGFEARSQAAAPTAYTPLDV

AQAYQFPEGLDGQGQCIAIIELGGGYDEASLAQYFASLGVPAPQVVSVSV

DGASNQPTGDPKGPDGEVELDIEVAGALAPGAKFAVYFAPDTTAGFLDAI

TTAIHDPTLKPSVVSISWSGPEDSWTSAAIAAMNRAFLDAAALGVTVLAA

AGDSGSTGGEQDGLYHVHFPAASPYVLACGGTRLVASGGRIAQETVWNDG

-continued

PDGGATGGGVSRIFPLPAWQEHANVPPSANPGASSGRGVPDLAGNADPAT

GYEVVIDGEATVIGGTSAVAPLFAALVARINQKLGKAVGYLNPTLYQLPA

DVFHDITEGNNDIANRAQIYQAGPGWDPCTGLGSPIGVRLLQALLPSASQ

PQP, or a processed version thereof.

In one embodiment, the method comprises administering Homologue 4 or full length mutant Homologue 4 (SEQ ID NOs: 75, 89, and/or 98), or processed versions thereof, together with the one or more of the further polypeptides disclosed herein, including but not limited to KumaMa™x (SEQ ID NO: 90), or a processed version thereof. As shown in the examples that follow, Homologue 4 (SEQ ID NO: 98) has increased activity against γ-gliadin peptide (amino acid sequence IQPQQPAQL (SEQ ID NO: 92)) compared to Kumamolisin polypeptides. Thus, administering a combination of Homologue 4 (SEQ ID NO: 98) or a processed version thereof and one or more Kumamolisin polypeptides (such as KumaMax™ (SEQ ID NO: 90), or a processed version thereof) may provide an improved therapy for gluten digestion. In a further embodiment, the Homologue 4 polypeptide comprises or consists of the full length Hom 4 mutant (SEQ ID NO: 89) or a processed version thereof, which is shown in the examples below to provide significantly improved activity against degradation products of gluten in the stomach that have been specifically linked to celiac disease: the 33mer peptide (LQLQP-FPQPQLPYPQPQLPYPQPQLPYPQPQPF (SEQ ID NO: 72)) and the 26mer peptide (FLQPQQP-FPQQPQQPYPQQPQQPFPQ (SEQ ID NO: 73)).

In another embodiment, the method comprises administering Homologue 1 (SEQ ID NO: 74), Homologue 6 (SEQ ID NO: 77), and/or the Homologue 6 mutant (SEQ ID NO: 78), or processed versions thereof, together with the one or more of the further polypeptides disclosed herein, including but not limited to KumaMax™ (SEQ ID NO: 90), or a processed version thereof. As demonstrated in the examples that follow, Homologue 1 (SEQ ID NO: 74) is optimally active through pH 5, and the Homologue 6 mutant demonstrates optimal activity at a pH level below that of the other homologues and the further Kumamolisin related polypeptides. As a result, Homologue 1 (SEQ ID NO: 74), Homologue 6 (SEQ ID NO: 77), and/or the Homologue 6 mutant (SEQ ID NO: 78), or processed versions thereof can be used alone in appropriate pH environments, or used in combination with the one or more further polypeptides to expand the pH profile of the one or more further polypeptides, to for example, more accurately mimic the pH of the stomach.

In a further embodiment, the method comprises administering Homologue 26 (SEQ ID NO: 88 or 111) or a processed version thereof, together with the one or more further polypeptides, including but not limited to KumaMax™ (SEQ ID NO: 90), or a processed version thereof. As shown in the examples that follow, Homologue 26 (SEQ ID NO: 111) has very strong activity in breaking down the 33mer gliadin peptide, and thus can be used for treating celiac sprue disease, either alone or on combination with the one or more further polypeptides, including but not limited to KumaMax™ (SEQ ID NO: 90).

Celiac sprue (also known as celiac disease or gluten intolerance) is a highly prevalent disease in which dietary proteins found in wheat, barley, and rye products known as 'glutens' evoke an immune response in the small intestine of genetically predisposed individuals. The resulting inflammation can lead to the degradation of the villi of the small intestine, impeding the absorption of nutrients. Symptoms can appear in early childhood or later in life, and range widely in severity, from diarrhea, fatigue, weight loss, abdominal pain, bloating, excessive gas, indigestion, constipation, abdominal distension, nausea/vomiting, anemia, bruising easily, depression, anxiety, growth delay in children, hair loss, dermatitis, missed menstrual periods, mouth ulcers, muscle cramps, joint pain, nosebleeds, seizures, tingling or numbness in hands or feet, delayed puberty, defects in tooth enamel, and neurological symptoms such as ataxia or paresthesia. There are currently no effective therapies for this lifelong disease except the total elimination of glutens from the diet. Although celiac sprue remains largely underdiagnosed, its'prevalence in the U.S. and Europe is estimated at 0.5-1.0% of the population.

As used herein, "treating celiac sprue" means accomplishing one or more of the following: (a) reducing the severity of celiac sprue; (b) limiting or preventing development of symptoms characteristic of celiac sprue; (c) inhibiting worsening of symptoms characteristic of celiac sprue; (d) limiting or preventing recurrence of celiac sprue in patients that have previously had the disorder; (e) limiting or preventing recurrence of symptoms in patients that were previously symptomatic for celiac sprue; and (f) limiting development of celiac sprue in a subject at risk of developing celiac sprue, or not yet showing the clinical effects of celiac sprue.

The subject to be treated according to the methods of the invention may be any subject suffering from celiac sprue, including human subjects. The subject may be one already suffering from symptoms or one who is asymptomatic.

In one embodiment, the subject may have an HLA-DQ2 serotype; in another embodiment, the subject may have an HLA-DQA serotype. Polypeptides with increased activity against γ-gliadin (Homologues 1, 4, 5, and 9 (SEQ ID NOs: 74, 75, 76, 79, 89, 98, 99, and 102)) may be particularly useful for treating subjects with an HLA-DQ8 serotype. Polypeptides with increased activity against α2-gliadin and α9-gliadin and/or the 33-mer and 26-mer degradation products of gluten described herein (Homologues 4 mutant (SEQ ID NO: 89) and Homologues 13 and 26 (SEQ ID NOs: 82, 88, 105, and 111)) may be particularly useful for treating subjects with an HLA-DQ2 serotype.

As used herein, an "amount effective" refers to an amount of the polypeptide that is effective for treating celiac sprue. The polypeptides are typically formulated as a pharmaceutical composition, such as those disclosed above, and can be administered via any suitable route, including orally, parentally, by inhalation spray, or topically in dosage unit formulations containing conventional pharmaceutically acceptable carriers, adjuvants, and vehicles. In a preferred embodiment, the pharmaceutical compositions and formulations are orally administered, such as by tablets, pills, lozenges, elixirs, suspensions, emulsions, solutions, or syrups.

Dosage regimens can be adjusted to provide the optimum desired response (e.g., a therapeutic or prophylactic response). A suitable dosage range may, for instance, be 0.1 ug/kg-100 mg/kg body weight; alternatively, it may be 0.5 ug/kg to 50 mg/kg; 1 ug/kg to 25 mg/kg, or 5 ug/kg to 10 mg/kg body weight. The polypeptides can be delivered in a single bolus, or may be administered more than once (e.g., 2, 3, 4, 5, or more times) as determined by an attending physician.

In another aspect, the present invention provides isolated polypeptides selected from the group consisting of the following polypeptides, or processed versions thereof.

Homologue 2
(SEQ ID NO: 95)
MQRGTKEGLNMARHLQADREPRIVPESKCLGQCDPAERIHVTIMLRRQEE

GQLDALVHQLATGDARAKPVSRDAFAQRFSANPDDIRKTEDFAHRHQLTV

DRVDPVESVVVLSGT(I/V/D)AQFEAAFSVKLERFEHRSIGQYRGRSGP

IVLPDDIGDAVTAVLGLDSRPQARPHFRFRPPFKPARGAAAVTFTPIQLA

SLYDFPAGDGAGQCIAIIELGGGYRAADIQQYFRGLGITTPPKLVDVNVG

TGRNAPTGEP(N/S/K/G)GPDGEVALDIEIAGAIAPAAKIAVYFAP(N/

D)(S/T)(D/A/T/N)AGFIQAVNAAVTDKTNQPSVISISW(G/S)GPEA

IWQAQSAQAFNRVLQAAAAQGITVCAASGD(S/N)GS(G/T/A)(D/N/G)

GL(Q/D)DGADHV(D/S/H)FPASSPYVLGCGGTQLDALPGQGIRSEVTW

NDEASGGGAGGGGVSALFDLPAWQQGLKVARADGTTTPLAKRGVPDVAGD

ASPQTGYEVSVAGTPAVMGGTSAVAPLWAALIARINAANGASAGWINPVL

YKHPGALRDITKGSNGTYAAASGWDACTGLGSPNGAQLATILARKPSS, wherein one, two, three, four, five, six, seven, eight, nine, ten, or all eleven of the following are true: (i) AA residue 116 is V or D; (ii) AA residue 255 is S, K, or G; (iii) AA residue 284 is D; (iv) AA residue 285 is T; (v) AA residue 286 is A, T, or N; (vi) AA residue 312 is S; (vii) AA residue 347 is N; (viii) AA residue 350 is T or A; (ix) AA residue 351 is N or G; (x) AA residue 354 is D; and (xi) AA residue 361 is S or H;

Homologue 4
(SEQ ID NO: 75)
MANHPLNGSERECLKDAQPIGKADPNERLEVTMLVRRRSHDAFEKHISAL

AAQGASAKHIDHDEFTKHFGADSADLAAVHAFAQKHGLSVVESHEARRAV

VLSGT(V/D)AQFDAAFGVSLQQYEHDGGTYRGRTGPIHLPDELNGVVDA

VMGLDNRPQARPSFRTRAQGNVRWTARAAGASTFTPVQLASLYDFPQGDG

QNQCIGIIELGGGYRPADLKTYFASLNMKAPSVTAVSVDHGRNHPTDP (N/S/K/G)GPDGEVMLDIEVAGAVAPGAKIVVYFAP(N/D)(T/S)(D/

A/T/N)AGFIDAIGTAIHDTKNKPSVISISW(G/S)GPESAWTQQAMNAF

DQAFQSAAALGVTICAASGD(N/S)GS(G/T/A)(D/N/G)GV(G/Q/D)

DGADHV(D/S/H)FPASSPYALGCGGTSLQASGNGIASETVWNDGANGGA

TGGGVSSFFALPAWQEGLRVTRAGGAHSPLAMRGVPDVAGNADPVTGYEV

RVDGHDMVIGGTSAVAPLWAGLIARINAIKGAPVGYINPHLYKDPLALVD

ITKGNNDDFHATAGWDACTGLGRPDGKKVKDAVS;

wherein one, two, three, four, five, six, seven, eight, nine, ten, or all eleven of the following are true: (i) AA residue 106 is D; (ii) AA residue 246 is S, K, or G; (iii) AA residue 275 is D; (iv) AA residue 276 is S; (v) AA residue 277 is A, T, or N; (vi) AA residue 303 is S; (vii) AA residue 338 is S; (viii) AA residue 341 is T or A; (ix) AA residue 342 is N or G; (x) AA residue 345 is Q or D; and (xi) AA residue 352 is S or H;

Homologue 5
(SEQ ID NO: 76)
MNHDHSPTGGELSNWVRVPGSERAAVQGSRKVGPADPNEQMSVTVVVRRP

AADTAVTSMIEKVGAQPLSERRHLTREEFASTHGANPADLSKVEKFAHEH

NLQVKEVNAAAGTMVLSGT(V/D)TSFSKAFGVELSTYEHPDFTYRGRIG

HVHIPDYLADTIQSVLGLDNRPQASPRFRVLKEEGGVTTAHAGRTSYTPL

EVAALYNFPSIHCKDQCIGILELGGGYRPADLQTYFNGLGIPQPNITDVS

VGGAANRPTGDP(N/S/K/G)GPDGEVVLDIEVAAAVTPGAKIAVYFAD (N/D)(S/T)(D/A/T/N)DGFLNAITTAIHDTRNKPSVISISW(G/S)K

AEIGWTPQAINAMNQAFRDAAALGVTICCASGD(D/S/N)GS(T/A)

(D//N/G)RV(Q/D)DGRYHV(D/S/H)FPASSPYVLACGGTRLESSGST

ITQEVVWNEGALGGGATGGGVSDVFDRPNWQANANVPTSANPERRIGRGV

PDWAGNADPATGYQILVDGTRAVIGGTSAVAPLFAGLIAIINQKLGHSVG

FINPILYNLSAQHNVFHDITSGNNDMSGQNGPYEAQPGWDACTGLGSPDG

TKLMNAISEAHRLVSVG;

wherein one, two, three, four, five, six, seven, eight, nine, ten, or all eleven of the following are true: (i) AA residue 120 is D; (ii) AA residue 259 is S, K, or G; (iii) AA residue 288 is D; (iv) AA residue 289 is T; (v) AA residue 290 is A, T, or N; (vi) AA residue 316 is S; (vii) AA residue 351 is S or N; (viii) AA residue 354 is A; (ix) AA residue 355 is N or G; (x) AA residue 358 is D; and (xi) AA residue 365 is S or H;

Homologue #6 mutant:
(SEQ ID NO: 78)
MAPEERRTLPGSAMPRPAGAQVLGQIPDDERVEVTVVLQPRAPLPEPGPT

PMSRAELADLRSPPEGALEAIARYVAGQGLEVIAADAPRRRIVLAGSAAR

IAALFGISFVRLQLEGRRYRTYEGEISLPAELAPLVVAVLGLDTRPFARS

HRRPAVAPNAPTTAPTVARAYDFPTAYDGRGTTIGFIELGGGFQESDLVR

YCEGLGLSTPQVSVVGVDGARNAPTGDPNGPDAEVMLDLEVATGVANGAD

LVLYMAANTDAAFYSAIATALRDATHAPVAISISWSAPEESYPATTIAAF

ESVLEEAVHVGVTVLVAAGDQGSTGGVDDGRAHVHYPAASPYVLACGGTR

LDLDGTTIVAETVWNDLPNGGATGGGISALFPVPSWQAGIAMPPSANPGA

GPGRGVPDVAGNADPDTGYRIVVDGVATVVGGTSAVAPLWAGLVARCHQA

GARGGFWNPLLYAARGSSAFHEITVGSNGAYDAGPIWNACCGLGSPNGTA

ILQTLRA;

Homologue 9
(SEQ ID NO: 79)
MTKQPVSGSSDKIHPDDAKCIGDCDPSEQIEVIVMLRRKDEAGFRQMMSR

IDAGEAPGQAVSREEFDRRFTASDEDIDKVKAFAKQYGLSVERAETETRS

VVLKGT(I/V/D)EQFQKAFDVKLERFQHHNIGEYRGRTGPVNVPDEMHD

AVTAVLGLDSKPQARPHFRFRPPFKPLRGAAPASFSPVDLAKLYDFPGD

GAGQCIAIIELGGGYRDSDLSAYFSKLGVKAPTVVPVGVDGGKNAPTGNP (N/S/K/G)GPDGEVTLDIEIAGAIAPGARIAVYFAP(N/D)(S/T)(D/

A/T/N)AGFVDAVNRALHDAANKPSVISISW(G/S)GPESNWSPQSMSAF

-continued

NDVLQSAAALGVTVCAASGD(G/S/N)GS(A/T)(D/N/G)GV(G/Q/D)

DGADHV(D/S/H)FPASSPYVLGCGGTSLAASGAGIAKEVVWNDGDQGGA

GGGGVSGTFALPVWQKGLSVTRNGKHIALAKRGVPDVAGDASPQTGYEVL

IDGEDTVVGGTSAVAPLWAALIARINAIDASPAGFVNPKLYKAKTAFRDI

TEGNNGSFSAAAGWDACTGMGSPDGGKIAAALKPAKPSQSAGQQ, wherein one, two, three, four, five, six, seven, eight, nine, ten, or all eleven of the following are true: (i) AA residue 107 is V or D; (ii) AA residue 245 is S, K, or G; (iii) AA residue 274 is D; (iv) AA residue 275 is T; (v) AA residue 276 is A, T, or N; (vi) AA residue 302 is S; (vii) AA residue 337 is S or N; (viii) AA residue 340 is T or A; (ix) AA residue 341 is N or G; (x) AA residue 344 is Q or D; and (xi) AA residue 351 is S or H;

Homologue 10
(SEQ ID NO: 80)
MGRLQGSYRPSLGTPVGPVPDDQPIDVTVVLRPTAADDFRADPDDVAAVR

AFAGRAGLDVAEVDEPARTVRLRGP(A/V/D)AAARTAFDTPLALYDSGG

RAIRGREGDLGLPDELDDRVVAVLGLDERPAARPRFQPAASARQGLTALQ

VARAYDFPAATGEGQTIAIIELGGGFGQADLDTYFGGLDLPTPAVSAVGV

QGAANVPGGDP(/S/K/G)DGADGEVLLDIEVAGAVAPGAAQVVYFAP (N/D)(T/S)(D/A/T/N)AGFLAAINAAAAATPRPAAISISWG(G/S)P

ESSWTAQAMRAYDQAFAAARAAGITVLAAAGD(A/S/N)GA(D/T/A)

(D/S/N/G)(A/Q/D)TDRLVA(D/S/H)FPAGSPNVIACGGTKLTLDAA

GARASEVVWNEAADSATGGGYSATFTRPAWQPAAVGRYRGLPDISGNADP

QTGYRVVVDGQPTVVGGTSAVAPLLAGLVARLAQLTGAPVADLAAVAYAN

PAAFTDITAGDNQGYPARSGWDPASGLGSPVGTKLLTAVGGPTPPPTTPP

PTTPPPTTPPPTIPPPTTPPTQTVDAADRALWSAVATWAGGTHTGANARA

AKAVRAWAQAKSLA, wherein one, two, three, four, five, six, seven, eight, nine, ten, or all eleven of the following are true: (i) AA residue 76 is V or D; (ii) AA residue 206 is S, K, or G; (iii) AA residue 235 is D; (iv) AA residue 236 is S; (v) AA residue 237 is A, T, or N; (vi) AA residue 262 is S; (vii) AA residue 297 is S or N; (viii) AA residue 300 is T or A; (ix) AA residue 301 is N or G; (x) AA residue 302 is Q or D; and (xi) AA residue 309 is S or H;

Homologue 12
(SEQ ID NO: 81)
MTQPRYTPLPGSEREAPLLAARSNATAARASRAQTASATVVLRRRSELPE

ALVLDQQFISSDELAARYGADPVDIEKVRSVLERFKVSVVEVDAASRRVK

VEGA(V/D)ADIERAFNIALHSASGTDPHSGRGFEYRYRTGVLSVPAELG

GIVTAVLGLDNRRQAETRLRVVPAAALGSSYTPVQLGEIYNFPQDATGAG

QRIAIIELGGGYTPAGLRRYFASLGVVPPKVAAVSVDGAQNAPGPDP(G/

S/K/G)ADGEVQLDVEVAGALAPGAHVLVYFAP(N/D)(T/S)(D/A/T/

N)QGFLDAVSQAAHATPPPTAISISW(G/S)ASEDSWTASARDALNQALR

DAAALGVTVTAAAGD(S/N)GS(S/T/A)(D/N/G)GV(P/Q/D)DRRAH

V(D/S/H)FPASSPYVLATGGTSLRADPATGVVQSETVWNDSQGSTGGGV

SDVFPRPAWQAHVDVPHAGRGVPDVSAVADPATGYQVLVDNQPAVIGGTS

AVAPLWAALVARLAESLGRPLGLLQPLVYPRTPGSTAYPGFRDITIGNNG

AYKAGKGWDAATGLGVPDGTELLAHLRGLNGSE, wherein one, two, three, four, five, six, seven, eight, nine, ten, or all eleven of the following are true: (i) AA residue 105 is D; (ii) AA residue 244 is S or K; (iii) AA residue 272 is D; (iv) AA residue 273 is S; (v) AA residue 274 is A, T, or N; (vi) AA residue 299 is S; (vii) AA residue 334 is N; (viii) AA residue 337 is T or A; (ix) AA residue 338 is N or G; (x) AA residue 341 is Q or D; and (xi) AA residue 348 is S or H;

Homologue 13
(SEQ ID NO: 82)
MARHLHAGSEPKVITESKCIGACDPAERIHVTVMLRREGEQALDALVDKL

ASGDPAAKPVSREDFAKRFGARADDIQHTEAFAKRHQLTVERVDPVQSVV

ELAGT(I/V/D)AQFENAFGVKLEKYEHHAIGSFRARTGAIALPDELHDA

VTAVLGLDTRPQAHPHFRFRPPFQPARSGAGTSYTPLQLASIYNFPEGDG

AGQCIALVELGGGYRAADIRQYFEQLGVKPPKLVDVSVNGGRNAPTDDP (N/S/K/G)GPDGEVALDIEVAGAIAPGATIAVYFAG(N/D)(S/T)(D/

A/T/N)AGFIQSVNQATHDSTNRPSVVSISW(G/S)GPEASWTQQSITAF

NNVLKTAASLGVTVCAASGD(S//N)GS(S/T/A)(D/N/G)GL(Q/D)D

GSNHV(D/S/H)FPASSPYVLACGGTTLDAQAGQGIRREVVWNDEAASGG

AGGGGVSAVFPAPSYQKGLSAKATGGGSTPLSQRGVPDVAGDASPTTGYI

ISIAGTTAVLGGTSAVAPLWAALIARINANGKSPVGWANPKLYAQPGAFH

DITQGNNGAFAASEGWDACTGLGSPDGAKVAAALQGASGGSQQGRATGA;

wherein one, two, three, four, five, six, seven, eight, nine, ten, or all eleven of the following are true: (i) AA residue 106 is V or D; (ii) AA residue 244 is S, K, or G; (iii) AA residue 273 is D; (iv) AA residue 274 is T; (v) AA residue 275 is A, T, or N; (vi) AA residue 301 is S; (vii) AA residue 336 is N; (viii) AA residue 339 is T or A; (ix) AA residue 340 is N or G; (x) AA residue 343 is D; and (viii) AA residue 350 is S or H;

Homologue 14
(SEQ ID NO: 83)
MTKHPLPGSERVLAPGSKVVAQCDPSETIEVVVVLRRKNEQQFAQMMKTI

EAGAAGARPLTREELEQRFGALPEDIAKLKAFAAQHGLSVVREDASARTV

VLSGR(I/V/D)EQFQQAFDVQLQHYEHQSMGRFRGRTGAISVPDELHGV

VTAVLGLDDRPQARPHFRIRPPFQPARAQSASSFTPLQLASLYRFPQGDG

SGQCIGIVELGGGYRTADLDSYFSSLGVGSPKVVAVGVDQSGNQPTGDP (N/S/K/G)GPDGEVTLDIEIAGALAPAATIAVYFTT(N/D)(S/T)(D/

A/T/N)AGFIDAVSQAVHDRTNQPSVISISW(G/S)APESMWTAQSMKAL

NDVLQSAAAIGVTVCAASGD(S/N)GS(S/T/A)(D/N/G)GV(G/Q/D)

DGRDHV(D/S/H)FPASSPYVLACGGTSLQGSGRTVAHEVVWNDGSNGGA

TGGGVSGAFPVPAWQEGLSTSAAQGGQRALTGRGVPDVAGDASPLTGYDV

IVDGNNTVIGGTSAVAPLWAALIARINGAKGAPVGFVNPKLYKASACNDI

TQGNNGSYAATTGWDACTGLGSPDGVKVAAAL, wherein one, two, three, four, five, six, seven, eight, nine, ten, or all eleven of the following are true: (i) AA residue 107 is V or D; (ii) AA residue 245 is S, K, or G; (iii) AA residue 274 is D; (iv) AA residue 275 is T; (v) AA residue 276 is A, T, or N; (vi) AA residue 302 is S; (vii) AA residue 337 is N; (viii) AA residue 340 is T or A; (ix) AA residue 341 is N or G; (x) AA residue 344 is Q or D; and (xi) AA residue 351 is S or H;

Homologue 15
(SEQ ID NO: 84)
MSPIASRRSALPLSERPAPENARALAAVEPDRTMTVSVLVRRKKPLVLAD

LEGKKLTHREFERRYGASEKDFATIAKFAAGHGLAVDHHASSLARRTVVL

RGT(A/V/D)RQMQQAFGVTLHDYEDSETQQRYHSFTGAITVPAAHARII

ESVLGLDARPIAKPHFRVRKRSAAATGAVSFNPPQVASLYSFPTGVDSGG

ETIGILELGGGYETSDIQQYFSGLGIQPPTVVAVSVDGAVNAPGNP(N/

S/K/G)GADGEVALDIQVAGSIAPGAKLAVYFAP(N/D)(T/S)(E/D/

A/T/N)QGFVDAITTAVHDTANKPSVLSISW(G/S)GPESSWPQAAAQSL

NNACESAAALGVTTTVASGD(N/S)GS(T/A)(D/N/G)GV(Q/D)DGQN

HV(D/S/H)FPASSPYVLACGGTYLAAVNNGVPQESVWDDLASGGGATGG

GVSALFPLPAWQTGANVPGGSMRGVPDVAGDASPESGYNVLVDGQPQVVG

GTSAVAPLWAALIALVNQQKGEAAGFVNAALYQNPSAFHDITQGSNGAYA

AAPGWDPCTGLGSPMGTAIAKILA, wherein one, two, three, four, five, six, seven, eight, nine, ten, or all eleven of the following are true: (i) AA residue 104 is V or D; (ii) AA residue 241 is S, K, or G; (iii) AA residue 270 is D; (iv) AA residue 271 is S; (v) AA residue 272 is D, A, T, or N; (vi) AA residue 398 is S; (vii) AA residue 33 is S; (viii) AA residue 336 is A; (ix) AA residue 337 is N or G; (x) AA residue 340 is D; and (xi) AA residue 347 is S or H;

Homologue 16
(SEQ ID NO: 85)
MSAFDQLVPLPGSEKTVPDAAPSQTLDPNEVLTVTIRIRRKRTLASLVST

TAPVTEVVSRSEYASRFGADPAIVKQVEAFASAYDLSLVEQSLARRSVLL

RGT(V/D)AQMEQAFGVSLANYQLADGTVFRGRTGVVNVPSELVEHIEGV

FGLDNRPQARAHFQVYKPEKGTKVAPRAGGISYTPPQLARLYNFPTGVTG

KGQCIAIIELGGGFRTADIKTYFGGLGLKPPTVVAVSVDGGHNAPSTA (D/S/K/G)SADGEVMLDIDVAGGVAPGAKIVVYFAP(N/D)(T/S)(D/

A/T/N)QGFLDAITTAMHDTKNKPSVISISW(G/S)AAESNWTPQALTSF

NQAFQAAAALGITVCAAAGD(T/S/N)GS(D/T/A)(D/N/G)SV(G/Q/

D)DGKAHV(D/S/H)FPASSPFVLACGGTKLTATDNVIASEVVWHESKTS

ATGGGVSDVFDLPDYQQKSHVPPSVNDKTRIGRGVPDVAAVADPVTGYAV

RVDGSNLVFGGTSAVAPLMAGLIALINQQRGKAVGFIHPLIYANPSAFRD

ITQGNNTTTTGNKGYAATTGWDACTGLGVADGKKLASVLTATPVA, wherein one, two, three, four, five, six, seven, eight, nine, ten, or all eleven of the following are true: (i) AA residue 104 is D; (ii) AA residue 245 is S, K, or G; (iii) AA residue 274 is D; (iv) AA residue 275 is S; (v) AA residue 276 is A, T, or N; (vi) AA residue 302 is S; (vii) AA residue 337 is S or N; (viii) AA residue 340 is T or A; (ix) AA residue 341 is N or G; (x) AA residue 344 is Q or D; and (xi) AA residue 351 is S or H;

Homologue 17
(SEQ ID NO: 86)
MAATPRFASQPRVTLPGSQKHPLTTDTEVPPPAPVKAAATKLSATPFTVT

VIVKRKNPLNLKQVLKPAGRLTHAAFAKAHGPSPDGVKLVKAFAKEFGLT

VAPAPGQGRRALYLTGT(A/V/D)AAMQTAFGVTFATKIMEGTKYRVREG

DICLPKELIGHVDAVLGLDNRPQAKPHFRHHKPAATSVSYTPVQVGQLYG

FPSGAKATGQTIGLIELGGGFRAADITAYFKTLGQTAPKVTAVLVDKAKN

TPTTS(S/K/G)SADGEVMLDIEVAAAVAPGANIAVYFAP(N/D)(T/S)

(D/A/T/N)QGFIDAISQAVHDTVNKPSVISISW(G/S)GPESTWTAQSL

AALDAACQSAAALGITITVAAGD(D/S/N)GS(T/A)(D/N/G)GV(K/

Q/D)GTVNHV(D/S/H)FPASSPHVLGCGGTKLLGSGTTITSEVVWNELT

ANEGATGGGVSNVFPLPTWQAKSNVPKPTVAAGGRGVPDVSGNADPSTGY

TVRVDGSTFPIGGTSAVAPLWAGLIALCNAQNKTTAGFINPALYAAAAAK

SFRDITSGNNGGFKAGPGWDACTGLGSPIGTAIAKTLAPATKSTSKTAVK

NAPEIRFRPHKKAPTKTAAKTPALRRLK, wherein one, two, three, four, five, six, seven, eight, nine, ten, or all eleven of the following are true: (i) AA residue 118 is V or D; (ii) AA residue 250 is K, or G; (iii) AA residue 279 is D; (iv) AA residue 280 is S; (v) AA residue 281 is A, T, or N; (vi) AA residue 307 is S; (vii) AA residue 342 is S or N; (viii) AA residue 345 is A; (ix) AA residue 346 is N or G; (x) AA residue 349 is Q or D; and (xi) AA residue 356 is S or H;

Homologue 19
(SEQ ID NO: 87)
MPTSSRFASQSRVPLPGSERKPFVPAGAPKAAKTPKVSTAVKTVPATGRI

RVSLIVPPKQPLDTKRLGKLDARLSRAQFAARHGADPASVRLVKAFAKEF

GLTVEPITQPGRCTVQLSGT(C/V/D)AAMRKAFAISLVEHTTEQGKFRL

REGEISLPAELEGHVLAVLGLDNRPQAKPHFRIAKPRATNVSYTPVQVAQ

MYGFPAGATATGQTIGIIELGGGYRAADLTAYFKTLGLPAPTVTAVPIDG

GKNTPGNA(N/S/K/G)GADGEVMLDIEVCAAVAQGAKIAVYFTT(N/D)

(T/S)(D/A/T/N)QGFIDAITTAVHDSTNKPSVISISW(G//S)GPESS

WTEQSMTALDAACQAAAAVGVTTTVAAGD(N/S)GS(S/T/S)(D/N/G)

GA(S/Q/D)GDNV(D/S/H)FPASSPHVLACGGTKLVGSGSTTTSEVVWD

ETSNDEGATGGGVSTVFALPTWQKNANVPSPTTSAGGRGVPDVSGDADPS

TGYTIRVDSETTVIGGTSAVAPLWAGLIALANAQNKVAAGFVNPALYAAG

AKKAFRDITQGNNGSFSAGPGWDACTGLGSPVGNLVIQAVAPKSTTTKKA

KKGKTK, wherein one, two, three, four, five, six, seven, eight, nine, ten, or all eleven of the following are true: (i) AA residue 121 is V or D; (ii) AA residue 253 is S, K, or G; (iii) AA residue 282 is D; (iv) AA residue 283 is S; (v) AA residue 284 is A, T, or N; (vi) AA residue 310 is S; (vii) AA residue 345 is S; (viii) AA residue 348 is T or A; (ix) AA residue 349 is N or G; (x) AA residue 352 is Q or D; and (xi) AA residue 357 is S or H; and Homologue 26
(SEQ ID NO: 88)
MHSYLKQQSHMQSYLEQENHMRSYLEMRKKPYFDDLANIRPGGLTPAQVC

QAYQFAKVQPVRPVKLGIVSLAGQYLSSDMSKAFTGYGLPTPVVSTAGSQ

VLGDLWSNVE(N/S/K/G)MMDIEIAGAAWAYATGTAATLLMQFEP(N/

D)(N/T/S)(E/D/A/T/N)TGIPNAINALVAAGCEVISISW(G/S)APA

NLQTMEAITARKEACKQAAVQNVHVFAASGD(E/S/N)SL(N/T/A)(D/

N/G)(G/Q/D)TNSRTP(D/S/H)DPCCDPNVWGVGGTRLVLQADGSIAQ

ESAWGDGNAADKGGGGGFDSREPLPDYQVGVVHSEHRGSPDSSANADPGT

GYAIVANGQWLIGGGTSASAPLTAGYVAAILSTLPGPISQSVLQRKLYTA

HKTAFRDILLGSNGAPARPGWEEATGLGSINGPGLAAALQS, wherein one, two, three, four, five, six, seven, eight, nine, or all ten of the following are true: (i) AA residue 111 is S, K, or G; (ii) AA residue 139 is D; (iii) AA residue 140 is T or S; (iv) AA residue 141 is D, A, T, or N; (v) AA residue 164 is S; (vi) AA residue 199 is S or N; (vii) AA residue 202 is T or A; (viii) AA residue 203 is N or G; (ix) AA residue 204 is Q or D; and (x) AA residue 211 is S or H.

The polypeptides may be processed versions of the recited polypeptides; the presently claimed polypeptides include any such processed versions of the recited polypeptides. Processed versions of the polypeptides are as defined above.

In one embodiment, the isolated polypeptide comprises the amino acid sequence of a polypeptide selected from Homologues 4, Homolog 6 mutant, and Homologs 13 and 26, or processed versions thereof. In another embodiment, the isolated polypeptide comprises the amino acid sequence of Hom 4 mutant:

(SEQ ID NO: 89)
MANHPLNGSERECLKDAQPIGKADPNERLEVTMLVRRRSHDAFEKHISAL

AAQGASAKHIDHDEFTKHFGADSADLAAVHAFAQKHGLSVVESHEARRAV

VLSGTVAQFDAAFGVSLQQYEHDGGTYRGRTGPIHLPDELNGVVDAVMGL

DNRPQARPSFRTRAQGNVRWTARAAGASTFTPVQLASLYDFPQGDGQNQC

IGIIELGGGYRPADLKTYFASLNMKAPSVTAVSVDHGRNHPTGDPNGPDG

EVMLDIEVAGAVAPGAKIVVYFAPNTDAGFIDAIGTAIHDTKNKPSVISI

SWSGPESAWTQQAMNAFDQAFQSAAALGVTICAASGDNGSGGGVGDGADH

VHFPASSPYALGCGGTSLQASGNGIASETVWNDGANGGATGGGVSSFFAL

PAWQEGLRVTRAGGAHSPLAMRGVPDVAGNADPVTGYEVRVDGHDMVIGG

TSAVAPLWAGLIARINAIKGAPVGYINPHLYKDPLALVDITKGNNDDFHA

TAGWDACTGLGRPDGKKVKDAVS,
or a processed version thereof.

The polypeptides disclosed herein have been identified as having similar, improved, or complimentary activity compared to Kumamolisin-related polypeptides in hydrolyzing proline (P)- and glutamine (Q)-rich components of gluten known as 'gliadins' believed responsible for the bulk of the immune response in most celiac sprue patients. Numerous other Kumamolisin homologues tested by the inventors possessed little or no such gliadin hydrolyzing activity. Thus, the polypeptides can be used to treat celiac sprue. The polypeptides of this aspect of the invention degrade gliadins at various pHs. Such degradation occurs under the conditions disclosed in the examples that follow.

As used throughout the present application, the term "polypeptide" is used in its broadest sense to refer to a sequence of subunit amino acids, whether naturally occurring or of synthetic origin. The polypeptides of the invention may comprise L-amino acids, D-amino acids (which are resistant to L-amino acid-specific proteases in vivo), or a combination of D- and L-amino acids. The polypeptides described herein may be chemically synthesized or recombinantly expressed. They polypeptides may be linked to other compounds to promote an increased half-life in vivo, such as by PEGylation, HESylation, PASylation, or glycosylation. Such linkage can be covalent or non-covalent as is understood by those of skill in the art. They polypeptides may be linked to any other suitable linkers, including but not limited to any linkers that can be used for purification or detection (such as FLAG or His tags).

In a further aspect, the invention provides compositions, comprising
(a) one or more polypeptides comprising the amino acid sequence of a polypeptide selected from the group consisting of SEQ ID NOs: 74-78, 80-88, 95, 97-99, and 102-111, or processed versions thereof; and
(b) one or more further polypeptides comprising an amino acid sequence selected from the group consisting of:
  (A) an amino acid sequence at least 75%, 80%, 85%, 90%, 95%, or 100% identical to the amino acid sequence of SEQ ID NO: 35, wherein
    (i) the polypeptide degrades a PQPQLP (SEQ ID NO: 34) peptide at pH 4; and
    (ii) residue 278 is Ser, residue 78 is Glu, and residue 82 is Asp
  (B) an an amino acid sequence at least 75%, 80%, 85%, 90%, 95%, or 100% identical to the amino acid sequence of SEQ ID NO: 1, wherein
    (i) the polypeptide degrades a PQPQLP (SEQ ID NO: 34) peptide at pH 4; and
    (ii) residue 467 is Ser, residue 267 is Glu, and residue 271 is Asp.

The one or more further polypeptides can be any as described above. For example, the one or more further polypeptides may comprise or consist of an amino acid sequence at least 75%, 80%, 85%, 90%, 95%, or 100% identical to any one of SEQ ID NOS: 2-33 or 36-67, or, alternatively, 2-32 or 36-66. In another embodiment, the one or more further polypeptides comprise or consist of Kuma-Max™ (SEQ ID NO: 90), or a processed version thereof.

In one embodiment, the composition comprises Homologue 4 (SEQ ID NO: 75 or 98) or full length mutant Homologue 4 (SEQ ID NO: 89), or processed versions thereof, together with the one or more of the further polypeptides disclosed herein, including but not limited to KumaMax™ (SEQ ID NO: 90), or a processed version thereof. In another embodiment, the composition comprises SEQ ID NO: 74, SEQ ID NO: 77, and/or SEQ ID NO: 78 (Homologue 1, Homologue 6, and/or the Homologue 6 mutant), or processed versions thereof, together with the one or more of the further polypeptides disclosed herein, including but not limited to KumaMax™ (SEQ ID NO: 90), or a processed version thereof. In a further embodiment, the method comprises administering SEQ ID NO: 88 and/or 111 (Homologue 26) or a processed version thereof, together with the one or more further polypeptides, including but not limited to KumaMax™ (SEQ ID NO: 90), or a processed version thereof.

In another aspect, the present invention provides isolated nucleic acids encoding the polypeptide of any aspect or embodiment of the invention. The isolated nucleic acid sequence may comprise RNA or DNA. As used herein, "isolated nucleic acids" are those that have been removed from their normal surrounding nucleic acid sequences in the genome or in cDNA sequences. Such isolated nucleic acid sequences may comprise additional sequences useful for promoting expression and/or purification of the encoded protein, including but not limited to polyA sequences, modified Kozak sequences, and sequences encoding epitope tags, export signals, and secretory signals, nuclear localization signals, and plasma membrane localization signals. It will be apparent to those of skill in the art, based on the teachings herein, what nucleic acid sequences will encode the polypeptides of the invention.

In a further aspect, the present invention provides nucleic acid expression vectors comprising the isolated nucleic acid of any embodiment of the invention operatively linked to a suitable control sequence. "Recombinant expression vector" includes vectors that operatively link a nucleic acid coding region or gene to any control sequences capable of effecting expression of the gene product. "Control sequences" operably linked to the nucleic acid sequences of the invention are nucleic acid sequences capable of effecting the expression of the nucleic acid molecules. The control sequences need not be contiguous with the nucleic acid sequences, so long as they function to direct the expression thereof. Thus, for example, intervening untranslated yet transcribed sequences can be present between a promoter sequence and the nucleic acid sequences and the promoter sequence can still be considered "operable linked" to the coding sequence. Other such control sequences include, but are not limited to, polyadenylation signals, termination signals, and ribosome binding sites. Such expression vectors can be of any type known in the art, including but not limited plasmid and viral-based expression vectors. The control sequence used to drive expression of the disclosed nucleic acid sequences in a mammalian system may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). The construction of expression vectors for use in transfecting prokaryotic cells is also well known in the art, and thus can be accomplished via standard techniques. (See, for example, Sambrook, Fritsch, and Maniatis, in: Molecular Cloning, A Laboratory Manual, Cold Spring Harbor Laboratory Press, 1989; *Gene Transfer and Expression Protocols*, pp. 109-128, ed. E. J. Murray, The Humana Press Inc., Clifton, N.J.), and the Ambion 1998 Catalog (Ambion, Austin, Tex.). The expression vector must be replicable in the host organisms either as an episome or by integration into host chromosomal DNA. In a preferred embodiment, the expression vector comprises a plasmid. However, the invention is intended to include other expression vectors that serve equivalent functions, such as viral vectors.

In another aspect, the present invention provides recombinant host cells comprising the nucleic acid expression vectors of the invention. The host cells can be either prokaryotic or eukaryotic. The cells can be transiently or stably transfected or transduced. Such transfection and transduction of expression vectors into prokaryotic and eukaryotic cells can be accomplished via any technique known in the art, including but not limited to standard bacterial transformations, calcium phosphate co-precipitation, electroporation, or liposome mediated-, DEAE dextran mediated-, polycationic mediated-, or viral mediated transfection. (See, for example, *Molecular Cloning: A Laboratory Manual* (Sambrook, et al, 1989, Cold Spring Harbor Laboratory Press: *Culture of Animal Cells- A Manual of Basic Technique*, $2^{nd}$ Ed. (R. I. Freshney, 1987. Liss, Inc. New York, N.Y.). A method of producing a polypeptide according to the invention is an additional part of the invention. The method comprises the steps of (a) culturing a host according to this aspect of the invention under conditions conducive to the expression of the polypeptide, and (b) optionally, recovering the expressed polypeptide. The expressed polypeptide can be recovered from the cell free extract, cell pellet, or recovered from the culture medium. Methods to purify recombinantly expressed polypeptides are well known to the man skilled in the art.

In a still further aspect, the present invention provides pharmaceutical compositions, comprising the polypeptide, nucleic acid, nucleic acid expression vector, the recombinant host cell, or composition of any aspect or embodiment of the invention, together with a pharmaceutically acceptable carrier. The pharmaceutical compositions of the invention can be used, for example, in the methods of the invention described below. The pharmaceutical composition may comprise in addition to the polypeptides, nucleic acids, etc. of the invention (a) a lyoprotectant; (b) a surfactant; (c) a bulking agent; (d) a tonicity adjusting agent; (e) a stabilizer; (f) a preservative and/or (g) a buffer.

In some embodiments, the buffer in the pharmaceutical composition is a Tris buffer, a histidine buffer, a phosphate buffer, a citrate buffer or an acetate buffer. The pharmaceutical composition may also include a lyoprotectant, e.g. sucrose, sorbitol or trehalose. In certain embodiments, the pharmaceutical composition includes a preservative e.g. benzalkonium chloride, benzethonium, chlorohexidine, phenol, m-cresol, benzyl alcohol, methylparaben, propylparaben, chlorobutanol, o-cresol, p-cresol, chlorocresol, phenylmercurie nitrate, thimerosal, benzoic acid, and various mixtures thereof. In other embodiments, the pharmaceutical composition includes a bulking agent, like glycine. In yet other embodiments, the pharmaceutical composition includes a surfactant e.g. polysorbate-20, polysorbate-40, polysorbate-60, polysorbate-65, polysorbate-80, polysorbate-85, poloxamer-188, sorbitan monolaurate, sorbitan monopalmitate, sorbitan monostearate, sorbitan monooleate, sorbitan trilaurate, sorbitan tristcarate, sorbitan trioleaste, or a combination thereof. The pharmaceutical composition may also include a tonicity adjusting agent, e.g. a compound that renders the formulation substantially isotonic or isoosmotic with human blood. Exemplary tonicity adjusting agents include sucrose, sorbitol, glycine, methionine, mannitol, dextrose, inositol, sodium chloride, arginine and arginine hydrochloride. In other embodiments, the pharmaceutical composition additionally includes a stabilizer, e.g. a molecule which, when combined with a protein of interest substantially prevents or reduces chemical and/or physical instability of the protein of interest in lyophilized or liquid form. Exemplary stabilizers include sucrose, sorbitol, glycine, inositol, sodium chloride, methionine, arginine, and arginine hydrochloride.

The polypeptides, nucleic acids, etc. of the invention may be the sole active agent in the pharmaceutical composition, or the composition may further comprise one or more other active agents suitable for an intended use.

The pharmaceutical compositions described herein generally comprise a combination of a compound described herein and a pharmaceutically acceptable carrier, diluent, or excipient. Such compositions are substantially free of non-pharmaceutically acceptable components, i.e., contain amounts of non-pharmaceutically acceptable components lower than permitted by U.S. regulatory requirements at the time of filing this application. In some embodiments of the aspect, if the compound is dissolved or suspended in water, the composition further optionally comprises an additional pharmaceutically acceptable carrier, diluent, or excipient. In other embodiments, the pharmaceutical compositions described herein are solid pharmaceutical compositions (e.g., tablet, capsules, etc.).

These compositions can be prepared in a manner well known in the pharmaceutical art, and can be administered by any suitable route. Ina preferred embodiment, the pharmaceutical compositions and formulations are designed for oral administration. Conventional pharmaceutical carriers, aqueous, powder or oily bases, thickeners and the like may be necessary or desirable.

The pharmaceutical compositions can be in any suitable form, including but not limited to tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

EXAMPLES

Celiac disease is an autoimmune disorder that afflicts approximately 1% of the population (1, 2). This disease is characterized by an inflammatory reaction to gluten, the major protein in wheat flour, and to related proteins in barley and rye (2). Gluten is composed of a heterogeneous mixture of the glycoproteins gliadin and glutenin (3). Upon ingestion, α-gliadin is partially degraded by gastric and intestinal proteases to oligopeptides, which are resistant to further proteolysis due to their unusually high proline and glutamine content (3). Immunogenic oligopeptides that result from incomplete proteolysis are enriched in the PQ motif (4, 5), which stimulate inflammation and injury in the intestine of people with Celiac disease. Currently the only treatment for this disease is complete elimination of gluten from the diet, which is difficult to attain due to the ubiquity of this protein in modern food products (6).

Oral enzyme therapy (OET) in which orally administered proteases are employed to hydrolyze immunogenic peptides before they are capable of triggering inflammation is currently being explored as a treatment for gluten intolerance. For this purpose, several different proteases have been considered due tot heir specificity for cleavage after either proline or glutamine residues. however, these enzymes often demonstrate characteristics that hinder their use in OET for gluten degradation. Most of these peptidases exhibit optimal catalytic activity at neutral pH; however, the pH of the human stomach ranges from 2 to 4. These enzymes are therefore most active when they reach the pH-neutral small intestine, which is too late for effective prevention of Celiac disease as this is the site where gluten-derived pathology develops. Additionally, several of these enzymes demonstrate instability in the low pH of the human stomach, are susceptible to proteolysis by digestive proteases, or require extensive refolding procedures during their purification, which are all characteristics that hamper efforts for clinical use.

The ideal protease for the application of OET in the treatment of gluten intolerance would combine the following traits: optimal activity at low pH, easy purification, stability under the conditions of the human stomach, and high specificity for amino acid motifs found in gluten-derived immunogenic oligopeptides. We previously identified a protease that is highly active in acidic conditions, Kumamolisin-As (KumaWT) from the acidophilic bacterium *Alicyclobacillus sendaiensis*, and used computational modeling tools to engineer it toward the desired oligopeptide specificity. An exemplary computationally designed enzyme, designated KumaMax™, exhibited over 100-fold increased proteolytic activity and an 800-fold switch in substrate specificity for the targeted PQ motif compared to wild-type KumaWT. In addition, KumaMax™ demonstrates resistance to common gastric proteases and is produced at high yields in *E. coli* without the need for refolding. The previously designed proteins were assessed for catalytic activity against a PQLP (SEQ ID NO: 68) peptide; exemplary results are provided in Table 2

TABLE 2

Table 2. Fold change in hydrolytic activity on PQ motif of all purified and sequenced mutants, relative to wild type Kumamolysin-As. These are the fold-change results for all mutants that were purified, sequenced, and tested against wild-type Kumamolysin in the pure protein assay. The assay took place at pH 4, with enzyme final concentration of 0.0125 mg/mL and substrate concentration of 5 µM.

| Mutations to Wild Type Kumamolysin-As (Preprocessed) | Fold Change in Activity of PQ Hydrolysis Relative to Wild Type Kumamolysin-As |
| --- | --- |
| Wild Type (WT) | 1.0 |
| T357A | 2.0 |
| G319S, D368S | 2.0 |
| D358G | 3.0 |
| D293A | 3.0 |
| D358N | 4.0 |
| G319S, S354N, D358G, D368H | 5.0 |
| D358G, D368H | 6.0 |
| G319S, D358G, D368H | 7.0 |
| N291D, Q361D | 7.5 |
| S354N, D358G, D368H | 9.0 |
| N291D | 10.0 |
| N291D, D293A, Q361D, D358N | 14.8 |
| N291D, D293A | 15.0 |
| N291D, D293A, D358G, Q361D | 15.0 |
| N291D, D358N | 18.9 |
| N291D, Q361D, D358G | 20.0 |
| N291D, G319S, D358G, Q361D, D368H | 23.1 |
| N291D, D293A, D358N | 24.0 |
| S262G, T292S, N291D, G319S, D358G, D368H | 29.0 |
| N291D, D293A, G319S, D358G, Q361D, D368H | 40.9 |
| T292S, N291D, G319S, D358G, D368H | 49.0 |
| N291D, G319S, S354N, D358G, Q361D, D368H | 50.0 |
| N291D, G319S, S354N, D358G, D368H | 54.6 |
| N291D, D293A, G319S, S354N, D358G, Q361D, D368H | 58.0 |
| D293T, N291D, G319S, D358G, D368H | 58.0 |
| S262K, D293N, N291D, G319S, D358G, D368H | 62.0 |
| N291D, G319S, D358G, D368H | 93.0 |
| V119D, S262K, D293T, N291D, G319S, D358G, D368H | 120.0 |

Table 2. Fold Change in Hydrolytic Activity on PQ Motif of all Purified and Sequenced Mutants, Relative to Wild Type Kumamolysin-As.

These are the fold-change results for all mutants that were purified, sequenced, and tested against wild-type Kumamolysin in the pure protein assay. The assay took place at pH 4, with enzyme final concentration of 0.0125 mg/mL and substrate concentration of 5 µM.

In the present study, the inventors tested a large number of Kumamolisin homologues obtained from a wide variety of organisms for activity in degrading gliadin proteins. They share the catalytic triad present in Kumamolisin-As ($Ser^{467}$-$Glu^{267}$-$Asp^{271}$ in the Kumamolisin-As pre-processed form). while Homologue 4 has increased activity against this peptide, suggesting that Homologue 4, alone or in combination therapy with Kumamolisin-related polypeptides, may be an effective therapy for gluten digestion.

TABLE 3

| Homologue # | γ-gliadin (IQPQQPAQL) (SEQ ID NO: 92) | α2-gliadin (PQPQLPYSQPQPFR) (SEQ ID NO: 93) | α9-gliadin (QLQPFPQPQLPY) (SEQ ID NO: 70) | Glia_56-79 (LQLQPFPQPQLPYPQPQLPY) (SEQ ID NO: 94) |
|---|---|---|---|---|
| 1 | ++/−; 29% | ++ (undetect) | −; 80% | ++; 1.6% |
| 2 | +/−; 65% | ++ (undetect) | ++/−; 37%; | ++; 0.2% |
| 3 | −; 108% | −; 123% | −; 116% | −; 104% |
| 4 | +; 12% | ++ (undetect) | ++/−; 25%; | ++; 0.6% |
| 5 | ++/−; 40% | ++ (undetect) | ++/−; 34%; | ++; 0.4% |
| 6 | −; 102% | −; 87% | −; 114% | −; 85% |
| 7 | −; 106% | −; 109% | −; 115% | −; 101% |
| 8 | −; 92% | ++ (undetect) | −; 105% | ++/−; 34% |
| 9 | ++/−; 32% | ++ (undetect) | +/−; 62% | +; 9% |
| Kumamolisin (WT) | ++/−; 39% | ++ (undetect) | ++; 2%; | +++; 0.2% |
| Max | +/−; 55% | +/−; 65% | ++; 0.9% | ++++ |

In order to assess the relative abilities of these homologues to target gluten, the purified homologue were incubated with protein with purified peptides that represent the immunogenic regions throughout gliadin, which is the problematic fraction of gluten for celiac patients.

Homologues were assessed for their ability to break down a fluorescent analogue of gliadin, a hexapeptide (QPQLPY (SEQ ID NO: 91)) that was conjugated to a fluorophore and a quencher, in simulated lab gastric conditions (NaOAc buffer pH 4.0 at 37° C.). The rate of degradation can be calculated from measurement of the fluorescence signal over time. The activity was compared to that of Kumamolisin (denoted below as KWT). Kumamolisin has some activity breaking down these gliadin substrates. Exemplary results are shown in FIG. 1. As can be noted, only a subset of the homologues (1, 2, 4, 8, and 9) tested had activity comparable to or better than Kumamolisin under these conditions.

Figure 2:
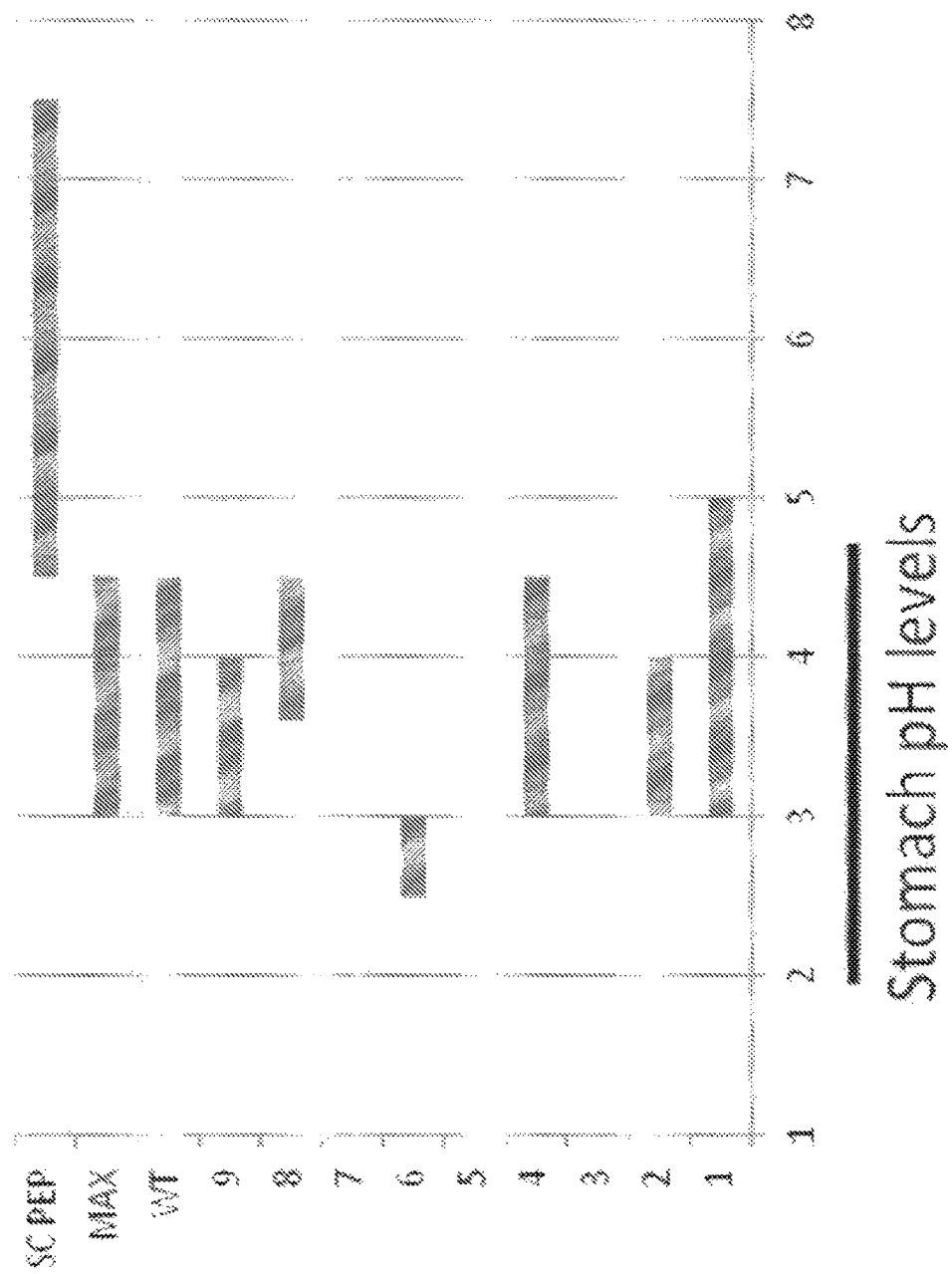
FIG. 2 is a graph showing polypeptide activity in breaking down a fluorescent analogue of gliadin at various pH levels. SC PEP: prolyl endopeptidase from *Sphingomonas capsulata*. WT: Kumamolisin-As. Max: KumaMax™. Blue bars represent optimal protease activity at the indicated pH level.

In a further study, the pH levels were varied and the homologues tested for activity at the different pH levels. The data is shown in FIG. 2. Most of the homologues tested demonstrated activities within the pH range of both Kumamolisin (designated below as "WT") and KumaMax™ (designated as "Max"). Interestingly, two of the homologues had expanded pH ranges compared to Kumamolisin. Homologue 1, was optimally active through pH 5, and Homologue 6 demonstrated optimal activity at a pH level below that of the other homologues and Kumamolisin/KumaMax, explaining why no activity was seen for this homologue in the fluorescent experiment conducted at pH 4. This indicated that homologues 1 and 6 could be used, for example, to expand the pH profile of Kumamolisin-related polypeptides, to more closely mimic pH conditions in the stomach.

We further tested the ability of these homologues to break down different non-fluorescently-labeled peptides that had been linked to celiac disease. Results are provided in Table 3; + and − represents a visual indication of the homologue's ability to break down the indicated peptide: −<+/−<++/−<+<++<+++<++++. The number is the % of peptide that is degraded by the homologue after an 80-min incubation (so the smaller the number, the more effective the homologue); (undetect) means that the peptide was below detection limit after 80 min.

Figure 3:
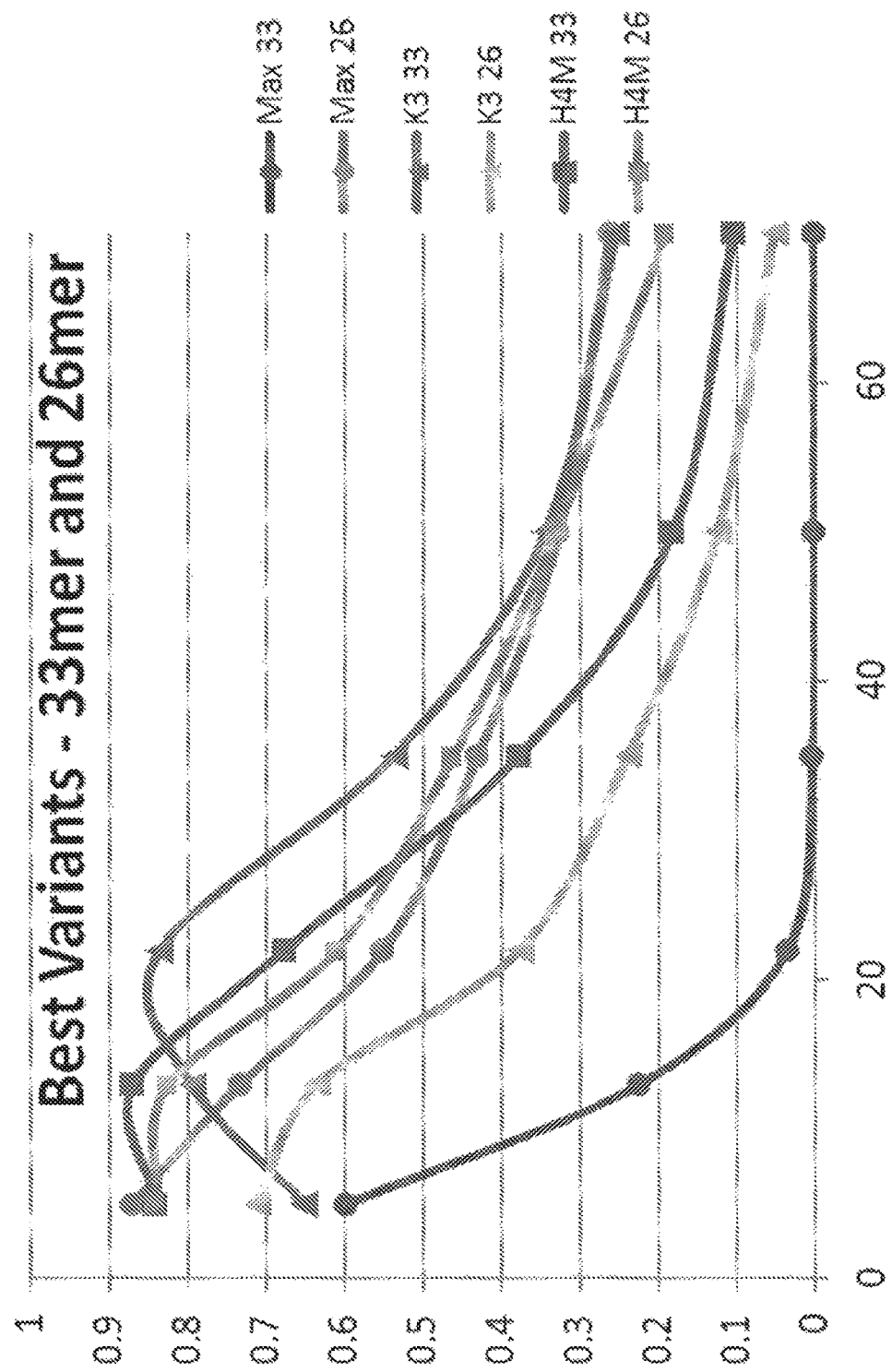
FIG. 3 is a graph showing the activity of various polypeptides to break down two peptides that are degradation products of gluten. On the X-axis is time in minutes, and the Y-axis is fraction of peptide remaining. Max=KumaMax™; K3=Kumamolisin-As active site mutant; H4M=Homologue 4 (SEQ ID NO: 75) KumaMax™-mutant; 33=33mer peptide (SEQ ID NO: 72); 26=26mer peptide (SEQ ID NO: 73).

As can be seen, Kumamolisin and KumaMax™ have fairly low levels of activity against the γ-gliadin peptide, Since these are the homologues of Kumamolisin with a low percentage of sequence identity, we made the same mutations in homologues as were made to Kumamolisin in order to generate KumaMax. We tested the activities of these homologues on two peptides that are degradation products of gluten in the stomach and have been specifically linked to celiac disease: the 33mer peptide (LQLQP-FPQPQLPYPQPQLPYPQPQLPYPQPQPF (SEQ ID NO: 72)) and the 26mer peptide (FLQPQQP-FPQQPQQPYPQQPQQPFPQ (SEQ ID NO: 73)). In particular, the 33mer peptide has been strongly linked to celiac disease. Additionally, the KumaMax™ mutations in the homologues inspired us to make these three active-site mutations alone on the Kumamolisin background (note that KumaMax™ contains a total of 7 mutations from Kumamolisin, but only 3 are within the active site). This mutant, which only contains these active-site mutations, is called the K3 mutant below. The data are provided in Table 4 and FIG. 3. We found that several these homologues demonstrated activity against these two very important peptides, and interestingly, that on Homologue 4 (SEQ ID NO: 75) the KumaMax™ (SEQ ID NO: 90) mutations increased activity against both peptides; in fact, the Homologue 4 Mutant (SEQ ID NO: 89) is the best overall enzyme tested in the experiment shown below, which includes KumaMax™ (SEQ ID NO: 90). This also shows that the K3 mutant could also be combined with KumaMax™ (SEQ ID NO: 90) to generate a more potent therapeutic. (NA=No Activity).

TABLE 4

| Homologue | 33mer | 26mer |
|---|---|---|
| KumaMax | 0.1% | 26% |
| K3 Mutant | 26% | 5% |
| KumaWT | 18% | NA |
| Hom #1 | 46% | NA |
| Hom #1 Max | NA | NA |
| Hom #2 | 31% | NA |
| Hom #2 Max | 29% | NA |
| Hom #4 | 38% | NA |
| Hom #4 Max | 10% | 19% |
| Hom #5 | NA | NA |
| Hom #5 Max | NA | NA |
| Hom #9 | NA | 52% |

TABLE 4-continued

| Homologue | 33mer | 26mer |
|---|---|---|
| Hom #9 Max | NA | 60% |
| Hom #10 | NA | NA |
| Hom #10 Max | NA | NA |

Figure 4:
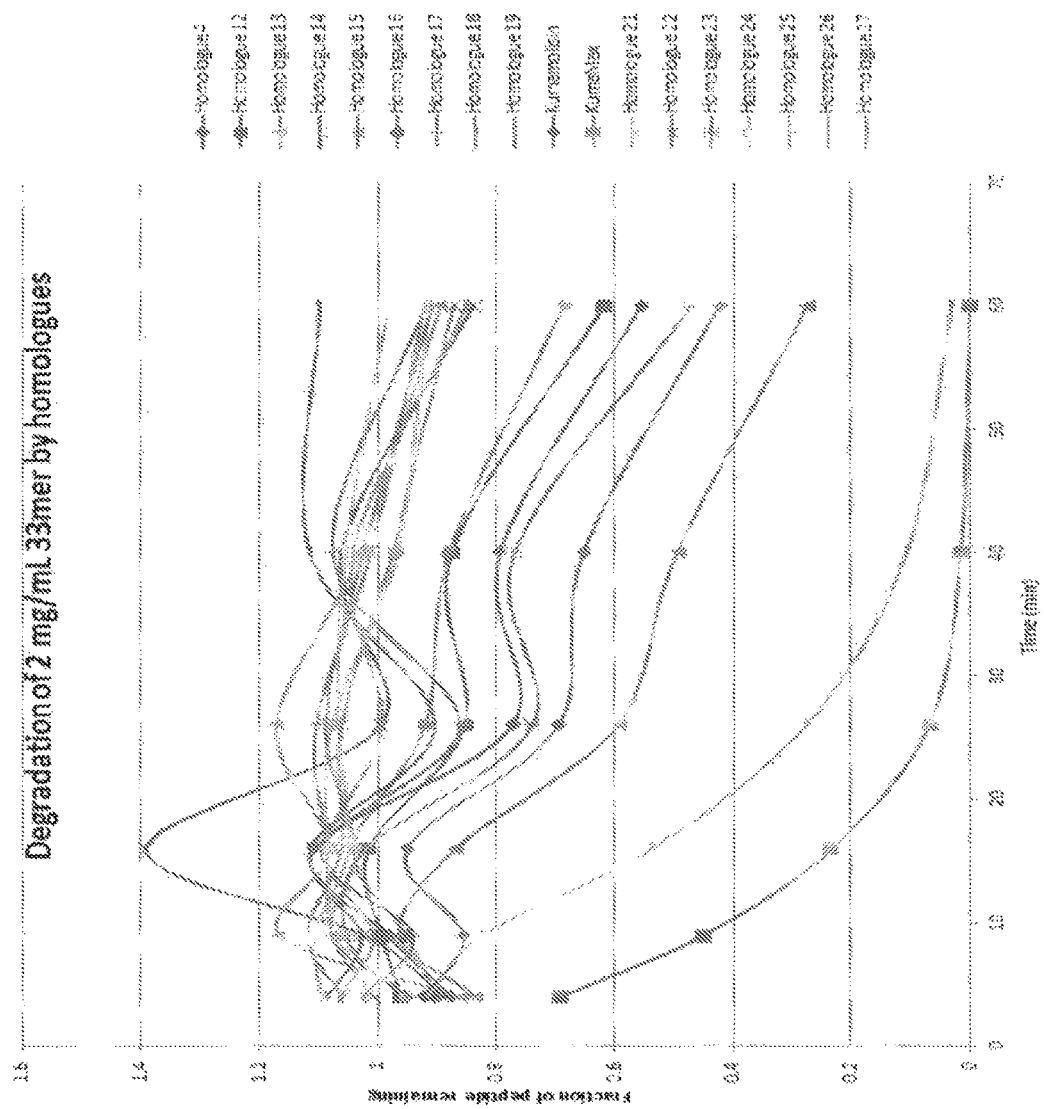
FIG. 4 is a graph showing the activity of various additional polypeptides to break down the 33mer peptide degradation product of gluten (SEQ ID NO: 72).

Further studies were done using additional homologues of Kumamolisin. A subset of these homologues (homologues 13 and 26) demonstrated significant activity against the 33mer peptide: see FIG. 4. In particular, homologue 26 in its wild type form had very strong activity comparable to KumaMax™ at breaking down the 33mer peptide.

We then looked at the profile of digested 33mers via HPLC after a 60 minute incubation: degrading the 33-mer at more than one location provides a significant therapeutic advantage. Wild type Kumamolysin degrades the 33-mer down at only a single location (WT-like), while Kuma-Max™ degrades the 33-mer at multiple locations (Max-like). The data are shown in Table 5.

TABLE 5

| Homologue | Degradation pattern of 33mer (60 min) |
|---|---|
| H4 | WT-like |
| H12 | WT-like |
| H13 | Max-like |
| H14 | WT-like - minor |
| H15 | WT-like |
| H16 | WT-like |
| H17 | WT-like - minor |
| H18 | Undegraded |
| H19 | WT-like - minor |
| H21 | Undegraded |
| H22 | Undegraded |
| H23 | Undegraded |
| H24 | Undegraded |
| H25 | Undegraded |
| H26 | Max-like |
| H27 | Undegraded |

An overall summary of the data is that several homologues, including Homologue 4 (SEQ ID NO: 75) and the Homologue 4 mutant (SEQ ID NO: 89)), 13, and 26, can be used as therapeutics to treat celiac disease. Homologue 26 (SEQ ID NO: 88) is almost as potent as KumaMax™ (SEQ ID NO: 90) and this is in the absence of any engineering, and Homologue 4 (demonstrated increased activity with the mutations that were made to KumaMax™. Furthermore, pH profiles from these homologues (in particular, Homologue 6 (including the Homologue 6 mutant) and Homologue 1) suggest that these homologues, alone or in combination, can expand the pH range of therapeutic efficacy in the human stomach.

METHODS

Protein Expression and Purification

The genes encoding each protein of interest, harbored in the pET29b plasmid, were transformed into *Escherichia coli* BL21 (DE3) cells. Individual colonies were picked, inoculated into Terrific Broth™ with 50 µg/µL Kanamycin (TB+Kan), and incubated overnight at 37° C. 500 uL of the overnight culture was added to 500 mL autoinduction media (5 g tryptone, 2.5 g yeast extract, 465 mL ddH$_2$O), and shaken at 37° C. for roughly 4 hours, then the autoinduction components were added (500 uL MgSO$_4$, 500 uL 1000× trace metals, 25 mL 20×NPS, 10 mL 20×5052, 500 uL 50 mg/mL Kan). The cultures were then shaken at 18° C. for 30 hours before being spun down. Pellets were resuspended in 10 mL 1×PBS, then lysed via sonication with 5 mL lysis buffer (50 mM HEPES, 500 mM NaCl, 1 mM bME, 2 mg/mL lysozyme, 0.2 mg/mL DNase, ddH$_2$O) and spun down. The proteins were then purified over 1 mL TALON cobalt affinity columns: KumaMax, KumaWT, and SC Pep were washed three times with 20 mL was buffer (10 mM imidazole, 50 mM HEPES, 500 mM, NaCl, 1 mM bME, ddH$_2$O), and then eluted in 15 mL of elution buffer (200 mM imidazole, 50 mM HEPES, 500 mM NaCl, 1 mM bME). EP-B2 had to be refolded on the column, so after lysis the pellets were resuspended in 10 mL of EP-B2 buffer, which differs from the wash buffer only in that it is diluted in guanidine hydrochloride instead of ddH$_2$O to allow for denaturation of the EP-B2 inclusion bodies. This resuspension was pelleted, and the supernatant (containing denatured EP-B2) was filtered with a 0.8 µm filter onto the column. EP-B2 was washed once with 20 mL of the EP-B2 buffer, before being washed twice with 20 mL of the wash buffer to refold the protein on the column. Protein was eluted with 15 ml of the elution buffer. All proteins were concentrated from 15 mL down to ~500 uL, then dialyzed once in 1 L dialysis buffer (20% glycerol, 50 mM HEPES, 500 mM NaCl, 1 mM bME). Protein concentration was calculated spectrophotometrically with extinction coefficients of 53,985 M$^{-1}$ cm$^{-1}$ for KumaWT and all KumaWT variants, 152,290 M$^{-1}$cm$^{-1}$ for SC Pep, and 58,245 M$^{-1}$cm$^{-1}$ for EP-B2.

Purified Enzyme Assay

The variants of Kumamolisin-As that displayed the most activity on the FQ substrate in the activity screen were sequenced, then purified in small scale. 500 uL of TB+Kan overnight cultures were added to 50 mL TB+Kan and grown at 37° C. until reaching an optical density of 0.5-0.8. IPTG was added to 0.5 mM, and the cultures were expressed at 22° C. for 16-24 hours. The cells were spun down, resuspended in 500 uL of wash buffer (1×PBS, 5 mM imidazole, ddH$_2$O), transferred to a 2 mL Eppendorf tube, and lysed in 1 mL lysis buffer (1×PBS, 5 mM imidazole, 2×Bug Buster™, 2 mg/mL lysozyme, 0.2 mg/mL DNase, ddH$_2$O). After centrifugation, the supernatant was decanted into a fresh tube. Columns with 200 uL of TALON cobalt resin were placed in Eppendorf tubes, and the supernatant was poured over the columns and rocked for 20 minutes before spinning down and discarding the flow-through. The proteins were washed three times with 500 uL wash buffer, discarding the flow-through between washes. Enzymes were eluted in 200 uL elution buffer (1×PBS, 200 mM imidazole, dd H$_2$O), and concentrations were calculated spectrophotometrically using an extinction coefficient of 53,985 M$^{-1}$cm$^{-1}$.

For the assay, the Kumamolisin-As mutants were incubated for 15 minutes in pH 4 100 mM sodium acetate buffer. Enzyme was added to 5 µM substrate so that the final protein concentration was 0.0125 mg/mL. The fluorescence was measured at 30-second intervals for 1 hour.

Kinetic Characterization

Enzyme variant proclivity for gluten degradation was measured by hydrolysis of the fluorescently quenched α-gliadin hexapeptide analogue QXL520-PQPQLP-K(5-FAM)-NH2 (FQ) (SEQ ID NO: 69) as a substrate. Each enzyme was incubated at room temperature for 15 minutes in 100 mM pH 4 sodium acetate buffer. After 15 minutes, 50 uL of fluorescent substrate was added ranging in final concentration between 100, 50, 25, 12.5, 6.25, and 0 µM peptide, and maintaining concentrations of 0.05 µM KumaMax™, 0.5 µM KumaWT, 0.5 µM SC Pep, and 0.5 µM EP-B2 across all variations in substrate concentration. The plate was read immediately on the spectrophotometer for an hour, using 455 nm wavelength for excitation and reading 485 nm wavelength for emission.

The enzymes were also tested for specificity to different dipeptide motifs using a variety of chromogenic substrates that release p-nitroaniline (pNA) upon hydrolysis: [Suc-APQ-pNA], [Suc-AQP-pNA], [Suc-APE-pNA], and [Suc-APR-pNA]. Again, each enzyme was incubated at room temperature for 15 minutes in 100 mM pH 4 sodium acetate buffer. After 15 minutes, 20 uL of substrate was added to the enzyme incubation so that the final concentrations of substrate ranged between 1000, 500, 250, 125, 62.5, 31.25, 15.625, and 0 µM, and all enzymes being tested ended in a concentration of 0.5 µM. The plate was read immediately on the spectrophotometer for an hour, monitoring absorption by the reactions at 385 nm.

The standard curve for the fluorescent peptide involved mixing substrate and product together at varying concentrations in pH 4 buffer. Substrate concentrations were 100, 50, 25, 12.5, 6.25, and 0 µM, and product concentrations were 20, 5, 1.25, 0.3125, 0.078125, 0 µM.

The standard curve for the absorbent peptide involved product concentrations of 100, 50, 25, 12.5, 6.25, 3.125, 1.5625, 0.78125, 0.390625, 0.1953125, 0.09765625, and 0 µM diluted in pH 4 buffer.

Protease Stability

Enzyme stability was determined in the presence the digestive proteases, pepsin and trypsin. KumaWT, KumaMax™, SC Pep, and EP-B2 were incubated in buffer matching the native pH environment of each digestive protease. pH 3.5 100 mM sodium acetate was used to pre-incubate the enzymes for pepsin digestion assays, and pH 7.5 dialysis buffer (see "Protein Expression and Purification") for the trypsin digestion assays. Each experimental enzyme was incubated at 37° C. for 15 minutes in each buffer, at a concentration of 0.2 mg/mL.

After pre-incubation in the appropriate buffer, 0.1 mg/mL digestive protease was added. The reactions were done in triplicate, and were incubated at 37° C. for 30 minutes. Adding SDS and boiling for 5 minutes ensured digestive protease inactivation. An SDS-PAGE gel allowed quantification of enzyme-degradation, using Imagel.

The rate of protein self-proteolysis was determined at pH 4 and 7.5 in the absence of pepsin or trypsin. Each enzyme, at a concentration of 0.2 mg/mL, was incubated in pH 4 100 mM sodium acetate and pH 7.5 dialysis buffer. At 20, 40, and 60 minutes, timepoints were taken. SDS was added, and the aliquots were boiled for 5 minutes to ensure denaturation of the enzymes and inhibition of further self-proteolysis. Again, an SDS-PAGE gel in conjunction with Imagel allowed quantification of enzyme self-proteolysis.

LCMS Gliadin Degradation Assay

Enzyme activity on full-length α9-gliadin was measured using high-performance liquid-chromatography mass spectrometry. For each enzyme, 7 µL of pH 4 1 M sodium acetate buffer was added to 28 µL of 5 µM enzyme, and incubated alongside separate tubes of 3 µL gliadin at 37° C. for 15 minutes. Next 27 µL of each enzyme mixture, and 27 µL of dialysis buffer as a control, were added to each tube of gliadin. These were incubated once more at 37° C., and 5 µL samples were taken at 10, 20, 30, 40, and 50 minutes. Each timepoint sample was quenched in 95 µL of 80% acetonitrile with 1% formic acid and approximately 33 µM leupeptin. The samples were analyzed on the HPLC to compare gliadin degradation by the different proteases over time.

REFERENCES

1. Armstrong, M. J., Hegade, V.S. & Robins, G. Advances in coeliac disease. *Curr Opin Gastroenterol* 28, 104-12 (2012).
2. Sollid, L. M. Coeliac disease: dissecting a complex inflammatory disorder. *Nat Rev Immunol* 2, 647-55 (2002).
3. Wieser, H. Chemistry of gluten proteins. *Food Mircrobiol* 24, 115-9 (2007).
4. Shan, L. et al. Structural basis for gluten intolerance in celiac sprue. *Science* 297, 2275-9 (2002).
5. Shan, L. Identification and analysis of multivalent proteolytically resistant peptides from gluten: implications for celiac sprue. *Journal of Proteome Research* (2005).
6. Chand, N. & Mihas, A. A. Celiac disease: current concepts in diagnosis and treatment. *J Clin Gastroenterol* 40, 3-14 (2006).
7. Shan, L., Marti, T., Sollid, L. M., Gray, G. M. & Khosia, C. Comparative biochemical analysis of three bacterial prolyl endopeptidases: implications for coeliac sprue. *Biochem J* 383, 311-8 (2004).
8. Seigel, M. et al. Rational design of combination enzyme therapy for celiac sprue. *Chem Biol* 13, 649-58 (2006).
9. Stepniak, D. et al. Highly efficient gluten degradation with a newly identified prolyl endoprotease: implications for celiac disease. *Am J Physiol Gastrointest Liver Physiol* 291, G621-9 (2006).
10. Ehren, J. et al. A food-grade enzyme preparation with modest gluten detoxification properties. *PLoS One* 4, e6313 (2009).
11. Bethune, M. T., Strop, P., Tang, Y., Sollid, L. M. & Khosla, C. Heterologous expression, purification, refolding, and structural-functional characterization of EP-B2, a self-activating barley cysteine endoprotease. *Chem Biol* 13, 637-47 (2006).
12. Okubo, A. et al. Processing, catalytic activity and crystal structures of kumamolisin-As with an engineered active site. *FEBS J* 273, 2563-76 (2006).
13. Gardner, J. D., Ciociola, A. A. & Robinson, M. Measurement of meal-stimulated gastric acid secretion by in vivo gastric autotitration. *J Appl Physiol* 92, 427-34 (2002).
14. Wlodawer, A. et al. Crystallographic and biochemical investigations of kumamolisin-As, a serine-carboxyl peptidase with collagenase activity. *J Biol Chem* 279, 21500-10 (2004).
15. Ehren, J., Govindarajan, S., Moron, B., Minshull, J. & Khosla, C. Protein engineering of improved prolyl endopeptidases for celiac sprue therapy. *Protein Eng Des Sel* 21, 699-707 (2008).
16. Bethume, M. T. & Khosla, C. Oral enzyme therapy for celiac sprue. *Methods Enzymol* 502, 241-71 (2012).
17. Gass, J., Vora, H., Bethume, M. T., Gray, G.M. & Khosla, C. Effect of barley endoprotease EP-B2 on gluten digestion in the intact rat. *J Pharmacol Exp Ther* 318, 1178-86 (2006).
18. Vora, H., McIntire, J., Kumar, P., Deshpande, M. & Khosla, C. A scaleable manufacturing process for pro-EP-B2, a cysteine protease from barley indicated for celiac sprue. *Biotechnol Bioeng* 98, 177-85 (2007).

We claim:

1. A method for treating celiac sprue, comprising administering to a subject with celiac sprue an amount effective to treat the celiac sprue of one or more polypeptides comprising or consisting of the amino acid sequence of a polypeptide selected from the group consisting of SEQ ID NOS: 74-89, 95, 97-98, and 102-111, or processed versions thereof wherein said processed versions thereof are devoid of at least 1-42 residues from said SEQ ID NOs.

2. The method of claim 1, wherein the one or more polypeptides comprise one or more polypeptides comprising or consisting of the amino acid sequence of a polypeptide selected from the group consisting of SEQ ID NOs: 74, 75, 77, 78, 82, 88, 98, 105, and 111, or processed versions thereof.

3. The method of claim 1, wherein the one or more polypeptides comprise a polypeptide with the amino acid sequence of SEQ ID NO: 89.

4. The method of claim 1, further comprising administering to the subject an amount of one or more further polypeptides comprising an amino acid sequence selected from the group consisting of:

(A) an amino acid sequence at least 75% identical to the amino acid sequence of SEQ ID NO: 35, wherein (i) the polypeptide degrades a PQPQLP (SEQ ID NO: 34) peptide at pH 4; and
(ii) residue 278 is Ser, residue 78 is Glu, and residue 82 is Asp (B) an amino acid sequence at least 75% identical to the amino acid sequence of SEQ ID NO: 1, wherein (i) the polypeptide degrades a PQPQLP (SEQ ID NO: 34) peptide at pH 4; and
(ii) residue 467 is Ser, residue 267 is Glu, and residue 271 is Asp.

5. The method of claim 4, wherein the one or more further polypeptides comprise an amino acid sequence at least 85% identical to the amino acid sequence of SEQ ID NO: 1 or SEQ ID NO: 35.

6. The method of claim 5, wherein the one or more further polypeptides comprise an amino acid sequence at least 95% identical to the amino acid sequence of SEQ ID NO: 1 or SEQ ID NO: 35.

7. The method of claim 6, wherein the one or more further polypeptides comprise the amino acid sequence of SEQ ID NO: 1 and/or SEQ ID NO: 35.

8. The method of claim 4, wherein the one or more further polypeptides comprise the amino acid sequence of any one of SEQ ID NO: 2-33 or 36-67.

9. The method of claim 4 wherein the one or more further polypeptides comprises the amino acid sequence of SEQ ID NO: 90.

10. The method of claim 4, therein the one or more polypeptides comprise SEQ ID NO: 75, SEQ ID NO: 89, and/or SEQ ID NO: 98, or said processed versions thereof.

11. The method of claim 4, wherein the one or more polypeptides comprise SEQ ID NO: 74, 77, and/or 78, or said processed versions thereof.

12. The method of claim 4, wherein the one or more polypeptides comprise SEQ ID NO: 88 and/or SEQ ID NO: 111, or said processed versions thereof.

13. The method of claim 1, wherein the polypeptide and, when present, the further polypeptide, are administered orally.

14. An isolated polypeptide selected from the group consisting of a polypeptide comprising the amino acid sequence selected from the following group, or processed versions thereof wherein said processed versions thereof are devoid of at least 1-42 residues from the following SEQ ID NOs:

(a) SEQ ID NO: 95, wherein one, two, three, four, five, six, seven, eight, nine, ten, or all eleven of the following are true: (i) amino acid (AA) residue 116 is V or D; (ii) AA residue 255 is S, K, or G; (iii) AA residue 284 is D; (iv) AA residue 285 is T; (v) AA residue 286 is A, T, or N; (vi) AA residue 312 is S; (vii) AA residue 347 is N; (viii) AA residue 350 is T or A; (ix) AA residue 351 is N or G; (x) AA residue 354 is D; and (xi) AA residue 361 is S or H;

(b) SEQ ID NO: 75, wherein one, two, three, four, five, six, seven, eight, nine, ten, or all eleven of the following are true: (i) AA residue 106 is D; (ii) AA residue 246 is S, K, or G; (iii) AA residue 275 is D; (iv) AA residue 276 is S; (v) AA residue 277 is A, T, or N; (vi) AA residue 303 is S; (vii) AA residue 338 is S; (viii) AA residue 341 is T or A; (ix) AA residue 342 is N or G; (x) AA residue 345 is Q or D; and (xi) AA residue 352 is S or H;

(c) SEQ ID NO: 76, wherein one, two, three, four, five, six, seven, eight, nine, ten, or all eleven of the following are true: (i) AA residue 120 is D; (ii) AA residue 259 is S, K, or G; (iii) AA residue 288 is D; (iv) AA residue 289 is T; (v) AA residue 290 is A, T, or N; (vi) AA residue 316 is S; (vii) AA residue 351 is S or N; (viii) AA residue 354 is A; (ix) AA residue 355 is N or G; (x) AA residue 358 is D; and (xi) AA residue 365 is S or H;

(d) SEQ ID NO: 78;

(e) SEQ ID NO: 79, wherein one, two, three, four, five, six, seven, eight, nine, ten, or all eleven of the following are true: (i) AA residue 107 is V or D; (ii) AA residue 245 is S, K, or G; (iii) AA residue 274 is D; (iv) AA residue 275 is T; (v) AA residue 276 is A, T, or N; (vi) AA residue 302 is S; (vii) AA residue 337 is S or N; (viii) AA residue 340 is T or A; (ix) AA residue 341 is N or G; (x) AA residue 344 is Q or D; and (xi) AA residue 351 is S or H;

(f) SEQ ID NO: 80, wherein one, two, three, four, five, six, seven, eight, nine, ten, or all eleven of the following are true: (i) AA residue 76 is V or D; (ii) AA residue 206 is S, K, or G; (iii) AA residue 235 is D; (iv) AA residue 236 is S; (v) AA residue 237 is A, T, or N; (vi) AA residue 262 is S; (vii) AA residue 297 is S or N; (viii) AA residue 300 is T or A; (ix) AA residue 301 is N or G; (x) AA residue 302 is Q or D; and (xi) AA residue 309 is S or H;

(g) SEQ ID NO: 81, wherein one, two, three, four, five, six, seven, eight, nine, ten, or all eleven of the following are true: (i) AA residue 105 is D; (ii) AA residue 244 is S or K; (iii) AA residue 272 is D; (iv) AA residue 273 is S; (v) AA residue 274 is A, T, or N; (vi) AA residue 299 is S; (vii) AA residue 334 is N; (viii) AA residue 337 is T or A; (ix) AA residue 338 is N or G; (x) AA residue 341 is Q or D; and (xi) AA residue 348 is S or H;

(h) SEQ ID NO: 82, wherein one, two, three, four, five, six, seven, eight, nine, ten, or all eleven of the following are true: (i) AA residue 106 is V or D; (ii) AA residue 244 is S, K, or G; (iii) AA residue 273 is D; (iv) AA residue 274 is T; (v) AA residue 275 is A, T, or N; (vi) AA residue 301 is S; (vii) AA residue 336 is N; (viii) AA residue 339 is T or A; (ix) AA residue 340 is N or G; (x) AA residue 343 is D; and (viii) AA residue 350 is S or H;

(i) SEQ ID NO: 83, wherein one, two, three, four, five, six, seven, eight, nine, ten, or all eleven of the following are true: (i) AA residue 107 is V or D; (ii) AA residue 245 is S, K, or G; (iii) AA residue 274 is D; (iv) AA residue 275 is T; (v) AA residue 276 is A, T, or N; (vi) AA residue 302 is S; (vii) AA residue 337 is N; (viii) AA residue 340 is T or A; (ix) AA residue 341 is N or G; (x) AA residue 344 is Q or D; and (xi) AA residue 351 is S or H;

(j) SEQ ID NO: 84, wherein one, two, three, four, five, six, seven, eight, nine, ten, or all eleven of the following are true: (i) AA residue 104 is V or D; (ii) AA residue 241 is S, K, or G; (iii) AA residue 270 is D; (iv) AA residue 271 is S; (v) AA residue 272 is D, A, T, or N; (vi) AA residue 398 is S; (vii) AA residue 33 is S; (viii) AA residue 336 is A; (ix) AA residue 337 is N or G; (x) AA residue 340 is D; and (xi) AA residue 347 is S or H;

(k) SEQ ID NO: 85, wherein one, two, three, four, five, six, seven, eight, nine, ten, or all eleven of the following are true: (i) AA residue 104 is D; (ii) AA residue 245 is S, K, or G; (iii) AA residue 274 is D; (iv) AA residue 275 is S; (v) AA residue 276 is A, T, or N; (vi) AA residue 302 is S; (vii) AA residue 337 is S or N; (viii) AA residue 340 is T or A; (ix) AA residue 341 is N or G; (x) AA residue 344 is Q or D; and (xi) AA residue 351 is S or H;

(l) SEQ ID NO: 86, wherein one, two, three, four, five, six, seven, eight, nine, ten, or all eleven of the following are true: (i) AA residue 118 is V or D; (ii) AA residue 250 is K, or G; (iii) AA residue 279 is D; (iv) AA residue 280 is S; (v) AA residue 281 is A, T, or N; (vi) AA residue 307 is S; (vii) AA residue 342 is S or N; (viii) AA residue 345 is A; (ix) AA residue 346 is N or G; (x) AA residue 349 is Q or D; and (xi) AA residue 356 is S or H;

(m) SEQ ID NO: 87, wherein one, two, three, four, five, six, seven, eight, nine, ten, or all eleven of the following are true: (i) AA residue 121 is V or D; (ii) AA residue 253 is S, K, or G; (iii) AA residue 282 is D; (iv) AA residue 283 is S; (v) AA residue 284 is A, T, or N; (vi) AA residue 310 is S; (vii) AA residue 345 is S; (viii) AA residue 348 is T or A; (ix) AA residue 349 is N or G; (x) AA residue 352 is Q or D; and (xi) AA residue 357 is S or H;

(n) SEQ ID NO: 88, wherein one, two, three, four, five, six, seven, eight, nine, or all ten of the following are true: (i) AA residue 111 is S, K, or G; (ii) AA residue 139 is D; (iii) AA residue 140 is T or S; (iv) AA residue 141 is D, A, T, or N; (v) AA residue 164 is S; (vi) AA residue 199 is S or N; (vii) AA residue 202 is T or A; (viii) AA residue 203 is N or G; (ix) AA residue 204 is Q or D; and (x) AA residue 211 is S or H; and
   (o) SEQ ID NO: 89.

15. The isolated polypeptide of claim 14, selected from the group consisting of the following, or said processed versions thereof wherein said processed versions thereof are devoid of at least 1-42 residues from the following SEQ ID NOs:
   (i) SEQ ID NO: 75, wherein one, two, three, four, five, six, seven, eight, nine, ten, or all eleven of the following are true: (i) AA residue 106 is D; (ii) AA residue 246 is S, K, or G; (iii) AA residue 275 is D; (iv) AA residue 276 is S; (v) AA residue 277 is A, T, or N; (vi) AA residue 303 is S; (vii) AA residue 338 is S; (viii) AA residue 341 is T or A; (ix) AA residue 342 is N or G; (x) AA residue 345 is Q or D; and (xi) AA residue 352 is S or H;
   (ii) SEQ ID NO: 78;
   (iii) SEQ ID NO: 82, wherein one, two, three, four, five, six, seven, eight, nine, ten, or all eleven of the following are true: (i) AA residue 106 is V or D; (ii) AA residue 244 is S, K, or G; (iii) AA residue 273 is D; (iv) AA residue 274 is T; (v) AA residue 275 is A, T, or N; (vi) AA residue 301 is S; (vii) AA residue 336 is N; (viii) AA residue 339 is T or A; (ix) AA residue 340 is N or G; (x) AA residue 343 is D; and (viii) AA residue 350 is S or H;
   (iv) SEQ ID NO: 88, wherein one, two, three, four, five, six, seven, eight, nine, or all ten of the following are true: (i) AA residue 111 is S, K, or G; (ii) AA residue 139 is D; (iii) AA residue 140 is T or S; (iv) AA residue 141 is D, A, T, or N; (v) AA residue 164 is S; (vi) AA residue 199 is S or N; (vii) AA residue 202 is T or A; (viii) AA residue 203 is N or G; (ix) AA residue 204 is Q or D; and (x) AA residue 211 is S or H; and
   (v) SEQ ID NO: 89.

16. The isolated polypeptide of claim 14, comprising the amino acid sequence of SEQ ID NO: 89, or said processed version thereof.

17. The isolated polypeptide of claim 14, comprising the amino acid sequence of SEQ ID NO: 78, or said processed version thereof.

18. A nucleic acid encoding the polypeptide of claim 14.

19. A nucleic acid expression vector comprising the nucleic acid of claim 18.

20. A recombinant host cell comprising the nucleic acid expression vector of claim 19.

21. A composition, comprising
   (a) one or more polypeptides comprising the amino acid sequence of a polypeptide selected from the group consisting of SEQ ID NOs: 74-89, 95, 97-99, and 102-111, or processed versions thereof; and
   (b) one or more further polypeptides comprising an amino acid sequence selected from the group consisting of:
      (A) an amino acid sequence at least 75% identical to the amino acid sequence of SEQ ID NO: 35, wherein
         (i) the polypeptide degrades a PQPQLP (SEQ ID NO: 34) peptide at pH 4; and
         (ii) residue 278 is Ser, residue 78 is Glu, and residue 82 is Asp
      (B) an amino acid sequence at least 75% identical to the amino acid sequence of SEQ ID NO: 1, wherein
         (i) the polypeptide degrades a PQPQLP (SEQ ID NO: 34) peptide at pH 4; and
         (ii) residue 467 is Ser, residue 267 is Glu, and residue 271 is Asp.

22. The composition of claim 21, wherein the one or more polypeptides comprise SEQ ID NO: 75, SEQ ID NO: 89, and/or SEQ ID NO: 98, or said processed versions thereof.

23. The composition of claim 21, wherein the one or more polypeptides comprise SEQ ID NO: 74, 77, and/or 78, or said processed versions thereof.

24. The composition of claim 21, wherein the one or more polypeptides comprise SEQ ID NO: 88 and/or SEQ ID NO: 111, or said processed versions thereof.

25. The composition of claim 21, wherein the one or more further polypeptides comprise the amino acid sequence of SEQ ID NO: 1 and/or SEQ ID NO: 35.

26. The composition of claim 21, wherein the one or more further polypeptides comprise the amino acid sequence of any one of SEQ ID NO: 2-33 or 36-67.

27. The composition of claim 21 wherein the one or more further polypeptides comprises the amino acid sequence of SEQ ID NO: 90, or said processed version thereof.

28. A pharmaceutical composition, comprising the isolated polypeptide of claim 14, and a pharmaceutically acceptable carrier.

29. The pharmaceutical composition of claim 28, wherein the composition is formulated for oral delivery.

* * * * *